US007504420B2

(12) United States Patent
Ghosh et al.

(10) Patent No.: US 7,504,420 B2
(45) Date of Patent: Mar. 17, 2009

(54) COMPOUNDS WHICH INHIBIT BETA-SECRETASE ACTIVITY AND METHODS OF USE

(75) Inventors: Arun K. Ghosh, West Lafayette, IN (US); Nagaswamy Kumaragurubaran, Tamil Nadu (IN); Chunfeng Liu, Oklahoma City, OK (US); Thippeswamy Devasamudram, Edmond, OK (US); Hui Lei, Edmond, OK (US); Lisa M. Swanson, Oklahoma City, OK (US); Sudha V. Ankala, Oklahoma City, OK (US); Jordan J. N. Tang, Edmond, OK (US); Geoffrey M. Bilcer, Edmond, OK (US)

(73) Assignees: CoMentis, Inc., South San Francisco, CA (US); The Board of Trustees of the University of Illinois, Urbana, IL (US); Oklahoma Medical Research Foundation, Oklahoma City, OK (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 11/463,558

(22) Filed: Aug. 9, 2006

(65) Prior Publication Data
US 2007/0117793 A1 May 24, 2007

Related U.S. Application Data

(63) Continuation of application No. PCT/US2006/013342, filed on Apr. 10, 2006.

(60) Provisional application No. 60/717,541, filed on Sep. 14, 2005, provisional application No. 60/669,541, filed on Apr. 8, 2005.

(51) Int. Cl.
*A61K 31/44* (2006.01)
*C07D 417/101* (2006.01)

(52) U.S. Cl. .................. 514/342; 514/336; 514/340; 514/365; 514/374.2; 546/193; 546/269.7; 546/271.4; 548/204; 548/205; 548/235

(58) Field of Classification Search .................. 514/318, 514/326, 336, 340, 342, 365, 374; 546/193, 546/196, 197, 202, 208, 209, 210, 214, 229, 546/269.7, 271.4; 548/204, 205, 235
See application file for complete search history.

(56) References Cited

U.S. PATENT DOCUMENTS

| 4,801,575 | A | 1/1989 | Pardridge |
| 4,861,760 | A | 8/1989 | Mazuel et al. |
| 4,863,905 | A | 9/1989 | Hudspeth et al. |
| 4,911,920 | A | 3/1990 | Jani et al. |
| 5,120,718 | A | 6/1992 | Goldman et al. |
| 5,212,162 | A | 5/1993 | Missel et al. |
| 5,403,841 | A | 4/1995 | Lang et al. |
| 6,180,603 | B1 | 1/2001 | Frey, II |
| 6,287,792 | B1 | 9/2001 | Pardridge et al. |
| 6,313,093 | B1 | 11/2001 | Frey, II |
| 6,372,250 | B1 | 4/2002 | Pardridge |
| 7,034,182 | B2 | 4/2006 | Fang et al. |
| 7,176,242 | B2 * | 2/2007 | John et al. ................... 514/615 |
| 7,214,715 | B2 * | 5/2007 | Beck et al. ................... 514/616 |
| 2002/0013276 | A1 | 1/2002 | Nadin et al. |
| 2002/0128255 | A1 * | 9/2002 | Beck et al. ............. 514/211.15 |
| 2003/0095958 | A1 | 5/2003 | Bhisetti et al. |
| 2003/0215398 | A1 | 11/2003 | Frey, II |
| 2003/0215432 | A1 | 11/2003 | Matalon |
| 2003/0216589 | A1 | 11/2003 | Gschneider et al. |
| 2004/0101904 | A1 | 5/2004 | Pardridge et al. |
| 2004/0102369 | A1 | 5/2004 | Wu et al. |
| 2004/0110928 | A1 | 6/2004 | Crisanti et al. |
| 2004/0121947 | A1 | 6/2004 | Ghosh et al. |
| 2004/0209925 | A1 | 10/2004 | Pulley et al. |
| 2005/0032848 | A1 | 2/2005 | Aquino et al. |
| 2005/0043290 | A1 | 2/2005 | Cumming et al. |
| 2005/0239684 | A1 * | 10/2005 | Ghosh et al. ................... 514/2 |
| 2006/0025459 | A1 | 2/2006 | Demont et al. |
| 2006/0234944 | A1 | 10/2006 | Ghosh et al. |
| 2007/0032470 | A1 | 2/2007 | Wu et al. |
| 2007/0149569 | A1 | 6/2007 | Neitz et al. |
| 2008/0176939 | A1 | 7/2008 | Ghosh et al. |

FOREIGN PATENT DOCUMENTS

| EP | 0 569 811 A1 | 11/1993 |
| EP | 0 569 811 B1 | 11/1993 |
| EP | 0 609 625 A1 | 8/1994 |
| WO | WO-88/03927 A2 | 6/1988 |
| WO | WO-88/03927 A3 | 6/1988 |
| WO | WO-89/07109 A1 | 8/1989 |
| WO | WO-89/10134 A1 | 11/1989 |
| WO | WO-96/05309 A2 | 2/1996 |

(Continued)

OTHER PUBLICATIONS

MedicineNet.com. Tacrine. (2007).*
PCT search report.*
Xue et al. "Preparation of 2-hydroxy . . . " CA 147:30947 (2007).*
Braga et al. "Making crystals . . . " Chem. Commun. (2005) pp. 3635-3645.*
Varghese, J. (Mar. 2006). "Human β-Secretase (BACE) and BACE inhibitors: Progress Report," *Current Topics in Medicinal Chemistry* 6(6):569-578.
Abbott, N.J. et al. (1992). *Physiology and Pharmacology of the Blood-Brain Barrier*, Bradbury, M.W.B. ed., Springer-Verlag:Berlin, Germany, pp. XI-XXIII. (Table of Contents Only.)
Abbott, N.J. et al. (Mar. 1996). "Transporting Therapeutics Across the Blood-brain Barrier," *Mol. Med. Today* 2(3):106-113.

(Continued)

*Primary Examiner*—Celia Chang
(74) *Attorney, Agent, or Firm*—Morrison & Foerster LLP

(57) ABSTRACT

The present invention provides novel beta-secretase inhibitors and methods for their use, including methods of treating Alzheimer's disease.

48 Claims, No Drawings

FOREIGN PATENT DOCUMENTS

| | | |
|---|---|---|
| WO | WO-96/05309 A3 | 2/1996 |
| WO | WO-02/02506 A2 | 1/2002 |
| WO | WO-02/02506 A3 | 1/2002 |
| WO | WO-02/02512 A2 | 1/2002 |
| WO | WO-02/02512 A3 | 1/2002 |
| WO | WO-02/02518 A2 | 1/2002 |
| WO | WO-02/02518 A3 | 1/2002 |
| WO | WO-02/02520 A2 | 1/2002 |
| WO | WO-02/02520 A3 | 1/2002 |
| WO | WO-02/053594 A2 | 7/2002 |
| WO | WO-02/053594 A3 | 7/2002 |
| WO | WO-02/088101 A2 | 11/2002 |
| WO | WO-02/088101 A3 | 11/2002 |
| WO | WO-02/094768 A2 | 11/2002 |
| WO | WO-02/094768 A3 | 11/2002 |
| WO | WO-02/098849 A2 | 12/2002 |
| WO | WO-02/098849 A3 | 12/2002 |
| WO | WO-02/100399 A1 | 12/2002 |
| WO | WO-02/100410 A1 | 12/2002 |
| WO | WO-02/100856 A1 | 12/2002 |
| WO | WO-03/000261 A1 | 1/2003 |
| WO | WO-03/006423 A1 | 1/2003 |
| WO | WO-03/020370 A1 | 3/2003 |
| WO | WO-03/027068 A2 | 4/2003 |
| WO | WO-03/027068 A3 | 4/2003 |
| WO | WO-03/029169 A2 | 4/2003 |
| WO | WO-03/029169 A3 | 4/2003 |
| WO | WO-03/039454 A2 | 5/2003 |
| WO | WO-03/039454 A3 | 5/2003 |
| WO | WO-03/040096 A2 | 5/2003 |
| WO | WO-03/040096 A3 | 5/2003 |
| WO | WO-03/043987 A2 | 5/2003 |
| WO | WO-03/043987 A3 | 5/2003 |
| WO | WO-03/045378 A1 | 6/2003 |
| WO | WO-03/050073 A1 | 6/2003 |
| WO | WO-03/057721 A2 | 7/2003 |
| WO | WO-03/057721 A3 | 7/2003 |
| WO | WO-03/072535 A2 | 9/2003 |
| WO | WO-03/072535 C1 | 9/2003 |
| WO | WO-03/099202 A2 | 12/2003 |
| WO | WO-03/099202 A3 | 12/2003 |
| WO | WO-03/106405 A1 | 12/2003 |
| WO | WO-2004/013098 A1 | 2/2004 |
| WO | WO-2004/019932 A1 | 3/2004 |
| WO | WO-2004/022523 A2 | 3/2004 |
| WO | WO-2004/022523 A3 | 3/2004 |
| WO | WO-2004/024081 A2 | 3/2004 |
| WO | WO-2004/024081 A3 | 3/2004 |
| WO | WO-2004/024675 A1 | 3/2004 |
| WO | WO-2004/037179 A2 | 5/2004 |
| WO | WO-2004/037179 A3 | 5/2004 |
| WO | WO-2004/043916 A1 | 5/2004 |
| WO | WO-2004/050609 A1 | 6/2004 |
| WO | WO-2004/050619 A1 | 6/2004 |
| WO | WO-2004/062625 A2 | 7/2004 |
| WO | WO-2004/062625 A3 | 7/2004 |
| WO | WO-2004/080376 A2 | 9/2004 |
| WO | WO-2004/080376 A3 | 9/2004 |
| WO | WO-2004/094430 A1 | 11/2004 |
| WO | WO-2005/005469 A2 | 1/2005 |
| WO | WO-2005/005469 A3 | 1/2005 |
| WO | WO-2005/014540 A1 | 2/2005 |
| WO | WO-2005/016876 A2 | 2/2005 |
| WO | WO-2005/016876 A3 | 2/2005 |
| WO | WO-2005/030709 A1 | 4/2005 |
| WO | WO-2005/113525 A1 | 12/2005 |
| WO | WO-2006/034277 A1 | 3/2006 |
| WO | WO-2006/110668 A1 | 10/2006 |
| WO | WO-2007/017509 A1 | 2/2007 |
| WO | WO-2007/017510 A2 | 2/2007 |
| WO | WO-2007/047305 A1 | 4/2007 |
| WO | WO-2007/061930 A1 | 5/2007 |

OTHER PUBLICATIONS

Anderson, R.N. (Oct. 12, 2001). "Deaths: Leading Causes for 1999," *Natl. Vital Stat. Rep.* 49(11):1-87.

Banks, W.A. et al. (Nov./Dec. 1992). "Permeability of the Blood-Brain Barrier to Peptides: An Approach to the Development of Therapeutically Useful Analogs," *Peptides* 13(6):1289-1294.

Begley, D.J. (Feb. 1996). "The Blood-Brain Barrier: Principles for Targeting Peptides and Drugs to the Central Nervous System," *J. Pharm. Pharmacol.* 48(2):136-146.

Berge, S.M. et al. (Jan. 1977). "Pharmaceutical Salts," *J. Pharm. Sci.* 66(1):1-19.

Bertling, W.M. et al. (Jun. 1991). "Use of Liposomes, Viral Capsids and Nanoparticles as DNA Carriers," *Biotechnol. Appl. Biochem.* 13(3):390-405.

Bickel, U. et al. (Mar. 1, 2001). "Delivery of Peptides and Proteins Through the Blood-brain Barrier," *Adv. Drug Deliv. Rev.* 46(1-3):247-279.

Bieth, J. (1974). "Some Kinetic Consequences of the Tight Binding of Protein-Proteinase-Inhibitors to Proteolytic Enzymes and Their Application to the Determination of Dissociation Constants," *Bayer-Symposium V "Proteinase Inhibitors"*, Proceedings of the 2nd International Research Conference on Proteinase Inhibitors, Grosse Ledder, Fed. Rep. Germany, Oct. 16-20, 1973, pp. 463-469.

Black, K.L. et al. (Nov. 1994). "Enzymatic Barrier Protects Brain Capillaries From Leukotriene $C_4$," *J. Neurosurg.* 81(5):745-751.

Bobo, R.H. et al. (Mar. 15, 1994). "Convection-enhanced Delivery of Macromolecules in the Brain," *Proc. Natl. Acad. Sci. USA* 91(6):2076-2080.

Bodor, N. et al. (Dec. 18, 1981). "Site-Specific, Sustained Release of Drugs to the Brain," *Science* 214(4527):1370-1372.

Bodor, N. et al. (1995). "Molecular Packaging," Chapter 14 in *Peptide-Based Drug Design: Controlling Transport and Metabolism*, Taylor, M.D. et al. eds., American Chemical Society: Washington, DC, pp. 317-337.

Bodor, N. et al. (Oct.-Dec. 1997). "Drug Targeting via Retrometabolic Approaches," *Pharmacol. Ther.* 76(1-3):1-27.

Brem, H. et al. (Jul./Aug. 1996). "Polymer-Based Drug Delivery to the Brain," *Sci. Med.* 3(4):52-61.

Brem, H. et al. (Jul 2001). "Biodegradable Polymer Implants to Treat Brain Tumors," *J. Control. Release* 74(1-3):63-67.

Calvo, P. et al. (Aug. 2001). "Long-Circulating PEGylated Polycyanoacrylate Nanoparticles as new Drug Carrier for Brain Delivery," *Pharm. Res.* 18(8):1157-1166.

CAPLUS Database Accession No. 1992:506860. (1992). One page.

Capobianco et al. (Jul. 1992). "Application of a Fluorogenic Substrate in the Assay of Proteolytic Activity and in the Discovery of a Potent Inhibitor of *Candida albicans* Aspartic Proteinase," *Anal. Biochem.* 1204(1):96-102.

Chang, W-P. et al. (Jun. 2004). "In Vivo Inhibition of Aβ Production by Memapsin 2 (β-secretase) Inhibitors," *J. Neurochem.* 89(6):1409-1416.

Chavany, C. et al. (Apr. 1992). "Polyalkylcyanoacrylate Nanoparticles as Polymeric Carriers for Antisense Oligonucleotides," *Pharm. Res.* 9(4):441-449.

Chavany, C. et al. (Sep. 1994). "Adsorption of Oligonucleotides Onto Polyisohexylcyanoacrylate Nanoparticles Protects Them Against Nucleases and Increases Their Cellular Uptake," *Pharm. Res.* 11(9):1370-1378.

Chen, P. et al. (Sep. 24, 1998). "Strategies to Target Kyotorphin Analogues to the Brain," *J. Med. Chem.* 41(20):3773-3781.

Coburn, C.A. et al. (Dec. 2, 2004). "Identification of a Small Molecule Nonpeptide Active Site β-Secretase Inhibitor That Displays a Nontraditional Binding Mode for Aspartyl Proteases," *J. Med. Chem.* 47(25):6117-6119.

Coloma, M.J. et al. (Mar. 2000). "Transport Across the Primate Blood-Brain Barrier of a Genetically Engineered Chimeric Monoclonal Antibody to the Human Insulin Receptor," *Pharm. Res.* 17(3):266-274.

Cutfield, S. et al. (1993). "Crystallization of Inhibited Aspartic Proteinase from *Candida albicans*," *J. Mol. Bio.* 234(4):1266-1269.

De Strooper, B. et al. (Jan. 22, 1998). "Deficiency of Presenilin-1 Inhibits the Normal Cleavage of Amyloid Precursor Protein," *Nature* 391:387-390.

Doran, S.E. et al. (May 1995). "Gene Expression From Recombinant Viral Vectors in the Central Nervous System After Blood-Brain Barrier Disruption," *Neurosurg.* 36(5):965-970.

Emerich, D.F. et al. (2001). "The Development of the Bradykinin Agonist Labradimil as a Means to Increase the Permeability of the Blood-Brain Barrier: From Concept to Clinical Evaluation," *Clin. Pharmacokinet.* 40(2):105-123.

Epps, D.E. et al. (Jul. 1991). "Determination of Dissociation Constants of High Affinity (PM) Humanrenin Inhibitors: Application to Analogues of Ditekiren (U-72, 038)," *J. Med. Chem.*, 34(7):2107-2112.

Ermolieff, J. et al. (Oct. 10, 2000). "Proteolytic Activation of Recombinant Pro-memapsin 2 (Pro-β-secretase) Studied With New Fluorogenic Substrates," *Biochemistry* 39(40):12450-12456.

Fingl, E. et al. (1975). "General Principles," Chapter 1 in *The Pharmacological Basis of Therapeutics*, 5th Edition, Macmillan Publishing Co., Inc: New York, NY, pp. 1-46.

Fray, A.H. et al. (1986). "A Short, Stereoselective Synthesis of the Lactone Precursor to 2R, 4S, 5S Hydroxyethylene Dipeptide Isosteres," *J. Org. Chem.* 51(25):4828-4833.

Gennaro, A.R. ed. (1985). Remington's Pharmaceutical Sciences, 17th Edition, Mack Publishing Company: Easton, PA, five pages. (Table of Contents Only.)

Ghosh, A.K. (2004). "Structure Based Design of Inhibitors of Human Brain Memapsin (β-secretase)," *36th Central Regional Meeting of the American Chemical Society*, Jun. 2-4, 2004, pp. 67 (Abstract No. INV-075).

Ghosh, A.K. (2005). "Structure-Based Design and Synthesis of Aspartyl Protease Inhibitors," *230th ACS National Meeting*, Washington, D.C., Aug. 28-Sep. 1, 2005, Abstract No. MEDI-242.

Ghosh, A.K. (2006). "Structure-Based Design of Potent and Highly Selective Memapsin 2 (BACE) Inhibitors," *232nd ACS National Meeting*, San Francisco, CA, Sep. 10-14, 2006, Abstract MEDI-289.

Ghosh, A.K. et al. (Apr. 12, 2000). "Design of Potent Inhibitors for Human Brain Memapsin 2 (β-Secretase)," *J. Amer. Chem. Soc.* 122(14):3522-3523.

Ghosh, A.K. et al. (Aug. 30, 2001). "Structure-Based Design: Potent Inhibitors of Human Brain Memapsin 2 (β-secretase)," *J. Med. Chem.* 44(18):2865-2868.

Ghosh, A.K. et al. (Jun. 2002). "β-Secretase as a Therapeutic Target for Inhibitor Drugs," *Curr. Med. Chem.* 9(11):1135-1144.

Ghosh, A.K. et al. (2003). "Structure-Based Design of Inhibitors of Human Brain Memapsin 2," *226th ACS National Meeting*, New York, NY, Sep. 7-11, 2003, Abstract No. MEDI-48.

Ghosh, A.K. et al. (2005). "Recent Developments of Structure Based β-Secretase Inhibitors for Alzheimer's Disease," *Curr. Topics Med. Chem.* 5(16):1609-1622.

Ghosh, A.K. et al. (Apr. 26, 2006). "Design, Synthesis and X-ray Structure of Protein-Ligand Complexes: Important Insight into Selectivity of Memapsin 2 (β-Secretase) Inhibitors," *J. Amer. Chem. Soc.* 128(16):5310-5311.

Ghosh, A.K. et al. (May 17, 2007). "Design, Synthesis, and X-ray Structure of Potent Memapsin 2 (β-secretase) Inhibitors With Isophthalamide Derivatives as the $P_2$-$P_3$-Ligands," *J. Med. Chem.* 50(10):2399-2407.

Golden, P.L. et al. (Jan. 1997). "Human Blood-Brain Barrier Leptin Receptor. Binding and Endocytosis in Isolated Human Brain Microvessels," *J. Clin. Invest.* 99(1):14-18.

Greene, T.W. et al. (1981). *Protective Groups in Organic Synthesis*, John Wiley & Sons:New York,NY, pp. ix-x. (Table of Contents Only.).

Han, J.M. et al. (Apr. 24, 2003). "Aromatic Reduced Amide Bond Peptidomimetics as Selective Inhibitors of Neuronal Nitric Oxide Synthase," *J. Med. Chem.* 46(9):1661-1669.

Han, H.-K. et al. (2000). "Targeted Prodrug Design to Optimize Drug Delivery," *AAPS PharmSci* 2(1):1-11.

Harbaugh, R.E. et al. (Dec. 1988). "Use of Implantable Pumps for Central Nervous System Drug Infusions to Treat Neurological Disease," *Neurosurg.* 23(6):693-698.

Hom, R.K. et al. (2004). "Design and Synthesis of Hyrdoxyethylene-Based Peptidomimetic Inhibitors of Human β-Secretase," *J. Med. Chem.* 47(1):158-164.

Hong, L. et al. (Aug. 2002). "Memapsin 2 (β-secretase) as a Therapeutic Target," *Biochem. Soc. Trans.* 30(4):530-534.

Hong, L. et al. (Apr. 27, 2004). "Flap Position of Free Memapsin 2 (β-secretase), a Model for Flap Opening in Aspartic Protease Catalysis," *Biochem.* 43(16):4689-4695.

Hsiao, K. et al. (Oct. 4, 1996). "Correlative Memory Deficits, Aβ Elevation, and Amyloid Plaques in Transgenic Mice," *Science* 274:99-102.

Huang, T.-Y. et al. (1999). "ACNU, MTX and 5-FU Penetration of Rat Brain Tissue and Tumors," *J. Neurooncol.* 45(1):9-17.

Hussain, I. et al. (Jun. 29, 2001). "Prodomain Processing of Asp1 (BACE2) Is Autocatalytic," *J. Biol. Chem.* 276(26):23322-23328.

Huwyler, J. et al. (Nov. 26, 1996). "Brain Drug Delivery of Small Molecules Using Immunoliposomes," *Proc. Natl. Acad. Sci. USA* 93(24):14164-14169.

Huwyler, J. et al. (Sep. 1997). "Receptor Mediated Delivery of Daunomycin Using Immunoliposomes: Pharmacokinetics and Tissue Distribution in the Rat," *J. Pharmcol. Exp. Ther.* 282(3):1541-1546.

Illum, L. (Dec. 2002). "Nasal Drug Delivery: New Developments and Strategies," *Drug Discov. Today* 7(23):1184-1189.

Kaldor, S.W. et al. (1995). "Isophthalic Acid Derivatives: Amino Acid Surrogates for the Inhibition of HIV-1 Protease," *Bioorg. Med. Chem. Lett.* 5(7):721-726.

Koelsch, G. et al. (2003). "Memapsin 2, A Drug Target for Alzheimer's Disease," *Biochem. Soc. Symp.* (70):213-220.

Koelsch, G. et al. (2005). "Analysis of Amyloid precursor Protein Processing Protease β-Secretase: Tools for Memapsin 2 (β-Secretase) Inhibition Studies," Chapter 4 in *Amyloid Precursor Protein: A Practical Approach*, Xia, W. et al. eds. CRC Press: Boca Raton, FL, pp. 41-50.

Kreil, G. et al. (Sep. 1995). "Hyaluronidases—a Group of Neglected Enzymes," *Protein Sci.* 4(9):1666-1669.

Kreuter, J. (Mar. 23, 2001). "Nanoparticulate Systems for Brain Delivery of Drugs," *Adv. Drug Deliv. Rev.* 47(1):65-81.

Kreuter, J. (2002). "Transport of Drugs Across the Blood-Brain Barrier by Nanoparticles," *Curr. Med. Chem.* 2(3):241-249.

Kreuter, J. et al. (Mar. 13, 1995). "Passage of Peptides Through the Blood-Brain Barrier With Colloidal Polymer Particles (Nanoparticles)," *Brain Res.* 674(1):171-174.

Krewson, C.E. et al. (May 22, 1995). "Distribution of Nerve Growth Factor Following Direct Delivery to Brain Interstitium," *Brain Res.* 680(1-2):196-206.

Kroll, R.A. et al. (Apr. 1996). "Increasing Volume of Distribution to the Brain With Interstitial Infusion: Dose, Rather Than Convection, Might be the Most Important Factor," *Neurosurg.* 38(4):746-754.

Kroll, R.A. et al. (May 1998). "Outwitting the Blood-Brain Barrier for Therapeutic Purposes: Osmotic Opening and Other Means," *Neurosurg.* 42(5):1083-1100.

Kumagai, A.K. et al. (Nov. 5, 1987). "Absorptive-Mediated Endocytosis of Cationized Albumin and a β-Endorphin-Cationized Albumin Chimeric Peptide by Isolated Brain Capillaries. Model System of Blood-Brain Barrier Transport," *J. Biol. Chem.* 262(31):15214-15219.

Kumar, S.K.P. et al. (2002). "Insight into the Selective Inhibition of *Candida albicans* Secreted Aspartyl Protease: A Docking Analysis Study," *Bioorg. & Med. Chem. Lett.* 10:1153-1170.

Lambert, D.M. (Oct. 2000). "Rationale and Applications of Lipids as Prodrug Carriers," *Eur. J. Pharm. Sci.* 11(Suppl. 2):S15-S27.

Li, J.Y. et al. (Sep. 1999). "Genetically Engineered Brain Drug Delivery Vectors: Cloning, Expression and in Vivo Application of an Anti-Transferrin Receptor Single Chain Antibody-Streptavidin Fusion Gene and Protein," *Protein Engineering* 12(9):787-796.

Lin, X. et al. (Feb. 15, 2000). "Human Aspartic Protease Memapsin 2 Cleaves the β-Secretase Site of β -Amyloid Precursor Protein," *Proc. Natl. Acad. Sci. USA* 97(4):1456-1460.

Liu, X. et al. (Feb. 24, 2003). "Synthesis and Preliminary Biological Evaluation of 6-O-[$^{11}$C]-[(methoxymethyl)benzyl]guanines, New Potential PET Breast Cancer Imaging Agents for the DNA Repair Protein AGT," *Bioorg. Med. Chem. Lett.* 13(4):641-644.

Lo, E.H. et al. (Dec. 2001). "Drug Delivery to Damaged Brain," *Brain Res. Rev.* 38(1-2):140-148.

Matsukado, K. et al. (Jul. 1996). "Enhanced Tumor Uptake of Carboplatin and Survival in Glioma-Bearing Rats by Intracarotic Infusion of Bradykinin Analog, RMP-7," *Neurosurgery* 39(1):125-134.

Miller, G. (Aug. 16, 2002). "Drug Targeting. Breaking Down Barriers," *Science* 297(5584):1116-1118.

Misra, A. et al. (May-Aug. 2003). "Drug Delivery to the Central Nervous System: A Review," *J. Pharm. Pharmaceut. Sci.* 6(2):252-273.

NCBI Accession No. NP_036236, created Jun. 26, 2007, located at <http://www.ncbi.nlm.nih/gov/entrez/viewer.fcgi?db=Protein&id=6912266>, last visited Jul. 17, 2007, four pages.

NCBI Accession No. NP_036237, created Jun. 3, 2007, located at <http://www.ncbi.nlm.nih.gov/entrez/viewer.fcgi?db=Protein&id=19923395>, last visited Jul. 17, 2007, four pates.

Neuwelt, E.A. ed. (1989). *Implications of the Blood-Brain Barrier and Its Manipulation: Volume 2 Clinical Aspects*, Plenum Press: New York, NY, pp. xvii-xxvi. (Table of Contents Only.).

Neuwelt, E.A. et al. (1994). "Therapeutic Dilemma of Disseminated CNS Germinoma and the Potential of Increased Platinum-Based Chemotherapy Delivery With Osmotic Blood-Brain Barrier Disruption," *Pediatr. Neurosurg.* 21(1):16-22.

Neuwelt, E.A. et al. (Nov. 1994). "Effect of Blood-Brain Barrier Disruption on Intact and Fragmented Monoclonal Antibody Localization in Intracerebral Lung Carcinoma Xenografts," *J. Nucl. Med.* 35(11):1831-1841.

Ostermann, N. et al. (Jan. 13, 2006). "Crystal Structure of Human BACE2 in Complex With a Hydroxyethylamine Transition-State Inhibitor," *J. Mol. Biol.* 355(2):249-261.

Palomino, E. et al. (Mar. 1989). "A Dihydropyridine Carrier System for Sustained Delivery of 2', 3'-dideoxynucleosides to the Brain," *J. Med. Chem.* 32(3):622-625.

Pardridge, W.M. (Aug. 1986). "Receptor-Mediated Peptide Transport Through the Blood-Brain Barrier," *Endocrine Rev.* 7(3):314-330.

Pardridge, W.M. et al. (Jun. 1995). "Human Insulin Receptor Monoclonal Antibody Undergoes High Affinity Binding to Human Brain Capillaries in Vitro and Rapid Transcytosis Through the Blood-Brain Barrier in Vivo in the Primate," *Pharm. Res.* 12(6):807-816.

Pardridge, W.M. (1999). "Vector-Mediated Drug Delivery to the Brain," *Adv. Drug Deliv. Rev.* 36(2,3):299-321.

Pardridge, W.M. (Feb. 2002). "Drug and Gene Targeting to the Brain With Molecular Trojan Horses," *Nat. Rev. Drug Discov.* 1(2):131-139.

Patel, S. et al. (2004). "Apo and Inhibitor Complex Structures of BACE (β-Secretase)," *J. Mol. Biol.* 343(2):407-416.

Rapoport, S.I. (Apr. 2000). "Osmotic Opening of the Blood-Brain Barrier: Principles, Mechanism, and Therapeutic Applications," *Cell Mol. Neurobiol.* 20(2):217-230.

Schwarze, S.R. et al. (Sep. 3, 1999). "In Vivo Protein Transduction: Delivery of a Biologically Active Protein Into the Mouse," *Science* 285(5344):1569-1572.

Selkoe, D.J. (Jun. 24, 1999). "Translating Cell Biology Into Therapeutic Advances in Alzheimer's Disease," *Nature* 399(6738 Suppl.):A23-A31.

Somogyi, G. et al. (May 11, 1998). "Targeted Drug Delivery to the Brain via Phosphonate Derivatives I. Design, Synthesis and Evaluation of an Anionic Chemical Delivery System for Testosterone," *Int. J. Pharm.* 166(1):15-26.

Statchel, S.J. et al. (Nov. 11, 2004). "Structure-Based Design of Potent and Selective Cell-Permeable Inhibitors of Human β-secretase (BACE-1)," *J. Med. Chem.* 47(26):6447-6450.

Tamai, I. et al. (Jan. 1997). "Structure-Internalization Relationship for Absorptive-Mediated Endocytosis of Basic Peptides at the Blood-Brain Barrier," *J. Pharmacol. Exp. Ther.* 280(1):410-415.

Tang, J. et al. (2003). "Study of Memapsin 2 (β-secretase) and Strategy of Inhibitor Design," *J. Mol. Neurosci.* 20(3):299-304.

Thorne, R.G. et al. (Sep. 18, 1995). "Quantitative Analysis of the Olfactory Pathway for Drug Delivery to the Brain," *Brain Res.* 692(1-2):278-282.

Thorne, R.G. et al. (2001). "Delivery of Neurotrophic Factors to the Central Nervous System: Pharmacokinetic Considerations," *Clin. Pharmacokinet.* 40(12):907-946.

Turner, R.T. et al. (Aug. 28, 2001). "Subsite Specificity of Memapsin 2 (β-Secretase): Implications for Inhibitor Design," *Biochem.* 40(34):10001-10006.

Turner, R.T. et al. (Jan. 11, 2005). "Structural Locations and Functional Roles of New Subsites $S_5$, $S_6$, and $S_7$ in Memapsin 2 (β-secretase)," *Biochem.* 44(1):105-112.

Umbreen, S. et al. (2006). "Norstatines From Aldehydes by Sequential Organocatalytic α-Amination and Passerini Reaction," *Euro. J. Org. Chem.* 20:4585-4595.

Wender, P.A. et al. (Nov. 21, 2000). "The Design, Synthesis, and Evaluation of Molecules That Enable or Enhance Cellular Uptake: Peptoid Molecular Transporters," *Proc. Natl. Acad. Sci USA* 97(24):13003-13008.

Wu, D. et al. (Oct. 1, 1997). "Drug Targeting of a Peptide Radiopharmaceutical Through the Primate Blood-Brain Barrier in Vivo With a Monoclonal Antibody to the Human Insulin Receptor," *J. Clin. Invest.* 100(7):1804-1812.

Wu, J. et al. (Jul. 2002). "Synthesis and Biological Evaluations of Brain-Targeted Chemical Delivery Systems of [$Nva^2$]-TRH," *J. Pharm. Pharmacol.* 54(7):945-950.

Yoshikawa, T. et al. (Nov. 1992). "Biotin Delivery to Brain With a Covalent Conjugate of Avidin and a Monoclonal Antibody to the Transferrin Receptor," *J. Pharmacol. Exp. Ther.* 263(2):897-903.

Zobel, H.P. et al. (Oct. 1997). "Cationic Polyhexylcyanoacrylate Nanoparticles as Carriers for Antisense Oligonucleotides," *Antisense Nucleic Acid Drug Dev.* 7(5):483-493.

Zordan-Nudo, T. et al. (Dec. 15, 1993). "Effects of Nonionic Detergents on P-Glycoprotein Drug Binding and Reversal of Multidrug Resistance," *Cancer Res.* 53(24):5994-6000.

Ghosh, A.K. et al. (2008). "Potent Memapsin 2 (β-Secretase) Inhibitors: Design, Synthesis, Protein-Ligand X-Ray Structure, and In Vivo Evaluation," *Bioorganic and Medicinal Chemistry Letters*, 6 pages. (article in press doi:10.1016/j.bmcl.2007.12.028).

Banner, D. et al. (1993). "Serine Proteases: 3D Structures, Mechanisms of Action and Inhibitors," Chapter 3 in *Perspectives in Medicinal Chemistry*, Testa, B. et al. eds., Verlag Helvetica Chimica acta: Basel, Switzerland, pp. 27-43.

\* cited by examiner

COMPOUNDS WHICH INHIBIT BETA-SECRETASE ACTIVITY AND METHODS OF USE

CROSS-REFERENCES TO RELATED APPLICATIONS

This application is a continuation of International Application No. PCT/US2006/013342, filed Apr. 10, 2006, which claims the benefit of U.S. Patent Application No. 60/669,541, filed Apr. 8, 2005, and U.S. Patent Application No. 60/717,541, filed Sep. 14, 2005, each of which is incorporated herein by reference in its entirety as if fully set forth by this reference for all purposes.

STATEMENT AS TO RIGHTS TO INVENTIONS MADE UNDER FEDERALLY SPONSORED RESEARCH OR DEVELOPMENT

The invention was made with government support under grants AG-18933 and AI-38189 awarded by the National Institutes of Health. The Government has certain rights in the invention.

BACKGROUND OF THE INVENTION

Alzheimer's disease is a progressive mental deterioration in a human resulting, inter alia, in loss of memory, confusion and disorientation. Alzheimer's disease accounts for the majority of senile dementias and is a leading cause of death in adults (Anderson, R. N., *Natl. Vital Stat. Rep.* 49:1-87 (2001), the teachings of which are incorporated herein in their entirety). Histologically, the brain of persons afflicted with Alzheimer's disease is characterized by a distortion of the intracellular neurofibrils and the presence of senile plaques composed of granular or filamentous argentophilic masses with an amyloid protein core, largely due to the accumulation of β-amyloid protein (Aβ) in the brain. Aβ accumulation plays a role in the pathogenesis and progression of the disease (Selkoe, D. J., *Nature* 399: 23-31 (1999)) and is a proteolytic fragment of amyloid precursor protein (APP). APP is cleaved initially by β-secretase (also referred to as memapsin 2) followed by γ-secretase to generate Aβ (Lin, X., et al., *Proc. Natl. Acad. Sci. USA* 97:1456-1460 (2000); De Stropper, B., et al, *Nature* 391:387-390 (1998)).

There is a need to develop effective compounds and methods for the treatment of Alzheimer's disease. The present invention fulfills these and other needs.

BRIEF SUMMARY OF THE INVENTION

The present invention provides novel β-secretase inhibitors and methods for their use, including methods of treating Alzheimer's disease.

In one aspect, the present invention provides a β-secretase inhibitor compound having the formula:

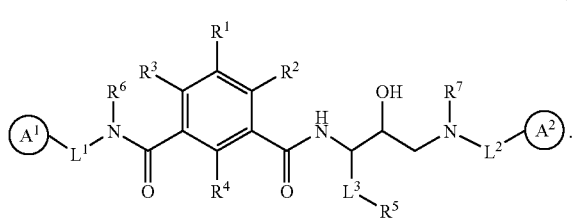

(I)

In Formula (I), $R^1$ is halogen, —OH, —$CF_3$, —$NO_2$, —$NR^8R^9$, —$OR^{10}$, —$S(O)_nR^{11}$, —$C(O)R^{12}$, hydrogen, substituted or unsubstituted $C_3$-$C_{20}$ alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^4$-Y.

$R^5$ is halogen, —OH, —$CF_3$, —$NO_2$, —$NR^8R^9$, —$OR^{10}$, —$S(O)_nR^{11}$, —$C(O)R^{12}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ and $R^3$ are independently halogen, —$CF_3$, —$NO_2$, —$NR^8R^9$, —$OR^{10}$, —$S(O)_nR^{11}$, —$C(O)R^{12}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^4$-Y.

$R^4$ is halogen, —OH, —$CF_3$, —$NO_2$, —$NR^8R^9$, —$OR^{10}$, —$S(O)_nR^{11}$, —$C(O)R^{12}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^4$-Y.

$R^6$ and $R^7$ are independently —$S(O)_2R^{11}$, —$C(O)R^{12}$, —$NR^8R^9$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^4$-Y.

The symbol n represents integers from 0 to 2.

$R^8$ is independently —$C(O)R^{13}$, —$S(O)_2R^{14}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10}$ is independently —$C(O)R^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{11}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. If n is 2, then $R^{11}$ is optionally —$NR^{15}R^{16}$. If n is 1 or 2, then $R^{11}$ is not hydrogen.

$R^{12}$ is independently —$NR^{18}R^{19}$, —$OR^{19}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{13}$ is independently —$OR^{19}$, —$NR^{18}R^{19}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{14}$ is independently —$NR^{18}R^{19}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{18}$ and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{15}$ and $R^{16}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ and $L^3$ are independently a bond, $—NR^{17}—$, $—S(O)_q—$, substituted or unsubstituted alkylene, or substituted or unsubstituted heteroalkylene. $L^2$ is substituted or unsubstituted alkylene, $—NR^{17}—$, $—S(O)_q—$, or substituted or unsubstituted heteroalkylene.

$R^{17}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The symbol q represents an integer from 0 to 2.

$A^1$ and $A^2$ are independently substituted or unsubstituted cycloalkyl, substituted or unsubstituted heterocycloalkyl, substituted or unsubstituted aryl, or substituted or unsubstituted heteroaryl. Y is a carrier moiety.

$L^4$ is a bond, $—OP(OH)_2O—$, $—C(O)OR^{20}—$, $—C(O)NHR^{21}—$, $—S(O)_2NHR^{22}—$, substituted or unsubstituted alkylene, substituted or unsubstituted heteroalkylene, or a peptidyl linker.

$R^{20}$, $R^{21}$, and $R^{22}$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect of the present invention, the β-secretase inhibitor compounds of the invention can be employed in methods to decrease memapsin 2 catalytic activity, decrease hydrolysis of a β-secretase site of a memapsin 2 substrate, and/or decrease the accumulation of β-amyloid protein relative to the amount of memapsin 2 catalytic activity, hydrolysis of a β-secretase site, and accumulation of β-amyloid protein, respectively, in the absence of the β-secretase inhibitor.

In another aspect, the present invention provides pharmaceutical compositions comprising a memapsin 2 β-secretase inhibitor compound of the invention or a memapsin 2 β-secretase inhibitor compound in combination with a pharmaceutically acceptable carrier.

In another aspect of the present invention, the β-secretase inhibitor compounds of the invention can be employed in the treatment of diseases or conditions associated with β-secretase activity, hydrolysis of a β-secretase site of a β-amyloid precursor protein, and/or β-amyloid protein accumulation. Typically, a mammal is treated for the disease or condition. In an exemplary embodiment, the disease is Alzheimer's disease.

DETAILED DESCRIPTION OF THE INVENTION

Abbreviations and Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker ($—O—$).

The term "alkylene" by itself or as part of another substituent means a divalent radical derived from an alkyl, as exemplified, but not limited, by $—CH_2CH_2CH_2CH_2—$, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2—,$ $—S(O)—CH_3$, $—CH_2—CH_2—S(O)_2—CH_3$, $—CH=CH—O—CH_3$, $—Si(CH_3)_3$, $—CH_2—CH=N—OCH_3$, $—CH=CH—N(CH_3)—CH_3$, O$—CH_3$, $—O—CH_2—CH_3$, and $—CN$. Up to two heteroatoms may be consecutive, such as, for example, $—CH_2—NH—OCH_3$ and $—CH_2—O—Si(CH_3)_3$. Similarly, the term "heteroalkylene" by itself or as part of another substituent means a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as $—C(O)R'$, $—C(O)NR'$, $—NR'R''$, $—OR'$, $—SR'$, and/or $—SO_2R'$. Where "heteroalkyl" is recited, followed by recitations of specific heteroalkyl groups, such as $—NR'R''$ or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

The term "alkylsulfonyl" as used herein means a moiety having the formula —S($O_2$)—R', where R' is an alkyl group as defined above. R' may have a specified number of carbons (e.g. "$C_1$-$C_4$ alkylsulfonyl").

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O) NR"R"', —NR"C(O)$_2$R', —NR—C(NR'R"R"')=NR"", —NR—C(NR'R")=NR"', —S(O)R', —S(O)$_2$R', —S(O)$_2$ NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C (NR'R"R"')=NR"", —NR—C(NR'R")=NR"', —S(O)R', —S(O)$_2$R', —S(O)$_2$NR'R", —NRSO$_2$R', —CN and —NO$_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'- or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"RR"')$_d$—, where s and d are independdently integers of from 0 to 3, and X' is —O—, —NR'—, —S—, —S(O)—, —S(O)$_2$—, or —S(O)$_2$NR'—. The substituents R, R', R" and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures), succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

A "hydrophobic" group is a group that does not reduce the solubility of a compound in octane or increases the solubility of a compound in octane. Examples of hydrophobic groups include aliphatic groups, aryl groups, and aralkyl groups.

As used herein, the term "natural amino acid" refers to the twenty-three natural amino acids known in the art, which are as follows (denoted by their three letter acronym): Ala, Arg, Asn, Asp, Cys, Cys-Cys, Glu, Gln, Gly, His, Hyl, Hyp, Ile, Leu, Lys, Met, Phe, Pro, Ser, Thr, Trp, Tyr, and Val. The term "side-chain of an amino acid", as used herein, is the substituent on the alpha-carbon of a natural amino acid.

The term "non-natural amino acid" refers to compounds of the formula $NH_2—C(R_{32})_2—COOH$, where $R_{32}$ for each occurrence is, independently, any side chain moiety recognized by those skilled in the art; examples of non-natural amino acids include, but are not limited to: hydroxyproline, homoproline, 4-amino-phenylalanine, norleucine, cyclohexylalanine, α-aminoisobutyric acid, N-methyl-alanine, N-methyl-glycine, N-methyl-glutamic acid, tert-butylglycine, α-aminobutyric acid, tert-butylalanine, ornithine, α-aminoisobutyric acid, 2-aminoindane-2-carboxylic acid, etc. and the derivatives thereof, especially where the amine nitrogen has been mono- or di-alkylated.

A peptide substituent is a sequence of natural or non-natural amino acids that are linked together via an amide bond which is formed by reaction of the α-amine of one amino acid with the α-carboxylic acid of an adjacent amino acid. Preferably, a peptide sequence includes only natural amino acids. In one embodiment, a peptide substituent is a sequence of about 6 natural amino acids. In another embodiment, a peptide substituent is a sequence of 2 natural amino acids. In yet another embodiment, a peptide substituent is 1 natural amino acid.

A "transition state isostere," or "isostere," as used herein, is a compound comprising the hydroxyethylamine linking group —CH(OH)—CH$_2$—NH—. This isostere is also referred to herein as a "hydroxyethylamine isostere." The hydroxyethylamine linking group may be found between a pair of natural or non-natural amino acids of a peptide. A hydroxyethylamine group is an isostere of the transition state of hydrolysis of an amide bond.

"Memapsin 2," as used herein, refers to proteins identified by National Center for Biotechnology Information ("NCBI") accession number NP_036236 (sometimes referred to as "β-site APP-cleaving enzyme 1" or "BACE-1"), including homologs, isoforms and subdomains thereof that retain proteolytic activity (also referred to as a β secretase). Sequence identities of active memapsin 2 proteins and protein fragments (and nucleic acid coding sequences thereof) have been previously disclosed and discussed in detail in copending U.S. Application No. 20040121947, and International Application No. PCT/USO2/34324 (Publication No. WO 03/039454), each of which are herein incorporated by reference in their entirety for all purposes. A "memapsin 2 protein," as used herein, means a full-length memapsin 2 protein or fragment thereof that retains proteolytic activity.

"Memapsin 1," as used herein, refers to proteins identified by National Center for Biotechnology Information ("NCBI") accession number NP_036237 (sometimes referred to as "β-site APP-cleaving enzyme 2" or "BACE-2") and/or those previously disclosed and discussed in detail in copending U.S. Application No. 20040121947, and International Application No. PCT/USO2/34324 (Publication No. WO 03/039454), incorporated by reference herein in their entirety for all purposes, including homologs, isoforms and subdomains thereof that retain proteolytic activity.

"Cathepsin D," as used herein, refers to proteins identified by National Center for Biotechnology Information ("NCBI") accession number NP_036236 (sometimes referred to as "β-site APP-cleaving enzyme 1" or "BACE-1") and or proteins identified by Enzyme Structure Database subclass EC 3.4.23.5., including homologs, isoforms and subdomains thereof that retain proteolytic activity.

A "β-secretase site" is an amino acid sequence that is cleaved by an active memapsin 2 or active fragment thereof. Specific β-secretase sites have also been previously set forth and discussed in detail in copending U.S. Application No. 20040121947, and International Application No. PCT/USO2/34324 (Publication No. WO 03/039454), which are herein incorporated by reference for all purposes in their entirety, and include the Swedish mutation sequence, and the native β-amyloid precursor protein cleavage sequence. Thus, β-secretase inhibitors may be tested for their ability to decrease the hydrolysis of the β-secretase site of a substrate, such as the β-amyloid precursor protein, analogs of β-amyloid precursor protein, or fragments of β-amyloid precursor protein.

A "beta-secretase inhibitor" (i.e. β-secretase inhibitor) refers to a compound capable of reducing the proteolytic activity of memapsin 2 relative to the activity in the absence of inhibitor.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

An "effective amount" of a compound of the present invention is the amount effective to achieve its intended purpose. The term "effective amount," when used in the context of a method of treating a subject (e.g. a mammal, human, etc.) is a therapeutically effective amount (i.e. the amount effective to achieve therapeutically effective results against the stated disease or disease state). "Treatment" or "treating" includes prevention and amelioration of a particular disease or disease state, and in some cases, curing a disease.

I. β-Secretase Inhibitors

In one aspect, the present invention provides compounds that inhibit (i.e. decrease) the catalytic activity of the β-secretase enzyme (memapsin 2). These compounds may be referred to herein as "compounds of the present invention," "β-secretase inhibitor compounds," or "memapsin 2 β-secretase inhibitors." In this aspect, the compounds have the formula:

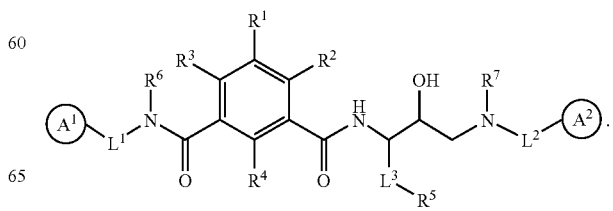

(I)

In Formula (I), $R^1$ is halogen, —OH, —$CF_3$, —$NO_2$, —$NR^8R^9$, —$OR^{10}$, —$S(O)_nR^{11}$, —$C(O)R^{12}$, hydrogen, substituted or unsubstituted $C_3$-$C_{20}$ alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^4$-Y.

$R^5$ is halogen, —OH, —$CF_3$, —$NO_2$, —$NR^8R^9$, —$OR^{10}$, —$S(O)_nR^{11}$, —$C(O)R^{12}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ and $R^3$ are independently halogen, —$CF_3$, —$NO_2$, —$NR^8R^9$, —$OR^{10}$, —$S(O)_nR^{11}$, —$C(O)R^{12}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^4$-Y.

$R^4$ is halogen, —OH, —$CF_3$, —$NO_2$, —$NR^8R^9$, —$OR^{10}$, —$S(O)_nR^{11}$, —$C(O)R^{12}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^4$-Y.

$R^6$ and $R^7$ are independently —$S(O)_2R^{11}$, —$C(O)R^{12}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -$L^4$-Y.

The symbol n represents integers from 0 to 2.

$R^8$ is independently —$C(O)R^{13}$, —$S(O)_2R^{14}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10}$ is independently —$C(O)R^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{11}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. If n is 2, then $R^{11}$ is optionally —$NR^{15}R^{16}$. If n is 1 or 2, then $R^{11}$ is not hydrogen.

$R^{12}$ is independently —$NR^{18}R^{19}$, —$OR^{19}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{13}$ is independently —$OR^{19}$, —$NR^{18}R^{19}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{14}$ is independently —$NR^{18}R^{19}$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{18}$ and $R^{19}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{15}$ and $R^{16}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ and $L^3$ are independently a bond, —$NR^{17}$—, —$S(O)_q$—, substituted or unsubstituted alkylene, or substituted or unsubstituted heteroalkylene. $L^2$ is substituted or unsubstituted alkylene, —$NR^{17}$—, —$S(O)_q$—, or substituted or unsubstituted heteroalkylene.

$R^{17}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The symbol q represents an integer from 0 to 2.

$A^1$ and $A^2$ are independently substituted or unsubstituted cycloalkyl, substituted or unsubstituted heterocycloalkyl, substituted or unsubstituted aryl, or substituted or unsubstituted heteroaryl. Y is a carrier moiety.

$L^4$ is a bond, —OP(OH)$_2$O—, —$C(O)OR^{20}$—, —$C(O)NHR^{21}$—, —$S(O)_2NHR^{22}$—, substituted or unsubstituted alkylene, substituted or unsubstituted heteroalkylene, or a peptidyl linker.

$R^{20}$, $R^{21}$, and $R^{22}$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $L^3$ is unsubstituted $C_1$-$C_5$ (e.g. $C_1$-$C_3$) alkylene. $L^3$ may also be unsubstituted 2 to 5 membered heteroalkylene. In other embodiments, $L^3$—(CH$_2$)$_e$—S—. The symbol e represents an integer from 0 to 10. In some embodiments, e is 1.

In some embodiments, $R^1$ is hydrogen, halogen, —$NR^8R^9$, —$OR^{10}$, or —$S(O)_nR^{11}$. In other embodiments, $R^1$ is hydrogen, —$NR^9S(O)_nR^{14}$, —$OR^{10}$, or —$S(O)_nR^{11}$. $R^1$ may also be hydrogen or —$NR^9S(O)_nR^{14}$.

$R^5$, R8, $R^9$, $R^{10}$, and $R^{11}$ may independently be hydrogen, substituted or unsubstituted $C_1$-$C_{20}$ alkyl, substituted or unsubstituted 2 to 20 membered heteroalkyl, substituted or unsubstituted $C_5$-$C_7$ cycloalkyl, substituted or unsubstituted 5 to 7 membered heterocycloalkyl, substituted or unsubstituted aryl, substituted or unsubstituted heteroaryl, or -$L^4$-Y.

In some embodiments of Formula (I), each substituted or unsubstituted alkylene is an $R^{23}$-substituted or unsubstituted $C_1$-$C_{20}$ alkylene, each substituted or unsubstituted heteroalkylene is an $R^{23}$-substituted or unsubstituted 2 to 20 membered heteroalkylene, each substituted or unsubstituted alkyl is an $R^{23}$-substituted or unsubstituted $C_1$-$C_{20}$ alkyl, each substituted or unsubstituted heteroalkyl is an $R^{23}$-substituted or unsubstituted 2 to 20 membered heteroalkyl, each substituted or unsubstituted cycloalkyl is an $R^{23}$-substituted or unsubstituted $C_5$-$C_7$ cycloalkyl, each substituted or unsubstituted heterocycloalkyl is an $R^{23}$-substituted or unsubstituted 5 to 7 membered heterocycloalkyl, each substituted or unsubstituted heteroaryl is an $R^{24}$-substituted or unsubstituted heteroaryl, and each substituted or unsubstituted aryl is an $R^{24}$-substituted or unsubstituted aryl.

$R^{23}$ is independently oxo, halogen, —CN, —CF$_3$, —OCF$_3$, —OR$^{27}$, —S(O)$_t$R$^{27}$, —OCH$_3$, —C(O)R$^{27}$, —NR$^{28}$R$^{29}$, —NR$^{28}$C(O)R$^{27}$, —C(O)NR$^{28}$R$^{29}$, R$^{25}$-substituted or unsubstituted C$_1$-C$_{20}$ alkyl, R$^{25}$-substituted or unsubstituted 2 to 20 membered heteroalkyl, R$^{25}$-substituted or unsubstituted C$_5$-C$_7$ cycloalkyl, R$^{25}$-substituted or unsubstituted 5 to 7 membered heterocycloalkyl, R$^{26}$-substituted or unsubstituted heteroaryl, or R$^{26}$-substituted or unsubstituted aryl.

$R^{24}$ is independently halogen, —CN, —CF$_3$, —OCF$_3$, —OCH$_3$, OR$^{27}$, —S(O)$_t$R$^{27}$, —OCH$_3$, —C(O)R$^{27}$, —NR$^{28}$R$^{29}$, —NR$^{28}$C(O)R$^{27}$, —C(O)NR$^{28}$R$^{29}$, R$^{25}$-substituted or unsubstituted C$_1$-C$_{20}$ alkyl, R$^{25}$-substituted or unsubstituted 2 to 20 membered heteroalkyl, R$^{25}$-substituted or unsubstituted C$_5$-C$_7$ cycloalkyl, R$^{25}$-substituted or unsubstituted 5 to 7 membered heterocycloalkyl, R$^{26}$-substituted or unsubstituted heteroaryl, or R$^{26}$-substituted or unsubstituted aryl.

The symbol t is independently an integer form 0 to 2.

$R^{27}$, $R^{28}$, and $R^{29}$ are independently hydrogen, R$^{25}$-substituted or unsubstituted C$_1$-C$_{20}$ alkyl, R$^{25}$-substituted or unsubstituted 2 to 20 membered heteroalkyl, R$^{25}$-substituted or unsubstituted C$_5$-C$_7$ cycloalkyl, R$^{25}$-substituted or unsubstituted 5 to 7 membered heterocycloalkyl, R$^{26}$-substituted or unsubstituted heteroaryl, or R$^{26}$-substituted or unsubstituted aryl. If t is 1 or 2, then R$^{27}$ is not hydrogen.

$R^{25}$ is independently oxo, halogen, —CN, —OH, —CF$_3$, —OCF$_3$, —OCH$_3$, unsubstituted C$_1$-C$_{20}$ alkyl, unsubstituted 2 to 20 membered heteroalkyl, unsubstituted C$_5$-C$_7$ cycloalkyl, unsubstituted 5 to 7 membered heterocycloalkyl, unsubstituted aryl, or unsubstituted heteroaryl. $R^{26}$ is independently halogen, —CN, —OH, —CF$_3$, —OCF$_3$, —OCH$_3$, unsubstituted C$_1$-C$_{20}$ alkyl, unsubstituted 2 to 20 membered heteroalkyl, unsubstituted C$_5$-C$_7$ cycloalkyl, unsubstituted 5 to 7 membered heterocycloalkyl, unsubstituted aryl, or unsubstituted heteroaryl.

In some embodiments, $A^1$ and/or $A^2$ are independently R$^{23}$-substituted or unsubstituted C$_5$-C$_7$ cycloalkyl, R$^{23}$-substituted or unsubstituted 5 to 7 membered heterocycloalkyl, R$^{24}$-substituted or unsubstituted heteroaryl, or R$^{24}$-substituted or unsubstituted aryl.

In other embodiments, $R^2$, $R^3$, $R^8$, $R^9$, $R^{10}$, $R^{11}$, and/or $R^{12}$ are independently hydrogen, R$^{23}$-substituted or unsubstituted C$_1$-C$_{20}$ alkyl, R$^{23}$-substituted or unsubstituted 2 to 20 membered heteroalkyl, R$^{23}$-substituted or unsubstituted C$_5$-C$_7$ cycloalkyl, R$^{23}$-substituted or unsubstituted 5 to 7 membered heterocycloalkyl, R$^{24}$-substituted or unsubstituted heteroaryl, or R$^{24}$-substituted or unsubstituted aryl. $R^2$, $R^3$, $R^8$, $R^9$, $R^{10}$, $R^{11}$, and/or $R^{12}$ may be substituted or unsubstituted C$_1$-C$_{20}$ alkyl or substituted or unsubstituted heterocycloalkyl. $R^2$, $R^3$, $R^4$, $R^8$, $R^9$, $R^{10}$, $R^{11}$, and/or $R^{12}$ may also be unsubstituted C$_1$-C$_{20}$ alkyl. $R^2$, $R^3$, $R^8$, $R^9$, $R^{10}$, $R^{11}$, and/or $R^{12}$ may also be unsubstituted C$_1$-C$_5$ alkyl.

$R^4$, $R^6$, and/or $R^7$ may independently be hydrogen, R$^{23}$-substituted or unsubstituted C$_1$-C$_{20}$ alkyl, R$^{23}$-substituted or unsubstituted 2 to 20 membered heteroalkyl, R$^{23}$-substituted or unsubstituted C$_5$-C$_7$ cycloalkyl, R$^{23}$-substituted or unsubstituted 5 to 7 membered heterocycloalkyl, R$^{24}$-substituted or unsubstituted heteroaryl, or R$^{24}$-substituted or unsubstituted aryl. $R^4$, $R^6$, and/or $R^7$ may also independently be hydrogen, or unsubstituted C$_1$-C$_{20}$ alkyl. In some embodiments, $R^4$, $R^6$, and/or $R^7$ are independently hydrogen, or unsubstituted C$_1$-C$_5$ alkyl.

$R^{27}$, $R^{28}$, and $R^{29}$ may independently be hydrogen, R$^{25}$-substituted or unsubstituted C$_1$-C$_{20}$ alkyl, or R$^{25}$-substituted or unsubstituted 2 to 20 membered heteroalkyl. $R^{23}$ may independently be oxo, halogen, —CN, —CF$_3$, —OCF$_3$, —OR$^{27}$, —S(O)$_t$R$^{27}$, —OCH$_3$, —C(O)R$^{27}$, —NR$^{28}$R$^{29}$, —NR$^{28}$C(O)R$^{27}$, —C(O)NR$^{28}$R$^{29}$, R$^{25}$-substituted or unsubstituted C$_1$-C$_{20}$ alkyl, or R$^{25}$-substituted or unsubstituted 2 to 20 membered heteroalkyl. $R^{24}$ may independently be halogen, —CN, —CF$_3$, —OCF$_3$, —OCH$_3$, —OR$^{27}$, —S(O)$_t$R$^{27}$, —OCH$_3$, —C(O)R$^{27}$, —NR$^{28}$R$^{29}$, —NR$^{28}$C(O)R$^{27}$, —C(O)NR$^{28}$R$^{29}$, R$^{25}$-substituted or unsubstituted C$_1$-C$_{20}$ alkyl, or R$^{25}$-substituted or unsubstituted 2 to 20 membered heteroalkyl.

In some embodiments, $R^2$ and $R^3$ may independently be hydrogen, halogen, or unsubstituted C$_1$-C$_{20}$ alkyl.

$R^5$ may be R$^{23}$-substituted or unsubstituted C$_5$-C$_7$ cycloalkyl, R$^{23}$-substituted or unsubstituted 5 to 7 membered heterocycloalkyl, R$^{24}$-substituted or unsubstituted heteroaryl, or R$^{24}$-substituted or unsubstituted aryl. $R^5$ may also be R$^{24}$-substituted or unsubstituted heteroaryl, or R$^{24}$-substituted or unsubstituted aryl. In some embodiments, $R^5$ is R$^{24}$-substituted or unsubstituted aryl. In some related embodiments, $R^{24}$ is halogen, —CN, —OH, —CF$_3$, unsubstituted C$_1$-C$_{20}$ alkyl, or unsubstituted alkoxy (e.g. C$_1$-C$_{20}$ alkoxy). $R^5$ may also be halophenyl (e.g. difluorophenyl) or phenyl. In some related embodiments, $L_3$ is unsubstituted C$_1$-C$_5$ (e.g. C$_1$-C$_3$) alkylene.

In some embodiments, $R^5$ is selected from substituted or unsubstituted tetrahydrofuranyl, substituted or unsubstituted tetrahydropyranyl, and substituted or unsubstituted pyridylmethyl. In some related embodiments, $L^3$ is unsubstituted C$_1$-C$_5$ alkyl. In other related embodiments, $L_3$ is methylene.

In some embodiments, $R^5$ is R$^{24}$-substituted or unsubstituted aryl, or R$^{24}$-substituted or unsubstituted heteroaryl (e.g. substituted or unsubstituted thiazolyl, substituted or unsubstituted oxazolyl, substituted or unsubstituted imidazolyl, or substituted or unsubstituted pyrazolyl). In some embodiments, $R^5$ is R$^{24}$-substituted or unsubstituted phenyl (e.g. halophenyl such as 3,5-difluorophenyl), or R$^{24}$-substituted or unsubstituted thiazolyl. In a further related embodiment, $L^3$ is methylene.

In some embodiments, $R^5$ is selected from substituted or unsubstituted phenyl, substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothieno-pyrazolyl, substituted or unsubstituted thianaphthenyl, substituted or unsubstituted carbazolyl, substituted or unsubstituted benzimidazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisoxazolyl, substituted or unsubstituted dimethylhydantoin, substituted or unsubstituted pyrazinyl, substituted or unsubstituted tetrahydrofuranyl, substituted or unsubstituted pyrrolinyl, substituted or unsubstituted pyrrolidinyl, substituted or unsubstituted morpholinyl, substituted or unsubstituted indolyl, substituted or unsubstituted diazepinyl, substituted or unsubstituted azepinyl, substituted or unsubstituted thiepinyl, or substituted or unsubstituted oxepinyl.

A¹ and A² may independently be substituted or unsubstituted $C_5$-$C_7$ cycloalkyl, substituted or unsubstituted 5 to 7 membered heterocycloalkyl, substituted or unsubstituted aryl, or substituted or unsubstituted heteroaryl. A¹ and/or A² may also independently be substituted or unsubstituted aryl (e.g. phenyl), or substituted or unsubstituted heteroaryl (e.g. pyridyl).

In some embodiments, A¹ and A² are independently substituted or unsubstituted phenyl, substituted or unsubstituted pyrazolyl, substituted or unsubstituted furanyl, substituted or unsubstituted imidazolyl, substituted or unsubstituted isoxazolyl, substituted or unsubstituted oxadiazolyl, substituted or unsubstituted oxazolyl, substituted or unsubstituted pyrrolyl, substituted or unsubstituted pyridyl, substituted or unsubstituted pyrimidyl, substituted or unsubstituted pyridazinyl, substituted or unsubstituted thiazolyl, substituted or unsubstituted triazolyl, substituted or unsubstituted thienyl, substituted or unsubstituted dihydrothieno-pyrazolyl, substituted or unsubstituted thianaphthenyl, substituted or unsubstituted carbazolyl, substituted or unsubstituted benzimidazolyl, substituted or unsubstituted benzothienyl, substituted or unsubstituted benzofuranyl, substituted or unsubstituted indolyl, substituted or unsubstituted quinolinyl, substituted or unsubstituted benzotriazolyl, substituted or unsubstituted benzothiazolyl, substituted or unsubstituted benzooxazolyl, substituted or unsubstituted benzimidazolyl, substituted or unsubstituted isoquinolinyl, substituted or unsubstituted isoindolyl, substituted or unsubstituted acridinyl, substituted or unsubstituted benzoisoxazolyl, substituted or unsubstituted dimethylhydantoin, substituted or unsubstituted pyrazinyl, substituted or unsubstituted tetrahydrofuranyl, substituted or unsubstituted pyrrolinyl, substituted or unsubstituted pyrrolidinyl, substituted or unsubstituted morpholinyl, substituted or unsubstituted indolyl, substituted or unsubstituted diazepinyl, substituted or unsubstituted azepinyl, substituted or unsubstituted thiepinyl, substituted or unsubstituted piperidinyl, or substituted or unsubstituted oxepinyl.

In some embodiments, $L^3$ and $L^1$ are independently a bond, unsubstituted alkylene, or unsubstituted heteroalkylene. In other embodiments, $L^3$ and $L^1$ are independently a bond, unsubstituted $C_1$-$C_{20}$ alkylene, or unsubstituted 2 to 20 membered heteroalkylene. $L^3$ and $L^1$ may also independently be a bond, unsubstituted $C_1$-$C_5$ alkylene, or unsubstituted 2 to 5 membered heteroalkylene. $L^3$ may also be $C_1$-$C_5$ alkylene. $L^1$ may be a branched unsubstituted $C_1$-$C_5$ alkylene.

In some embodiments, $L^2$ is an unsubstituted $C_1$-$C_{20}$ alkylene, or unsubstituted 2 to 20 membered heteroalkylene. In other embodiments, $L^2$ is unsubstituted $C_1$-$C_5$ alkylene, or unsubstituted 2 to 5 membered heteroalkylene. $L^2$ may be unsubstituted $C_1$-$C_5$ alkylene. $L^2$ may be a branched unsubstituted $C_1$-$C_5$ alkylene. $L^2$ may also be methylene. In some related embodiments, A² is substituted or unsubstituted heteroaryl (e.g. pyridyl) or substituted or unsubstituted aryl (e.g. phenyl). In some related embodiments, A¹ is substituted or unsubstituted heteroaryl (e.g. pyridyl) or substituted or unsubstituted aryl (e.g. phenyl).

In some embodiments, where $R^1$ is —NR⁸R⁹ and R⁸ is —S(O)₂R¹⁴, then R⁶ is hydrogen. R⁷ may be substituted or unsubstituted alkyl. R⁷ may be unsubstituted $C_1$-$C_5$ alkyl. R² and R³ may both be hydrogen. Thus, in some embodiments, $R^1$ is —NR⁸R⁹, R⁸ is —S(O)₂R¹⁴, R⁶ is hydrogen, R⁷ is unsubstituted $C_1$-$C_5$ alkyl, and R² and R³ are hydrogen.

In some embodiments, where $R^1$ is hydrogen, then R⁶ is not hydrogen. In some related embodiments, R⁶ is substituted or unsubstituted alkyl. In some related embodiments, R⁶ is unsubstituted $C_1$-$C_5$ alkyl. In some related embodiments, R⁶ is substituted or unsubstituted $C_3$-$C_6$ cycloalkyl. In some related embodiments, R⁶ is substituted or unsubstituted cyclopropyl. In some related embodiments, R⁷ is hydrogen. In some related embodiments, R² and R³ are hydrogen.

In some embodiments, $R^1$ is hydrogen. R², R³, and R⁴ may be hydrogen. A¹ may be substituted or unsubstituted heteroaryl, or substituted or unsubstituted heterocycloalkyl. In some related embodiments, A¹ is substituted or unsubstituted heteroaryl (e.g. substituted or unsubstituted thioazolyl, substituted or unsubstituted oxazolyl, substituted or unsubstituted imidazolyl, or substituted or unsubstituted pyrazolyl). A² may be substituted or unsubstituted aryl or heteroaryl. A² may also be substituted or unsubstituted phenyl, or substituted or unsubstituted pyridyl. R⁶ may be substituted or unsubstituted alkyl, or substituted or unsubstituted cycloalkyl (e.g. unsubstituted ($C_1$-$C_6$) alkyl or unsubstituted ($C_3$-$C_6$) cycloalkyl). $L^1$ may be unsubstituted methylene. $L^2$ may be unsubstituted methylene. In some related embodiments, R⁶ is methyl or cyclopropyl, R⁷ is hydrogen, $L^1$ is unsubstituted methylene, and $L^2$ is unsubstituted methylene. $L^3$ may be unsubstituted methylene. R⁵ may be substituted or unsubstituted phenyl. In some related embodiments, A¹ is substituted or unsubstituted 2-thiazolyl (e.g. unsubstituted 2-thiazolyl or 2-thiazolyl substituted with substituted or unsubstituted alkyl, such as one or more unsubstituted ($C_1$-$C_5$) alkyl(s)). For example, A¹ may be 2-(4-methylthiazolyl). A² may be substituted or unsubstituted 3-pyridyl or substituted or unsubstituted phenyl (e.g. 3-(5-substituted pyridyl) or meta-substituted phenyl). In some embodiments, the 3-(5-substituted pyridyl) and meta-substituted phenyl are substituted with substituted or unsubstituted alkyl (e.g. unsubstituted $C_1$-$C_5$ alkyl or $C_1$-$C_5$ haloalkyl). Some or all of the embodiments for each substituent definition in this paragraph may be combined to form an appropriate subgenus. Thus, in some embodiments, $R^1$, $R^2$, $R^3$, and R⁴ are hydrogen, A¹ is substituted or unsubstituted 2-thiazolyl, A² is substituted or unsubstituted 3-pyridyl or substituted or unsubstituted phenyl, R⁶ is unsubstituted ($C_1$-$C_6$) alkyl or unsubstituted ($C_3$-$C_6$)cycloalkyl, R⁷ is hydrogen, and $L^1$, $L^2$, and $L^3$ are unsubstituted methylene.

In some embodiments, $R^1$ is —NR⁹S(O)ₙR¹⁴. R⁶ may be hydrogen. A¹ may be substituted or unsubstituted phenyl. A² may be substituted or unsubstituted phenyl, or substituted or unsubstituted pyridyl. In some related embodiments, n is 2, R⁹ is unsubstituted ($C_1$-$C_5$) alkyl (e.g. methyl), and R¹⁴ is unsubstituted ($C_1$-$C_5$) alkyl (e.g. methyl). $L^2$ may be unsubstituted methylene. $L^1$ may be methylmethylene. R², R³, and R⁴ may be hydrogen.

Some or all of the embodiments for each substituent definition in this paragraph may be combined to from an appropriate subgenus. Thus, in some embodiments, $R^1$ is —NR⁹S(O)ₙR¹⁴, R⁶ is hydrogen, A¹ is substituted or unsubstituted phenyl, A² is substituted or unsubstituted phenyl or substituted or unsubstituted pyridyl, n is 2, R⁹ is unsubstituted ($C_1$-$C_5$) alkyl (e.g. methyl), R¹⁴ is unsubstituted ($C_1$-$C_5$) alkyl (e.g. methyl), $L^2$ is unsubstituted methylene, $L^1$ is methylmethylene, and R², R³, and R⁴ are hydrogen.

In some embodiments, the β-secretase inhibitor compound has the formula:

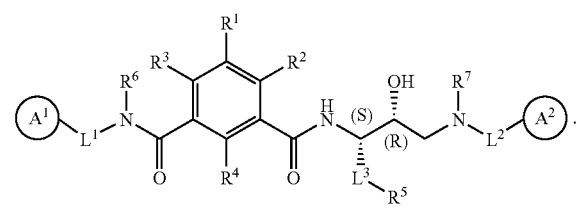

(II)

In Formula (II), $L^1$, $L^2$, $L^3$, $R^1$, $R^2$, $R^3$, $R^4$, $R^5$, $R^6$, $R^7$, $A^1$ and $A^2$ are as defined above in the discussion of Formula (I).

In some embodiments, the β-secretase inhibitor compound has the formula:

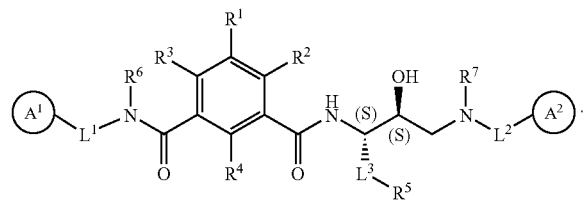

(III)

In Formula (III), $L^1$, $L^2$, $L^3$, $R^1$, $R^2$, $R^3$, $R^4$, $R^5$, $R^6$, $R^7$, $A^1$ and $A^2$ are as defined above in the discussion of Formula (I).

In another embodiment, the β-secretase inhibitor compound has the formula:

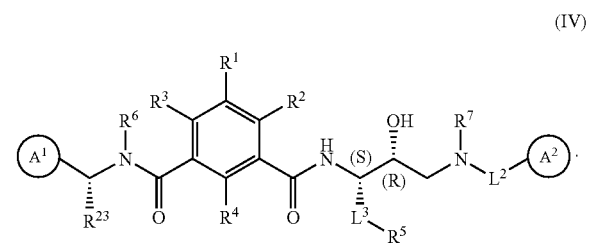

(IV)

In Formula (II), $L^1$, $L^2$, $L^3$, $R^1$, $R^2$, $R^3$, $R^4$, $R^5$, $R^6$, $R^7$, $R^{23}$, $A^1$ and $A^2$ are as defined above in the discussion of Formula (I). In some embodiments, $R^{23}$ is an unsubstituted $C_1$-$C_5$ alkyl.

In another embodiment, the β-secretase inhibitor compound has the formula:

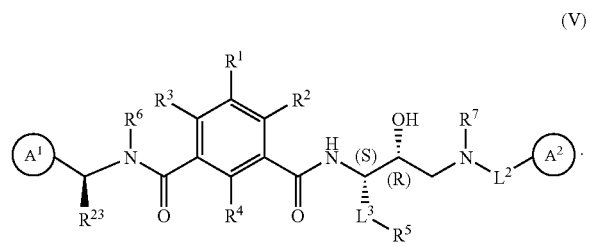

(V)

In Formula (V), $L^1$, $L^2$, $L^3$, $R^1$, $R^2$, $R^3$, $R^4$, $R^5$, $R^6$, $R^7$, $R^{23}$, $A^1$ and $A^2$ are as defined above in the discussion of Formula (I). In some embodiments, $R^{23}$ is an unsubstituted $C_1$-$C_5$ alkyl.

In another embodiment, the β-secretase inhibitor compound has the formula:

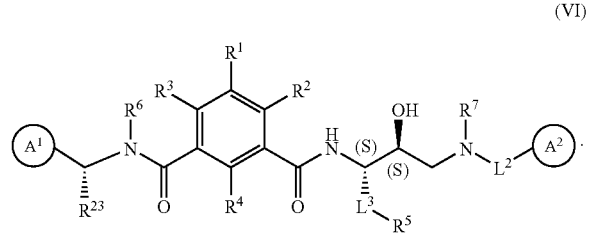

(VI)

In Formula (VI), $L^1$, $L^2$, $L^3$, $R^1$, $R^2$, $R^3$, $R^4$, $R^5$, $R^6$, $R^7$, $R^{23}$, $A^1$ and $A^2$ are as defined above in the discussion of Formula (I). In some embodiments, $R^{23}$ is an unsubstituted $C_1$-$C_5$ alkyl.

In another embodiment, the β-secretase inhibitor compound has the formula:

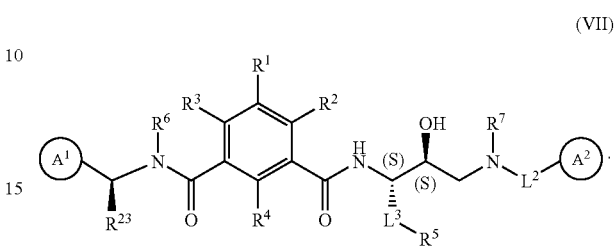

(VII)

In Formula (VII), $L^1$, $L^2$, $L^3$, $R^1$, $R^2$, $R^3$, $R^4$, $R^5$, $R^6$, $R^7$, $R^{23}$, $A^1$ and $A^2$ are as defined above in the discussion of Formula (I). In some embodiments, $R^{23}$ is an unsubstituted $C_1$-$C_5$ alkyl.

In some embodiments, each substituted group described above in the compound of Formulae (I)-(VII) is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, or substituted heteroalkylene described above in the compounds of Formulae (I)-(VII) is substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formulae (I)-(VII), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, and each substituted or unsubstituted heteroalkylene is a substituted or unsubstituted 2 to 20 membered heteroalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, and each substituted or unsubstituted heteroalkylene is a substituted or unsubstituted 2 to 8 membered heteroalkylene.

In some embodiments, the compounds of the present invention include any one or all of the compounds of Table 1. In some embodiments, the compounds of the present invention include t any one or all of the compounds of Example 4 below.

A. Carrier Moieties

In copending U.S. Application No. 20040121947, and International Application No. PCT/USO2/34324 (Publication No. WO 03/039454), which are herein incorporated by reference for all purposes, isostere β-secretase inhibitors with and without a carrier moiety were shown to effectively reduce Aβ production in tg2576 mice expressing the Swedish mutation of the human amyloid precursor protein (Hsiao, K., et al., *Science* 274, 99-102 (1996)). Thus, one of skill in the art will recognize that the compounds of the invention may be administered with or without a carrier moiety. A carrier moiety may be attached to any appropriate site on the compounds of the present invention.

A "carrier moiety," as used herein, refers to a chemical moiety covalently or non-covalently attached to a β-secretase inhibitor compound of the invention that enhances the ability of the compound to traverse the blood-brain barrier (BBB). The β-secretase inhibitors of the invention may be attached or conjugated to the carrier moiety by covalent interactions (e.g., peptide bonds) or by non-covalent interactions (e.g., ionic bonds, hydrogen bonds, van der Waals attractions).

The blood-brain barrier is a permeability barrier that exists between the extracellular fluid in the brain and the blood in the capillary lumen. The barrier stems from structural differences between the capillaries in the brain and capillaries found in other tissues. Most significant among the structural differences of brain capillaries are the tight junctions between endothelial cells. These specialized tight junctions create a very high trans-endothelial electrical resistance of 1500-2000 ohms/cm$^2$ compared to 3-33 ohms/cm$^2$ in capillary endothelial cells lying outside the brain, reducing the aqueous based para-cellular diffusion observed in other organs (Brightman, M. in Bradbury MWB (ed) *Physiology and Pharmacology of the blood-brain barrier. Handbook of experimentalpharmacology* 103, Springer-Verlag, Berlin, (1992); Lo, E. H., et al., *Brain Res. Rev.*, 38:140-148, (2001)). Thus, in some embodiments, the compounds of the present invention are covalently attached to a carrier moiety (represented by the symbol Y in the formulae above).

Any appropriate carrier moiety may be used in the present invention. Useful carrier moieties include, for example, lipophilic carrier moieties, enzymatic substrate carrier moieties, peptidyl carrier moieties, and nanoparticle carrier moieties. Carrier moieties may also include an oligosaccharide unit or other molecule linked to the compound by phosphoester or lipid-ester or other hydrolyzable bonds which are cleaved by glycosidases, phosphatases, esterases, lipases, or other hydrolases in the lysosomes and endosomes. The carrier moieties may contain contain guanidine, amino, or imidizole functional groups.

1. Lipophilic Carrier Moieties

Lipophilic carrier moieties increase the overall lipophilicity of a compound, thereby aiding in passage through the BBB. Lipophilicity can be quantified using any suitable approach known in the art. For example, the partition coefficient between octanol and water (log $P_{o/w}$) may be measured thereby indicating the degree of lipophilicity. In some embodiments, the lipophilic carrier moiety has a log $P_{o/w}$ of 1.5-2.5. Lipophilic carrier moieties are widely known in the art and are discussed in detail, for example, in Lambert, D. M., *Eur J Pharm Sci.*, 11:S15-27 (2000). Exemplary lipophilic carrier moieties used to increase the lipophilicity of a compound include modified and unmodified diglycerides, fatty acids, and phospholipids.

Some lipophilic carrier moieties undergo enzyme mediated oxidation after traversing the BBB, resulting in a hydrophilic membrane impermeable form of the carrier moiety that remains trapped behind the BBB (Bodor et al., *Pharmacol Ther* 76:1-27 (1997); Bodor et al., *American Chemical Society*, Washington, D.C. pp 317-337 (1995); Chen et al., *J Med Chem* 41:3773-3781 (1998); Wu et al., *J Pharm Pharmacol* 54:945-950 (2002)). Exemplary lipophilic carrier moieties that undergo enzyme mediated oxidation include 1,4-dihydrotrigonelline (Palomino et al., *J Med Chem*, 32:622-625 (1989)); alkyl phosphonate carrier moieties that have been successfully used to transport testosterone and zidovudine across the blood-brain barrier (Somogyi, G., et al., *Int J Pharm*, 166:15-26 (1998)); and the lipophilic dihydropyridine carrier moieties that are enzymatically oxidized to the ionic pyridinium salt (Bodor et al., *Science*, 214(18):1370-1372 (1981)).

2. Peptidyl Carrier Moieties

Peptidyl carrier moieties are moieties partially or wholly composed of a peptide (including polypeptides, proteins, antibodies, and antibody fragments) used to aid in the transport of compounds across the BBB (Wu et al., *J Clin Invest* 100:1804-1812 (1997); U.S. Pat. No. 4,801,575; Pardridge et al., *Adv Drug Deliv Rev*, 36:299-321 (1999)).

Peptidyl carrier moieties may interact with specific peptide transport systems, receptors, or ligands, that target the corresponding ligand or receptor on an endothelial cell of the BBB. Specific transport systems may include either carrier-mediated or receptor-mediated transport across the BBB (U.S. Pat. App. No. 20040110928). Exemplary peptidyl carrier moieties include insulin (Pardridge et al., *Nat Rev Drug Discov*, 1:131-139 (2002)); small peptides such as enkephalin, thyrotropin-releasing hormone, arginine-vassopressin (Bergley, *J Pharm Pharmacol*, 48:136-146 (1996)), Banks et al., *Peptides*, 13:1289-1294 (1992)), Han et al., *AAPS Pharm. Si.*, 2:E6 (2000)); chimeric peptides such as those described in WO-A-89/10134; amino acid derivatives such as those disclosed in U.S. Pat. App. No. 20030216589; tat peptide (Schwarze, S. R., et al., *Science* 285:1569-1572 (1999); polyarginine peptide (Wender, P. A., et al., *Proc. Natl. Acad. Sci. USA* 97:13003-13008 (2000)); insulin-like-growth factor-1; insulin-like-growth factor-2; transferrin; leptin; low-density lipoprotein (Pardridge, *Nat. Rev. Drug Discov.* 1:131-139 (2002); Colma et al., *Pharm. Res.* 17:266-274 (2000); Pardridge, *Endocrine Rev*, 7:314-330 (1986); Golden, et al., *J Clin Invest*, 99:14-18 (1997); Bickel et al., *Adv. Drug Deliv. Rev.* 46(1-3):247-79 (2001)); and basic fibroblast growth factor (bFGF) (U.S. Pat. App. No. 20040102369).

Copending U.S. Application No. 20040121947, and International Application No. PCT/USO2/34324 (Publication No. WO 03/039454), disclose that confocal microscopic images of cells incubated with a fluorescent tat-conjugated isosteric β-secretase inhibitor showed uneven distribution inside cells. Some high fluorescence intensity was associated with the endosome and lysosome intracellular vesicular structures. This indicated that the tat carrier moiety may have been modified by proteases within the lysosome or endosome resulting in an inhibitor that was unable to exit the lysosomal or endosomal compartment. Lysosomes and endosomes contain many proteases, including hydrolase such as cathepsins A, B, C, D, H and L. Some of these are endopeptidase, such as cathepsins D and H. Others are exopeptidases, such as cathepsins A and C, with cathepsin B capable of both endo- and exopeptidase activity. The specificities of these proteases are sufficiently broad to hydrolyze a tat peptide away from the inhibitor compound, thus, hydrolyzing the carrier peptide away from the isosteric inhibitor. Thus, it has been shown that tat and other carrier peptides may be particularly useful for specific delivery of isosteric inhibitors to lysosomes and endosomes. When administered to a mammal by a mechanism such as injections, the conjugated compound will penetrate cells and permeate to the interior of lysosomes and endosomes. The proteases in lysosomes and endosomes will then hydrolyze tat, thereby preventing to escape from lysosomes and endosomes.

The carrier peptide may be tat or other basic peptides, such as oligo-L-arginine, that are hydrolyzable by lysosomal and endosomal proteases. Specific peptide bonds susceptible for the cleavage of lysosomal or endosomal proteases may be installed, thereby facilitating the removal of the carrier compound from the inhibitor. For example, dipeptides Phe-Phe, Phe-Leu, Phe-Tyr and others are cleaved by cathepsin D.

In one embodiment, the peptidyl carrier molecule includes cationic functional groups, such as the tat-peptide (Schwarze, S. R., et al., *Science* 285: 1569-1572 (1999)), or nine arginine residues (Wender, P. A., et al., *Proc. Natl. Acad. Sci. USA* 97:13003-13008 (2000)). Useful cationic functional groups include, for example, guanidine, amino, and imidazole functional groups. Thus, cationic functional groups also include amino acid side chains such as side chains of lysine, arginine, and histidine residues. In some embocients, the peptidyl carrier molecule may includes from 1-10 cationic functional groups. When a compound of the invention is conjugated or attached to a carrier moiety, the resulting conjugate may be referred to herein as a "Carrier Peptide-Inhibitor" conjugate or "CPI." The CPI conjugate can be administered to an in vitro sample or to a mammal thereby serving as a transport vehicle for a compound or compounds of the invention into a cell in an in vitro sample or in a mammal. The carrier moieties and CPI conjugates result in an increase in the ability of the compounds of the invention to effectively penetrate cells and the blood brain barrier to inhibit memapsin 2 from cleaving APP to subsequently generate Aβ.

Adsorptive-meditated transcytosis (AME) provides an alternative mechanism whereby peptidyl carrier moieties may cross the BBB. AME differs from other forms of transcytosis in that the initial binding of the carrier moiety to the luminal plasma membrane is mediated through either electrostatic interactions with anionic sites, or specific interactions with sugar residues. Uptake through AME is determined by the C-terminal structure and basicity of the carrier moiety. Exemplary adsorptive peptidyl carrier moieties include peptides and proteins with basic isoeletric points (cationic proteins), and some lectins (glycoprotein binding proteins). See Tamai, I., et al., J. Pharmacol. Exp. Ther. 280:410-415 (1997); Kumagai, A. K., et al., *J. Biol. Chem.* 262: 15214-15219 (1987).

Peptidyl carrier moieties also include antibody carrier moieties. Antibody carrier moieties are carrier moieties that include an antibody or fragment thereof. Typically, the antibody or antibody fragment is, or is derived from, a monoclonal antibody. Antibody carrier moieties bind to cellular receptors, or transporters expressed on the luminal surface of brain capillary endothelial cells (U.S. Patent App No. 20040101904). Exemplary antibodies, or fragments thereof, include MAb 83-14 that binds to the human insulin receptor (Pardridge et al., *Pharm Res.* 12:807-816 (1995)); anti-transferrin antibody (Li, J. Y., et al., *Protein Engineering* 12:787-796 (1999)); and monoclonal antibodies that mimic an endogenous protein or peptide which is known to cross the BBB as discussed above.

3. Nanoparticle Carrier Moieties

Nanoparticle carrier moieties are solid colloidal carriers generally less than a micron in diameter or length. The compound may be encapsulated in, adsorbed onto, or covalently linked to the surface of the nanoparticle carrier moiety. Nanoparticle carrier moieties have been used to successfully deliver a variety of compounds to the brain, including hexapeptide dalagrin, an enkephalin analog; loperamide; tubocerarine; and doxorubicin (Ambikanandan, et al., *J. Pharm Pharmaceut Sci* 6(2):252-273 (2003)). In addition to aiding transport into the brain, nonionic detergents such as polysorbate-80, which can be used to coat the nanoparticle, may be used to inhibit the efflux pump. Zordan-Nudo, T., et al., *Cancer Res,* 53:5994-6000 (1993). Exemplary materials for the manufacture of nanoparticle carrier moieties include polyalkylcyanoacrylate (PACA) (Bertling et al., *Biotechnol. Appl. Biochem.* 13: 390-405 (1991)); polybutylcyanoacrylate (PBCA) (Chavany et al., *Pharm. Res.* 9: 441-449 (1992)); polybutylcyanoacrylate with the peptide-drug complex absorbed onto the surface and coated with polysorbate 80 (Kreuter, J., et al., *Brain Res,* 674:171-174 (1995), Kreuter, J., *Adv Drug Deliv Rev,* 47:65-81, (2001), Kreuter, J., *Curr Med Chem,* 2:241-249 (2002)); polyisohexylcyanoacrylate (PI-HCA) (Chavany et al., *Pharm. Res.* 11: 1370-1378 (1994)); polyhexylcyanoacrylate (PHCA) (Zobel et al., *Antisense Nucleic Acid Drug Dev.* 7:483-493 (1997)); and PEGylated polycyanoacrylate (Pilar, C., et al., *Pharm Res* 18(8):1157-1166 (2001)).

4. Linker Moieties

Linker moieties may be used to attach the carrier moiety to the β-secretase inhibitors of the present invention. For example, steric hinderance between the compound and the carrier can be prevented using polymer technology (e.g. PEGylation) in conjunction with the linker molecule to introduce a long spacer arm (Yoshikawa, T., et al., *J Pharmacol Exp Ther,* 263:897-903, 1992). Linker moieties may be cleavable or non-cleavable.

Cleavable linker molecules include a cleavable moiety. Any appropriate cleavable moiety is useful in the present invention, including for example, phosphoesters, esters, disulfides, and the like. Cleavable moieties also include those moieties capable of being cleaved by biological enzymes, such as peptidases, glycosidases, phosphatases, esterases, lipases, or other hydrolases. Cleavable linker molecules are especially useful where the carrier moiety interferes with the biological activity of the compound. Exemplary cleavable linker molecules include N-succinimidyl-3-2-pyridyldithio-proprionate (SPDP), or N-hydrosuccinimide (NHS).

Non-cleavable linker molecules are those that involve the attachment of a carrier moiety to the compound through a linkage that is generally stable to biological conditions and enzymes. Non-cleavable linker molecules are typically used when the carrier moiety does not interfere with the biological activity of the compound. Exemplary non-cleavable linker molecules include thio-ether (e.g., m-maleimidobenzoyl N-hydroxysuccinimide ester (MBS)); amide (e.g., N-hydrosuccinimide (NHS—XX—); extended amide (e.g., N-hydrosuccinimide polyethylene glycol (NHS-PEG); and extended hydrazide linkages (e.g., hydrazide-PEG-biotin-); avidin-biotin; and PEG linkers (Ambikanandan et al., *J. Pharm Pharmaceut Sci* 6(2):252-273 (2003); Pardridge, *Adv Drug Deliv Rev,* 36:299-321 (1999); U.S. Pat. No. 6,287,792).

II. Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

Scheme 1

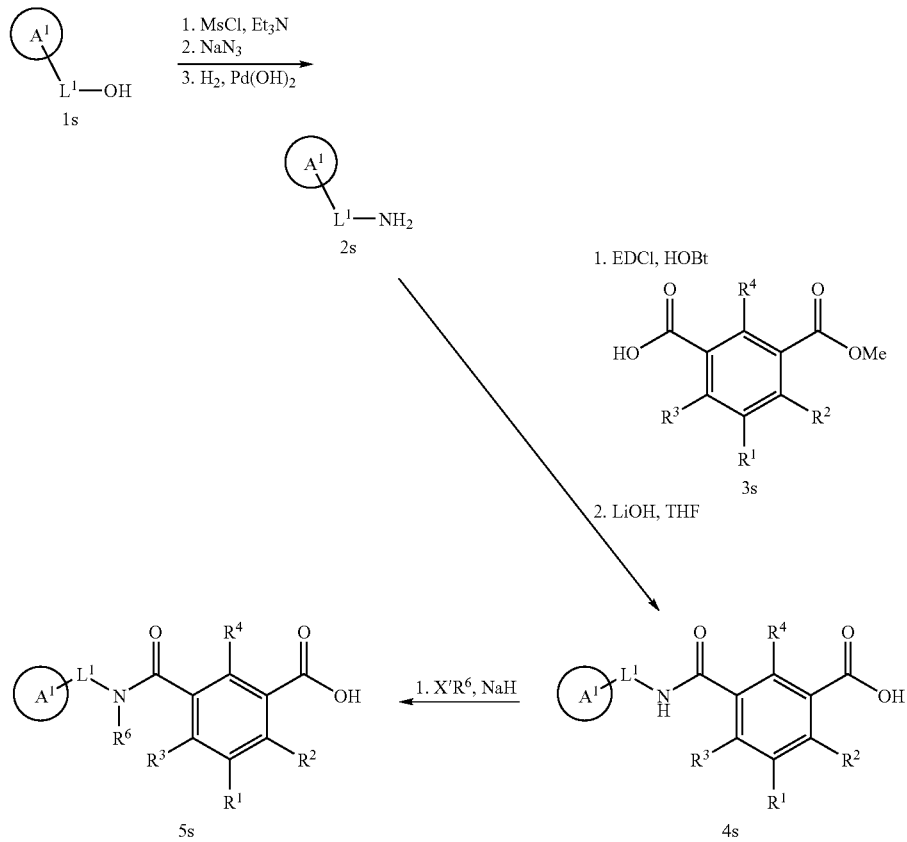

In Schemes 1, 2, and 3, $L^1$, $L^2$, $L^3$, $R^1$, $R^2$, $R^3$, $R^4$, $R^5$, $R^6$, $R^7$, $A^1$ and $A^2$ are as defined above. Synthesis of certain 1s and 2s compounds is detailed in the Examples section below. Treatment of 1s with triethylamine and mesyl chloride followed by sodium azide followed by palladium reduction yields the methylamine substituted ring 2s. The isophthalamide 4s is formed by amide bond formation between the partially protected isophthalic acid 3s and methylamine 2s. Finally, the alkylated amide 5s is produced via a sodium hydride-mediated alkylation using an alkyl halide.

Scheme 2

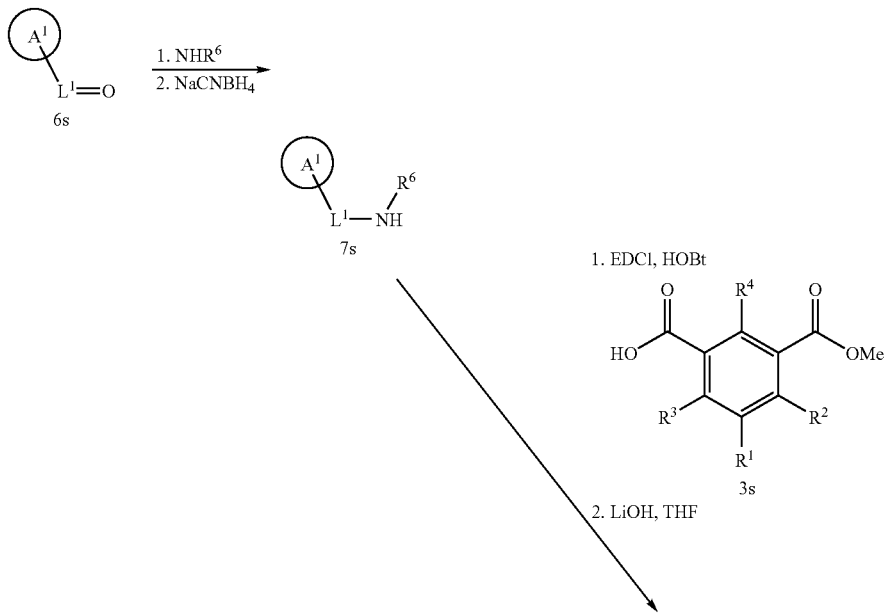

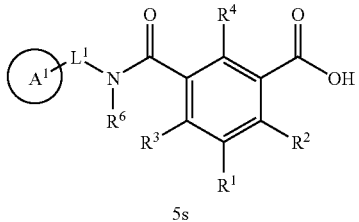

5s

Alternatively compound 5s can be prepared following the sequence in Scheme 2 wherein reductive amination of aldehyde 6s with an appropriate amine and sodium cyanoborohydride yields amine 7s. Amine 7s is then coupled with 3s followed by ester hydrolysis to yield alkylated amide 5s.

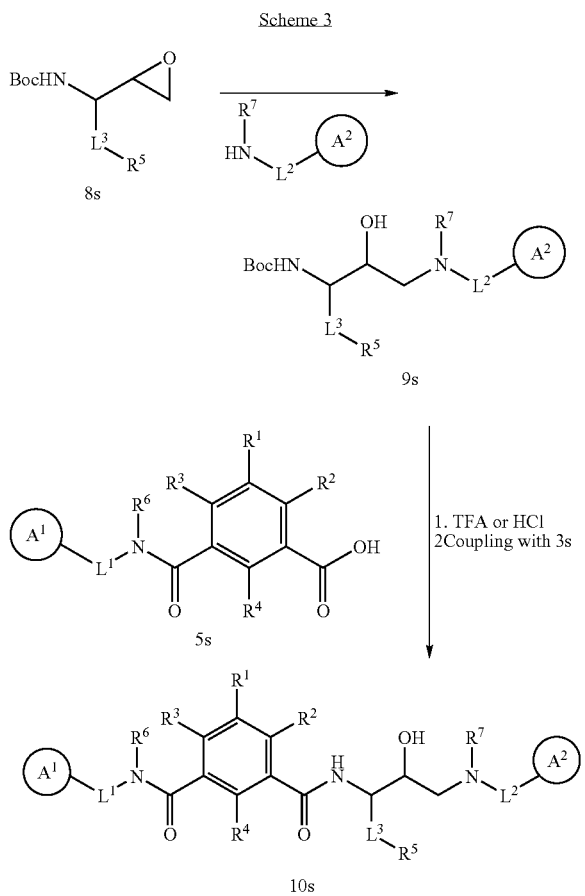

Treatment of epoxide 8s with an appropriate amine yields aminoalcohol 9s. Removal of the Boc protecting group with acid followed by coupling with fragment 5s (Scheme 1) gives rise to final inhibitor 10s.

III. Beta-Secretase Inhibitor Activity

To develop useful β-secretase inhibitors, candidate inhibitors capable of selectively decreasing memapsin 2 catalytic activity may be identified in vitro and subsequently tested for their ability to reduce the production of Aβ. The activity of the inhibitor compounds can be assayed utilizing methods known in the art and/or those methods presented herein.

Compounds that decrease memapsin 2 catalytic activity may be identified and tested using biologically active memapsin 2, either recombinant or naturally occurring. Memapsin 2 can be found in native cells, isolated in vitro, or co-expressed or expressed in a cell. Measuring the reduction in the memapsin 2 catalytic activity in the presence of an inhibitor relative to the activity in the absence of the inhibitor may be performed using a variety of methods known in the art.

For example, the compounds may be tested for their ability to cause a detectable decrease in hydrolysis of a β-secretase site of a peptide in the presence of memapsin 2. These data can be expressed, for example, as $K_i$, $K_i$ apparent, Vi/Vo, or percentage inhibition. $K_i$ is the inhibition equilibrium constant which indicates the ability of compounds to inhibit a given enzyme (such as memapsin 2, memapsin 1, and/or cathepsin D). Numerically lower $K_i$ values indicate a higher affinity of the compounds of the invention for the enzyme. The $K_i$ value is independent of the substrate, and converted from $K_i$ apparent.

$K_i$ apparent is determined in the presence of substrate according to established techniques (see, for example, Bieth, J., Bayer-Symposium V: Proteinase Inhibitors, pp. 463-469, Springer-Verlag, Berlin (1994)). The standard error for the $K_i$ apparent is the error from the nonlinear regression of the Vi/Vo data measured at different concentrations of the compounds of the invention (e.g., between about 10 nM to about 1000 nM) employing well-known techniques (see, for example, Bieth, J., Bayer-Symposium V: Proteinase Inhibitors, pp. 463-469, Springer-Verlag, Berlin (1994), Ermolieff, J., et al., Biochemistry 39:12450-12456 (2000), the teachings of which are incorporated herein by reference in their entirety). Vi/Vo depicts the ratio of initial conversion velocites of an enzyme substrate (Ermolieff, et al., Biochemistry 40:12450-12456 (2000)) by an enzyme in the absence (Vo) or presence (Vi) of an inhibitor. A Vi/Vo value of 1.0 indicates that a compound does not inhibit the enzyme. A Vi/Vo value less than 1.0 indicates that a compound of the invention inhibits enzyme activity.

Once compounds are identified that are capable of reducing the hydrolysis of a β-secretase site of a peptide in the presence of memapsin 2, the compounds may be further tested for their ability to selectively inhibit memapsin 2 relative to other enzymes. Typically, the other enzyme is a peptide hydrolase, such as memapsin 1 or cathepsin D. Compounds that decrease cathepsin D catalytic activity or memapsin 1 catalytic activity are tested using biologically active enzyme, either recombinant or naturally occurring. Cathepsin D or memapsin 1 catalytic activity can be found in native cells, isolated in vitro, or co-expressed or expressed in a cell. Inhibition by a compound of the invention is measured using standard in vitro or in vivo assays such as those well known in the art or as otherwise described herein.

For example, selectivity may be measured by determining the extent to which memapsin 2 hydrolyzes a substrate peptide compared to the extent to which the same compound inhibits memapsin 1 and/or cathepsin D cleaving of a β-secretase site of a substrate peptide. Exemplary substrate peptides are useful in determining the activity of memapsin 2 includes APP and derivatives thereof, such as FS-2 (Bachem Americas, Torrance, Calif.). Exemplary substrate peptides are useful in determining the activity of memapsin 1 and cathepsin D include, for example, peptides with include the sequence ELDLAVEFWHDR (SEQ ID NO.:1). These data can be expressed, for example, as $K_i$, $K_i$ apparent, Vi/Vo, or percentage inhibition and depict the inhibition of a compound for memapsin 2 catalytic activity relative to memapsin 1 or cathepsin D catalytic activity. For example, if the $K_i$ of a reaction between an inhibitor compound of the invention and memapsin 1 or cathepsin D is 1000 and the $K_i$ of a reaction between an inhibitor compound of the invention and memapsin 2 is 100, the inhibitor compound inhibits the β-secretase activity of memapsin 2 ten fold, relative to memapsin 1.

Compounds demonstrating the ability to cause a detectable decrease in hydrolysis of a β-secretase site of a peptide in the presence of memapsin 2 (or, in addition, selectivity of action toward memapsin 2), may be tested in cell models or animal models for their ability to cause a detectable decrease in the amount or production of β-amyloid protein (Aβ). For example, isosteric inhibitors of memapsin 2 have been tested for their ability to decrease Aβ production in cultured cells (copending U.S. Application No. 20040121947, and International Application No. PCT/USO2/34324 (Publication No. WO 03/039454)). Briefly, inhibitors may be added to a culture of cells (e.g. human embryonic kidney (HEK293) cells, HeLa cells, Chinese hamster ovary cells, or neuroblastoma line M17 cells) stably transfected with a nucleic acid constructs that encode human APP Swedish mutant (or London mutation or double mutant) and, if needed, a nucleic acid construct encoding human memapsin 2. Immunoprecipitation of Aβ followed by SDS-gel electrophoresis allows detection and quantitation of the amount of Aβ produced in the presence and absence of inhibitor.

In addition to cell cultures, animal models may be used to test inhibitors of memapsin 2 for their ability to decrease Aβ production. For example, an animal (e.g. tg2576 mice) expressing the Swedish mutation of the human amyloid precursor protein (Hsiao, K., et al., *Science* 274, 99-102 (1996) may be injected intraperitoneally with an inhibitor. The plasma may then be collected and Aβ levels determined by capture ELISA (BioSource International, Camarillo, Calif.).

The presence of inhibitors in organs of animal models or within cellular compartments may be ascertained using a fluorescent tag conjugated to the inhibitor and visualization via confocal microscopy (copending U.S. Application No. 20040121947, and International Application No. PCT/USO2/34324 (Publication No. WO 03/039454)).

The sample obtained from the mammal can be a fluid sample, such as a plasma or serum sample; or can be a tissue sample, such as a brain biopsy. The amount of β-amyloid protein or a decrease in the production of β-amyloid protein can be measured using standard techniques (e.g. western blotting and ELISA assays).

Further examples of assays for identifying memapsin 2-β-secretase inhibitors are set forth in the Examples section below. Other methods for assaying the activity of memapsin 2, memapsin 1, and cathepsin D and the activity of agents that decrease the activity of these enzymes are known in the art. The selection of appropriate assay methods is well within the capabilities of those of skill in the art.

IV. Pharmaceutical Compositions

In another aspect, the present invention provides pharmaceutical compositions comprising a β-secretase inhibitor compound of the invention or a β-secretase inhibitor compound in combination with a pharmaceutically acceptable carrier. The pharmaceutical compositions include optical isomers, diastereomers, or pharmaceutically acceptable salts of the inhibitors disclosed herein. For example, in some embodiments, the pharmaceutical compositions include a compound of the present invention and citrate as a pharmaceutically acceptable salt. The β-secretase inhibitor included in the pharmaceutical composition may be covalently attached to a carrier moiety, as described above. Alternatively, the β-secretase inhibitor included in the pharmaceutical composition is not covalently linked to a carrier moiety.

A "pharmaceutically suitable carrier," as used herein refers to pharmaceutical excipients, for example, pharmaceutically, physiologically, acceptable organic, or inorganic carrier substances suitable for enteral or parenteral application which do not deleteriously react with the extract. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the compounds of the invention.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

A. Formulations

The β-secretase inhibitors of the present invention can be prepared and administered in a wide variety of oral, parenteral and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the 5 preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

B. Effective Dosages

Pharmaceutical compositions provided by the present invention include compositions wherein the active ingredient is contained in a therapeutically effective amount, i.e., in an amount effective to achieve its intended purpose (defined above). The actual amount effective for a particular application will depend, inter alia, on the condition being treated. For example, when administered in methods to treat Alzheimer's disease, such compositions will contain an amount of active ingredient effective to achieve the desires result (e.g. decreasing β-secretase activity or β-amyloid production). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, including a disease that results in increased activity of memapsin 2 or increased accumulation of β-amyloid protein, whether the mammal suffers from another disease, and its route of administration; size, age, sex, health, body weight, body mass index, and diet of the recipient; nature and extent of symptoms of the disease being treated (e.g., Alzheimer's disease), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of reducing the activity of memapsin 2 catalytic activity, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring memapsin 2 inhibition and adjusting the dosage upwards or downwards, as described above. Adjusting the dose to achieve maximal efficacy in humans based on the methods described above and other methods as are well-known in the art is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

V. Methods of Reducing the Catalytic Activity of Memapsin 2

In another aspect of the present invention, the β-secretase inhibitor compounds of the invention can be employed in methods to decrease memapsin 2 catalytic activity, decrease hydrolysis of a β-secretase site of a memapsin 2 substrate, and/or decrease the accumulation of β-amyloid protein relative to the amount of memapsin 2 catalytic activity, hydrolysis of a β-secretase site, and accumulation of β-amyloid protein, respectively, in the absence of the β-secretase inhibitor.

In an exemplary embodiment, a method of reducing memapsin 2 catalytic activity is provided. The method includes contacting a memapsin 2 protein with an effective amount of a β-secretase inhibitor compound of the present invention. The memapsin 2 may be contacted in any appropriate environment. The memapsin 2 catalytic activity is decreased relative the amount of activity in the absence of β-secretase inhibitor.

In another exemplary embodiment, a method is provided of selectively reducing memapsin 2 catalytic activity using an inhibitor of the present invention. Selective reduction of the activity of memapsin 2 means that memapsin 2 is not only reduced relative to its activity in the absence of inhibitor, but is reduced to a greater extent as compared to the reduction in activity due to inhibitor action against another peptide hydrolase. For example, as described above, the reduction in activity of an enzyme may be expressed in terms of the inhibitory constant ($K_i$). Where an inhibitor selectively reduces the activity of memapsin 2, the $K_i$ of the reaction between an inhibitor compound of the invention and memapsin 2 is less than the $K_i$ of the reaction between an inhibitor compound of the invention and another peptide hydrolase.

In an exemplary embodiment, the $K_i$ of the reaction between an inhibitor compound of the invention and memapsin 2 is at least 2 times less than the $K_i$ of the reaction between an inhibitor compound of the invention and another peptide hydrolase. In another exemplary embodiment, the $K_i$ of the reaction between an inhibitor compound of the invention and memapsin 2 is at least 10 times less than the $K_i$ of the reaction between an inhibitor compound of the invention and another peptide hydrolase. In another exemplary embodiment, the $K_i$ of the reaction between an inhibitor compound of the invention and memapsin 2 is at least 100 times less than the $K_i$ of the reaction between an inhibitor compound of the invention and another peptide hydrolase. In another exemplary embodiment, the $K_i$ of the reaction between an inhibitor compound of the invention and memapsin 2 is at least 1000 times less than the $K_i$ of the reaction between an inhibitor compound of the invention and another peptide hydrolase. In another exemplary embodiment, the $K_i$ of the reaction between an inhibitor compound of the invention and memapsin 2 is at least 10000 times less than the $K_i$ of the reaction between an inhibitor compound of the invention and another peptide hydrolase.

In some related embodiments, the inhibitor selectively reduces the activity of memapsin 2 as compared to memapsin 1. In other related embodiments, the inhibitor selectively reduces the activity of memapsin 2 as compared to cathepsin D.

Thus, the present invention provides methods of selectively reducing the activity of memapsin 2. The method includes contacting a memapsin 2 protein with an effective amount of a β-secretase inhibitor compound of the present invention. In a related embodiment, the method includes contacting the memapsin 2 with a β-secretase inhibitor in the presence of memapsin 1. In an alternative related embodiment, the method includes contacting the memapsin 2 with an effective amount of a β-secretase inhibitor in the presence of cathepsin D. In yet another related embodiment, the method includes contacting the memapsin 2 with an effective amount of a β-secretase inhibitor in the presence of cathepsin D and memapsin 1.

In some embodiments, the activity of β-secretase may be determined by measuring the hydrolysis of a β-secretase site of a β-secretase substrate. Thus, the present invention also relates to a method of decreasing the hydrolysis of a β-secretase site of a β-secretase substrate by contacting a memapsin 2 protein with a β-secretase inhibitor compound of the present invention. In some embodiments, the hydrolysis of a β-secretase site is decreased relative the amount of hydrolysis in the absence of the inhibitor. In other embodiments, the hydrolysis is selectively reduced as compared to hydrolysis by memapsin 1 and/or cathepsin D. Thus, a method of selectively decreasing hydrolysis of a β-secretase site of a β-amyloid precursor protein relative to memapsin 1 and/or cathepsin D in a sample is provided. The method includes contacting a memapsin 2 protein with a β-secretase inhibitor compound of the present invention.

In another embodiment, the present invention relates to a method of decreasing the amount of β-amyloid protein in a sample by contacting the memapsin 2 with an effective amount of a β-secretase inhibitor compound of the present invention. The amount of β-amyloid protein in a sample is decreased relative the amount of β-amyloid protein in the sample in the absence of the inhibitor. Thus, the accumulation of β-amyloid protein is thereby decreased.

Memapsin 2 may be contacted in any suitable environment or any suitable sample. For example, memapsin 2 may be contacted in vitro, within a cell, or within a mammal. Typically, in vitro solutions are selected such that the components do not substantially interfere with the enzymatic activity of memapsin 2 (e.g. aqueous solutions). In some embodiments, the in vitro solution includes a biological sample, such as a mammalian sample. Exemplary mammalian samples include plasma or serum samples and tissue samples, such as a brain biopsy. Any appropriate cell or cellular sample may be selected in which to contact the memapsin 2 with the inhibitor. The cell may contain endogenous memapsin 2 or recombinant memapsin 2 as previously described (copending U.S. Application No. 20040121947, and International Application No. PCT/USO2/34324 (Publication No. WO 03/039454)). Exemplary cells include human embryonic kidney (HEK293) cells, HeLa cells, Chinese hamster ovary cells, or neuroblastoma line M17 cells Hela cells, 293 cells. In an exemplary embodiment, the compounds of the invention are administered to a mammal to inhibit the hydrolysis of a β-secretase site of a β-amyloid precursor protein (e.g. a mouse, rabbit or human).

VI. Methods of Treating Alzheimer's Disease

In another aspect of the present invention, the β-secretase inhibitor compounds of the invention can be employed in the treatment of diseases or conditions associated with β-secretase activity, hydrolysis of a β-secretase site of a β-amyloid precursor protein, and/or β-amyloid protein accumulation. Typically, a mammal is treated for the disease or condition. In an exemplary embodiment, the disease is Alzheimer's disease.

Thus, in some embodiments, the invention provides a method of treating Alzheimer's disease in a mammal comprising the step of administering to the mammal an effective amount of a β-secretase inhibitor of the invention. The mammals treated with the inhibitors may be human primates, nonhuman primates and/or non-human mammals (e.g., rodents, canines). In one embodiment, the mammal is administered a compound of the invention that reduces β3-secretase activity (inhibits memapsin 1 and memapsin 2 catalytic activity). In another embodiment, the mammal is administered a compound that selectively reduces memapsin 2 catalytic activity. In a related embodiment, the compound has minimal or no effect on reducing memapsin 1 catalytic activity. Therefore, the present invention also provides a method of treating Alzheimer's disease in a subject in need thereof, the method comprising administering to the subject a β-secretase inhibitor compound. In an exemplary embodiment, the β-secretase inhibitor compound is part of a pharmaceutical formulation, as described above.

The inhibitor compounds of the invention can be employed in the treatment of diseases or conditions associated with β-secretase activity, which can halt, reverse or diminish the progression of the disease or condition, in particular Alzheimer's disease. In addition to compounds that decrease memapsin 2 catalytic activity, compounds that selectively reduce memapsin 2 catalytic activity are useful to treat diseases or conditions or biological processes association with memapsin 2 catalytic activity rather than diseases or conditions or biological processes associated with both memapsin 2 catalytic activity and another peptide hydrolase (such as cathepsin D or memapsin 1).

For example, both memapsin 1 and memapsin 2 cleave amyloid precursor protein (APP) at a β-secretase site to form β-amyloid protein (also referred to herein as Aβ or β-amyloid protein). Thus, both memapsin 1 and memapsin 2 have β-secretase activity (Hussain, I., et al., *J. Biol. Chem.* 276: 23322-23328 (2001)). However, the β-secretase activity of memapsin 1 is significantly less than the β-secretase activity of memapsin 2 (Hussain, I., et al., *J. Biol. Chem.* 276:23322-23328 (2001)). Memapsin 2 is localized in the brain, and pancreas, and other tissues (Lin, X., et al., *Proc. Natl. Acad Sci. USA* 97:1456-1460 (2000)) and memapsin 1 is localized preferentially in placentae (Lin, X., et al., *Proc. Natl. Acad Sci. USA* 97:1456-1460 (2000)). Alzheimer's disease is associated with the accumulation of Aβ in the brain as a result of cleaving of APP by β-secretase (also referred to herein as memapsin 2, ASP2 and BACE). Thus, methods employing the compounds which selectively inhibit memapsin 2 catalytic activity relative to memapsin 1 catalytic activity may be important in the treatment of memapsin 2-related diseases, such as Alzheimer's disease. Selective inhibition of memapsin 2 catalytic activity makes the compounds of the invention suitable drug candidates for use in the treatment of Alzheimer's disease.

A. Methods of Administering Beta-Secretase Inhibitors to the CNS

The inhibitor compounds of the present invention may be administered to the CNS through either invasive or non-invasive methods. Non-invasive methods of administration include those methods that do not require the use of a mechanical or physical means to breach the integrity of the blood-brain barrier. Typically, non-invasive methods include the use of immunoliposomes, blood-brain barrier disruption (BBBD), or the olfactory pathway.

Immunoliposomes are liposomes with antibodies or antibody fragments that bind to receptors or transporters expressed on brain capillary endothelial cells attached to the surface of the liposome. An exemplary immunoliposome combines polymer (e.g. PEGylation) technology with that of chimeric peptide technology. For example, the β-secretase inhibitor may be packaged into a unilamellar lipid vesicle containing a $PEG^{2000}$ derivative that contains a reactive groups at one end, for attachment to a complimentary reactive group of an antibody or fragment thereof. Complimentary reactive groups are well known in the art and, include, fro example, amine and activated carboxylic acids, thiols and maleimides, and the like (Ambikanandan et al., *J. Pharm Pharmaceut Sci* 6(2):252-273 (2003); Huwyler et al., *Proc. Natl. Acad. Sci. USA,* 93:14164-14169 (1996); and Huwyler et al., *J Pharmcol Exp Ther.* 282:1541-1546 (1997); and U.S. Pat. No. 6,372,250).

Blood-brain barrier disruption is a temporal loss of the integrity of the tight junctions between endothelial cells that comprise the blood brain barrier. Typically, the compound is administered via systemic or intercarotid injection in conjuction with transient blood-brain barrier disruption (BBBD). Exemplary agents useful for inducing BBBD include solvents such as dimethyl sulfoxide (DMSO); ethanol (EtOH); metals (e.g. aluminum); X-irradiation; induction of pathological conditions (e.g. hypertension, hypercapnia, hypoxia, or ischemia); anti-neoplastic agents (e.g. VP-16, cisplatin, hydroxyurea, flurouracil and etoposide); or concurrent systemic administration of the convulsant drug metrazol and the anti-convulsant drug pentobarbital (Ambikanandan et al., *J. Pharm Pharmaceut Sci* 6(2):252-273 (2003)); vasoactive leukotrienes (Black et al., *J Neurosurg,* 81(5):745-751 (1994)); intracarotid infusion of bradykinin, histamine, or the synthetic bradykinin analog RMP-7 (Miller et al., *Science* 297: 1116-1118 (2002), Matsukado, et al., *Neurosurgery* 39:125-133 (1996), Abbott, et al., *Mol Med Today* 2:106-113 (1996), Emerich et al., *Clin Pharmacokinet* 40:105-123 (2001)); hyaluronidase (U.S. Pat App No. 20030215432, Kreil, et al. *Protein Sci.,* 4(9):1666-1669 (1995)); and intercarotid injection of inert hypertonic solutions such as mannitol, or arabinose (Neuwelt, E. A., et al., in Neuwelt E A (ed), *Implications of the Blood Brain Barrier and its Manipulation: Clinical Aspects.* Vol. 2, *Plenum Press*, New York, (1989), Neuwelt, et al., *J Nucl Med,* 35:1831-1841 (1994), Neuwelt et al., *Pediatr Neurosurg* 21:16-22 (1994), Kroll et al., *Neurosurg,* 42:1083-1099 (1998), Rapoport, *Cell Mol Neurobiol* 20:217-230 (2000), and Doran et al., *Neurosurg* 36:965-970, (1995)).

Olfactory pathway administration is the intranasal delivery of the compound to the olfactory nerves in the upper third of the nasal passages. After intranasal delivery, the compound is transported back along the sensory olfactory neurons to yield significant concentrations in the cerebral spinal fluid (CSF) and olfactory bulb (Thorne et al., *Brain Res,* 692(1-2):278-282 (1995); Thorne et al., *Clin Pharmacokinet* 40:907-946 (2001); Illum, *Drug Discov Today* 7:1184-1189 (2002); U.S. Pat. No. 6,180,603; U.S. Pat. No. 6,313,093; and U.S. Pat App No. 20030215398).

Invasive methods of administration are those methods that involve a physical breach of the blood-brain barrier typically through a mechanical or physical means to introduce the compound into the CSF, or directly into the parenchyma of the brain. Typically, invasive methods of administration may include injection or surgical implantation of the compound.

In injection methods, a needle is used to physically breach the BBB and deliver the compound directly into the CSF. Exemplary injection methods include intraventricular, intrathecal, or intralumbar routes of administration and may also involve infusion of the compound through a reservoir external to the body (Krewson et al., *Brain Res* 680:196-206 (1995); Harbaugh et al., *Neurosurg.* 23(6):693-698 (1988); Huang et al., *J Neurooncol* 45:9-17 (1999); Bobo et al., *Proc Natl Acad Sci USA* 91:2076-2082 (1994); Neuwalt et al., *Neurosurg.* 38(4):1129-1145 (1996)).

In surgical implantation methods, the compound is placed directly into the parenchyma of the brain. Exemplary surgical implantation methods may include incorporation of the compound into a polyanhydride wafer placed directly into the interstitium of the brain (Bremet al., *Sci Med* 3(4): 1-11 (1996); Brem et al., *J Control Release* 74:63-67 (2001)).

VII. Crystallized Complexes

In another aspect, the present invention provides a crystallized complex containing a memapsin 2 protein and a β-secretase inhibitor of the present invention. Memapsin 2 proteins useful in forming co-crystals with isostere compounds (e.g. memapsin 2 protein fragments, transmembrane proteins, etc.) have been previously discussed in detail (copending U.S. Application No. 20040121947, and International Application No. PCT/USO2/34324 (Publication No. WO 03/039454)). These memapsin 2 proteins are equally useful in forming crystallized complexes with β-secretase inhibitors of the present invention.

The crystallized complex may be formed employing techniques described in copending U.S. Application No. 20040121947, and International Application No. PCT/USO2/34324 (Publication No. WO 03/039454). Briefly, a nucleic acid construct encoding the protein is generated, is expressed in a host cell, such as a mammalian host cell (e.g., Hela cell, 293 cell) or a bacterial host cell (e.g., *E. coli*), is purified and is crystallized with a compound or compounds of the invention. The diffraction resolution limit of the crystallized protein can be determined, for example, by x-ray diffraction or neutron diffraction techniques.

In an exemplary embodiment, the crystallized protein may have an x-ray diffraction resolution limit not greater than about 4.0 Å. The crystallized protein may also have an x-ray diffraction resolution limit not greater than about 4.0 Å, about 3.5 Å, about 3.0 Å, about 2.5 Å, about 2.0 Å, about 1.5 Å, about 1.0 Å, or about 0.5 Å. In some embodiments, the crystallized protein may also have an x-ray diffraction resolution limit not greater than about 2 Å. The diffraction resolution limit of the crystallized protein can be determined employing standard x-ray diffraction techniques.

In an other exemplary embodiment, the β-secretase inhibitor of the crystallized complex is in association with said protein at an $S_3'$ binding pocket, an $S_4'$ binding pocket and/or an $S_4$ binding pocket. $S_3'$, $S_4'$, and $S_4$ binding pockets are discussed in detail in copending U.S. Application No. 20040121947, and International Application No. PCT/USO2/34324 (Publication No. WO 03/039454).

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the β-secretase inhibitors of the present invention are equally applicable to the methods of treating disease states and/or the pharmaceutical compositions described herein. All publications, patents, and patent applications cited herein are hereby incorporated by reference in their entirety for all purposes.

VIII. EXAMPLES

The following examples are for illustrative purposes only and are not intended to limit the scope of the invention.

Example 1

Preparation of Selected Beta-Secretase Inhibitor Compounds

Example 1.1

Synthesis of tert-butyl 3-hydroxy-4-(3-methoxybenzylamino)-1-phenylbutan-2-ylcarbamate Methylthiazole (1.0 g, 10.1 mnol) in THF at −78° C. was treated with n-BuLi (1.6 M, 7.56 mL) for 30 min, DMF (1.4 mL, 18.2 mmol) was added dropwise. The resulting reaction mixture was warmed to r.t. After the starting material was disappeared (by TLC), the reaction mixture was recooled to 0° C. and LAH (0.69 g, 18.5 mmol) was added. The mixture was warmed to r.t. and stirred for 1 h, the reaction was quenched with aqueous $NH_4Cl$, diluted with EtOAc. The organic solution was separated, extracted twice with EtOAc, dried with $Na_2SO_4$, and concentrated. The residue was purified with flash chromatography to give the corresponding alcohol as a light yellow oil. $^1$H-NMR: (300 MHz, $CDCl_3$), δ: 6.89 (s, 1H); 4.95 (s, 2H); 2.48 (s, 3H).

Methylthiazole methanol (0.57 g, 4.4 mmol) was treated with mesyl chloride (0.42 mL, 5.4 mmol) and triethyl ethylamine at 0° C. in dichloromethane. The resulting mixture was stirred for 20 minutes followed by quenching with aqueous $NH_4Cl$. Evaporation of the solvent from the organic layer and flash chromatography of the residue afforded the corresponding mesylate as an oil. The mesylate (0.25 g, 1.2 mmol) was then dissolved in DMF and sodium azide (0.62 g, 9.6 mmol) was added. The mixture was heated to reflux for 2 hours followed by cooling and washing with aqueous $NH_4Cl$. Evaporation of the solvent from the organic layer resulted in the corresponding azide. The azide (0.14 g, 0.91 mmol) was dissolved in ethyl acetate, $Pd(OH)_2$ (0.07 g) was added, and the suspension was stirred under a hydrogen atmosphere for 5 hours. The suspension was filtered through Celite. Evaporation of the solvent and flash chromatography of the residue afforded methylthiazole methylamine as a yellow oil. $^1$H-NMR: (300 MHz, $CDCl_3$), δ: 6.74 (m, 1H); 4.09 (m, 2H); 2.37 (s, 3H).

Mono-Methyl isophthalate (0.054 g, 0.30 mmol) was treated with EDCI (0.064 g, 0.33 mmol), HOBt (0.046 g, 0.34 mmol), DIPEA (0.07 mL, 0.4 mmol), and methylthiazole methylamine (0.046 g, 0.36 mmol). The resulting mixture was stirred at room temperature for 15 h under argon followed by quenching with water. The layers were separated and the aqueous layer was extracted with $CHCl_3$ (2×20 mL). The combined organic layers were dried with $Na_2SO_4$ and concentrated under reduced pressure. The resulting oil was dissolved in THF (5 mL) to which was added 3 mL of 1.0N $LiOH_{(aq)}$. The resulting mixture was stirred rapidly for 1.5 h. The volatiles were removed via rotary evaporation and the resulting aqueous solution was extracted with $CHCl_3$ (×3). The aqueous solution was then acidified to pH 1 with 1N $HCl_{(aq)}$ and extracted with $CHCl_3$ (×3). The combined organic layers were dried with $Na_2SO_4$ and concentrated under reduced pressure to provide the corresponding isophthalic acid. This product (0.042 g, 0.11 mmol) was dissolved in DMF and treated with NaH (0.015 g, 0.62 mmol) and MeI (0.04 mL, 0.64 mmol) and stirred overnight. The volatiles were removed via rotary evaporation and the resulting solution was diluted with 1N LiOH and extracted with $CHCl_3$ (×3). The aqueous solution was then acidified to pH 1 with 1N $HCl_{(aq)}$ and extracted with $CHCl_3$ (×3). The combined organic layers were dried with $Na_2SO_4$ and concentrated under reduced pressure to provide N-Methyl-N-(4-methylthiazol-2-ylmethyl)-isophthalamic acid. $^1$H-NMR: (300 MHz, $CDCl_3$), δ: 8.16 (m, 2H), 7.70 (m, 1H), 7.51 (m, 1H), 6.91 (s, 1H), 5.05 (s, 1.5H), 4.75 (s, 0.5H), 3.2-3.0 (m, 3H), 2.46 (s, 3H).

To a stirred solution of tert-Butyl (1-oxiranyl-2-phenylethyl)carbamate (0. 5 g, 1.9 mmol) in iPrOH was added 3-methoxybenzyl amine (0.28 mL, 2.1 mmol). The mixture was heated to reflux overnight followed by cooling and removal of the volatiles under reduced pressure. Flash chromatography of the residue resulted in the corresponding aminoalcohol as a solid. $^1$H NMR (300 MHz, $CDCl_3$): δ 7.35-7.17 (m, 6H), 6.93-6.78 (m, 3H), 4.65 (d, 1H), 3.90-3.7 (m, 5H), 3.51 (m, 1H), 3.15-2.65 (m, 6H), 1.34 (s, 9H).

To a stirred solution of tert-butyl 3-hydroxy-4-(3-methoxybenzylamino)-1-phenylbutan-2-ylcarbamate (0.032 g, 0.079 mmol) in dichloromethane was added TFA. The resulting mixture was stirred for 1 hour followed by removal of the volatiles under reduced pressure. This amine was dissolved in dichloromethane, treated with DIPEA, and added to a solution of N-Methyl-N-(4-methyl-thiazol-2-ylmethyl)-isophthalamic acid (0.021 g, 0.071 mmol), EDCI (0.015 g, 0.078 mmol), and HOBt (0.011 g, 0.081 mmol) in dichloromethane. The resulting mixture was stirred at room temperature overnight followed by washing with water, drying with $Na_2SO_4$, and removal of volatiles under reduced pressure. Flash chromatography of the residue provided the target molecule. $^1$H NMR (300 MHz, $CDCl_3$): δ 7.8-7.1 (m, 11H), 6.94-6.76 (m, 4H), 4.95 (s, 1.5H), 4.63 (s, 0.5H), 4.38 (m, 1H), 3.90-3.64 (m, 5H), 3.18-2.74 (m, 9H), 2.44 (s, 3H).

Example 1.2

Synthesis of N1-(3-hydroxy-4-(3-methoxybenzylamino)-1-phenylbutan-2-yl)-5-(N-methylmethylsulfonamido)-N3-(1-phenylethyl)isophthalamide Tert-butyl 3-hydroxy-4-(3-methoxybenzylamino)-1-phenylbutan-2-ylcarbamate was obtained in a single step by the ring opening reaction of tert-butyl-(1-oxiranyl-2-phenylethyl)-carbamate with 3-methoxybenzylamine under reflux condition in 2-propanol. Deprotection of Boc group by treatment of TFA in $CH_2Cl_2$ or methanolic HCl provided 3-amino-1-(3-methoxybenzylamino)-4-phenylbutan-2-ol, which was directly exposed to peptide coupling reaction with 3-(N-methylmethylsulfonamido)-5-(1-phenylethylcarbamoyl)benzoic acid in presence of N-ethyl-N'-(dimethylaminopropyl)carbodiimde hydrochloride (EDC), 1-hydroxybenzotriazole hydrate and diisopropylethylamine in a mixture of DMF and $CH_2Cl_2$ to afford N1-(3-hydroxy-4-(3-methoxybenzylamino)-1-phenylbutan-2-yl)-5-(N-methylmethylsulfonamido)-N3-(1-phenylethyl)isophthalamide.

Dimethyl 5-aminoisophthalate was mesylated by treating with methane sulfonylchloride and pyridine in dichloromethane. Then N-alkylation with methyl iodide under NaH/DMF condition gave dimethyl 5-(N-methylmethylsulfonamnido)isophthalate. Selective hydrolysis of dimethyl 5-(N-methylmethylsulfonamido)isophthalate, followed by EDC/HOBT/DIPEA mediated coupling with cc-methylbezylamine provided methyl 3-(N-methylmethylsulfonamido)-5-(1-phenylethylcarbamoyl)benzoate. Ester hydrolysis using aq. 1N NaOH in presence of THF/MeOH provided pure 3-(N-methylmethylsulfonamido)-5-(1-phenylethylcarbamoyl) benzoic acid as white solid.

To a stirred solution of tert-butyl-(1-oxiranyl-2-phenylethyl)-carbamate (131.6 mg, 0.5 mmol), 3-methoxy-benzylamine (0.25 mL, 2 mmol) in 3 mL of 2-propanol was heated to reflux for 12 h to afford tert-butyl 4-(3-methoxybenzy-lamino)-3-hydroxy-1-phenylbutan-2-ylcarba-mate. The solvent was evaporated and the crude product was purified by silica gel flash column chromatography (5-10% MeOH in CHCl$_3$) to give 4 in 77% yield (154 mg) as a colorless solid.

To a stirred solution of dimethyl 5-aminoisophthalate (2.09 g, 10 mmol) in dichloromethane (30 mL), pyridine (2.43 mL, 30 mmol) was added at room temperature. At 0° C., methanesulfonyl chloride (0.86 mL, 11 mmol) was added and the resulting mixture was stirred at room temperature for overnight. Then the reaction mixture was concentrated under reduced pressure and ethyl acetate (50 mL) was added. The resulting white precipitate was filtered and washed with hexanes to give the sulfonamide in 95% (2.715 g) yield as a white solid.

To a stirred suspension of NaH (0.24 g, 10 mmol, 60% in oil dispersion) in 10 mL of DMF was added the above sulfonamide (1.435 g, 5 mmol) followed by iodomethane (0.62 mL, 10 mmol) at room temperature. After 5 hours, the reaction was quenched by H$_2$O (25 mL). Then the reaction mixture was extracted with EtOAc, further washed with H$_2$O to remove excess of DMF, dried over anhydrous Na$_2$SO$_4$ and concentrated. The crude product thus obtained was washed with hexanes to give dimethyl 5-(N-methylmethylsulfonamido)isophthalate as a white solid in 91% (1.37 g) yield.

dimethyl 5-(N-methylmethylsulfonamido)isophthalate. (0.842 g, 2.8 numol) was dissolved in THF:MeOH (1:1) (8 mL) and H$_2$O (3 mL). Solid NaOH (0.112 g, 2.8 mmol) was added and stirred at room temperature for 18 hours. The reaction mixture was concentrated under reduced pressure. Saturated NaHCO$_3$ (10 mL) solution was added to the reaction mixture and extracted with toluene (to remove <10% unreacted starting material). The aqueous solution was acidified with dilute HCl (10%), extracted with EtOAc, and dried over anhydrous Na$_2$SO$_4$. The solvent was evaporated and dried under reduced pressure to give the 3-(methoxycarbo-nyl)-5-(N-methylmethan-5-ylsulfonamido)benzoic acid: as a white solid (75%, 0.598 g) which was used for further reaction without purification.

To a stirred solution of 3-(Methoxycarbonyl)-5-(N-meth-ylmethan-5-ylsulfonamido)benzoic acid (0.215 g, 0.75 mmol), EDC (0.172 g, 0.9 mmol), HOBt (0.122 g, 0.9 mmol) in DMF/CH$_2$Cl$_2$ (1:5 mL) at room temperature was added cc-methylbezylamine (0.1 mL, 0.75 mmol) followed by diisopropylethylamine (0.5 mL). The reaction mixture was stirred at room temperature for 16 h. Then water was added and the reaction mixture was extracted with EtOAc. The organic layers were dried over Na$_2$SO$_4$ and concentrated. The crude product thus obtained was purified by silica gel flash column chromatography (3% MeOH in CHCl$_3$) to provide the corresponding amide 10 (0.343 g) which was dissolved in THF:MeOH (1:1) (6 mL) and H$_2$O (2 mL). Solid NaOH (80 mg, 2.0 mmol) was added and stirred at room temperature for 6 hours. The reaction mixture was concentrated under reduced pressure. Saturated NaHCO$_3$ (10 mL) solution was added to the reaction mixture and extracted with toluene (to remove organic impurities). The aqueous reaction mixture was acidified with diluted HCl (10%), extracted with EtOAc, dried over anhydrous Na$_2$SO$_4$ The solvent was evaporated and dried under reduced pressure to give 3-(N-methyl-methan-5-ylsulfonamido)-5-((1-phenylethyl)carbomoyl) benzoic acid (0.198 g, 60%,) as a white solid.

To a solution of tert-butyl 3-hydroxy-4-(3-methoxybenzy-lamino)-1-phenylbutan-2-ylcarbamate (40 mg, 0.1 mmol) in CH$_2$Cl$_2$ (1 mL) was added TFA (0.5 mL) at room temperature. The reaction mixture was stirred at room temperature for 30 min. After this period, the mixture was concentrated under reduced pressure and dissolved in CH$_2$Cl$_2$ (1 mL) and stirred with diisopropylethylamine (0.2 mL). This mixture was added to a stirred solution of 3-(N-methylmethan-5-ylsul-fonamido)-5-((1-phenylethyl)carbomoyl)benzoic acid (37.6 mg, 0.1 mmol), EDC (24 mg, 0.125 mmol), HOBt (16.9 mg, 0.125 mmol) in DMF/CH$_2$Cl$_2$ (1:2 mL). The reaction mixture was stirred at room temperature for 19 h. Then water was added and the reaction mixture was extracted with EtOAc. The organic layers were dried over Na$_2$SO$_4$ and concentrated. The crude product N$^1$-(4-(3-methoxybenzylamino)-3-hy-droxy-1-phenylbutan-2-yl)-5-(N-meth-ylmethan-5-ylsul-fonamido)-N$^3$-(1-pheynylethyl)isophthalamide thus obtained was purified by silica gel flash column chromatography (10% MeOH in CHCl$_3$) to provide the target molecule (22.3 mg, 34%) as white solid. $^1$H NMR (500 MHz, CDCl$_3$): δ 1.58 (3H, d), 2.72 (3H, s), 2.74-2.83 (4H, m), 3.22 (3H, s), 3.69-3.83 (6H, m), 4.29-4.33 (1H, m), 5.26 (1H, q), 6.78 (1H, dd), 6.85-6.86 (2H, m), 7.13-7.37 (12H, m), 7.76 (1H, s), 7.89 (2H, s), 8.11 (1H, s).

Example 2

Syntheses of Selected Precursor Compounds

The precursor compounds synthesized below are useful in the methods of making compounds of the present invention provided herein. Using the guidance provided in the Exemplary Syntheses and Example 1 above, one skilled in the art will immediately recognize that the below precursor compounds may be elaborated by modifying the below syntheses using well known techniques to arrive at a wide variety of inhibitor compounds.

Example 2.1

1-(pyridin-3-yl)ethanarnine

To a solution of 3-acetylpridine (82.6 mmol) in methanol (200 mL) was added ammonium acetate (1.03 mol) in one portion at room temperature. After the mixture has been stirred for 20 min, sodium cyanoborohydride (57.8 mmol) was added to this mixture. After being stirring for one day, 6 M hydrochloric acid was added to the reaction mixture. The resulting solution was washed with diethyl ether, and then the aqueous phase was basified to PH=10 with potassium hydroxide. The liberated amine was extracted with chloroform, and the combined organic extracts were dried over anhydrous sodium sulfate. After removal of the solvent under reduced pressure, the crude amine was obtained as a colorless oil, which was further purified by distillation under reduced pressure. $^1$H NMR (300 MHz, CDCl$_3$), δ: 8.552 (d, 1H), 8.453 (dd, 1H), 7.678 (m, 1H), 7.206-7.261 (m, 1H), 4.148 (q, 1H), 1.378 (d, 3H).

The above procedure was also used to produce the following compounds:

1-(3-methoxyphenyl)ethanamine: $^1$H NMR (300 MHz, CDCl$_3$), δ: 7.274-7.219 (m, 1H), 6.941-6.905 (m, 2H), 6.796-6.757 (m, 1H), 4.090 (q, 1H), 3.811 (s, 3H), 1.382 (d, 3H).

1-(3-fluorophenyl)ethanamine: $^1$H NMR (300 MHz, CDCl$_3$), δ: 7.297-7.224 (m, 1H), 7.105-7.032 (m, 2H), 6.903-6.862 (m, 1H), 4.100 (q, 1H), 1.352 (d, 3H).

Example 2.2 tert-butyl(3-methylisoxazol-5-yl)methylcarbamate

A solution of 321 mg (2.27 mmol) of 2-(3-methylisoxazol-5-yl)acetic acid, 0.5 mL (2.32 mmol) of diphenylphosphorylazide (DPPA), and 0.35 mL (2.51 mmol) of triethylamine in 30 mL of distilled tert-butyl alcohol was refluxed for 13.5 hours. The solution was concentrated, and the crude residue was dissolved in EtOAc. The organic layer was washed with 1N HCl (3×10 mL) and saturated NaHCO$_3$ solution (3×10 mL). The organic layer was dried over sodium sulfate, filtered, concentrated. Purification by flash silica gel chromatography (28% EtOAc/hexanes) provided 50 mg (10% yield) of the protected amine as a pale yellow solid.

Example 2.3

(3-(methoxymethyl)phenyl)methanamnine 1,3-phenylenedimethanol was converted to (3-(methoxymethyl)phenyl)methanol using the procedure found in the following reference: Liu, Xuan; Zheng, Qi-Huang; Fei, Xiangshu; Wang, Ji-Quan; Ohannesian, David W.; Erickson, Leonard C.; Stone, K. Lee; Hutchins, Gary D.; *Bioorg. Med. Chem. Lett.* 2003, 13, 641-644. (3-(methoxymethyl)phenyl) methanol was converted to the target molecule following standard reactions including formation of the azide with DPPA and reduction.

Example 2.4 tert-butyl 3-acetaniidobenzylcarbamate

To a stirred solution of tert-butyl 3-aminobenzylcarbamate (Hah, Jung-Mi; Martasek, Pavel; Roman, Linda J.; Silverman, Richard B.; *J. Med. Chem.*; 2003, 46,1661-1669) (287 mg, 1.29 mmol) in CH$_2$Cl$_2$ (10 mL) at 0° C. was added Et$_3$N (0.27 mL, 2.0 mmol) and acetyl chloride (0.10 mL, 1.4 mmol) and the resulting solution was warmed up to room temperature slowly. After further stirring of 4 h, the reaction was quenched with saturated aqueous NH$_4$Cl. The layers were separated and the aqueous layer was extracted with CH$_2$Cl$_2$ (2×20 mL). The combined organic layer was washed with H$_2$O, brine, dried with Na$_2$SO$_4$ and concentrated under reduced pressure. The residue oil was purified by column chromatography (60% EtOAc in hexanes) to provide acetamide (123.1 mg, 36%).

Example 2.5 tert-butyl 3-(methylamino)benzylcarbamate

Tert-butyl 3-aminobenzylcarbamate was converted to the target molecule following standard reductive amination conditions using formaldehyde and sodium cyanoborohydride.

Example 2.6

5-fluoroisophthalic acid

To a gently refluxing solution of 1.9 g (15.3 mmol) of 5-fluoro-m-xylene in about 13.5 mL of pyridine and about 9.5 mL of water was added 13.8 g (87.3 mmol) of KMnO$_4$ in several portions. After the mixture was refluxed for about 7 h, sodium sulfite was added to quench the excess KMnO$_4$. The warm mixture was filtered, and 1N HCl was added to a pH=3. The filtrate was washed with EtOAc, saturated with NaCl, and extracted with the extract of a mixture of (80 mL CHCl$_3$: 10 mL MeOH: 10 mL H$_2$O) 3-4 times. The combined extracts were dried over sodium sulfate, filtered, and concentrated to give about 400 mg (14% yield) of diacid as a pale yellow solid.

Example 2.7 methyl 5-(benzyloxy)nicotinate

A mixture of 818 mg (5.34 mmol) of 5-hydroxynicotinic acid, 1.70 g (12.3 mmol) of K$_2$CO$_3$, and 1.0 mL (8.41 mmol) of benzyl bromide in 25 mL of DMF was heated at 60° C. under Ar for 16 h. The mixture was filtered through cotton, and the residue was dissolved in CHCl$_3$. The organic layer was washed with water (2×30 mL), brine (30 mL), dried over Na$_2$SO$_4$, filtered, and concentrated. Purification by flash silica gel chromatography provided 363 mg of the benzyl ether in 28% yield as an orange oil.

Example 2.8

(5-(benzyloxy)pyridin-3-yl)methanol

To a stirring solution of 363 mg (1.49 mmol) of methyl 5-(benzyloxy)nicotinate in 10 mL of THF at 0° C. was added 141 mg (3.71 mmol) of LiAlH$_4$. The ice bath was removed, and after 55 min., 20.5 mg of LiAlH$_4$ was added. After 40 min., the reaction was quenched by adding successively 160 μL of H$_2$O, 160 μL of 15% aqueous NaOH, and 480 μL of brine. Purification by flash silica gel chromatography (2 mL MeOH/100 mL CHCl$_3$) provided 250 mg of alcohol (yellow oil) in 78% yield.

Example 2.9

3-(azidomethyl)-5-(benzyloxy)pyridine

To a stirring solution of 250 mg (1.17 mmol) of (5-(benzyloxy)pyridin-3-yl)methanol in 8 mL of toluene was added 310 μL (1.44 mmol) of DPPA. The mixture was cooled to 0° C. and 210 μL (1.44 mmol) of 1,8-diazabicyclo[5.4.0]-undec-7-ene] (DBU) was added. The ice bath was removed, and stirring was continued with wanning to room temperature. After about 20 h, the solution was diluted with EtOAc, and 1N HCl was added to a pH between 7 and 8. The organic layer was washed with water (2×15 mL) and brine (15 mL) and dried over Na$_2$SO$_4$. After filtration and concentration, the crude product was purified by flash silica gel chromatography (56-60% EtOAc/hexanes) to give 181 mg (65% yield) of the azide as a colorless oil.

Example 2.10

(5-(benzyloxy)pyridin-3-yl)methanamine

To a stirring solution of 181 mg of 3-(azidomethyl)-5-(benzyloxy)pyridine in 6 mL of THF at 0° C. was added 80.6 mg (2.12 mmol) of LiAlH$_4$. The ice bath was removed and stirring was continued with warming to r.t. After 30 min. the reaction was quenched by adding successively 160 μL of H$_2$O, 160 μL of 15% aqueous NaOH, and 480 μL of brine. The mixture was filtered through Celite and concentrated. The crude product was used for the next reaction without further purification.

Example 2.11

(5-methylpyridin-3-yl)methanol

To stirring solution of 233 mg (1.70 mmol) of 5-methylnicotinic acid (synthesized following the general procedure for 5-fluoro-isophthalic acid) in 30 mL of THF at 0° C. was added 181 mg (4.76 mmol) of LiAlH$_4$. After 25 min., the reaction was quenched by adding successively 180 μL of H$_2$O, 180 μL of 15% aqueous NaOH, and 540 μL of brine. The mixture was filtered through Celite and concentrated to give 87 mg of crude alcohol which was used for the next reaction without further purification.

Example 2.12

(5-methylpyridin-3-yl)methanamine

The precursor compound was synthesized from the corresponding alcohol following the general procedure as described above for the nicotinic acid benzyl ether derivative.

Example 2.13

(5-methoxypyridin-3-yl)methanamine

The precursor compound was synthesized from the hydroxynicotinate following the general procedure as described above for the nicotinic acid benzyl ether derivative.

Example 2.14

4-fluoro-isophthalic acid

The precursor compound was synthesized from 2-fluoro-5-methylbenzoic acid following the procedure described for 5-fluoro-isophthalic acid.

Example 2.15

4-methyl-isophthalic acid

The precursor compound was synthesized from 2,5-dimethylbenzoic acid following the procedure described for 5-fluoro-isophthalic acid.

Example 2.16 tert-butyl 1-(4-methylthiazol-2-yl)ethylcarbamate

A mixture of BOC-alanine-thioamide (1.39 g, 6.81 mmoles), chloroacetone (0.65 mL, 8.18 mmoles) and calcium carbonate (1.0 g, 10.22 mmoles) were refluxed in ethanol (25 mL) for 4 h. The reaction was cooled to room temperature and quenched with 2OmL of saturated aq. NaHCO$_3$ solution. Ethanol was evaporated under reduced pressure and extracted with ethyl acetate (2×30 mL). The combined organic layers was dried over Na$_2$SO$_4$ and concentrated. The residue was chromatographed on silica gel (20% ethyl acetate/80% hexane) to yield 48% of the desired product.

Example 2.17 tert-butyl 4-((1H-benzo[d]imidazol-2-yl)methylamino)-3-hydroxy-1-phenylbutan-2-ylcarbamate A solution of tert-butyl 1-(oxiran-2-yl)-2-phenylethylcarbamate (185 mg, 0.7 mmoles), (1H-benzo[d]imidazol-2-yl)methanamine dihydrochloride salt (232 mg, 1.01 mmoles) and Hunig's base (0.49 mL, 2.8 mmoles) in iPrOH (6 mL) was refluxed for 12 h. The reaction was cooled to room temperature, solvent evaporated under reduced pressure and chromatographed (5% MeOH/95% CHCl$_3$) to obtain 175 mg (61%) of the desired product.

Example 2.18

N1-(3-hydroxy-4-((1-isobutylpiperidin-4-yl)methylanino)-1-phenylbutan-2-yl)-5-(N-methylmethylsulfonamido)-N3-(1-phenylethyl)isophthalamde dihydrochloride 1-(oxiran-2-yl)-N-((oxoboryl)methylene)-2-phenylethanamine (1.61 mmol, 424 mg) and benzyl 4-(aminomethyl)piperidine-1-carboxylate (1.94 nmnol, 480 mg) in isopropanol (20 mL) was heated at 80° C. for overnight. Evaporated the solvent and purified by flash chromatography to get benzyl 4-((2-hydroxy-3-((oxoboryl)methyleneamino)-4-phenylbutylamino)methyl)piperidine-1-carboxylate (880 mg). $^1$H NMR (300 MHz, CDCl$_3$), δ: 7.363-7.174 (m, 10H), 5.118 (s, 2H), 4.767 (br, 1H), 4.187 (m, 2H), 3.786 (m, 1H), 3.458 (m, 1H), 3.023-2.671 (m, 6H), 2.484 (d, J=6.6 Hz, 2H), 1.733 (m, 2H), 1.600 (m, 1H), 1.347 (s, 9H), 1.135 (m, 2H).

benzyl 4-((2-hydroxy-3-((oxoboryl)methyleneamino)-4-phenylbutylamino)methyl) piperidine-1-carboxylate (1.04 mmol, 530 mg) in dichloromethane was added TFA (7.6 mL) and stirred for 40 min at room temperature. The solvent was evaporated. The residue was dissolved in dichloromethane, added diisopropylethylamine (4.14 imol, 0.72 mL) and tirred for 30 min. Then acid (1.04 mmol, 390 mg) and BOP reagent (1.14 mmol, 504 mg) were added to the flask. The resulting mixture was stirred for overnight and the solvent was evaporated. The residue was dissolved into chloroform, washed with water and brine. Finally the yellow residue was purified by flash chromatography to get the product (320 mg). $^1$H NMR (300 MHz, CDCl$_3$), δ: 7.992 (s, 1H), 7.865 (m, 1H), 7.715 (s, 1H), 7.383-7.106 (m, 15H), 5.241 (m, 1H), 5.093 (s, 2H), 4.291 (m, 1H), 4.146 (m , 2H), 3.843 (m, 1H), 3.232 (s, 3H), 3.065 (m, 1H), 2.962-2.626(m, 7H), 2.779 (s, 3H), 1.714 (m, 3H), 1.579 (d, J=6.9 Hz, 3H), 1.120 (m, 2H).

The above compound (318 mg, 0.413 mmol) was dissolved into anhydrous methanol, followed by triethylamine (0.2 mL, excess) and t-butyl dicarbonate (108.3 mg 0.5 mmol). The resulting mixture was stirred for overnight. The solvent was then evaporated and the residue was dissolved methanol, hydrogenated with Pd(OH)$_2$ at 1 atm. After the filtration the solvent was evaporated and the residue was purified by flash chromatography to get the product (215 mg). $^1$H NMR (300 MHz, CDCl$_3$+CD$_3$OD), δ: 8.227-7.802 (m, 3H), 7.365-7.059 (m, 10H), 5.214 (m, 1H), 4.308 (br, 1H), 3.885 (m, 1H), 3.467 (m, 1H), 3.293-2.879 (m, 6H), 3.211 (s, 3H), 2.805-2.668 (m, 3H), 2.782 (s, 3H), 1.717 (m, 3H), 1.562 (d, J=6.9 Hz, 3H), 1.386 (s, 9H), 1.174 (m, 2H).

The amine (50 mg, 0.068 mmol) dissolved in methanol/acetonitrile(5/1) was added isobutyraldehyde (0.1 mL, excess) and stirred for 15 min, NaBCNH$_3$ (12.8 mg, 0.2 mmol)was then added and continued to stir for 30 min. 5 drops of acetic acid was added to the reaction mixture and continued to stir for overnight. The solvent was evaporated. The white solid was then dissolved in chloroform, washed with aqueous NaHCO$_3$, brine, filtrated and dried with anhydrous Na$_2$SO$_4$. The resulting residue was purified by flash chromatography to get the product (40 mg). $^1$H NMR (300 MHz, CDCl$_3$), δ: 8.014 (s, 1H), 7.902 (s, 1H), 7.798 (s, 1H), 7.372-7.087 (m, 10H), 5.261 (m, 1H), 4.340 (m, 1H), 3.870 (m, 1H), 3.420-3.207(m, 3H), 3.282 (s, 3H), 3.103-2.890 (m, 4H), 2.841 (s, 3H), 2.610 (m, 3H), 2.132 (m, 2H), 1.935-1.774 (m, 3H), 1.569 (d, J=6.9 Hz, 3H), 1.422 (s, 9H), 1.302 (m, 2H), 0.979 (d, J=6.6 Hz, 3H), The above compound was dissolved in 4 M HCl dioxane solution and stirred for 1 hr. Evaporated the solvent and recovered N1-(3-hydroxy-4-((1-isobutylpiperidin-4-yl)methylamino)-1-phenylbutan-2-yl)-5-(N-methylmethylsulfonamido)-N3-(1-phenylethyl)isophthalamide dihydrochloride as a white solid.

Example 2.19 methyl 3-(isopropyl((4-methylthiazol-2-yl)methyl)carbamoyl)benzoate

Et$_3$N (1 drop, catalytic) was added to a stirred suspension of mono-Methyl isophthalate (0.294 mmol, 1.0 eq) in 2 ml SOCl$_2$ under Ar. The mixture was heated to reflux at 90° C. for 2 h. The reaction was cooled to RT, and the solvent was removed in vacuo. The residue was placed under an Ar atmosphere and dissolved in 2 ml anh CH$_2$Cl$_2$. The resulting solution was treated with a solution of N-((4-methylthiazol-2-yl)methyl)propan-2-amine (0.294 mmol, 1.0 eq made from reductive amination of 4-methylthiazole-2-carbaldehyde with isopropylamine) dissolved in 1 ml anh CH$_2$Cl$_2$ under Ar. After stirring at RT for 30 min, the reaction was treated with ET$_3$N (0.294 mmol, 1 eq). After stirring at RT for 30 min, the reaction is poured into a seperatory funnel, washed with sat. NaHCO$_3$ (×1), water (×3), brine (×1), and dried over Na$_2$SO$_4$. The inorganics were removed via filtration, and the solvent was removed in vacuo yielding the crude product in 93% yield.

Example 2.20 tert-butyl(3-methylisoxazol-5-yl)methylcarbamate

A solution of 321 mg (2.27 mmol) of 2-(3-methylisoxazol-5-yl)acetic acid, 0.5 mL (2.32 mmol) of diphenylphosphorylazide (DPPA), and 0.35 mL (2.51 mmol) of triethylamine in 30 mL of distilled tert-butyl alcohol was refluxed for 13.5 hours. The solution was concentrated, and the crude residue was dissolved in EtOAc. The organic layer was washed with 1N HCl (3×10 mL) and saturated NaHCO$_3$ solution (3×10 mL). The organic layer was dried over sodium sulfate, filtered, concentrated. Purification by flash silica gel chromatography (28% EtOAc/hexanes) provided 50 mg (10% yield) of tert-butyl (3-methylisoxazol-5-yl)methylcarbamate as a pale yellow solid.

Example 2.21

5-fluoroisophthalic acid

To a gently refluxing solution of 1.9 g (15.3 mmol) of 5-fluoro-m-xylene in about 13.5 mL of pyridine and about 9.5 mL of water was added 13.8 g (87.3 mmol) of KMnO$_4$ in several portions. After the mixture was refluxed for about 7 h, sodium sulfite was added to quench the excess KMnO$_4$. The warm mixture was filtered, and 1N HCl was added to a pH=3. The filtrate was washed with EtOAc, saturated with NaCl, and extracted with the extract of a mixture of (80 mL CHCl$_3$: 10 mL MeOH: 10 mL H$_2$O) 3-4 times. The combined extracts were dried over sodium sulfate, filtered, and concentrated to give about 400 mg (14% yield) of 5-fluoroisophthalic acid as a pale yellow solid.

Example 2.22

(5-(benzyloxy)pyridin-3-yl)methananiine

A mixture of 818 mg (5.34 mmol) of 5-hydroxynicotinic acid, 1.70 g (12.3 mmol) of K$_2$CO$_3$, and 1.0 mL (8.41 mmol) of benzyl bromide in 25 mL of DMF was heated at 60° C. under Ar for 16 h. The mixture was filtered through cotton, and the residue was dissolved in CHCl$_3$. The organic layer was washed with water (2×30 mL), brine (30 mL), dried over Na$_2$SO$_4$, filtered, and concentrated. Purification by flash silica gel chromatography provided 363 mg of methyl 5-(benzyloxy)nicotinate in 28% yield as an orange oil.

To a stirring solution of 363 mg (1.49 mmol) of methyl 5-(benzyloxy)nicotinate in 10 mL of THF at 0° C. was added 141 mg (3.71 mmol) of LiAlH$_4$. The ice bath was removed, and after 55 min., 20.5 mg of LiAlH$_4$ was added. After 40 min., the reaction was quenched by adding successively 160 µL of H$_2$O, 160 µL of 15% aqueous NaOH, and 480 µL of brine. Purification by flash silica gel chromatography (2 mL MeOH/100 mL CHCl$_3$) provided 250 mg of (5-(benzyloxy)pyridin-3-yl)methanol (yellow oil) in 78% yield.

To a stirring solution of (5-(benzyloxy)pyridin-3-yl)methanol 250 mg (1.17 mmol) in 8 mL of toluene was added 310 µL (1.44 mmol) of DPPA. The mixture was cooled to 0° C. and 210 µL (1.44 mmol) of 1,8-diazabicyclo[5.4.0]-undec-7-ene] (DBU) was added. The ice bath was removed, and stirring was continued with warming to room temperature. After about 20 h, the solution was diluted with EtOAc, and 1N HCl was added to a pH between 7 and 8. The organic layer was washed with water (2×15 mL) and brine (15 mL) and dried over Na$_2$SO$_4$. After filtration and concentration, the crude product was purified by flash silica gel chromatography (56-60% EtOAc/hexanes) to give 181 mg (65% yield) of 3-(azidomethyl)-5-(benzyloxy)pyridine as a colorless oil.

To a stirring solution of 181 mg of 3-(azidomethyl)-5-(benzyloxy)pyridine in 6 mL of THF at 0° C. was added 80.6 mg (2.12 mmol) of LiAlH$_4$. The ice bath was removed and stirring was continued with warming to r.t. After 30 min. the reaction was quenched by adding successively 160 µL of H$_2$O, 160 µL of 15% aqueous NaOH, and 480 µL of brine. The mixture was filtered through Celite and concentrated to yield crude (5-(benzyloxy)pyridin-3-yl)methanamine. The crude product was used without further purification.

Example 2.23

(5-methylpyridin-3-yl)methanol

To stirring solution of 233 mg (1.70 mmol) of 5-methylnicotinic acid (synthesized following the general procedure for 5-fluoro-isophthalic acid) in 30 mL of THF at 0° C. was added 181 mg (4.76 mmol) of LiAlH$_4$. After 25 min., the reaction was quenched by adding successively 180 µL of H$_2$O, 180 µL of 15% aqueous NaOH, and 540 µL of brine. The mixture was filtered through Celite and concentrated to give 87 mg of crude (5-methylpyridin-3-yl)methanol which was used for the next reaction without further purification.

Example 2.24

1,5-bis(chloromethyl)-2,4-dimethylbenzene

A solution of 3 mL (24.4 mmol) of m-xylene, 2.6 g (28.5 mmol) of 1,3,5-trioxane, and 2.6 g (19.0 mmol) of ZnCl$_2$ in 100 mL of 1.0 M HCl in acetic acid was heated at 90° C. After 23 h, water, NaHCO$_3$, and EtOAc were added. The layers were separated, and the organic layer was washed with water (3-4×) and brine, dried over Na$_2$SO$_4$, filtered, and concentrated. Purification by flash silica gel chromatography (hexanes to 3% EtOAc/hexanes) provided 2.45 g of 1,5-bis(chloromethyl)-2,4-dimethylbenzene as a colorless solid in 49% yield.

Example 2.25

(5-ethylpyridin-3-yl)methanol

To a stirring mixture of 1.08 g (12.0 mmol) of CuCN in 20 mL of THF at −78° C. was added 24 mL of EtMgBr (1M in THF). After stirring for 20 min., 387 mg of 5-(5-bromopyridin-3-yl)methanol in 20 mL of THF was added and stirring was continued at −78° C. for 3 h. The reaction mixture was then allowed to warm to r.t., stirred for about 17 h, and ammonium hydroxide was added. The mixture was stirred until the color became a royal blue and was allowed to stand overnight. It was extracted with $CHCl_3$ (2×), dried over $Na_2SO_4$, filtered, and concentrated. Purification by flash silica gel chromatography (2.5% MeOH/$CHCl_3$) provided 37 mg of (5-ethylpyridin-3-yl)methanol as a yellow oil in 13% yield.

Example 2.26 methyl 5-fluoronicotinate

To a stirring solution of 243 mg (1.6 mmol) of methyl 5-aminonicotinate in 5 mL of HF-pyridine at 0° C. was added 119 mg (1.72 mmol) of $NaNO_2$. The mixture was stirred at 0° C. for 30 min. and at 50° C. for 1 h. The reaction was quenched by ice and sat. $NaHCO_3$ solution. The aqueous layer was extracted with $CHCl_3$, dried over $Na_2SO_4$, filtered, and concentrated. Purification by flash silica gel chromatography (1% MeOH/$CHCl_3$) provided 139 mg of methyl 5-fluoronicotinate as a yellow solid in 56% yield.

Example 2.27

2-chloro-1-(2,4-difluoro-5-methylphenyl)ethanone

To a stirring solution of 2,4-difluorotoluene was added 6.3 g (47.3 mmol) of $AlCl_3$, and 3.4 mL (42.6 mmol) of chloroacetyl chloride at 0° C. After the mixture was stirred for 10 min. at 0° C. and then at 45° C. for 30 min. The mixture was allowed to cool to r.t., about 16 mL of conc. HCl, 25 mL of water, and 100 mL of EtOAc were added. The organic layer was separated and washed with brine and sat. $NaHCO_3$ (2×), and dried over $Na_2SO_4$. The solution was filtered and concentrated to give 9.0 g of 2-chloro-1-(2,4-difluoro-5-methylphenyl)ethanone as a colorless solid that was used without further purification.

Example 2.28 methyl 5-isopropoxynicotinate

A solution of 677 mg (3.28 mmol) of dicyclohexylcarbodiimide (DCC), 0.3 mL (3.92 mmol) of isopropanol, and 7.7 mg (0.078 mmol) of CuCl was heated at 60° C. After 13 h, 460 mg (3.0 mmol) of 5-hydroxynicotinic acid methyl ester and 10 mL of benzene were added and heated at 105° C. for 24.5 h. The mixture was diluted with chloroform and filtered. The organic layer was washed with 15 mL of sat. $NaHCO_3$, water, and brine and dried over $Na_2SO_4$. Purification by flash silica gel chromatography (100% $CHCl_3$) provided 274 mg of methyl 5-isopropoxynicotinate as a yellow oil in 47% yield.

Example 2.29

1-(3-methylisoxazol-5-yl)ethanol

To a stirring solution of 5.2 mL (84.9 mmol) of acetaldehyde oxime, 6.7 mL (85.5 mmol) of 3-butyn-2-ol, and 1.2 mL (8.6 mmol) of $Et_3N$ in 20 mL of $CH_2Cl_2$ at 0° C. was added 275 mL of NaOCl over a period of 2 h 45 min. The ice bath was removed and stirring was continued at r.t. for 18 h. Chloroform was added, and the layers were separated. The organic layer was extracted with $CHCl_3$ (2×) and with the extract of a mixture of (80 mL $CHCl_3$: 10 mL $H_2O$: 10 mL MeOH) (2×). The combined extracts were dried over $Na_2SO_4$, filtered and concentrated. Purification by flash silica gel chromatography (2% MeOH/$CHCl_3$) provided 2.2 g of 1-(3-methylisoxazol-5-yl)ethanol as an orange-yellow oil in 20% yield.

Example 2.30

(4-methoxypyridin-2-yl)methanamine

To a stirring mixture of 1.2 g (9.67 mmol) of 4-methoxypyridine-N-oxide in 18 mL of $CH_2Cl_2$ at r.t. was added 1.6 mL (12.0 mmol) of TMSCN. After 5 min. 0.9 mL (9.8 mmol) of dimethylcarbamoyl chloride. The solution was stirred at r.t. for 13 h and $CHCl_3$ and 20 mL of 10% $K_2CO_3$ was added. The aqueous layer was extracted with $CHCl_3$ 3 times, and the combined extracts were dried over $Na_2SO_4$, filtered, and concentrated. Purification by flash silica gel chromatography (38-44% EtOAc/hexanes) provided 949 mg of 4-methoxypicolinonitrile as a colorless solid in 73% yield.

To a stirring solution of 949 mg of 4-methoxypicolinonitrile in 15 mL of THF at 0° C. was added about 0.6 g of $LiAlH_4$. The reaction became very exothermic. The mixture was allowed to warm to r.t. and after 40 min., the following were added in succession: 0.4 mL of $H_2O$, 0.4 mL of 15% NaOH (aq.), and 1.2 mL of brine. The mixture was stirred at r.t. for 75 min. and then filtered through Celite and concentrated to give 377 mg of (4-methoxypyridin-2-yl)methanamine which was used for the next reaction without further purification.

Example 2.31 methyl 5-(dimethylamino)nicotinate

To a stirring solution of 283 mg (1.86 mmol) of methyl 5-aminonicotinate in 19 mL of $CH_3CN$ and 19 mL of 37% formaldehyde in $H_2O$ was added 353 mg (5.62 mmol) of $NaCNBH_3$, and 50 drops of acetic acid. The solution was stirred at r.t. for 18.5 h and 40 mL of EtOAc and 40 mL of sat. $NaHCO_3$ solution was added. The layers were separated, and the organic layer was washed with 25 mL of sat. $NaHCO_3$ and 25 mL of brine, dried over $Na_2SO_4$, filtered, and concentrated. Purification by flash silica gel chromatography (0.5% MeOH/$CHCl_3$) resulted in 124 mg of methyl 5-(dimethylamino)nicotinate as a yellow oil in 37% yield.

Example 2.32 methyl 3-(2,2-dimethyl-1-((4-methylthiazol-2-yl)methyl)hydrazinecarbonyl)benzoate To the acid 3-(methoxycarbonyl)benzoic acid (253 mg, 1.40 mmol) in $CH_2Cl_2$ at rt, EDCI (312 mg, 1.64 mmol) and HOBT (189 mg, 1.40 mmol) were added and stirred at rt for 20 min. To that mixture, N,N-dimethyl hydrazine was added followed by DIPEA (404 mg, 14.0 mmol). Reaction mixture was stirred at rt for 16 h. Then reaction mixture was diluted with chloroform, washed with water, brine and dried. Crude residue was purified by column chromatography to yield 60% of methyl 3-(2,2-dimethylhydrazinecarbonyl)benzoate.

To the sodium hydride (16 mg, 0.68 mmol) in THF (3 ml) at 0° C., methyl 3-(2,2-dimethylhydrazinecarbonyl)benzoate (100 mg, 0.45 nmol) was added. After 10 min, 4-methyl-2-bromo methyl thiazole (103 mg, 0.54 mmol) was added and reaction mixture stirred at 3-4° C. overnight. Reaction mixture was quenched with MeOH and diluted with ethylacetate. Organic layer was washed with water, brine and dried. Crude residue was purified by column chromatography to yield 70% of methyl 3-(2,2-dimethyl-1-((4-methylthiazol-2-yl)methyl)hydrazinecarbonyl)benzoate.

Example 2.33 tert-butyl 3-(fluoromethyl)benzylcarbamate

To the DAST (600 mg, 3.72 mmol) in $CH_2Cl_2$ (30 ml) at −78° C., alcohol tert-butyl 3-(hydroxymethyl)benzylcarbamate (630 mg, 2.65 mmol) was slowly added. Reaction mixture was stirred for 1h at −78° C. and a further 1h at rt. Then reaction mixture was quenched with methanol, followed by sodium bicarbonate. After solvent removal, crude residue was column chromatographed to yield 60% of tert-butyl 3-(fluoromethyl)benzylcarbamate.

Example 2.34

(3-isopropylphenyl)methanamine

To the methyl triphenylphosphoniumbromide (4.3 grn, 12 mmol) in THF at 0° C., n-BuLi (1.6M, 7.5 ml, 12 mmol) was added and stirred for 30 min. Then 3-acetylbenzonitrile in THF was slowly added and the reaction mixture was stirred at 0° C. for further 3 h. Then reaction mixture was quenched with aqeous ammonium chloride and diluted with ethyl acetate. Organic layer was washed with water, brine and dried. Crude residue after column purification yielded 3-(prop-1-en-2-yl)benzonitrile in 86% yield.

To 3-(prop-1-en-2-yl)benzonitrile (1.2 gm, 8.3 mmol) in ethyl acetate (30 ml) 10% Pd/C (120 mg) was added and stirred under hydrogen atmosphere for 16 h. Then the reaction mixture was filtered and solvent evaporated to obtain 3-isopropylbenzonitrile in quantitative yield.

To 3-isopropylbenzonitrile in THF at 0° C., LAH (1.74 gin, 45.7 mmol) was slowly added and the reaction mixture was allowed to come to rt and stirred at rt for 48 h. Then reaction mixture was cooled to 0° C., diluted with ether and quenched with saturated sodium sulfate solution. The residue was filtered and solvent was evaporated to obtain the amine (3-isopropylphenyl)methanamine in quantitative yield.

Example 2.35

3-(3-methoxy-4-methylphenyl)propan-1-amine

To methyl 3-methoxy-4-methylbenzoate (3 gm, 16.6 mmol) in THF (60 ml) at 0° C., LAH (3 gm, 66.6 mmol) was slowly added. After stirring at 0° C. for further 30 min, reaction mixture was worked up as described above to obtain the alcohol (3-methoxy-4-methylphenyl)methanol in quantitative yield.

Dess-Martin periodinane (3 gm, 7.07 mmol) was added to (3-methoxy-4-methylphenyl)methanol (1 gm, 6.57 mmol) in $CH_2Cl_2$ (35 ml) at 0° C. After stirring at 0° C. for 0.5 h, some of the $CH_2Cl_2$ was removed, reaction mixture was diluted with ether, washed with sodium bicarbonate solution, sodium thiosulfate solution and water. Organic layer was dried and evaporated to obtain 3-methoxy-4-methylbenzaldehyde in quantitative yield.

Wittig reaction of 3-methoxy-4-methylbenzaldehyde with cyanomethyl triphenylphosphorane gave 3-(3-methoxy-4-methylphenyl)acrylonitrile in 77% yield which was further transformed to 3-(3-methoxy-4-methylphenyl)propan-1-amine using the above described procedures.

Example 2.36 tert-butyl 4-(3-ethynylbenzylamino)-3-hydroxy-1-phenylbutan-2-ylcarbamate

To tert-butyl 3-bromobenzylcarbamate (220 mg, 1 mmol) in triethylamine (3 ml), trimethylsilyl acetylene (147 mg, 1.5 mmol) was added followed by cuprous iodide (8 mg, 0.04 mmol). After stirring for 5 min, dichloro bis (triphenylphosphine) palladium (II) (35 mg, 0.05 mmol) was added and the reaction mixture was heated at 90° C. for 18 h. Then the reaction mixture was filtered, diluted with ethyl acetate and washed with water. Organic layer was dried, evaporated and the crude residue was purified by column chromatography to obtain tert-butyl 3-((trimethylsilyl)ethynyl)benzylcarbamate in 67% yield.

Boc-group was removed from tert-butyl 3-((trimethylsilyl)ethynyl)benzylcarbamate and the resulting amine was used to open the epoxide, tert-butyl(S)-1-((S)-oxiran-2-yl)-2-phenethylcarbamate to obtain tert-butyl 3-hydroxy-1-phenyl-4-(3-((trimethylsilyl)ethynyl)benzylamino)butan-2-ylcarbamate in 60% yield.

To tert-butyl 3-hydroxy-1-phenyl-4-(3-((trimethylsilyl)ethynyl)benzylamino)butan-2-ylcarbamate in a mixture of THF (2 ml) and MeOH (2 ml), 1M $K_2CO_3$ (0.25 ml) was added and the reaction mixture was stirred at rt for 18 h. Then solvent was removed, crude residue was redissolved in ethyl acetate, washed with water, brine and dried. Column purification yielded tert-butyl 4-(3-ethynylbenzylamino)-3-hydroxy-1-phenylbutan-2-ylcarbamate in 85% yield.

Example 2.37 diethyl 5-(methylsulfonylmethyl)isophthalate

To diethyl 5-(hydroxymethyl)isophthalate (2.52 gm, 10 mmol) in THF (30 ml), triphenyl phosphine (5.25 gm, 20 mmol) was added followed by thiolacetic acid (1.52 gm, 20 mmol) and Diisopropylazodicarboxylate (4.04 gm, 20 mmol) at 0° C. Reaction mixture was then allowed to come to rt and stirred for 2 h. Then solvent was removed, crude was redissolved in minimum amount of $CH_2Cl_2$. With stirring, hexane was added and the resultant solids were discarded. Filtrtae was evaporated to dryness and the residue was column purified to yield diethyl 5-(acetylthiomethyl)isophthalate in 95% yield.

To diethyl 5-(acetylthiomethyl)isophthalate (1.02 gm, 3.30 mmol) in THF (10 ml) and MeOH (10 ml), sodium methoxide (207 mg, 3.63 mmol) was added and stirred at rt for 2 h. Then methyl iodide (0.69 ml, 10.9 mmol) were added in two portions. After stirring at rt for 4 h, THF and MeOH were removed in vacuum and the reaction mixture was diluted with ethyl acetate. Organic layer was washed with water, brine and dried. Column purification of the crude residue yielded diethyl 5-(methylthiomethyl)isophthalate in 55% yield.

m-CPBA (990 mg, 4.43 mmol) was added to the S-methyl compound (500 mg, 1.77 mmol) in $CH_2Cl_2$ (10 ml) at 0° C. After stirring for 15 min, reaction mixture was allowed to come to rt and stirred for 20 h. Then reaction mixture was diluted with $CH_2Cl_2$ and washed with sodium bicarbonate solution. Crude residue was column purified to obtain diethyl 5-(methylsulfonylmethyl)isophthalate in 73% yield.

Example 3

Inhibition of Memapsin 2 Catalytic Activity

Potency of compounds were determined by measurement of their inhibition of memapsin 2 catalytic activity toward a fluorescent substrate. Kinetic inhibition experiments were performed using the procedure as described in Ermolieff, et al. (*Biochemistry* 39:12450-12456 (2000), the teachings of which are incorporated hereby in their entirety). Briefly, assays were performed at pH 4, 37° C., by pre-incubation of memapsin 2 enzyme with compound for 20 minutes. Activity measure was initiated by addition of a fluorogenic substrate FS-2 (Bachem Americas, Torrance, Calif.). Fluorescent signal increase over time was measured as a rate of hydrolysis of the peptide substrate. Inhibition of hydrolytic rate was expressed relative to uninhibited controls and fit to a model for tight-binding inhibitors (J. Bieth, in "Proteinase Inhibitors," Bayer Symposium V, 463-469, 1974). The results are presented in Table 1 below.

TABLE 1

| Structure | M2K | CDK | M1K | Cell |
|---|---|---|---|---|
| N1-(3-hydroxy-4-(3-methoxybenzylamino)-1-phenylbutan-2-yl)-5-(N-methylmethylsulfonamido)-N3-(1-phenylethyl)isophthalamide | +++ | +++ | +++ | +++ |
| N1-(1-(2,5-dimethyloxazol-4-yl)ethyl)-N3-(3-hydroxy-4-(3-methoxybenzylamino)-1-phenylbutan-2-yl)-5-(N-methylmethylsulfonamido)isophthalamide | + | + | + | ++ |
| N1-((2,5-dimethyloxazol-4-yl)methyl)-N3-(3-hydroxy-4-(3-methoxybenzylamino)-1-phenylbutan-2-yl)-5-(N-methylmethylsulfonamido)isophthalamide | + | + | + | ++ |
| N1-(3-hydroxy-4-(3-(methoxymethyl)benzylamino)-1-phenylbutan-2-yl)-5-(N-methylmethylsulfonamido)-N3-(1-phenylethyl)isophthalamide | + | + | + | + |
| methyl 3-((2-hydroxy-3-(3-(N-methylmethylsulfonamido)-5-(1-phenylethylcarbamoyl)benzamido)-4-phenylbutylamino)methyl)benzoate | + | + | + | +++ |
| N1-(3-hydroxy-1-phenyl-4-(pyridin-2-ylmethylamino)butan-2-yl)-5-(N-methylmethylsulfonamido)-N3-(1-phenylethyl)isophthalamide | +++ | + | + | +++ |
| N1-(3-hydroxy-1-phenyl-4-(pyridin-3-ylmethylamino)butan-2-yl)-5-(N-methylmethylsulfonamido)-N3-(1-phenylethyl)isophthalamide | +++ | + | ++ | +++ |
| N1-(4-(3-(benzyloxymethyl)benzylamino)-3-hydroxy-1-phenylbutan-2-yl)-5-(N-methylmethylsulfonamido)-N3-(1-phenylethyl)isophthalamide | ++ | + | +++ | |
| N1-(3-hydroxy-4-(3-(isopropylcarbamoyl)benzylamino)-1-phenylbutan-2-yl)-5-(N-methylmethylsulfonamido)-N3-(1-phenylethyl)isophthalamide | + | | + | + |
| N1-(2-hydroxy-1-(3-methoxybenzylamino)-5-methylhexan-3-yl)-5-(N-methylmethylsulfonamido)-N3-(1-phenylethyl)isophthalamide | + | | + | |
| N1-(2-hydroxy-1-(3-methoxybenzylamino)-5-methylhexan-3-yl)-5-(N-methylmethylsulfonamido)-N3-(1-phenylethyl)isophthalamide | + | | + | |
| N1-(3-hydroxy-4-(4-methoxyphenylsulfonamido)-1-phenylbutan-2-yl)-5-(N-methylmethylsulfonamido)-N3-(1-phenylethyl)isophthalamide | + | | | ++ |
| N1-(3-hydroxy-4-(3-methoxybenzylamino)-1-phenylbutan-2-yl)-5-(N-methylmethylsulfonamido)-N3-(1-(pyridin-3-yl)ethyl)isophthalamide | +++ | + | + | +++ |
| N1-(3-hydroxy-4-(3-methoxybenzylamino)-1-(2-methoxyphenyl)butan-2-yl)-5-(N-methylmethylsulfonamido)-N3-(1-phenylethyl)isophthalamide | ++ | | | + |
| N1-(3-hydroxy-4-(3-methoxybenzylamino)-1-phenylbutan-2-yl)-N3-methyl-N3-((4-methylthiazol-2-yl)methyl)isophthalamide | +++ | +++ | + | +++ |
| N1-(4-(2-(1H-indol-3-yl)ethylamino)-3-hydroxy-1-phenylbutan-2-yl)-5-(N-methylmethylsulfonamido)-N3-(1-phenylethyl)isophthalamide | | | | |
| N1-(3-hydroxy-1-phenyl-4-((tetrahydrofuran-2-yl)methylamino)butan-2-yl)-5-(N-methylmethylsulfonamido)-N3-(1-phenylethyl)isophthalamide | | | | |
| N1-(3-hydroxy-4-(3-methoxybenzylamino)-1-phenylbutan-2-yl)-5-(N-methylmethylsulfonamido)-N3-(1-(pyridin-3-yl)ethyl)isophthalamide | +++ | | | +++ |
| N1-(1-(hexahydrofuro[2,3-b]furan-3-yl)ethyl)-N3-(3- | + | | | |

TABLE 1-continued

| Structure | M2K | CDK | M1K | Cell |
|---|---|---|---|---|
| hydroxy-4-(3-methoxybenzylamino)-1-phenylbutan-2-yl)-5-(N-methylmethylsulfonamido)isophthalamide | | | | |
| N1-((hexahydrofuro[2,3-b]furan-3-yl)methyl)-N3-(3-hydroxy-4-(3-methoxybenzylamino)-1-phenylbutan-2-yl)-5-(N-methylmethylsulfonamido)isophthalamide | ++ | ++ | + | + |
| N1-(3-hydroxy-4-(3-methoxybenzylamino)-1-phenylbutan-2-yl)-N3-(3-methoxybenzyl)-5-(N-methylmethylsulfonamido)isophthalamide | +++ | +++ | + | ++ |
| N1-(3-hydroxy-1-phenyl-4-(1-phenylethylamino)butan-2-yl)-5-(N-methylmethylsulfonamido)-N3-(1-phenylethyl)isophthalamide | +++ | +++ | ++ | +++ |
| N1-(3-hydroxy-4-(3-methoxybenzylamino)-1-phenylbutan-2-yl)-N3-methyl-N3-((3-methylisoxazol-5-yl)methyl)isophthalamide | + | +++ | + | + |
| N1-(3-hydroxy-1-phenyl-4-(1-phenylethylamino)butan-2-yl)-N3-methyl-N3-((4-methylthiazol-2-yl)methyl)isophthalamide | + | + | +++ | ++ |
| N1-(3-hydroxy-1-phenyl-4-(pyridin-2-ylmethylamino)butan-2-yl)-5-(N-methylmethylsulfonamido)-N3-(1-phenylethyl)isophthalamide | +++ | | | +++ |
| N1-(1-(4-fluorophenyl)ethyl)-N3-(3-hydroxy-4-(3-methoxybenzylamino)-1-phenylbutan-2-yl)-5-(N-methylmethylsulfonamido)isophthalamide | +++ | +++ | +++ | +++ |
| N1-(3-hydroxy-4-(methyl((4-methylthiazol-2-yl)methyl)amino)-1-phenylbutan-2-yl)-5-(N-methylmethylsulfonamido)-N3-(1-phenylethyl)isophthalamide | + | + | + | |
| N1-(3-hydroxy-1-phenyl-4-(1-phenylpropylamino)butan-2-yl)-N3-methyl-N3-((4-methylthiazol-2-yl)methyl)isophthalamide | + | +++ | + | ++ |
| N1-(3-hydroxy-1-phenyl-4-(pyridin-4-ylmethylamino)butan-2-yl)-5-(N-methylmethylsulfonamido)-N3-(1-phenylethyl)isophthalamide | +++ | + | ++ | +++ |
| N1-(3-hydroxy-1-phenyl-4-(1-phenylpropylamino)butan-2-yl)-5-(N-methylmethylsulfonamido)-N3-(1-phenylethyl)isophthalamide | +++ | +++ | +++ | +++ |
| N1-(3-hydroxy-4-((4-methylthiazol-2-yl)methylamino)-1-phenylbutan-2-yl)-5-(N-methylmethylsulfonamido)-N3-(1-phenylethyl)isophthalamide | +++ | ++ | + | +++ |
| N1-(3-hydroxy-4-(3-methoxybenzylamino)-1-phenylbutan-2-yl)-5-(N-methylmethylsulfonamido)-N3-(1-(4-methylthiazol-2-yl)ethyl)isophthalamide | +++ | + | ++ | +++ |
| N-(3-hydroxy-4-(3-methoxybenzylamino)-1-phenylbutan-2-yl)-3-(2-methyl-2-phenylhydrazinecarbonyl)-5-(N-methylmethylsulfonamido)benzamide | +++ | +++ | + | +++ |
| N1-(3-hydroxy-4-(3-methoxybenzylamino)-1-phenylbutan-2-yl)-5-(N-methylmethylsulfonamido)-N3-(1-phenylpropyl)isophthalamide | +++ | +++ | +++ | +++ |
| N1-(4-(1-(4-fluorophenyl)ethylamino)-3-hydroxy-1-phenylbutan-2-yl)-5-(N-methylmethylsulfonamido)-N3-(1-phenylethyl)isophthalamide | +++ | +++ | +++ | +++ |
| N1-(3-hydroxy-4-(2-methoxybenzylamino)-1-phenylbutan-2-yl)-5-(N-methylmethylsulfonamido)-N3-(1-phenylethyl)isophthalamide | +++ | +++ | ++ | +++ |
| N1-(4-(benzylamino)-3-hydroxy-1-phenylbutan-2-yl)-5-(N-methylmethylsulfonamido)-N3-(1-phenylethyl)isophthalamide | +++ | +++ | +++ | +++ |
| N1-(4-(1-(4-fluorophenyl)ethylamino)-3-hydroxy-1-phenylbutan-2-yl)-5-(N-methylmethylsulfonamido)-N3-(1-phenylethyl)isophthalamide | +++ | +++ | +++ | +++ |
| N1-benzyl-N3-(3-hydroxy-4-(3-methoxybenzylamino)-1-phenylbutan-2-yl)-5-(N-methylmethylsulfonamido)isophthalamide | +++ | +++ | + | +++ |
| N1-(3-hydroxy-4-(3-methoxybenzylamino)-1-phenylbutan-2-yl)-5-nitro-N3-(1-phenylethyl)isophthalamide | ++ | +++ | +++ | +++ |
| N1-(3-hydroxy-1-phenyl-4-(1-phenylethylamino)butan-2-yl)-5-(N-methylmethylsulfonamido)-N3-(1-phenylethyl)isophthalamide | +++ | +++ | | +++ |
| N1-(4-(3-(dimethylamino)benzylamino)-3-hydroxy-1-phenylbutan-2-yl)-5-(N-methylmethylsulfonamido)-N3-(1-phenylethyl)isophthalamide | +++ | + | | +++ |
| N1-(3-hydroxy-1-phenyl-4-(pyrazin-2- | +++ | + | | +++ |

TABLE 1-continued

| Structure | M2K | CDK | M1K | Cell |
|---|---|---|---|---|
| ylmethylamino)butan-2-yl)-5-(N-methylmethylsulfonamido)-N3-(1-phenylethyl)isophthalamide | | | | |
| N1-(4-((1H-benzo[d]imidazol-2-yl)methylamino)-3-hydroxy-1-phenylbutan-2-yl)-5-(N-methylmethylsulfonamido)-N3-(1-phenylethyl)isophthalamide | +++ | +++ | | ++ |
| N1-(3-hydroxy-1-phenyl-4-(1-(pyridin-3-yl)ethylamino)butan-2-yl)-5-(N-methylmethylsulfonamido)-N3-(1-phenylethyl)isophthalamide | +++ | | | +++ |
| N1-(3-hydroxy-4-((3-methylisoxazol-5-yl)methylamino)-1-phenylbutan-2-yl)-5-(N-methylmethylsulfonamido)-N3-(1-phenylethyl)isophthalamide | +++ | +++ | | +++ |
| N1-(3-hydroxy-4-(3-methoxybenzylamino)-1-phenylbutan-2-yl)-N3-((5-hydroxypyridin-3-yl)methyl)-5-(N-methylmethylsulfonamido)isophthalamide | + | + | | +++ |
| N1-(4-(3-fluorobenzylamino)-3-hydroxy-1-phenylbutan-2-yl)-5-(N-methylmethylsulfonamido)-N3-(1-phenylethyl)isophthalamide | +++ | ++ | + | +++ |
| N1-(3-hydroxy-1-phenyl-4-(1-(pyridin-3-yl)ethylamino)butan-2-yl)-5-(N-methylmethylsulfonamido)-N3-(1-phenylethyl)isophthalamide | +++ | +++ | | +++ |
| 4- or 6-fluoro-N3-(3-hydroxy-4-(3-methoxybenzylamino)-1-phenylbutan-2-yl)-N1-(1-phenylethyl)isophthalamide | + | +++ | + | ++ |
| 4- or 6-fluoro-N3-(3-hydroxy-4-(3-methoxybenzylamino)-1-phenylbutan-2-yl)-N1-(1-phenylethyl)isophthalamide | + | +++ | ++ | +++ |
| N1-(3-hydroxy-4-((6-methylpyridin-2-yl)methylamino)-1-phenylbutan-2-yl)-5-(N-methylmethylsulfonamido)-N3-(1-phenylethyl)isophthalamide | ++ | + | ++ | +++ |
| N1-(3-hydroxy-4-(3-methoxybenzylamino)-1-phenylbutan-2-yl)-N3-(1-(pyridin-3-yl)ethyl)isophthalamide | + | + | + | + |
| N1-(3-hydroxy-4-(2-methyl-2-phenylhydrazinyl)-1-phenylbutan-2-yl)-5-(N-methylmethylsulfonamido)-N3-(1-phenylethyl)isophthalamide | ++ | + | + | + |
| N1-(4-((2,5-dimethyloxazol-4-yl)methylamino)-3-hydroxy-1-phenylbutan-2-yl)-5-(N-methylmethylsulfonamido)-N3-(1-phenylethyl)isophthalamide | | + | + | ++ |
| N1-(3-hydroxy-4-(1-(3-methoxyphenyl)ethylamino)-1-phenylbutan-2-yl)-N3-(1-(3-methoxyphenyl)ethyl)-5-(N-methylmethylsulfonamido)isophthalamide | +++ | +++ | +++ | +++ |
| N1-(3-hydroxy-4-(1-(3-methoxyphenyl)ethylamino)-1-phenylbutan-2-yl)-N3-(1-(3-methoxyphenyl)ethyl)-5-(N-methylmethylsulfonamido)isophthalamide | +++ | +++ | +++ | +++ |
| N1-(3-hydroxy-4-(1-(3-methoxyphenyl)ethylamino)-1-phenylbutan-2-yl)-N3-(1-(3-methoxyphenyl)ethyl)-5-(N-methylmethylsulfonamido)isophthalamide | +++ | +++ | ++ | +++ |
| N1-(3-hydroxy-4-(1-(3-methoxyphenyl)ethylamino)-1-phenylbutan-2-yl)-N3-(1-(3-methoxyphenyl)ethyl)-5-(N-methylmethylsulfonamido)isophthalamide | +++ | +++ | +++ | +++ |
| N1-(3-hydroxy-4-((5-methylpyridin-3-yl)methylamino)-1-phenylbutan-2-yl)-5-(N-methylmethylsulfonamido)-N3-(1-phenylethyl)isophthalamide | +++ | +++ | ++ | +++ |
| N1-(3-hydroxy-4-(2-hydroxybenzylamino)-1-phenylbutan-2-yl)-5-(N-methylmethylsulfonamido)-N3-(1-phenylethyl)isophthalamide | +++ | +++ | +++ | +++ |
| N1-(3-hydroxy-4-(1-(3-methoxyphenyl)ethylamino)-1-phenylbutan-2-yl)-5-(N-methylmethylsulfonamido)-N3-(1-phenylethyl)isophthalamide | +++ | +++ | +++ | +++ |
| N1-(3-hydroxy-4-(1-(3-methoxyphenyl)ethylamino)-1-phenylbutan-2-yl)-5-(N-methylmethylsulfonamido)-N3-(1-phenylethyl)isophthalamide | +++ | +++ | +++ | +++ |
| N1-(3-hydroxy-4-(1-(4-methylthiazol-2-yl)ethylamino)-1-phenylbutan-2-yl)-5-(N-methylmethylsulfonamido)-N3-(1-phenylethyl)isophthalamide | +++ | +++ | +++ | +++ |
| N1-(3-hydroxy-4-(3-methoxybenzylamino)-1-phenylbutan-2-yl)-N3-(1-(3-methoxyphenyl)ethyl)-5-(N-methylmethylsulfonamido)isophthalamide | +++ | ++ | + | +++ |
| N1-(3-hydroxy-4-(3-methoxybenzylamino)-1-phenylbutan-2-yl)-N3-(1-(3-methoxyphenyl)ethyl)-5-(N-methylmethylsulfonamido)isophthalamide | +++ | +++ | + | |

TABLE 1-continued

| Structure | M2K | CDK | M1K | Cell |
|---|---|---|---|---|
| N1-(3-hydroxy-4-(1-(4-methylthiazol-2-yl)ethylamino)-1-phenylbutan-2-yl)-5-(N-methylmethylsulfonamido)-N3-(1-phenylethyl)isophthalamide | +++ | ++ | + | +++ |
| N1-(3-hydroxy-4-(3-methoxybenzylamino)-1-phenylbutan-2-yl)-5-(N-methylmethylsulfonamido)-N3-(1-(4-methylthiazol-2-yl)ethyl)isophthalamide | ++ | +++ | + | +++ |
| N1-(4-(3-fluorobenzylamino)-3-hydroxy-1-phenylbutan-2-yl)-N3-methyl-N3-((4-methylthiazol-2-yl)methyl)isophthalamide | + | +++ | + | +++ |
| N1-(3-hydroxy-4-(3-methylbenzylamino)-1-phenylbutan-2-yl)-5-(N-methylmethylsulfonamido)-N3-(1-phenylethyl)isophthalamide | +++ | +++ | ++ | +++ |
| N3-(3-hydroxy-4-(3-methoxybenzylamino)-1-phenylbutan-2-yl)-4- or 6-methyl-N1-(1-phenylethyl)isophthalamide | ++ | +++ | ++ | ++ |
| N3-(3-hydroxy-4-(3-methoxybenzylamino)-1-phenylbutan-2-yl)-4- or 6-methyl-N1-(1-phenylethyl)isophthalamide | + | +++ | + | ++ |
| N1-(4-(3-acetamidobenzylamino)-3-hydroxy-1-phenylbutan-2-yl)-5-(N-methylmethylsulfonamido)-N3-(1-phenylethyl)isophthalamide | +++ | ++ | +++ | +++ |
| N1-(4-(3,5-difluorobenzylamino)-3-hydroxy-1-phenylbutan-2-yl)-5-(N-methylmethylsulfonamido)-N3-(1-phenylethyl)isophthalamide | +++ | +++ | + | +++ |
| N1-(3-hydroxy-4-(3-methylbenzylamino)-1-phenylbutan-2-yl)-N3-methyl-N3-((4-methylthiazol-2-yl)methyl)isophthalamide | + | +++ | + | +++ |
| 5-(N-ethylmethylsulfonamido)-N1-(3-hydroxy-4-(3-methoxybenzylamino)-1-phenylbutan-2-yl)-N3-(1-phenylethyl)isophthalamide | ++ | +++ | +++ | +++ |
| N1-cyclopropyl-N3-(3-hydroxy-4-(3-methoxybenzylamino)-1-phenylbutan-2-yl)-N1-((4-methylthiazol-2-yl)methyl)isophthalamide | +++ | +++ | + | |
| N1-(3-hydroxy-4-((5-methoxypyridin-3-yl)methylamino)-1-phenylbutan-2-yl)-5-(N-methylmethylsulfonamido)-N3-(1-phenylethyl)isophthalamide | +++ | +++ | ++ | |
| 4- or 6-fluoro-N3-(3-hydroxy-4-(3-methoxybenzylamino)-1-phenylbutan-2-yl)-N1-methyl-N1-((4-methylthiazol-2-yl)methyl)isophthalamide | +++ | +++ | +++ | |
| N1-(3-hydroxy-4-((6-methylpyridin-2-yl)methylamino)-1-phenylbutan-2-yl)-N3-methyl-N3-((4-methylthiazol-2-yl)methyl)isophthalamide | | | | |
| 4- or 6-fluoro-N3-(3-hydroxy-4-(3-methoxybenzylamino)-1-phenylbutan-2-yl)-N1-methyl-N1-((4-methylthiazol-2-yl)methyl)isophthalamide | | | | |
| N1-(4-(1-(3-fluorophenyl)ethylamino)-3-hydroxy-1-phenylbutan-2-yl)-5-(N-methylmethylsulfonamido)-N3-(1-phenylethyl)isophthalamide | +++ | +++ | | |
| N1-(4-(1-(3-fluorophenyl)ethylamino)-3-hydroxy-1-phenylbutan-2-yl)-5-(N-methylmethylsulfonamido)-N3-(1-phenylethyl)isophthalamide | +++ | +++ | | |
| N1-(3-hydroxy-4-(3-(methoxymethyl)benzylamino)-1-phenylbutan-2-yl)-5-(N-methylmethylsulfonamido)-N3-(1-phenylethyl)isophthalamide | +++ | +++ | | |
| N1-(3-hydroxy-4-(3-methoxyphenethylamino)-1-phenylbutan-2-yl)-5-(N-methylmethylsulfonamido)-N3-(1-phenylethyl)isophthalamide | +++ | +++ | | |
| N1-(3-hydroxy-4-(3-(methylamino)benzylamino)-1-phenylbutan-2-yl)-5-(N-methylmethylsulfonamido)-N3-(1-phenylethyl)isophthalamide | | +++ | | |
| N1-(1-(3-fluorophenyl)ethyl)-N3-(3-hydroxy-4-(3-methoxybenzylamino)-1-phenylbutan-2-yl)-5-(N-methylmethylsulfonamido)isophthalamide | +++ | ++ | | |
| N1-(1-(3-fluorophenyl)ethyl)-N3-(3-hydroxy-4-(3-methoxybenzylamino)-1-phenylbutan-2-yl)-5-(N-methylmethylsulfonamido)isophthalamide | +++ | +++ | | |
| N1-(3-hydroxy-4-(4-hydroxy-3-methoxybenzylamino)-1-phenylbutan-2-yl)-5-(N-methylmethylsulfonamido)-N3-(1-phenylethyl)isophthalamide | | | | |
| N1-(3-hydroxy-1-phenyl-4-(quinolin-3-ylmethylamino)butan-2-yl)-5-(N-methylmethylsulfonamido)-N3-(1-phenylethyl)isophthalamide | +++ | +++ | +++ | |
| N1-(4-(3-ethylbenzylamino)-3-hydroxy-1-phenylbutan-2-yl)-5-(N-methylmethylsulfonamido)-N3-(1-phenylethyl)isophthalamide | +++ | +++ | +++ | |

TABLE 1-continued

| Structure | M2K | CDK | M1K | Cell |
|---|---|---|---|---|
| N1-(3-hydroxy-4-((3-methylisoxazol-5-yl)methylamino)-1-phenylbutan-2-yl)-N3-methyl-N3-((4-methylthiazol-2-yl)methyl)isophthalamide | +++ | + | | + |
| N1-(3-hydroxy-4-(3-isopropylbenzylamino)-1-phenylbutan-2-yl)-5-(N-methylmethylsulfonamido)-N3-(1-phenylethyl)isophthalamide | +++ | +++ | | +++ |
| N1-(3-hydroxy-4-((5-methylfuran-2-yl)methylamino)-1-phenylbutan-2-yl)-5-(N-methylmethylsulfonamido)-N3-(1-phenylethyl)isophthalamide | +++ | +++ | | |
| 2-fluoro-N1-(3-hydroxy-4-(3-methoxybenzylamino)-1-phenylbutan-2-yl)-N3-methyl-N3-((4-methylthiazol-2-yl)methyl)isophthalamide | + | +++ | | ++ |
| N1-(4-(2-fluoro-3-methoxybenzylamino)-3-hydroxy-1-phenylbutan-2-yl)-5-(N-methylmethylsulfonamido)-N3-(1-phenylethyl)isophthalamide | +++ | +++ | | +++ |
| N1-(3-hydroxy-4-(N-(3-methoxybenzyl)-4-(2-morpholinoethylamino)-4-oxobutanamido)-1-phenylbutan-2-yl)-5-(N-methylmethylsulfonamido)-N3-(1-phenylethyl)isophthalamide | | | | ++ |
| methyl 5-((2-hydroxy-3-(3-(N-methylmethylsulfonamido)-5-(1-phenylethylcarbamoyl)benzamido)-4-phenylbutyl)(3-methoxybenzyl)amino)-5-oxopentanoate | | | | +++ |
| N1-(3-hydroxy-4-(3-isopropylbenzylamino)-1-phenylbutan-2-yl)-N3-methyl-N3-((4-methylthiazol-2-yl)methyl)isophthalamide | +++ | +++ | | +++ |
| N1-(4-(3-(fluoromethyl)benzylamino)-3-hydroxy-1-phenylbutan-2-yl)-5-(N-methylmethylsulfonamido)-N3-(1-phenylethyl)isophthalamide | +++ | +++ | | +++ |
| N1-(3-hydroxy-4-(3-methoxybenzylamino)-1-phenylbutan-2-yl)-N3-methyl-5-(N-methylmethylsulfonamido)-N3-((4-methylthiazol-2-yl)methyl)isophthalamide | +++ | +++ | | +++ |
| tert-butyl 2-hydroxy-3-(3-(N-methylmethylsulfonamido)-5-(1-phenylethylcarbamoyl)benzamido)-4-phenylbutyl(3-methoxybenzyl)carbamate | | | | |
| N1-(4-(3-((dimethylamino)methyl)benzylamino)-3-hydroxy-1-phenylbutan-2-yl)-5-(N-methylmethylsulfonamido)-N3-(1-phenylethyl)isophthalamide | +++ | + | | +++ |
| N1-(3-hydroxy-4-(3-methoxybenzylamino)-1-phenylbutan-2-yl)-4,6-dimethyl-N3-(1-phenylethyl)isophthalamide | ++ | +++ | | +++ |
| N1-(4-((5-ethylpyridin-3-yl)methylamino)-3-hydroxy-1-phenylbutan-2-yl)-5-(N-methylmethylsulfonamido)-N3-(1-phenylethyl)isophthalamide | +++ | +++ | | +++ |
| N1-(4-(3-(fluoromethyl)benzylamino)-3-hydroxy-1-phenylbutan-2-yl)-N3-methyl-N3-((4-methylthiazol-2-yl)methyl)isophthalamide | +++ | +++ | | +++ |
| N1-(4-(3-ethylbenzylamino)-3-hydroxy-1-phenylbutan-2-yl)-N3-methyl-N3-((4-methylthiazol-2-yl)methyl)isophthalamide | +++ | +++ | | +++ |
| N1-(4-(2-fluoro-6-methoxybenzylamino)-3-hydroxy-1-phenylbutan-2-yl)-5-(N-methylmethylsulfonamido)-N3-(1-phenylethyl)isophthalamide | +++ | +++ | | +++ |
| N1-(4-(2-(dimethylamino)-N-(3-methoxybenzyl)acetamido)-3-hydroxy-1-phenylbutan-2-yl)-5-(N-methylmethylsulfonamido)-N3-(1-phenylethyl)isophthalamide | | | | ++ |
| 3-(2,2-dimethyl-1-((4-methylthiazol-2-yl)methyl)hydrazinecarbonyl)-N-(3-hydroxy-4-(3-methoxybenzylamino)-1-phenylbutan-2-yl)benzamide | + | + | | + |
| N1-(3-hydroxy-4-(N-(3-methoxybenzyl)-4-oxo-4-(pyridin-3-ylmethylamino)butanamido)-1-phenylbutan-2-yl)-5-(N-methylmethylsulfonamido)-N3-(1-phenylethyl)isophthalamide | | | | + |
| N1-(3-hydroxy-4-(N-(3-methoxybenzyl)-5-oxo-5-(pyridin-3-ylmethylamino)pentanamido)-1-phenylbutan-2-yl)-5-(N-methylmethylsulfonamido)-N3-(1-phenylethyl)isophthalamide | | | | + |
| N1-(3-hydroxy-4-(2-morpholinoethylamino)-1-phenylbutan-2-yl)-5-(N-methylmethylsulfonamido)-N3-(1-phenylethyl)isophthalamide | ++ | + | | ++ |
| N1-(4-(1-cyclohexylethylamino)-3-hydroxy-1-phenylbutan-2-yl)-5-(N-methylmethylsulfonamido)-N3-(1-phenylethyl)isophthalamide | +++ | +++ | | +++ |

TABLE 1-continued

| Structure | M2K | CDK | M1K | Cell |
|---|---|---|---|---|
| N1-(3-hydroxy-4-(3-methoxyphenethylamino)-1-phenylbutan-2-yl)-N3-methyl-N3-((4-methylthiazol-2-yl)methyl)isophthalamide | + | ++ | | + |
| N1-(3-hydroxy-4-(N-(3-methoxybenzyl)-5-(2-morpholinoethylamino)-5-oxopentanamido)-1-phenylbutan-2-yl)-5-(N-methylmethylsulfonamido)-N3-(1-phenylethyl)isophthalamide | | | | + |
| N1-(3-hydroxy-4-(N-(3-methoxybenzyl)-5-(4-methylpiperazin-1-ylamino)-5-oxopentanamido)-1-phenylbutan-2-yl)-5-(N-methylmethylsulfonamido)-N3-(1-phenylethyl)isophthalamide | | | | + |
| N1-(1-cyclohexylethyl)-N3-(3-hydroxy-4-(3-methoxybenzylamino)-1-phenylbutan-2-yl)-5-(N-methylmethylsulfonamido)isophthalamide | +++ | +++ | | +++ |
| N1-(3-hydroxy-4-((5-methylisoxazol-3-yl)methylamino)-1-phenylbutan-2-yl)-5-(N-methylmethylsulfonamido)-N3-(1-phenylethyl)isophthalamide | +++ | +++ | | +++ |
| N1-(3-hydroxy-4-((5-methylisoxazol-3-yl)methylamino)-1-phenylbutan-2-yl)-N3-methyl-N3-((4-methylthiazol-2-yl)methyl)isophthalamide | ++ | ++ | | ++ |
| N1-(4-((5-fluoropyridin-3-yl)methylamino)-3-hydroxy-1-phenylbutan-2-yl)-5-(N-methylmethylsulfonamido)-N3-(1-phenylethyl)isophthalamide | +++ | +++ | | +++ |
| benzyl 4-((2-hydroxy-3-(3-(N-methylmethylsulfonamido)-5-(1-phenylethylcarbamoyl)benzamido)-4-phenylbutylamino)methyl)piperidine-1-carboxylate | +++ | +++ | | ++ |
| N1-(3-hydroxy-4-(4-methoxyphenethylamino)-1-phenylbutan-2-yl)-5-(N-methylmethylsulfonamido)-N3-(1-phenylethyl)isophthalamide | +++ | +++ | | +++ |
| N1-(3-hydroxy-1-phenyl-4-(2-(pyrrolidin-1-yl)ethylamino)butan-2-yl)-5-(N-methylmethylsulfonamido)-N3-(1-phenylethyl)isophthalamide | + | + | | + |
| N1-(3-hydroxy-4-(2-methoxyphenethylamino)-1-phenylbutan-2-yl)-5-(N-methylmethylsulfonamido)-N3-(1-phenylethyl)isophthalamide | +++ | +++ | | ++ |
| N1-(3-hydroxy-4-(3-isobutylbenzylamino)-1-phenylbutan-2-yl)-5-(N-methylmethylsulfonamido)-N3-(1-phenylethyl)isophthalamide | +++ | +++ | | +++ |
| N1-(3-hydroxy-1-phenyl-4-(2-(piperidin-1-yl)ethylamino)butan-2-yl)-5-(N-methylmethylsulfonamido)-N3-(1-phenylethyl)isophthalamide | + | + | | + |
| N1-(3-hydroxy-1-phenyl-4-(piperidin-4-ylmethylamino)butan-2-yl)-5-(N-methylmethylsulfonamido)-N3-(1-phenylethyl)isophthalamide | + | + | | + |
| N1-(3-hydroxy-1-phenyl-4-(piperidin-3-ylmethylamino)butan-2-yl)-5-(N-methylmethylsulfonamido)-N3-(1-phenylethyl)isophthalamide | + | + | | + |
| N1-(3-hydroxy-1-phenyl-4-(2-(pyrrolidin-1-yl)ethylamino)butan-2-yl)-N3-methyl-N3-((4-methylthiazol-2-yl)methyl)isophthalamide | + | + | | + |
| 4,6-difluoro-N1-(3-hydroxy-4-(3-methoxybenzylamino)-1-phenylbutan-2-yl)-N3-(1-phenylethyl)isophthalamide | + | +++ | | ++ |
| N1-(3-hydroxy-4-((1-methylpiperidin-3-yl)methylamino)-1-phenylbutan-2-yl)-5-(N-methylmethylsulfonamido)-N3-(1-phenylethyl)isophthalamide | + | + | | + |
| N1-(3-hydroxy-4-(N-(3-methoxybenzyl)-5-oxo-5-(2-(piperidin-1-yl)ethylamino)pentanamido)-1-phenylbutan-2-yl)-5-(N-methylmethylsulfonamido)-N3-(1-phenylethyl)isophthalamide | | | | |
| N1-(3-hydroxy-4-((5-isopropoxypyridin-3-yl)methylamino)-1-phenylbutan-2-yl)-N3-methyl-N3-((4-methylthiazol-2-yl)methyl)isophthalamide | +++ | | | +++ |
| 2-(3,4-bis(benzyloxy)-5-oxo-2,5-dihydrofuran-2-yl)-2-hydroxyethyl 4-((2-hydroxy-3-(3-(N-methylmethylsulfonamido)-5-(1-phenylethylcarbamoyl)benzamido)-4-phenylbutyl)(3-methoxybenzyl)amino)-4-oxobutanoate | | | | |
| 2-(3,4-dihydroxy-5-oxo-2,5-dihydrofuran-2-yl)-2-hydroxyethyl 4-((2-hydroxy-3-(3-(N- | | | | ++ |

TABLE 1-continued

| Structure | M2K | CDK | M1K | Cell |
|---|---|---|---|---|
| methylmethylsulfonamido)-5-(1-phenylethylcarbamoyl)benzamido)-4-phenylbutyl)(3-methoxybenzyl)amino)-4-oxobutanoate | | | | |
| N1-(3-hydroxy-4-(3-methoxybenzylamino)-1-phenylbutan-2-yl)-N3-(1-(4-(hydroxymethyl)oxazol-2-yl)ethyl)-5-(N-methylmethylsulfonamido)isophthalamide | +++ | + | | +++ |
| N1-(3-hydroxy-4-(3-methoxybenzylamino)-1-phenylbutan-2-yl)-N3-methyl-N3-(1-(4-methylthiazol-2-yl)ethyl)isophthalamide | +++ | +++ | | +++ |
| N1-(3-hydroxy-4-((5-isopropoxypyridin-3-yl)methylamino)-1-phenylbutan-2-yl)-5-(N-methylmethylsulfonamido)-N3-(1-phenylethyl)isophthalamide | +++ | +++ | | +++ |
| N1-(3-hydroxy-4-((5-isopropylpyridin-3-yl)methylamino)-1-phenylbutan-2-yl)-5-(N-methylmethylsulfonamido)-N3-(1-phenylethyl)isophthalamide | +++ | +++ | | +++ |
| N1-(3-hydroxy-4-(1-(3-methylisoxazol-5-yl)ethylamino)-1-phenylbutan-2-yl)-5-(N-methylmethylsulfonamido)-N3-(1-phenylethyl)isophthalamide | +++ | | | +++ |
| N1-(3-hydroxy-4-(3-isobutylbenzylamino)-1-phenylbutan-2-yl)-N3-methyl-N3-((4-methylthiazol-2-yl)methyl)isophthalamide | +++ | | | +++ |
| N1-(3-hydroxy-1-phenyl-4-((1-((2-(trimethylsilyl)ethoxy)methyl)-1H-pyrrol-2-yl)methylamino)butan-2-yl)-5-(N-methylmethylsulfonamido)-N3-(1-phenylethyl)isophthalamide | ++ | | | +++ |
| N1-(3-hydroxy-4-((1-methylpyrrolidin-2-yl)methylamino)-1-phenylbutan-2-yl)-5-(N-methylmethylsulfonamido)-N3-(1-phenylethyl)isophthalamide | + | | | + |
| N1-(3-hydroxy-4-((1-isopropylpyrrolidin-2-yl)methylamino)-1-phenylbutan-2-yl)-5-(N-methylmethylsulfonamido)-N3-(1-phenylethyl)isophthalamide | + | | | |
| N1-(3-hydroxy-4-(3-methoxybenzylamino)-1-phenylbutan-2-yl)-N3-((4-(hydroxymethyl)oxazol-2-yl)methyl)-5-(N-methylmethylsulfonamido)isophthalamide | ++ | | | + |
| N1-(3-hydroxy-1-phenyl-4-((1-((2-(trimethylsilyl)ethoxy)methyl)-1H-imidazol-4-yl)methylamino)butan-2-yl)-5-(N-methylmethylsulfonamido)-N3-(1-phenylethyl)isophthalamide | +++ | | | |
| N1-(4-((1H-imidazol-4-yl)methylamino)-3-hydroxy-1-phenylbutan-2-yl)-5-(N-methylmethylsulfonamido)-N3-(1-phenylethyl)isophthalamide | ++ | | | ++ |
| N1-(3-hydroxy-4-(3-(3-methoxy-4-methylphenyl)propylamino)-1-phenylbutan-2-yl)-5-(N-methylmethylsulfonamido)-N3-(1-phenylethyl)isophthalamide | +++ | | | ++ |
| N1-(4-((5-ethoxypyridin-3-yl)methylamino)-3-hydroxy-1-phenylbutan-2-yl)-5-(N-methylmethylsulfonamido)-N3-(1-phenylethyl)isophthalamide | +++ | | | +++ |
| N1-(3-hydroxy-4-(3-methoxybenzylamino)-1-phenylbutan-2-yl)-5-(N-methylmethylsulfonamido)-N3-(1-(4-methyloxazol-2-yl)ethyl)isophthalamide | +++ | | | +++ |
| N1-(3-hydroxy-4-((3-methoxycyclohexyl)methylamino)-1-phenylbutan-2-yl)-5-(N-methylmethylsulfonamido)-N3-(1-phenylethyl)isophthalamide | + | | | ++ |
| N1-(3-hydroxy-4-((3-methoxycyclohexyl)methylamino)-1-phenylbutan-2-yl)-5-(N-methylmethylsulfonamido)-N3-(1-phenylethyl)isophthalamide | | | | ++ |
| N1-(4-((5-ethoxypyridin-3-yl)methylamino)-3-hydroxy-1-phenylbutan-2-yl)-N3-methyl-N3-((4-methylthiazol-2-yl)methyl)isophthalamide | +++ | | | +++ |
| N1-(3-hydroxy-4-((5-isobutylpyridin-3-yl)methylamino)-1-phenylbutan-2-yl)-5-(N-methylmethylsulfonamido)-N3-(1-phenylethyl)isophthalamide | | | | +++ |
| N1-(3-hydroxy-4-((4-methoxypyridin-2-yl)methylamino)-1-phenylbutan-2-yl)-5-(N- | | | | +++ |

TABLE 1-continued

| Structure | M2K | CDK | M1K | Cell |
|---|---|---|---|---|
| methylmethylsulfonamido)-N3-(1-phenylethyl)isophthalamide | | | | |
| N1-(1-(3,5-difluorophenyl)-3-hydroxy-4-(3-methoxybenzylamino)butan-2-yl)-N3-methyl-N3-((4-methylthiazol-2-yl)methyl)isophthalamide | +++ | | | +++ |
| N1-(3-hydroxy-4-(3-methoxybenzylamino)-1-phenylbutan-2-yl)-N3-methyl-N3-((4-methyloxazol-2-yl)methyl)isophthalamide | +++ | | | +++ |
| N1-(3-hydroxy-1-phenyl-4-((1-((2-(trimethylsilyl)ethoxy)methyl)-1H-imidazol-2-yl)methylamino)butan-2-yl)-5-(N-methylmethylsulfonamido)-N3-(1-phenylethyl)isophthalamide | ++ | | | + |
| N1-(1-(3,5-difluorophenyl)-3-hydroxy-4-(3-methoxybenzylamino)butan-2-yl)-5-(N-methylmethylsulfonamido)-N3-(1-phenylethyl)isophthalamide | | | | +++ |
| N1-(3-hydroxy-4-((5-methoxypyridin-3-yl)methylamino)-1-phenylbutan-2-yl)-N3-methyl-N3-((4-methylthiazol-2-yl)methyl)isophthalamide | +++ | | | +++ |
| N1-(3-hydroxy-4-((5-methylpyridin-3-yl)methylamino)-1-phenylbutan-2-yl)-N3-methyl-N3-((4-methylthiazol-2-yl)methyl)isophthalamide | +++ | +++ | | +++ |
| N1-(3-hydroxy-4-((1-isobutylpiperidin-4-yl)methylamino)-1-phenylbutan-2-yl)-5-(N-methylmethylsulfonamido)-N3-(1-phenylethyl)isophthalamide dihydrochloride | | | | + |
| N1-(3-hydroxy-4-((1-(2-methoxybenzyl)piperidin-4-yl)methylamino)-1-phenylbutan-2-yl)-5-(N-methylmethylsulfonamido)-N3-(1-phenylethyl)isophthalamide dihydrochloride | | | | + |
| N1-(3-hydroxy-4-((1-(2-methoxybenzyl)piperidin-4-yl)methylamino)-1-phenylbutan-2-yl)-5-(N-methylmethylsulfonamido)-N3-(1-phenylethyl)isophthalamide | | | | ++ |
| N1-(3-hydroxy-4-((3-methyl-1H-pyrazol-5-yl)methylamino)-1-phenylbutan-2-yl)-5-(N-methylmethylsulfonamido)-N3-(1-phenylethyl)isophthalamide | + | | | |
| N1-(4-(3,4-dimethoxyphenethylamino)-3-hydroxy-1-phenylbutan-2-yl)-5-(N-methylmethylsulfonamido)-N3-(1-phenylethyl)isophthalamide | +++ | | | +++ |
| N1-(3-hydroxy-4-(3-methoxybenzylamino)-1-(thiazol-4-yl)butan-2-yl)-5-(N-methylmethylsulfonamido)-N3-(1-phenylethyl)isophthalamide | +++ | | | +++ |
| N1-(3-hydroxy-4-((5-isobutylpyridin-3-yl)methylamino)-1-phenylbutan-2-yl)-N3-methyl-N3-((4-methylthiazol-2-yl)methyl)isophthalamide | +++ | | | +++ |
| N1-(3-hydroxy-4-((5-isobutoxypyridin-3-yl)methylamino)-1-phenylbutan-2-yl)-N3-methyl-N3-((4-methylthiazol-2-yl)methyl)isophthalamide | +++ | | | +++ |
| N1-(3-hydroxy-4-((1-(3-methoxybenzyl)piperidin-4-yl)methylamino)-1-phenylbutan-2-yl)-5-(N-methylmethylsulfonamido)-N3-(1-phenylethyl)isophthalamide | + | | | + |
| N1-(3-hydroxy-4-(2-hydroxy-1-phenylethylamino)-1-phenylbutan-2-yl)-5-(N-methylmethylsulfonamido)-N3-(1-phenylethyl)isophthalamide | +++ | | | +++ |
| N1-(3-hydroxy-4-(3-hydroxy-4-methoxyphenethylamino)-1-phenylbutan-2-yl)-5-(N-methylmethylsulfonamido)-N3-(1-phenylethyl)isophthalamide | +++ | | | ++ |
| N1-(4-((5-(dimethylamino)pyridin-3-yl)methylamino)-3-hydroxy-1-phenylbutan-2-yl)-5-(N-methylmethylsulfonamido)-N3-(1-phenylethyl)isophthalamide | +++ | ++ | | +++ |
| N1-(4-((5-ethylpyridin-3-yl)methylamino)-3-hydroxy-1-phenylbutan-2-yl)-N3-methyl-N3-((4-methylthiazol-2-yl)methyl)isophthalamide | +++ | +++ | | +++ |
| N1-(3-hydroxy-4-(3-methoxybenzylamino)-1-phenylbutan-2-yl)-N3-(1-(3-methoxyphenyl)ethyl)-5-(N-methylmethylsulfonamido)isophthalamide | +++ | | | +++ |
| N1-(4-(benzo[d][1,3]dioxol-5-ylmethylamino)-3-hydroxy-1-phenylbutan-2-yl)-5-(N-methylmethylsulfonamido)-N3-(1-phenylethyl)isophthalamide | +++ | | | +++ |

TABLE 1-continued

| Structure | M2K | CDK | M1K | Cell |
|---|---|---|---|---|
| N1-(3-hydroxy-4-((5-isobutoxypyridin-3-yl)methylamino)-1-phenylbutan-2-yl)-5-(N-methylmethylsulfonamido)-N3-(1-phenylethyl)isophthalamide | +++ | | | +++ |
| N1-(3-hydroxy-1-phenyl-4-(3-(trifluoromethyl)benzylamino)butan-2-yl)-5-(N-methylmethylsulfonamido)-N3-(1-phenylethyl)isophthalamide | +++ | +++ | | +++ |
| N1-(4-(3-ethynylbenzylamino)-3-hydroxy-1-phenylbutan-2-yl)-5-(N-methylmethylsulfonamido)-N3-(1-phenylethyl)isophthalamide | +++ | | | +++ |
| N1-(4-(3-(difluoromethoxy)benzylamino)-3-hydroxy-1-phenylbutan-2-yl)-5-(N-methylmethylsulfonamido)-N3-(1-phenylethyl)isophthalamide | +++ | +++ | | +++ |
| N1-(4-(3-ethynylbenzylamino)-3-hydroxy-1-phenylbutan-2-yl)-N3-methyl-N3-((4-methylthiazol-2-yl)methyl)isophthalamide | +++ | | | +++ |
| N1-((2,5-dimethyloxazol-4-yl)methyl)-N3-(3-hydroxy-4-(3-methoxybenzylamino)-1-phenylbutan-2-yl)-N1-methylisophthalamide | +++ | | | +++ |
| N1-(3-hydroxy-4-(3-methoxybenzylamino)-1-phenylbutan-2-yl)-5-(N-methylmethylsulfonamido)-N3-(1-(thiazol-2-yl)ethyl)isophthalamide | +++ | | | +++ |
| N1-(3-hydroxy-4-(3-methoxybenzylamino)-1-phenylbutan-2-yl)-N3-isopropyl-N3-((4-methylthiazol-2-yl)methyl)isophthalamide | +++ | | | +++ |
| N1-(4-(3-ethoxybenzylamino)-3-hydroxy-1-phenylbutan-2-yl)-5-(N-methylmethylsulfonamido)-N3-(1-phenylethyl)isophthalamide | +++ | | | +++ |
| N1-(3-hydroxy-4-(3-methoxybenzylamino)-1-phenylbutan-2-yl)-N3-isobutyl-N3-((4-methylthiazol-2-yl)methyl)isophthalamide | +++ | | | |
| N1-(3-hydroxy-4-(1-(3-methoxyphenyl)ethylamino)-1-phenylbutan-2-yl)-5-(N-methylmethylsulfonamido)-N3-(1-phenylethyl)isophthalamide | +++ | | | +++ |
| N1-(4-(benzylamino)-3-hydroxy-1-phenylbutan-2-yl)-N3-methyl-N3-((4-methylthiazol-2-yl)methyl)isophthalamide | + | | | |
| N1-(4-(3-ethoxybenzylamino)-3-hydroxy-1-phenylbutan-2-yl)-N3-methyl-N3-((4-methylthiazol-2-yl)methyl)isophthalamide | +++ | | | |
| N1-(3-hydroxy-4-(3-isopropoxybenzylamino)-1-phenylbutan-2-yl)-N3-methyl-N3-((4-methylthiazol-2-yl)methyl)isophthalamide | +++ | +++ | | +++ |
| N1-(3-hydroxy-4-(3-methoxybenzylamino)-1-phenylbutan-2-yl)-5-(N-methylmethylsulfonamido)-N3-(1-phenylethyl)isophthalamide | + | | | |
| N1-(3-hydroxy-4-(3-isobutoxybenzylamino)-1-phenylbutan-2-yl)-N3-methyl-N3-((4-methylthiazol-2-yl)methyl)isophthalamide | +++ | | | |
| N1-(3-hydroxy-4-(2-methoxyphenethylamino)-1-phenylbutan-2-yl)-N3-methyl-N3-((4-methylthiazol-2-yl)methyl)isophthalamide | + | | | ++ |
| N1-(3-hydroxy-4-((5-isopropylpyridin-3-yl)methylamino)-1-phenylbutan-2-yl)-N3-methyl-N3-((4-methylthiazol-2-yl)methyl)isophthalamide | +++ | +++ | ++ | +++ |
| N1-(3-hydroxy-1-phenyl-4-(3-(trifluoromethyl)benzylamino)butan-2-yl)-N3-methyl-N3-((4-methylthiazol-2-yl)methyl)isophthalamide | +++ | +++ | + | +++ |
| N1-ethyl-N3-(3-hydroxy-4-(3-methoxybenzylamino)-1-phenylbutan-2-yl)-N1-((4-methylthiazol-2-yl)methyl)isophthalamide | +++ | | | +++ |
| N1-(4-(3-(difluoromethoxy)benzylamino)-3-hydroxy-1-phenylbutan-2-yl)-N3-methyl-N3-((4-methylthiazol-2-yl)methyl)isophthalamide | +++ | | | +++ |
| N1-(3-hydroxy-4-(3-methoxybenzylamino)-1-phenylbutan-2-yl)-N3-methyl-N3-((2-methylthiazol-4-yl)methyl)isophthalamide | +++ | | | +++ |
| N1-(3-hydroxy-4-(4-methoxyphenethylamino)-1-phenylbutan-2-yl)-N3-methyl-N3-((4-methylthiazol-2-yl)methyl)isophthalamide | + | | | ++ |
| N1-(3-hydroxy-4-(2-methoxybenzylamino)-1-phenylbutan-2-yl)-N3-methyl-N3-((4-methylthiazol-2-yl)methyl)isophthalamide | + | | | ++ |
| N1-(3-hydroxy-4-(3-methoxybenzylamino)-1-phenylbutan-2-yl)-N3-methyl-N3-((4-methylthiazol-2-yl)methyl)-5-nitroisophthalamide | +++ | | | +++ |

TABLE 1-continued

| Structure | M2K | CDK | M1K | Cell |
|---|---|---|---|---|
| N1-(3-hydroxy-4-(3-methoxybenzylamino)-1-phenylbutan-2-yl)-5-(methylsulfonylmethyl)-N3-(1-phenylethyl)isophthalamide | +++ | | | +++ |
| N1-((4-ethylthiazol-2-yl)methyl)-N3-(3-hydroxy-4-(3-methoxybenzylamino)-1-phenylbutan-2-yl)-N1-methylisophthalamide | +++ | | | +++ |
| N1-(3-hydroxy-1-phenyl-4-(3-(trifluoromethoxy)benzylamino)butan-2-yl)-5-(N-methylmethylsulfonamido)-N3-(1-phenylethyl)isophthalamide | +++ | | | +++ |
| N1-(3-hydroxy-4-(4-methoxybenzylamino)-1-phenylbutan-2-yl)-N3-methyl-N3-((4-methylthiazol-2-yl)methyl)isophthalamide | + | | | ++ |
| N1-(3-hydroxy-1-phenyl-4-(3-(trifluoromethoxy)benzylamino)butan-2-yl)-N3-methyl-N3-((4-methylthiazol-2-yl)methyl)isophthalamide | +++ | | | +++ |
| N1-benzyl-N3-(3-hydroxy-4-(3-methoxybenzylamino)-1-phenylbutan-2-yl)-N1-((4-methylthiazol-2-yl)methyl)isophthalamide | +++ | | | |
| N1-cyclopentyl-N3-(3-hydroxy-4-(3-methoxybenzylamino)-1-phenylbutan-2-yl)-N1-((4-methylthiazol-2-yl)methyl)isophthalamide | +++ | | | |
| N1-(3-hydroxy-4-(3-methoxybenzylamino)-1-phenylbutan-2-yl)-N3-methyl-N3-((2-methyloxazol-4-yl)methyl)isophthalamide | +++ | | | |
| N1-(3-hydroxy-1-phenyl-4-(1-phenylethylamino)butan-2-yl)-N3-methyl-N3-((4-methylthiazol-2-yl)methyl)isophthalamide | + | | | |
| N1-(3-hydroxy-4-(1-(3-methoxyphenyl)ethylamino)-1-phenylbutan-2-yl)-N3-methyl-N3-((4-methylthiazol-2-yl)methyl)isophthalamide | +++ | | | |
| N1-cyclohexyl-N3-(3-hydroxy-4-(3-methoxybenzylamino)-1-phenylbutan-2-yl)-N1-((4-methylthiazol-2-yl)methyl)isophthalamide | ++ | | | |
| N1-cyclopropyl-N3-(3-hydroxy-4-((5-isopropylpyridin-3-yl)methylamino)-1-phenylbutan-2-yl)-N1-((4-methylthiazol-2-yl)methyl)isophthalamide | +++ | +++ | +++ | +++ |
| N1-(3-hydroxy-4-(3-methoxybenzylamino)-1-phenylbutan-2-yl)-N3-methyl-N3-(pyrazin-2-ylmethyl)isophthalamide | + | | | |
| N1-(3-hydroxy-4-(4-methylbenzylamino)-1-phenylbutan-2-yl)-N3-methyl-N3-((4-methylthiazol-2-yl)methyl)isophthalamide | + | | | |
| N1-(3-hydroxy-4-(3-methoxybenzylamino)-1-phenylbutan-2-yl)-N3-methyl-5-(methylsulfonylmethyl)-N3-((4-methylthiazol-2-yl)methyl)isophthalamide | | | | |
| N1-cyclopropyl-N3-(3-hydroxy-4-(3-methoxybenzylamino)-1-phenylbutan-2-yl)-5-methoxy-N1-((4-methylthiazol-2-yl)methyl)isophthalamide | | | | |

In Table 1, for the Ki data, a "+" represents a Ki of greater than >501 nM, a "++" represents a Ki from 500 nm to 301 nm, and a "+++" represents a Ki of less than 300 nm. For the IC50 data, a "+" represents an IC50 of greater than 5 μM, a "++" represents an IC50 from 1 to 5 μM, and a "+++" represents an IC50 of less than 1 μM. In Table 1 above, compounds names that appear more than once include alternative sterochemical configurations.

Example 4

Characterization Data

N1-((2S,3R)-3-hydroxy-4-((4-methylthiazol-2-yl)methylamino)-1-phenylbutan-2-yl)-5-(N-methylmethylsulfonamido)-N3-((R)-1-phenylethyl)isophthalamide: 1H NMR (300 MHz, CDCl$_3$+CD$_3$OD): 1.56 (d, 3H), 2.36 (d, 3H), 2.85 (s, 3H), 2.78-3.00 (m, 4H), 3.30 (s, 3H), 3.68-3.78 (m, 1H), 4.01 (s, 2H), 4.30-4.40 (m, 1H), 5.20-5.35 (m, 1H), 6.80 (d, 1H), 7.10-7.40 (m, 10H), 7.79-7.82 (m, 1H), 7.90-7.92 (m, 1H), 8.01-8.05 (m, 1H).

N1-((2S,3R)-3-hydroxy-4-(3-methoxybenzylamino)-1-phenylbutan-2-yl)-5-(N-methylmethylsulfonamido)-N3-((R)-1-(4-methylthiazol-2-yl)ethyl)isophthalamide: 1H NMR (300 MHz, CDCl$_3$+CD$_3$OD): 1.68 (d, 3H), 2.41 (d, 3H), 2.85 (s, 3H), 2.70-3.02 (m, 4H), 3.31 (s, 3H), 3.75 (s, 3H), 3.70-3.83 (m, 2H), 4.30-4.40 (m, 1H), 5.50-5.60 (m, 1H), 6.72-6.90 (m, 3H), 7.10-7.30 (m, 7H), 7.79-7.82 (m, 1H), 7.90-7.92 (m, 1H), 8.05-8.10 (m, 1H).

N1-((2S,3R)-4-(benzylamino)-3-hydroxy-1-phenylbutan-2-yl)-5-(N-methylmethylsulfonamido)-N3-((R)-1-phenylethyl)isophthalamide: 1H NMR (300 MHz, CDCl$_3$+CD$_3$OD): 1.56 (d, 3H), 2.82 (s, 3H), 2.68-3.02 (m, 4H), 3.27 (s, 3H), 3.70-3.85 (m, 3H), 4.25-4.35 (m, 1H), 5.20-5.30 (m, 1H), 7.10-7.40 (m, 15H), 7.75-7.77 (m, 1H), 7.86-7.90 (m, 1H), 8.01-8.03 (m, 1H).

N1-benzyl-N3-((2S,3R)-3-hydroxy-4-(3-methoxybenzylamino)-1-phenylbutan-2-yl)-5-(N-methylmethylsulfonamido)isophthalamide: 1H NMR (300 MHz, CDCl$_3$+CD$_3$OD): 2.84 (s, 3H), 2.70-3.02 (m, 4H), 3.30 (s, 3H), 3.74 (s, 3H), 3.70-3.83 (m, 3H), 4.30-4.42 (m, 1H), 4.58 (s, 2H), 6.74-6.88 (m, 2H), 7.10-7.38 (m, 12H), 7.74-7.78 (m, 1H), 7.90-7.94 (m, 1H), 8.05-8.10 (m, 1H).

N1-((2S,3R)-3-hydroxy-4-(3-methoxybenzylamino)-1-phenylbutan-2-yl)-5-nitro-N3-((R)-1-phenylethyl)isophthalamide: 1H NMR (300 MHz, CDCl$_3$+CD$_3$OD): 1.59 (d, 3H), 2.70-3.02 (m, 4H), 3.73 (s, 3H), 3.70-3.85 (m, 3H), 4.28-4.39 (m, 1H), 5.20-5.35 (m, 1H), 6.72-6.88 (m, 2H), 7.10-7.40 (m, 12H), 8.42-8.44 (m, 1H), 8.55-8.57 (m, 1H), 8.74-8.77 (m, 1H).

N1-((2S,3R)-3-hydroxy-1-phenyl-4-(pyrazin-2-ylmethylamino)butan-2-yl)-5-(N-methylmethylsulfonamido)-N3-((R)-1-phenylethyl)isophthalamide: 1H NMR (300 MHz, CDCl$_3$+CD$_3$OD): 1.58 (d, 3H), 2.80 (s, 3H), 2.70-3.02 (m, 4H), 3.29 (s, 3H), 3.60-3.72 (m, 1H), 3.85-4.01 (m, 2H), 4.34-4.48 (m, 1H), 5.25-5.40 (m, 1H), 7.12-7.40 (m, 10H), 7.76-7.80 (m, 1H), 7.93-7.97 (m, 1H), 8.03-8.07(m, 1H), 8.40-8.42 (m, 1H), 8.46-8.48 (m, 1H), 8.59-8.61 (m, 1H). Melting point: 75-80° C.

N1-((2S,3R)-3-hydroxy-4-(3-methoxybenzylamino)-1-phenylbutan-2-yl)-5-(N-methylmethylsulfonamido)-N3-((R)-1-phenylethyl)isophthalamide: 1H NMR (500 MHz, CDCl$_3$): δ 1.58 (3H, d, J=7.0 Hz), 2.72 (3H, s), 2.74-2.83 (4H, m), 3.22 (3H, s), 3.69-3.83 (6H, m), 4.29-4.33 (1H, m), 5.26 (1H, m), 6.78 (1H, m), 6.85-6.86 (2H, m), 7.13-7.37 (12H, m), 7.76 (1H, s), 7.89 (2H, s), 8.11 (1H, s); mp 77-80° C.

N1-((2S,3R)-4-((1H-benzo[d]imidazol-2-yl)methylamino)-3-hydroxy-1-phenylbutan-2-yl)-5-(N-methylmethylsulfonamido)-N3-((R)-1-phenylethyl)isophthalamide: 1H NMR (300 MHz, CDCl$_3$+CD$_3$OD): 1.56 (d, 3H), 2.81 (s, 3H), 2.68-2.94 (m, 4H), 3.24 (s, 3H), 3.70-3.77 (m, 1H), 3.90-4.01 (m, 2H), 4.30-4.40 (m, 1H), 5.20-5.30 (m, 1H), 7.05-7.50 (m, 15H), 7.75-7.77 (m, 1H), 7.86-7.89 (m, 1H), 8.03-8.06 (m, 1H).

N1-((2S,3R)-4-((2,5-dimethyloxazol-4-yl)methylamino)-3-hydroxy-1-phenylbutan-2-yl)-5-(N-methylmethylsulfonamido)-N3-((R)-1-phenylethyl)isophthalamide: 1H NMR (300 MHz, CDCl$_3$+CD$_3$OD): 1.48 (d, 3H), 2.14 (s, 3H), 2.24 (s, 3H), 2.58-2.82 (m, 4H), 2.78 (s, 3H), 3.23 (s, 3H), 3.36 (s, 2H), 3.60-3.70 (m, 1H), 4.25-4.32 (m, 1H), 5.18-5.32 (m, 1H), 7.05-7.32 (m, 10H), 7.77-7.81 (m, 1H), 7.90-7.94 (m, 1H), 8.06-8.09 (m, 1H).

N1-((2S,3R)-3-hydroxy-4-((S)-1-(4-methylthiazol-2-yl)ethylamino)-1-phenylbutan-2-yl)-5-(N-methylmethylsulfonamido)-N3-((R)-1-phenylethyl)isophthalamide: 1H NMR (300 MHz, CDCl$_3$+CD$_3$OD): 1.45 (d, 3H), 1.55 (d, 3H, J=6.9 Hz) 2.37 (d, 3H), 2.74-2.84 (m, 2H), 2.81 (s, 3H), 2.95 (d, 2H), 3.30 (s, 3H), 3.58-3.65 (m, 1H), 4.00-4.12 (m, 1H), 4.30-4.42 (m, 1H), 5.22-5.34 (m, 1H), 6.79 (d, 1H) 7.10-7.32 (m, 10H), 7.74-7.78 (m, 1H), 7.94-7.96 (m, 1H), 8.02-8.05 (m, 1H). Melting point: 80-87° C.

N1-((2S,3R)-3-hydroxy-4-((R)-1-(4-methylthiazol-2-yl)ethylamino)-1-phenylbutan-2-yl)-5-(N-methylmethylsulfonamido)-N3-((R)-1-phenylethyl)isophthalamide: 1H NMR (300 MHz, CDCl$_3$+CD$_3$OD): 1.43 (d, 3H), 1.54 (d, 3H) 2.33 (d, 3H), 2.62-2.84 (m, 2H), 2.84 (s, 3H), 2.87 (d, 2H), 3.27 (s, 3H), 3.65-3.75 (m, 1H), 4.00-4.12 (m, 1H), 4.28-4.48 (m, 1H), 5.18-5.32 (m, 1H), 6.76 (d, 1H) 7.05-7.35 (m, 10H), 7.78-7.81 (m, 1H), 7.87-7.90 (m, 1H), 8.02-8.05 (m, 1H). Melting point: 85-90° C.

N1-((2S,3R)-3-hydroxy-4-(3-methoxybenzylamino)-1-phenylbutan-2-yl)-5-(N-methylmethylsulfonamido)-N3-((S)-1-(4-methylthiazol-2-yl)ethyl)isophthalamide: 1H NMR (300 MHz, CDCl$_3$+CD$_3$OD): 1.61 (d, 3H), 2.34 (s, 3H), 2.68-2.88 (m, 4H), 2.77 (s, 3H), 3.23 (s, 3H), 3.62-3.82 (m, 3H), 3.70 (s, 3H), 4.27-4.38 (m, 1H), 5.40-5.51 (m, 1H), 6.70-6.87 (m, 4H), 7.05-7.50 (m, 5H), 7.71-7.74 (m, 1H), 7.86-7.89 (m, 1H), 7.98-8.03 (m, 1H).
Melting point: 57-61° C.

5-(N-ethylmethylsulfonamido)-N1-((2S,3R)-3-hydroxy-4-(3-methoxybenzylamino)-1-phenylbutan-2-yl)-N3-((R)-1-phenylethyl)isophthalamide: 1H NMR (300 MHz, CDCl$_3$+CD$_3$OD): 1.06 (t, 3H), 1.58 (d, 3H), 2.68-3.02 (m, 4H), 2.87 (s, 3H), 3.62-3.84 (m, 3H), 3.75 (s, 3H), 4.25-4.36 (m, 1H), 5.20-5.33 (m, 1H), 6.73-6.90 (m, 4H), 7.07-7.42 (m, 10H), 7.66-7.72 (m, 1H), 7.83-7.87 (m, 1H), 8.02-8.06 (m, 1H).
Melting point: 110-116° C.

N1-((2S,3R)-3-hydroxy-4-(3-methoxyphenethylamino)-1-phenylbutan-2-yl)-5-(N-methylmethylsulfonamido)-N3-((R)-1-phenylethyl)isophthalamide: $^1$H NMR (300 MHz, CDCl$_3$): 1.60(d, 3H, J=7.2 Hz), 2.75 (s, 3H), 2.77-3.07 (m, 8H), 3.24 (s, 3H), 3.74 (s, 3H), 3.81-3.90 (m, 1H), 4.28-4.40 (m, 1H), 5.24-5.76 (m, 1H), 6.72-6.75 (m, 3H), 7.12-7.37 (m, 11H), 7.80-7.91 (m, 3H), 8.15 (s, 1H).

N1-((2S,3R)-3-hydroxy-4-(3-methylbenzylamino)-1-phenylbutan-2-yl)-N3-methyl-N3-((4-methylthiazol-2-yl)methyl)isophthalamide: $^1$H NMR (300 MHz, CDCl$_3$): 0.80-0.88 (m, 4H), 2.45 (s, 3H), 2.80-2.86 (m, 2H), 2.92-3.02 (m, 2H), 3.69-3.86 (m, 6H), 4.36-4.44 (m, 1H), 4.96-5.12 (m, 2H), 6.79-6.99 (m, 4H), 7.15-7.26 (m, 8H), 7.64-7.67 (m, 1H), 7.82 (s, 1H).

N1-((2S,3R)-3-hydroxy-4-(3-methylbenzylamino)-1-phenylbutan-2-yl)-5-(N-methylmethylsulfonamido)-N3-((R)-1-phenylethyl)isophthalamide: $^1$H NMR (300 MHz, CDCl$_3$): 1.64 (d, 3H, J=7.2 Hz), 2.33 (s, 3H), 2.79-3.33 (m, 7H), 3.29 (s, 3H), 3.82-3.91 (m, 3H), 4.24-4.41 (m, 1H), 5.29-5.42 (m, 1H), 6.93-7.43 (m, 14H), 7.83 (s, 1H), 7.94 (s, 1H), 8.13 (s, 1H).

N1-((2S,3R)-4-(3-fluorobenzylamino)-3-hydroxy-1-phenylbutan-2-yl)-N3-methyl-N3-((4-methylthiazol-2-yl)methyl)isophthalamide: $^1$H NMR (300 MHz, CDCl$_3$): 2.40 (s, 3H), 2.76-2.81 (m, 2H), 2.92-3.05 (m, 5H), 3.71-3.78 (m, 3H), 4.26-4.42 (m, 1H), 4.86-4.96 (m, 2H), 6.88-7.66 (m, 14H).

N1-((2S,3R)-3-hydroxy-4-((S)-1-(4-methylthiazol-2-yl)ethylamino)-1-phenylbutan-2-yl)-5-(N-methylmethylsulfonamido)-N3-((R)-1-phenylethyl)isophthalamide: $^1$H NMR (300 MHz, CDCl$_3$): 2.25 (s, 3H), 2.38 (s, 3H), 2.65-2.81 (m, 2H), 2.92-3.13 (m, 5H), 3.64-3.88 (m, 3H), 4.22-4.39 (m, 1H), 4.89 (s, 2H), 6.82-7.59 (m, 14H).

N1-((2S,3R)-3-hydroxy-4-(3-methoxybenzylamino)-1-phenylbutan-2-yl)-N3-methyl-N3-((3-methylisoxazol-5-yl)methyl)isophthalamide: $^1$H NMR (300 MHz, CDCl$_3$) δ 7.73-7.82 (m, 1H), 7.64-7.66 (m, 1H), 7.46-7.59 (m, 1H), 7.37-7.42 (m, 1H), 7.16-7.29 (m, 6H), 7.08-7.11 (m, 1H), 6.90-6.92 (m, 2H), 6.80-6.83 (m, 1H), 6.00-6.14 (m, 1H), 4.77 (m, 1.5H), 4.33-4.47 (m, 1.5H), 3.71-3.89 (m, 6H), 3.00-3.08 (m, 5H), 2.81-2.90 (m, 2H), 2.47 (s, 1H), 2.30 (s, 3H); m.p. 46-56° C.

N1-((2S,3R)-3-hydroxy-1-phenyl-4-(pyridin-2-ylmethylamino)butan-2-yl)-5-(N-methylmethylsulfonamido)-N3-((R)-1-phenylethyl)isophthalamide: $^1$H NMR (300 MHz, CDCl$_3$) δ 8.50-8.51 (m, 1H), 8.20 (s, 1H), 8.10-8.13 (m, 1H), 8.02 (s, 1H), 7.88 (s, 1H), 7.65-7.71 (m, 1H), 7.15-7.31 (m, 14H), 5.28-5.38 (m, 1H), 4.39-4.48 (m, 1H), 3.64-3.84 (m, 4H), 3.30 (s, 3H), 2.81-2.95 (m, 5H), 2.63-2.69 (m, 1H), 2.28 (s, 1H), 1.53 (d, 3H); m.p. 53-67° C.

N1-((2S,3R)-3-hydroxy-1-phenyl-4-(pyridin-4-ylmethylamino)butan-2-yl)-5-(N-methylmethylsulfonamido)-N3-((R)-1-phenylethyl)isophthalamide: $^1$H NMR (300 MHz, CDCl$_3$) δ 8.49-8.51 (m, 2H), 7.93 (s, 1H), 7.89 (s, 1H), 7.75 (s, 1H), 7.09-7.41 (m, 13H), 6.87-6.97 (m, 1H), 5.27-5.36 (m, 1H), 4.31-4.40 (m, 1H), 3.75-3.91 (m, 2H), 3.62-3.70 (m, 2H), 3.31 (d, 3H), 2.96-2.98 (m, 2H), 2.81 (s, 3H), 2.74-2.76 (m, 2H), 2.02 (s, 1H), 1.62 (d, 3H); m.p. 73-84° C.

N1-((2S,3R)-3-hydroxy-4-((3-methylisoxazol-5-yl)methylamino)-1-phenylbutan-2-yl)-5-(N-methylmethylsulfonamido)-N3-((R)-1-phenylethyl)isophthalamide: $^1$H NMR (300 MHz, CDCl$_3$) δ 8.05 (s, 1H), 7.97 (s, 1H), 7.78 (s, 1H), 7.20-7.40 (m, 10H), 7.08-7.18 (m, 1H), 6.97-7.08 (m, 1H), 5.98 (s, 1H), 5.26-5.41 (m, 1H), 4.33-4.43 (m, 1H), 3.82-4.01 (m, 2H), 3.61-3.65 (m, 2H), 3.33 (s, 3H), 2.99-3.02 (m, 2H), 2.83 (s, 3H), 2.75-2.76 (m, 2H), 2.21 (s, 3H), 1.70 (s, 1H), 1.62 (d, 3H).

N1-((2S,3R)-3-hydroxy-4-(3-methoxybenzylamino)-1-phenylbutan-2-yl)-N3-((5-hydroxypyridin-3-yl)methyl)-5-(N-methylmethylsulfonamido)isophthalamide: $^1$H NMR (300 MHz, CDCl$_3$) δ 8.15 (s, 1H), 7.81-7.98 (m, 3H), 7.72 (s, 1H), 7.06-7.27 (m, 9H), 6.86-6.89 (m, 2H), 6.79-6.81 (m, 1H), 4.34-4.46 (m, 2H), 4.22-4.34 (m, 2H), 3.95-4.03 (m, 1H), 3.88-3.91 (m, 2H), 3.60-3.80 (m, 4H), 3.21 (s, 3H), 2.77-2.98 (m, 7H), 2.27 (s, 1H); m.p. 100-113.5° C.

4- or 6-fluoro-N3-((2S,3R)-3-hydroxy-4-(3-methoxybenzylamino)-1-phenylbutan-2-yl)-N1-((R)-1-phenylethyl) isophthalamide: $^1$H NMR (300 MHz, CDCl$_3$) δ 8.25-8.29 (m, 1H), 7.78-7.85 (m, 1H), 6.89-7.37 (m, 17H), 6.66-6.82 (m, 1H), 5.28-5.37 (m, 2H), 4.32-4.44 (m, 1H), 3.76-3.92 (m, 5H), 2.95-3.06 (m, 2H), 2.77-2.95 (m, 2H), 2.17 (s, 1H), 1.60 (d, 3H).

6- or 4-fluoro-N3-((2S,3R)-3-hydroxy-4-(3-methoxybenzylamino)-1-phenylbutan-2-yl)-N1-((R)-1-phenylethyl) isophthalamide: $^1$H NMR (300 MHz, CDCl$_3$) δ 8.14-8.16 (m, 1H), 7.90-7.98 (m, 1H), 7.00-7.32 (m, 13H), 6.75-6.90 (m, 2H), 6.64-6.74 (m, 2H), 5.18-5.29 (m, 2H), 4.26-4.42 (m, 1H), 3.56-3.88 (m, 6H), 2.89-3.08 (m, 2H), 2.65-2.89 (m, 2H), 2.23(s, 1H), 1.53-1.55 (d, 3H); m.p. 55-67° C.

N1-((2S,3R)-3-hydroxy-4-((5-methylpyridin-3-yl)methylamino)-1-phenylbutan-2-yl)-5-(N-methylmethylsulfonamido)-N3-((R)-1-phenylethyl)isophthalamide: $^1$H NMR (300 MHz, CDCl$_3$) δ 8.46 (s, 1H), 8.33-8.36 (m 1H), 8.19 (s, 1H), 8.13 (s, 1H), 8.04-8.07 (m, 1H), 7.95-7.97 (m, 1H), 7.69-7.72 (m, 1H), 7.15-7.44 (m, 11H), 6.89-6.95 (m, 1H), 5.30-5.44 (m, 1H), 4.32-4.41 (m, 1H), 3.99-4.04 (m, 1H), 3.57-3.83 (m, 2H), 3.31 (s, 3H), 2.94-3.09 (m, 2H), 2.81 (s, 3H), 2.61-2.62 (m, 2H), 2.27 (s, 3H), 2.03 (s, 1H), 1.65 (d, 3H).

N1-((2S,3R)-3-hydroxy-4-(3-methoxybenzylamino)-1-phenylbutan-2-yl)-4- or 6-methyl-N3-((R)-1-phenylethyl) isophthalamide: $^1$H NMR (300 MHz, CDCl$_3$) δ 7.61-7.63 (m, 1H), 7.14-7.42 (m, 15H), 6.88-6.95 (m, 2H), 6.81-6.85 (m, 1H), 6.16-6.29 (m, 1H), 5.28-5.36 (m, 1H), 4.30-4.43 (m, 1H), 3.72-3.93 (m, 5H), 3.02-3.04 (m, 2H), 2.75-2.95 (m, 3H), 2.42 (s, 3H), 1.74 (s, 1H), 1.60 (d, 3H); m.p. 64-77° C.

N3-((2S,3R)-3-hydroxy-4-(3-methoxybenzylamino)-1-phenylbutan-2-yl)-6- or 4-methyl-N1-((R)-1-phenylethyl) isophthalamide: $^1$H NMR (300 MHz, CDCl$_3$) δ 7.66-7.91 (m, 1H), 7.49 (s, 1H), 7.08-7.40 (m, 13H), 6.87-6.90 (m, 2H), 6.77-6.83 (m, 1H), 6.57 (s, 1H), 6.32 (s, 1H), 5.25-5.37 (m, 1H), 4.30-4.43 (m, 1H), 3.65-3.90 (m, 5H), 2.95-3.16 (m, 2H), 2.72-2.95 (m, 3H), 2.13 (s, 3H), 2.02 (s, 1H), 1.60 (d, 3H).

N1-((2S,3R)-3-hydroxy-4-((5-methoxypyridin-3-yl)methylamino)-1-phenylbutan-2-yl)-5-(N-methylmethylsulfonamido)-N3-((R)-1-phenylethyl)isophthalamide: $^1$H NMR (300 MHz, CDCl$_3$) δ 8.25 (s, 1H), 8.09 (s, 1H), 7.98 (s, 1H), 7.76-7.82 (m, 1H), 7.72 (s, 1H), 7.16-7.44 (m, 14H), 6.77-6.86 (m, 1H), 5.30-5.45 (m, 1H), 4.30-4.42 (m, 1H), 4.00-4.12 (m, 1H), 3.73-3.87 (m, 2H), 3.55-3.73 (m, 2H), 3.33 (s, 3H), 2.98-3.03 (m, 2H), 2.82 (s, 3H), 2.60-2.69 (m, 2H), 1.70 (s, 1H), 1.66 (d, 3H).

4- or 6-fluoro-N1-((2S,3R)-3-hydroxy-4-(3-methoxybenzylamino)-1-phenylbutan-2-yl)-N3-methyl-N3-((4-methylthiazol-2-yl)methyl)isophthalamide: $^1$H NMR (300 MHz, CDCl$_3$) δ 8.06 (s, 1H), 7.61 (s, 1H), 7.05-7.28 (m, 10H), 6.85-7.05 (m, 2H), 6.78-6.81 (m, 1H), 4.89-5.02 (m, 2H), 4.36-4.52 (m, 1H), 3.69-3.87 (m, 5H), 3.59-3.69 (m, 1H), 2.96-3.16 (m, 5H), 2.72-2.84 (m, 2H), 2.44 (s, 3H), 2.04 (s, 1H).

6- or 4-fluoro-N3-((2S,3R)-3-hydroxy-4-(3-methoxybenzylamino)-1-phenylbutan-2-yl)-N1-methyl-N1-((4-methylthiazol-2-yl)methyl)isophthalamide: $^1$H NMR (300 MHz, CDCl$_3$) δ 7.61-7.81 (m, 2H), 7.03-7.45 (m, 10H), 6.87-6.98 (m, 2H), 6.77-6.87 (m, 1H), 4.99 (s, 2H), 4.32-4.46 (m, 1H), 3.77-3.98 (m, 5H), 3.62-3.70 (m, 1H), 2.96-3.04 (m, 5H), 2.76-2.93 (m, 2H), 2.46 (s, 3H), 1.68 (s, 1H).

N1-((2S,3R)-3-hydroxy-4-((6-methylpyridin-2-yl)methylamino)-1-phenylbutan-2-yl)-5-(N-methylmethylsulfonamido)-N3-((R)-1-phenylethyl)isophthalamide: 8.28 (s, 1H), 8.01 (m, 1H), 7.87 (m, 1H), 7.52-7.57 (m, 1H), 7.11-7.29 (m, 10H), 7.00-7.05 (m, 2H), 5.28-5.35 (m, 1H), 4.40-4.46 (m, 1H), 3.69-3.75 (m, 3H), 3.27 (s, 3H), 2.81-2.93 (m, 2H), 2.78 (s, 3H), 2.51-2.69 (m, 2H), 2.42 (s, 3H), 1.51 (d, 3H).

N1-((2S,3R)-3-hydroxy-4-(2-methyl-2-phenylhydrazinyl)-1-phenylbutan-2-yl)-5-(N-methylmethylsulfonamido)-N3-((R)-1-phenylethyl)isophthalamide: 7.88-7.90 (m, 1H), 7.84-7.85 (m, 1H), 7.68-7.69 (m, 1H), 7.16-7.37 (m, 12H), 6.76-6.86 (m, 3H), 5.22-5.28 (m, 1H), 4.37-4.42 (m, 1H), 4.11-4.14 (m, 1H), 3.41-3.43 (m, 2H), 3.27 (s, 3H), 3.00-3.14 (m, 2H), 2.96 (s, 3H), 2.83 (s, 3H), 1.60 (d, 3H).

N1-((2S,3R)-3-hydroxy-4-(2-hydroxybenzylamino)-1-phenylbutan-2-yl)-5-(N-methylmethylsulfonamido)-N3-((R)-1-phenylethyl)isophthalamide: 8.01 (s, 1H), 7.88 (s, 1H), 7.72 (s, 1H), 7.12-7.38 (m, 11H), 6.97-7.01 (m, 1H), 6.77-6.81 (m, 2H), 5.24-5.29 (m, 1H), 4.30 (m, 1H), 3.86-4.02 (m, 3H), 3.23 (s, 3H), 2.83-2.92 (m, 4H), 2.78 (s, 3H), 1.60 (d, 3H).

N1-((2S,3R)-4-(3-acetamidobenzylamino)-3-hydroxy-1-phenylbutan-2-yl)-5-(N-methylmethylsulfonamido)-N3-((R)-1-phenylethyl)isophthalamide: 8.27 (s, 1H), 7.90 (s, 1H), 7.80 (s, 1H), 7.50 (s, 1H), 7.38-7.41 (m, 3H), 7.11-7.26 (m, 10H), 5.25-5.30 (m, 1H), 4.26 (m, 1H), 3.84 (m, 1H), 3.64-3.76 (m, 2H), 3.19 (s, 3H), 2.75-2.85 (m, 4H), 2.73 (s, 3H), 1.98 (s, 3H), 1.60 (d, 3H).

N1-((2S,3R)-3-hydroxy-4-((6-methylpyridin-2-yl)methylamino)-1-phenylbutan-2-yl)-N3-methyl-N3-((4-methylthiazol-2-yl)methyl)isophthalamide: 7.67-7.70 (m, 1H), 7.51-7.56 (m, 2H), 7.35-7.40 (m, 1H), 7.16-7.25 (m, 6H), 7.02-7.06 (m, 2H), 6.88 (s, 1H), 4.95 (s, 2H), 4.43-4.48 (m, 1H), 3.94-4.01 (m, 2H), 3.79-3.82 (m, 1H), 2.92-3.10 (m, 7H), 2.50 (s, 3H), 2.44 (s, 3H).

N1-((2S,3R)-3-hydroxy-4-(3-(methoxymethyl)benzylamino)-1-phenylbutan-2-yl)-5-(N-methylmethylsulfonamido)-N3-((R)-1-phenylethyl)isophthalamide: 8.06 (s, 1H), 7.91-7.93 (m, 1H), 7.78-7.79 (m, 1H), 7.15-7.38 (m, 14H), 5.26-5.31 (m, 1H), 4.40 (s, 2H), 4.31-4.36 (m, 1H), 3.68-3.88 (m, 3H), 3.34 (s, 3H), 3.27 (s, 3H), 2.86-2.89 (m, 2H), 2.79-2.81 (m, 2H), 2.77 (s, 3H), 1.59 (d, 3H).

N1-((2S,3R)-3-hydroxy-4-(3-(methylamino)benzylamino)-1-phenylbutan-2-yl)-5-(N-methylmethylsulfonamido)-N3-((R)-1-phenylethyl)isophthalamide: 8.31 (s, 1H), 7.91 (s, 1H), 7.83 (s, 1H), 7.37-7.44 (m, 2H), 7.07-7.25 (m, 9H), 6.57-6.60 (m, 2H), 6.47-6.49 (m, 1H), 5.26-5.31 (m, 1H), 4.29-4.33 (m, 1H), 3.95-4.00 (m, 1H), 3.75-3.89 (m, 2H), 3.22 (s, 3H), 2.78-2.82 (m, 4H), 2.73 (s, 3H), 2.72 (s, 3H), 1.64 (d, 3H).

N1-((2S,3R)-3-hydroxy-4-(4-hydroxy-3-methoxybenzylamino)-1-phenylbutan-2-yl)-5-(N-methylmethylsulfonamido)-N3-((R)-1-phenylethyl)isophthalamide: 8.09-8.10 (m, 1H), 7.84-7.86 (m, 1H), 7.73-7.74 (m, 1H), 7.35-7.39 (m, 2H), 7.09-7.29 (m, 8H), 6.88 (s, 1H), 6.72 (s, 2H), 5.20-5.24 (m, 1H), 4.16-4.21 (m, 1H), 3.79-3.93 (m, 3H), 3.75 (s, 3H), 3.25 (s, 3H), 3.09-3.15 (m, 1H), 2.79-2.93 (m, 3H), 2.81 (s, 3H), 1.57 (d, 3H).

N1-((2S,3R)-3-hydroxy-4-(3-methoxybenzylamino)-1-phenylbutan-2-yl)-N3-methyl-N3-((4-methylthiazol-2-yl)methyl)isophthalamide: 1H NMR (300 MHz, CDCl$_3$): 2.44 (s, 3H), 2.80 (d, 2H), 2.98 (d, 3H), 2.95-3.14 (m, 2H), 3.77 (s, 3H), 3.64-3.86 (m, 3H), 4.33-4.45 (m, 1H), 4.63 (bs, 0.6H), 4.95 (bs, 1.4H), 6.76-6.92 (m, 4H), 7.13-7.29 (m, 7H), 7.33-7.40 (m, 1H), 7.50-7.84 (m, 3H).

N1-(1-(4-fluorophenyl)ethyl)-N3-((2S,3R)-3-hydroxy-4-(3-methoxybenzylamnino)-1-phenylbutan-2-yl)-5-(N-methylmethylsulfonamido)isophthalamide: 1H NMR (300 MHz, CDCl$_3$+CD$_3$OD): 1.53 (d, 3H), 2.77 (2s, 3H total), 2.80-2.91 (m, 3H), 3.24 (2s, 3H total), 3.74 (2s, 3H total), 3.64-3.86 (m, 3H), 4.27-4.40 (m, 1H), 5.17-5.29 (m, 2H), 6.73-6.81 (m, 1H), 6.82-6.88 (m, 2H), 6.90-7.02 (m, 2H), 7.12-8.36 (m, 9H), 7.72-7.78 (m, 1H), 7.87-7.96 (m, 2H), 8.01-8.07 (m, 1H).

N1-((2S,3R)-4-(3-fluorobenzylamino)-3-hydroxy-1-phenylbutan-2-yl)-5-(N-methylmethylsulfonamido)-N3-((R)-1-phenylethyl)isophthalamide: 1H NMR (300 MHz, CDCl$_3$+CD$_3$OD): 1.57 (d, 3H), 2.77 (s, 3H), 2,72-2.80 (m, 2H), 2.86-2.93 (m, 2H), 3.25 (s, 3H), 3.64-3.72 (m, 1H), 3.72-3.89 (m, 2H), 4.29-4.40 (m, 1H), 5.22-5.33 (m, 1H), 6.88-7.08 (m, 4H), 7.12-7.38 (m, 11H), 7.64 (d, 1H), 7.74-7.77 (m, 1H), 7.88-7.92 (m, 1H), 7.99-8.02 (m, 1H).

N1-((2S,3R)-3-hydroxy-1-phenyl-4-((S)-1-phenylethylamino)butan-2-yl)-5-(N-methylmethylsulfonamido)-N3-((R)-1-phenylethyl)isophthalamide: m.p. 103-108° C. $^1$H NMR (300 MHz, CDCl$_3$ plus a small amount of CD$_3$OD), δ: 7.939 (s, 1H), 7.791 (s, 1H), 7.631 (s, 1H), 6.985-7.296 (m, 15H), 5.142 (m, 1H), 4.055 (m, 1H), 3.788 (m, 1H), 3.674 (m, 1H), 3.176 (s, 3H), 2.969 (m, 1H), 2.785 (s, 3H), 2.785 (m, 1H), 2.567 (m, 2H), 1.488 (d, 3H), 1.371 (d, 3H).

N1-((2S,3R)-3-hydroxy-1-phenyl-4-((S)-1-phenylethylamino)butan-2-yl)-N3-methyl-N3-((4-methylthiazol-2-yl)methyl)isophthalamide: m.p. 46-51° C. $^1$H NMR (300 MHz, CDCl$_3$ plus a small amount of CD$_3$OD), δ: 7.485 (m, 2H), 7.374 (m, 1H), 7.292 (m, 1H), 6.935-7.123 (m, 10H), 6.803 (s, 3H), 4.782 (s, 1.3H), 4.496 (s, 0.7H), 4.180 (m, 1H), 3.611 (m, 1H), 3.530 (m, 1H), 2.893-2.945 (m, 1H), 2.834 (s 3H), 2.653 (m, 1H), 2.470 (m, 2H), 2.273 (s, 3H), 1.249 (m, 3H).

N1-((2S,3R)-3-hydroxy-1-phenyl-4-((R)-1-phenylethylamino)butan-2-yl)-N3-methyl-N3-((4-methylthiazol-2-yl)methyl)isophthalamide: $^1$H NMR (300 MHz, CDCl$_3$+CD$_3$OD), δ: 7.729 (m, 2H), 7.516 (m, 1H), 7.402 (m 1H), 7.327-7.110 (m, 10H), 6.861 (s, 1H), 4.938 (br, 1.2H), 4.634 (br, 0.8H), 4.360 (m, 1H), 3.752-3.635(m, 2H), 2.980 (s 3H), 2.894-2.557(m, 4H), 2.424 (s, 3H), 1.400 (d, J=6.6 Hz, 3H).

N1-((2S,3R)-3-hydroxy-1-phenyl-4-((S)-1-phenylpropylamino)butan-2-yl)-N3-methyl-N3-((4-methylthiazol-2-yl)methyl)isophthalamide: m.p. 50-55° C. $^1$H NMR (300 MHz, CDCl$_3$ plus a small amount of CD$_3$OD, δ: 7.304-7.561 (m, 4H), 6.998-7.208 (m, 10H), 6.838 (s, 1H), 4.836 (m, 2H), 4.154 (m, 1H), 3.551 (m, 1H), 3.367 (m, 1H), 2.876-2.998 (m, 1H), 2.876 (s, 3H), 2.730 (m, 1H), 2.493 (m, 2H), 2.328 (s 3H), 1.660-1.775 (m, 1H), 1.536-1.633 (m, 1H), 0.675 (t, 3H).

N1-((2S,3R)-3-hydroxy-1-phenyl-4-((S)-1-phenylpropylamino)butan-2-yl)-5-(N-methylmethylsulfonamido)-N3-((R)-1-phenylethyl)isophthalamide: m.p. 74-77° C. $^1$H NMR (300 MHz, CDCl$_3$ plus a small amount of CD$_3$OD), δ: 7.916 (m, 1H), 7.826 (m, 1H), 7.660 (m, 1H), 7.050-7.334 (m, 15H), 5.201(m, 1H), 4.214 (m, 1H), 3.598 (m, 1H), 3.411 (m, 1H), 3.229 (s, 3H), 3.938 (m, 1H), 2.805-2.728 (m, 1H), 2.805 (s 3H), 2.527 (m, 1H), 1.699-1.835 (m, 1H), 1.575-1.672 (m, 1H), 1.523 (d, 3H), 0.710 (t, 3H).

N1-((2S,3R)-3-hydroxy-4-(3-methoxybenzylamino)-1-phenylbutan-2-yl)-5-(N-methylmethylsulfonamido)-N3-((R)-1-phenylpropyl)isophthalamide: m.p. 92-94° C. $^1$H NMR (300 MHz, CDCl$_3$ plus a small amount of CD$_3$OD), δ: 7.969 (m, 1H), 7.814 (m, 1H), 7.693 (m, 1H), 7.026-7.307 (m, 11H), 6.697-6.815 (m, 3H), 4.913 (m, 1H), 4.212 (m, 1H), 3.625-3.787 (m, 3H), 3.680 (s, 3H), 3.217 (s, 3H), 2.993 (m, 1H), 2.650-2.816 (m, 3H), 2.791 (s, 3H), 1.807-1.912 (m, 2H), 0.891 (t, 3H).

N1-((2S,3R)-4-((R)-1-(4-fluorophenyl)ethylamino)-3-hydroxy-1-phenylbutan-2-yl)-5-(N-methylmethylsulfonamido)-N3-((R)-1-phenylethyl)isophthalamide: m.p. 102-109° C. $^1$H NMR (300 MHz, CDCl$_3$ plus a small amount of CD$_3$OD), δ: 7.979 (m, 1H), 7.850 (m, 1H), 7.718 (m, 1H), 7.038-7.348 (m, 12H), 6.889-6.947 (m, 2H), 5.245 (m, 1H), 4.177-4.245 (m, 1H), 3.646-3.748 (m, 2H), 3.259 (s, 3H), 2.830 (s, 3H), 2.700-3.013 (m, 2H), 2.431-2.648 (m, 2H), 1.546 (d, 3H), 1.357 (d, 3H).

N1-((2S,3R)-4-((S)-1-(4-fluorophenyl)ethylamino)-3-hydroxy-1-phenylbutan-2-yl)-5-(N-methylmethylsulfonamido)-N3-((R)-1-phenylethyl)isophthalamide: m.p. 95-97° C. $^1$H NMR (300 MHz, CDCl$_3$ plus a small amount of CD$_3$OD), δ: 7.956 (m, 1H), 7.850 (m, 1H), 7.696 (m, 1H), 7.066-7.362 (m, 12H), 6.900-6.957 (m, 2H), 5.233 (m, 1H), 4.194-4.261 (m, 1H), 3.625-3.768 (m, 2H), 3.261 (s, 3H), 2.950-3.013 (m, 1H), 2.771-2.849 (m, 1H), 2.830 (s, 3H), 2.497-2.634 (m, 2H), 1.553 (d, 3H), 1.352 (d, 3H).

N1-((2S,3R)-3-hydroxy-1-phenyl-4-((R)-1-phenylethylamino)butan-2-yl)-5-(N-methylmethylsulfonamido)-N3-((R)-1-phenylethyl)isophthalamide: m.p. 95-99° C. $^1$H NMR (300 MHz, CDCl$_3$ plus a small amount of CD$_3$OD), δ: 8.013 (m, 1H), 7.873 (m, 1H), 7.754 (m, 1H), 7.078-7.363 (m, 15H), 5.245 (m, 1H), 4.250 (m, 1H), 3.651-3.737 (m, 2H), 3.269 (s, 3H), 2.712-2.883 (m, 2H), 2.488-2.683 (m, 2H), 2.834 (s, 3H), 1.560 (d, 3H), 1.378 (d, 3H).

N1-((2S,3R)-3-hydroxy-1-phenyl-4-((S)-1-(pyridin-3-yl)ethylamino)butan-2-yl)-5-(N-methylmethylsulfonamido)-N3-((R)-1-phenylethyl)isophthalamide: m.p. 67-85° C. $^1$H NMR (300 MHz, CDCl$_3$ plus a small amount of CD$_3$OD), δ: 8.323-8.493 (m, 2H), 8.031 (m, 1H), 7.945 (s, 1H), 7.845-7.881 (m, 1H), 7.606-7.700 (m, 1H), 7.064-7.363 (m, 10H), 5.241 (m, 1H), 4.232 (m, 1H), 3.790 (m, 1H), 3.636 (m, 1H), 3.263 (s, 3H), 2.946-3.028 (m, 1H), 2.769-2.867(m, 1H), 2.834 (s, 3H), 2.587-2.650 (m, 1H), 2.467-2.520 (m, 1H), 1.555 (d, J=7.2 Hz, 3H), 1.379 (d, J=5.3 Hz, 3H).

N1-((2S,3R)-3-hydroxy-1-phenyl-4-((R)-1-(pyridin-3-yl)ethylamino)butan-2-yl)-5-(N-methylmethylsulfonamido)-N3-((R)-1-phenylethyl)isophthalamide: $^1$H NMR (300 MHz, CDCl$_3$ plus a small amount of CD$_3$OD), δ: 8.518 (s, 1H), 8.355-8.334 (m, 2H), 8.065 (s, 1H), 7.890 (m, 1H), 7.678-7.613 (m, 2H), 7.378-7.104 (m, 10H), 5.305-5.240 (m, 1H), 4.279-4.209 (m, 1H), 3.773-3.706 (m, 1H), 3.648-3.596 (m, 1H), 3.281 (s, 3H), 3.027-2.745 (m, 2H), 2.843 (s, 3H), 2.613-2.560 (m, 1H), 2.472-2.413 (m, 1H), 1.587 (d, 3H), 1.427 (d, 3H).

N1-((2S,3R)-3-hydroxy-4-(3-methoxybenzylamino)-1-phenylbutan-2-yl)-N3-(1-(pyridin-3-yl)ethyl)isophthalamide: m.p. 84-89° C. $^1$H NMR (300 MHz, CDCl$_3$ plus a small amount of CD₃OD), δ: 8.654 (s, 1H), 8.400-8.249 (m, 3H), 7.969 (d, 1H), 7.838-7.735 (m, 2H), 7.397 (m, 1H), 7.294-7.087 (m, 6H), 6.903-6.801 (m, 3H), 5.297 (m, 1H), 4.264 (m, 1H), 3.971-3.857 (m, 3H), 3.725 (s, 3H), 3.132-2.836 (m, 4H), 1.654-1.598 (m, 3H).

1-((2S,3R)-3-hydroxy-4-(1-(3-methoxyphenyl)ethylamino)-1-phenylbutan-2-yl)-N3-(1-(3-methoxyphenyl)ethyl)-5-(N-methylmethylsulfonamido)isophthalamide: ¹H NMR (300 MHz, CDCl₃), δ: 8.031 (m, 1H), 7.933 (m, 1H), 7.786 (m, 1H), 7.287-7.117 (m, 6H), 6.984-6.706 (m, 7H), 5.257 (m, 1H), 4.361 (m, 1H), 3.767 (m, 6H), 3.608-3.725 (m, 2H), 3.299 (s, 3H), 3.2.924 (m, 1H), 2.842 (m, 1H), 2.805 (m, 3H), 2.717-2.567 (m, 2H), 1.613-1.574 (m, 3H), 1.442-1.406 (m, 3H).

N1-((2S,3R)-3-hydroxy-4-((R)-1-(3-methoxyphenyl)ethylamino)-1-phenylbutan-2-yl)-5-(N-methylmethylsulfonamido)-N3-((R)-1-phenylethyl)isophthalamide: ¹H NMR (300 MHz, CDCl₃), δ: 8.025-7.919 (m, 2H), 7.809-7.765 (m, 1H), 7.391-7.117 (m, 11H), 6.942-6.754 (m, 3H), 5.359-5.249 (m, 1H), 4.419-4.301 (m, 1H), 3.744-3.576 (m, 2H), 3.762 (d, 3H), 3.298 (s, 3H), 2.804 (s, 3H), 2.936-2.565 (m, 4H), 1.613 (d, 1.5H), 1.604 (d, 1.5H), 1.427-1.393 (m, 3H).

N1-((2S,3R)-3-hydroxy-4-((S)-1-(3-methoxyphenyl)ethylamino)-1-phenylbutan-2-yl)-5-(N-methylmethylsulfonamido)-N3-((R)-1-phenylethyl)isophthalamide: m.p. 76-82° C. ¹H NMR (300 MHz, CDCl₃), δ: 8.026-7.922 (m, 2H), 7.812-7.770 (m, 1H), 7.401-7.120 (m, 11H), 6.933-6.756 (m, 3H), 5.363-5.252 (m, 1H), 4.420-4.302 (m, 1H), 3.761-3.581 (m, 2H), 3.764 (d, 3H), 3.303 (s, 3H), 2.806 (s, 3H), 2.938-2.564 (m, 4H), 1.629-1.598 (m, 3H), 1.434-1.401 (m, 3H).

N1-((2S,3R)-3-hydroxy-4-(3-methoxybenzylamino)-1-phenylbutan-2-yl)-N3-((S)-1-(3-methoxyphenyl)ethyl)-5-(N-methylmethylsulfonamido)isophthalamide: ¹H NMR (300 MHz, CDCl₃), δ: 8.007 (m, 1H), 7.913 (m, 1H), 7.780 (m, 1H), 7.275-7.126 (m, 6H), 6.972-6.742 (m, 7H), 5.297-5.195 (m, 1H), 4.405-4.320 (m, 1H), 3.951-3.672 (m, 3H), 3.772 (s, 3H), 3.753 (s, 3H), 3.277 (s, 3H), 2.920-2.882 (m, 2H), 2.791 (s, 5H), 1.580-1.558 (m, 3H).

N1-((2S,3R)-4-(3,5-difluorobenzylamino)-3-hydroxy-1-phenylbutan-2-yl)-5-(N-methylmethylsulfonamido)-N3-((R)-1-phenylethyl)isophthalamide: ¹H NMR (300 MHz, CDCl₃), δ: 8.007 (s, 1H), 7.945 (m, 1H), 7.800 (m, 1H), 7.408-7.141 (m, 9H), 6.909-6.837 (m, 2H), 6.748-6.638 (m, 2H), 5.350-5.256 (m, 1H), 4.415-4.321 (m, 1H), 3.832 (q, J=14.1; 37.2 Hz, 2H), 3.704-3.653 (m, 1H), 3.326 (s, 3H), 2.990 (d, 2H), 2.818 (s, 3H), 2.764-2.728 (m, 2H), 1.621 (d, 3H).

N1-((2S,3R)-4-((R or S)-1-(3-fluorophenyl)ethylamino)-3-hydroxy-1-phenylbutan-2-yl)-5-(N-methylmethylsulfonamido)-N3-((R)-1-phenylethyl)isophthalamide: ¹H NMR (300 MHz, CDCl₃), δ: 8.021-7.924 (m, 2H), 7.806-7.773 (m, 1H), 7.400-7.145 (m, 10H), 7.101-6.861 (m, 3H), 6.790 (m, 1H), 5.355-5.248 (m, 1H), 4.407-4.302 (m, 1H), 3.797-3.682 (m, 1H), 3.630-3.554 (m, 1H), 3.310 (d, 3H), 2.960-2.857 (m, 2H), 2.813 (s, 3H), 2.707-2.581 (m, 2H), 1.627-1.597 (m, 3H), 1.420-1.386 (m, 3H).

N1-((2S,3R)-4-((S or R)-1-(3-fluorophenyl)ethylamino)-3-hydroxy-1-phenylbutan-2-yl)-5-(N-methylmethylsulfonamido)-N3-((R)-1-phenylethyl)isophthalamide: m.p. 84-88° C. ¹H NMR (300 MHz, CDCl₃), δ: 8.027-7.926 (m, 2H), 7.814-7.781 (m, 1H), 7.407-7.169 (m, 10H), 7.109-6.866 (m, 3H), 6.771 (m, 1H), 5.360-5.260 (m, 1H), 4.407-4.302 (m, 1H), 3.822-3.697 (m, 1H), 3.640-3.554 (m, 1H), 3.321 (d, 3H), 2.965-2.893 (m, 2H), 2.818 (m, 2H), 2.675-2.561 (m, 2H), 1.636-1.607 (m, 3H), 1.432-1.405 (m, 3H).

N1-((R or S)-i-(3-fluorophenyl)ethyl)-N3-((2S,3R)-3-hydroxy-4-(3-methoxybenzylamino)-1-phenylbutan-2-yl)-5-(N-methylmethylsulfonamido)isophthalamide: ¹H NMR (300 MHz, CDCl₃), δ: 8.116 (m, 1H), 7.941 (m, 1H), 7.806 (m, 1H), 7.334-7.038 (m, 10H), 6.979-6.869 (m, 2H), 6.824-6.768 (m, 1H), 5.313-5.213 (m, 1H), 4.390 (m, 1H), 3.893-3.742 (m, 3H), 3.764 (s, 3H), 3.300 (s, 3H), 2.939 (m, 2H), 2.803 (m, 5H), 1.625-1.571 (m, 3H).

N1-((2S,3R)-3-hydroxy-4-(3-methoxybenzylamino)-1-phenylbutan-2-yl)-N3-isopropyl-N3-((4-methylthiazol-2-yl)methyl)isophthalamide: ¹H NMR (300 MHz, CDCl₃) δ 7.69-7.18 (m, 15H), 6.91-6.79 (m, 5H), 4.90 (broad s, 1.3H), 4.64 (broad s, 0.7H) 4.41 (m, 1H), 3.96-3.69 (m, 7H), 3.00 (m, 2H), 2.81 (m, 2H), 2.43 (s, 3H), 1.29-1.16 (m, 7H).

N1-((2S,3R)-3-hydroxy-4-(3-methoxybenzylamino)-1-phenylbutan-2-yl)-N3-isobutyl-N3-((4-methylthiazol-2-yl)methyl)isophthalamide: ¹H NMR (300 MHz, CDCl₃) δ 7.77-7.22 (m, 11H), 7.15-6.81 (m, 5H), 5.00 (broad s, 1.2H), 4.66 (broad s, 0.7H), 4.40 (m, 1H), 3.88-2.83 (m, 14H), 2.46 (s, 3H), 2.20-1.96 (m, 2H), 0.99-0.70 (m, 7H).

N1-ethyl-N3-((2S,3R)-3-hydroxy-4-(3-methoxybenzylamino)-1-phenylbutan-2-yl)-N1-((4-methylthiazol-2-yl)methyl)isophthalamide: ¹H NMR (300 MHz, CDCl₃) δ 7.71-7.18 (m, 12H), 7.08-6.79 (m, 5H), 4.96 (broad s, 1.2H), 4.63 (broad s, 0.7H) 4.40 (m, 1H), 3.86-3.30 (m, 8H), 3.02-2.82 (m, 5H), 2.44 (s, 3H), 1.11 (m, 4H).

N1-benzyl-N3-((2S,3R)-3-hydroxy-4-(3-methoxybenzylamino)-1-phenylbutan-2-yl)-N1-((4-methylthiazol-2-yl)methyl)isophthalamide: ¹H NMR (300 MHz, CDCl₃) δ 7.84-7.15 (m, 17H), 6.91-6.79 (m, 4H), 4.93-4.55 (m, 4H), 4.38 (m, 1H), 3.85-3.68 (m, 6H), 3.00-2.80 (m, 5H), 2.43 (s, 3H).

N1-cyclopentyl-N3-((2S,3R)-3-hydroxy-4-(3-methoxybenzylamino)-1-phenylbutan-2-yl)-N1-((4-methylthiazol-2-yl)methyl)isophthalamide: ¹H NMR (300 MHz, CDCl₃) δ 7.71-7.19 (m, 12H), 7.06-6.81 (m, 5H), 4.88 (broad s, 2H), 4.41 (m, 1H), 4.03-3.68 (m, 7H), 3.02-2.82 (m, 4H), 2.43 (s, 4H), 1.68-1.38 (m, 8H).

N1-((2S,3R)-4-(2-fluoro-3-methoxybenzylamino)-3-hydroxy-1-phenylbutan-2-yl)-5-(N-rmethylmethylsulfonamido)-N3-((R)-1-phenylethyl)isophthalarmide: ¹H-NMR (300 MHz, CDCl3) δ 7.93 (s, 1H), 7.83 (s, 1H), 7.68 (s, 1H), 7.01-7.29 (m, 10H), 6.92 (m, 1H), 6.76-6.81 (m, 2H), 5.19 (m, 1H), 4.26 (m, 1H), 3.71-3.82 (m, 2H), 3.77 (s, 3H), 3.59-3.64 (m, 1H), 3.16 (s, 3H), 2.63-2.78 (m, 4H), 2.69 (s, 3H), 1.49 (m, 3H).

N1-((2S,3R)-4-(3-((dimethylamino)methyl)benzylamino)-3-hydroxy-1-phenylbutan-2-yl)-5-(N-methylmethylsulfonamido)-N3-((R)-1-phenylethyl)isophthalamide: 8.10 (m, 1H), 7.99 (m, 1H), 7.96 (m, 1H), 7.19-7.33 (m, 2H), 7.03-7.20 (m, 12H), 5.26 (m, 1H), 4.88 (m, 1H), 3.68 (m, 1H), 3.34-3.51 (m, 3H), 3.29 (s, 3H), 3.17 (m, 1H), 3.00-3.04 (m, 2H), 2.77-2.87 (m, 1H), 2.79 (s, 3H), 2.63-2.70 (m, 1H), 2.17 (s, 6H), 1.57 (m, 3H)

N1-((2S,3R)-4-(2-fluoro-6-methoxybenzylamino)-3-hydroxy-1-phenylbutan-2-yl)-5-(N-methylmethylsulfonamido)-N3-((R)-1-phenylethyl)isophthalamide: 7.99 (s, 1H), 7.90 (m, 1H), 7.75 (m, 1H), 7.14-7.37 (m, 10H), 6.93 (m, 1H), 6.82-6.85 (m, 1H), 6.70-6.75 (m, 1H), 5.27 (m, 1H), 4.33 (m, 1H), 3.76-3.82 (m, 2H), 3.72 (s, 3H), 3.68-3.71 (m, 1H), 3.24 (s, 3H), 2.71-2.87 (m, 4H), 2.76 (s, 3H), 1.57 (m, 3H)

N1-((2S,3R)-3-hydroxy-4-(2-morpholinoethylamino)-1-phenylbutan-2-yl)-5-(N-methylmethylsulfonamido)-N3-((R)-1-phenylethyl)isophthalamide: 8.68 (s, 1H), 8.04-8.06 (m, 1H), 8.01 (m, 1H), 7.52-7.55 (m, 2H), 7.18-7.35 (m, 8H), 5.35 (m, 1H), 4.51 (m, 1H), 4.04 (m, 1H), 3.33-3.44 (m, 4H), 3.28 (s, 3H), 3.02-3.20 (m, 4H), 2.88-2.93 (m, 2H), 2.85 (s, 3H), 2.52-2.58 (m, 2H), 2.36 (m, 2H), 2.23 (m, 2H), 1.72 (m, 3H)

N1-((2 S,3R)-3-hydroxy-1-phenyl-4-(2-(pyrrolidin-1-yl)ethylamino)butan-2-yl)-5-(N-methylmethylsulfonamido)-N3-((R)-1-phenylethyl)isophthalamide: 8.18 (s, 1H), 7.95 (m, 1H), 7.86 (m, 1H), 7.40-7.43 (m, 2H), 7.19-7.32 (m, 8H), 5.31 (m, 1H), 4.46 (m, 1H), 3.75 (m, 1H), 3.31 (s, 3H), 3.06-3.13 (m, 1H), 2.94-3.01 (m, 1H), 2.80-2.89 (m, 4H), 2.82 (s, 3H), 2.69-2.71 (m, 2H), 2.58-2.62 (m, 4H), 1.74-1.77 (m, 4H), 1.64 (m, 3H)

N1-((2S,3R)-3-hydroxy-1-phenyl-4-(2-(piperidin-1-yl)ethylamino)butan-2-yl)-5-(N-methylmethylsulfonamido)-N3-((R)-1-phenylethyl)isophthalamide: 8.12 (s, 1H), 7.95 (m, 1H), 7.86 (m, 1H), 7.23-7.40 (m, 10H), 5.31 (m, 1H), 4.46 (m, 1H), 3.69 (m, 1H), 3.31 (s, 3H), 3.06-3.13 (m, 1H), 2.91-3.00 (m, 2H), 2.70-2.88 (m, 3H), 2.81 (s, 3H), 2.43-2.48 (m, 2H), 2.32-2.39 (m, 4H), 1.62 (m, 3H), 1.48-1.58 (m, 4H), 1.39-1.42 (m, 2H)

N1-((2S,3R)-3-hydroxy-1-phenyl-4-(2-(pyrrolidin-1-yl)ethylamino)butan-2-yl)-N3-methyl-N3-((4-methylthiazol-2-yl)methyl)isophthalamide: 7.72 (m, 1H), 7.42 (m, 2H), 7.17-7.29 (m, 6H), 6.89 (s, 1H), 4.96 (m, 2H), 4.42 (m, 1H), 3.66 (m, 1H), 2.99-3.12 (m, 6H), 2.76-2.82 (m, 4H), 2.60-2.64 (m, 2H), 2.56 (m, 4H), 2.44 (s, 3H), 1.78 (s, 3H)

N1-((2S,3R)-3-hydroxy-1-phenyl-4-((1-((2-(trimethylsilyl)ethoxy)methyl)-1H-pyrrol-2-yl)methylamino)butan-2-yl)-5-(N-methylmethylsulfonamido)-N3-((R)-1-phenylethyl)isophthalamide: 8.29 (m, 1H), 8.00 (m, 1H), 7.91 (m, 1H), 7.47-7.49 (m, 2H), 7.21-7.34 (m, 8H), 6.77 (m, 1H), 6.22 (m, 1H), 6.10 (m, 1H), 5.36 (m, 1H), 5.22 (m, 2H), 4.43 (m, 1H), 3.98 (m, 2H), 3.86 (m, 1H), 3.45-3.52 (m, 2H), 3.32 (s, 3H), 2.79-3.02 (m, 4H), 2.83 (s, 3H), 1.69 (m, 3H), 0.89 (m, 2H), 0.00 (s, 9H)

N1-((2S,3R)-3-hydroxy-1-phenyl-4-((1-((2-(trimethylsilyl)ethoxy)methyl)-1H-imidazol-4-yl)methylamino)butan-2-yl)-5-(N-methylmethylsulfonamido)-N3-((R)-1-phenylethyl)isophthalamide: 7.96-7.98 (m, 2H), 7.75 (m, 1H), 7.21-7.45 (m, 11H), 6.90 (s, 1H), 5.36 (m, 1H), 5.30 (s, 2H), 4.31 (m, 1H), 3.87 (m, 2H), 3.57 (m, 1H), 3.48 (m, 2H), 3.31 (s, 3H), 3.01 (m, 2H), 2.83 (s, 3H), 2.73 (m, 2H), 1.65 (m, 3H), 3.90 (m, 2H), 0.00 (s, 9H)

N1-((2S,3R)-4-((1H-imidazol-4-yl)methylamino)-3-hydroxy-1-phenylbutan-2-yl)-5-(N-methylmethylsulfonamido)-N3-((R)-1-phenylethyl)isophthalamide: 8.18 (s, 1H), 7.91 (m, 1H), 7.79 (m, 1H), 7.18-7.47 (m, 11H), 7.03 (s, 1H), 5.28 (m, 1H), 4.24 (m, 1H), 3.91 (m, 1H), 3.29 (s, 3H), 3.27-3.33 (m, 2H), 2.83-3.18 (m, 4H), 2.87 (s, 3H), 1.62 (m, 3H)

N1-((2S,3R)-3-hydroxy-1-phenyl-4-((1-((2-(trimethylsilyl)ethoxy)methyl)-1H-imidazol-2-yl)methylamino)butan-2-yl)-5-(N-methylmethylsulfonamido)-N3-((R)-1-phenylethyl)isophthalamide: 8.19 (s, 1H), 8.01 (m, 1H), 7.84 (m, 1H), 7.17-7.34 (m, 10H), 6.94 (m, 1H), 6.90 (m, 1H), 5.33 (m, 1H), 5.25 (s, 2H), 4.40 (m, 1H), 3.74-3.94 (m, 2H), 3.60 (m, 1H), 3.48-3.55 (m, 2H), 3.29 (s, 3H), 2.93-3.00 (m, 1H), 2.79-2.90 (m, 3H), 2.81 (s, 3H), 1.55 (m, 3H), 0.89-0.95 (m, 2H), 0.00 (s, 9H)

N1-((2S,3R)-3-hydroxy-4-((3-methyl-i H-pyrazol-5-yl)methylamino)-1-phenylbutan-2-yl)-5-(N-methylmethylsulfonamido)-N3-((R)-1-phenylethyl)isophthalamide: 8.22 (s, 1H), 8.12 (m, 1H), 8.09 (m, 1H), 7.16-7.44 (m, 10H), 5.99 (s, 1H), 5.38 (m, 1H), 4.96 (m, 1H), 3.85 (m, 1H), 3.53-3.66 (m, 2H), 3.40 (s, 3H), 3.30-3.36 (m, 1H), 3.11-3.22 (m, 1H), 2.91 (s, 3H), 2.76-2.98 (m, 2H), 2.30 (s, 3H), 1.70 (m, 3H).

N1-((2S,3R)-3-hydroxy-4-((5-methylfuran-2-yl)methylamino)-1-phenylbutan-2-yl)-5-(N-methylmethylsulfonamido)-N3-((R)-1-phenylethyl)isophthalamide: ¹H NMR (300 MHz, CDCl₃), δ: 8.093 (s, 1H), 7.946 (s, 1H), 7.850 (s, 1H), 7.054-7.379 (m, 10H), 6.094 (m, 1H), 5.875 (m, 1H), 5.343-5.248 (m, 1H), 4.428-4.334 (m, 1H), 3.777-3.667 (m, 3H), 3.286 (s, 3H), 2.951-2.750 (m, 4H), 2.789 (s, 3H), 2.167 (s, 3H), 1.583 (d, J=7.2 Hz, 3H).

tert-butyl(2R,3S)-2-hydroxy-3-(3-(N-methylmethylsulfonamido)-5-((R)-1-phenylethylcarbamoyl)benzamido)-4-phenylbutyl(3-methoxybenzyl)carbamate: ¹H NMR (300 MHz, CDCl₃), δ: 7.951 (m, 1H), 7.885 (s, 1H), 7.771 (s, 1H), 7.405-7.133 (m, 11H), 6.768 (m, 3H), 5.310 (m, 1H), 4.457-4.298 (m, 3H), 3.910 (m, 1H), 3.753 (s, 3H), 3.431-3.327 (m, 2H), 3.328 (s, 3H), 2.972 (m, 2H), 2.829 (s, 3H), 1.617 (d, J=6.9 Hz, 3H), 1.490 (s, 9H).

N1-((2S,3R)-4-((S)-1-cyclohexylethylamino)-3-hydroxy-1-phenylbutan-2-yl)-5-(N-methylmethylsulfonamido)-N3-((R)-1-phenylethyl)isophthalamide: ¹H NMR (300 MHz, CDCl₃), δ: 8.622 (m, 1H), 7.956 (m, 2H), 7.514-7.126 (m, 10H), 5.307-5.215 (m, 1H), 4.230 (m, 1H), 3.849 (m, 1H), 3.274 (s, 3H), 3.079-2.812 (m, 4H), 2.698 (m, 1H), 1.713 (d, J=6.93 Hz, 3H), 1.668-1.428 (m, 3H), 1.690 (d, J=6.6 Hz, 3H), 1.253-0.862(m, 8H).

benzyl 4-(((2R,3S)-2-hydroxy-3-(3-(N-methylmethylsulfonainido)-5-((R)-1-phenylethylcarbamoyl)benzamido)-4-phenylbutylamino)methyl)piperidine-1-carboxylate: ¹H NMR (300 MHz, CDCl₃), δ: 8.105 (s, 1H), 7.901 (m, 1H), 7.792 (m, 1H), 7.405-7.139 (m, 15H), 5.326-5.231 (m, 1H), 5.108 (s, 2H), 4.377-4.278 (m, 1H), 4.202-4.078 (m, 2H), 3.748 (m, 1H), 3.256 (s, 3H), 3.024-3.608 (m, 6H), 2.777 (s, 3H), 2.584 (m, 2H), 1.711 (m, 3H), 1.612 (d, J=6.9 Hz, 3H), 1.125 (m, 2H).

N1-((R)-1-cyclohexylethyl)-N3-((2S,3R)-3-hydroxy-4-(3-methoxybenzylamino)-1-phenylbutan-2-yl)-5-(N-methylmethylsulfonamido)isophthalamide: ¹H NMR (300 MHz, CDCl₃), δ: 8.023 (s, 1H), 7.905 (s, 1H), 7.780 (m, 1H), 7.274-7.134 (m, 5H), 6.893-6.772 (m, 4H), 4.377-4.312 (m, 1H), 4.050-3.977 (m, 1H), 3.867-3.712 (m, 3H), 3.768 (s, 3H), 3.315 (s, 3H), 3.014-2.733 (m, 4H), 2.846 (s, 3H), 1.802-1.605 (m, 6H), 1.468-1.369 (m, 1H), 1.238-0.974 (m, 4H), 1.188 (d, J=6.6 Hz, 3H).

N1-((2S,3R)-3-hydroxy-1-phenyl-4-(piperidin-4-ylmethylamino)butan-2-yl)-5-(N-methylmethylsulfonamido)-N3-((R)-1-phenylethyl)isophthalamide: ¹H NMR (300 MHz, CDCl₃+CD₃OD), δ: 8.226 (s, 1H), 7.844 (s, 1H), 7.757 (s, 1H), 7.384-7.041 (m, 10H), 5.184 (m, 1H), 4.268 (m, 1H), 4.126 (m, 1H), 3.174 (m, 3H), 2.778 (s, 3H), 3.373-2.775 (m, 10H), 2.118-1.861 (m, 3H), 1.578 (d, J=6.9 Hz, 3H), 1.567-1.421 (m, 2H).

N1-((2S,3R)-3-hydroxy-1-phenyl-4-(piperidin-3-ylmethylamino)butan-2-yl)-5-(N-methylmethylsulfonamido)-N3-((R)-1-phenylethyl)isophthalamide: ¹H NMR (300 MHz, CDCl₃+CD₃OD), δ: 7.879-7.678 (m, 3H), 7.528-7.115 (m, 10H), 5.261-5.142 (m, 1H), 4.479 (m, 1H), 3.892 (m, 1H), 3.324 (s, 3H), 3.328-2.568 (m, 10H), 2.875 (s, 3H), 1.992-1.133 (m, 3H), 1.560 (d, J=6.6 Hz, 3H), 1.536-1.362 (m, 2H).

N1-((2S,3R)-3-hydroxy-4-((1-methylpiperidin-3-yl)methylamino)-1-phenylbutan-2-yl)-5-(N-methylmethylsulfonamido)-N3-((R)-1-phenylethyl)isophthalamide: ¹H NMR (300 MHz, CDCl₃+CD₃OD), δ: 7.939-7.715 (m, 3H), 7.528-7.115 (m, 10H), 5.300-5.203 (m, 1H), 3.834 (m, 1H), 3.309 (s, 3H), 3.052-2.590 (m, 6H), 2.484-2.267 (m, 4H), 2.355 (s, 3H), 2.011-1.762 (m, 3H), 1.572 (br, s, 3H), 1.536-1.362 (m, 2H).

N1-((2S,3R)-3-hydroxy-4-(((R)-1-methylpyrrolidin-2-yl)methylamino)-1-phenylbutan-2-yl)-5-(N-methylmethylsulfonamido)-N3-((R)-1-phenylethyl)isophthalamide: ¹H NMR (300 MHz, CDCl₃+CD₃OD), δ: 7.961 (s, 1H), 7.881 (m, 1H), 7.685 (m, 1H), 7.401-7.089 (m, 10H), 5.276 (m, 1H), 4.398 (m, 1H), 3.862 (m, 1H), 3.315 (s, 3H), 3.280-2.646(m, 6H), 2.840 (s, 3H), 2.278 (s, 3H), 2.356-2.117 (m, 3H), 2.019-1.674 (m, 4H), 1.583 (d, J=6.9 Hz, 3H ).

N1-((2S,3R)-3-hydroxy-4-(((R)-1-isopropylpyrrolidin-2-yl)methylamino-1-phenylbutan-2-yl)-5-(N-methylmethylsulfonamido)-N3-((R)-1-phenylethyl)isophthalamide: $^1$H NMR (300 MHz, CDCl$_3$+CD$_3$OD), δ: 7.945 (s, 1H), 7.869 (s, 1H), 7.686 (s, 1H), 7.390-7.098 (m, 10H), 5.269 (m, 1H), 4.403 (m, 1H), 3.672 (m, 1H), 3.308 (s, 3H), 3.056-2.659(m, 6H), 2.836 (s, 3H), 2.447 (m, 4H), 2.011-1.707 (m, 4H), 1.576 (d, J=6.9 Hz, 3H), 0.953 (d, J=6.3 Hz, 3H), 0.921 (d, J=6.3 Hz, 3H).

N1-((2S,3R)-3-hydroxy-4-((3-methoxycyclohexyl)methylamnino)-1-phenylbutan-2-yl)-5-(N-methylmethylsulfonamido)-N3-((R)-1-phenylethyl)isophthalamide: $^1$H NMR (300 MHz, CDCl$_3$), δ: 8.273-7.879 (m, 3H), 7.395-7.061 (m, 10H), 5.263 (m, 1H), 4.249 (m, 1H), 4.029 (m, 1H), 3.496 (m, 1H), 3.287-3.178 (m, 6H), 3.139-2.677 (m, 6H), 2.771 (s, 3H), 2.077-1.466 (m, 12H).

N1-((2S,3R)-3-hydroxy-4-((1-isobutylpiperidin-4-yl)methylamino)-1-phenylbutan-2-yl)-5-(N-methylmethylsulfonamido)-N3-((R)-1-phenylethyl)isophthalamide dihydrochloride: $^1$H NMR (300 MHz, CDCl$_3$+CD$_3$OD), δ: 8.272-7.836 (br, 3H), 7.426-7.032 (m, 10H), 5.172 (br, 1H), 4.212 (br, 1H), 3.882 (br, 1H), 3.243 (br, 9H), 2.768 (br, 7H), 1.955 (br, 5H), 1.569 (br, 3H), 1.207 (br, 2H), 0.959 (br, 6H).

N1-((2S,3R)-3-hydroxy-4-((1-(2-methoxybenzyl)piperidin-4-yl)methylamino)-1-phenylbutan-2-yl)-5-(N-methylmethylsulfonamido)-N3-((R)-1-phenylethyl)isophthalamide dihydrochloride: $^1$H NMR (300 MHz, CDCl$_3$), δ: 8.108 (m, 1H), 7.894 (m, 1H), 7.778 (m, 1H), 7.395-7.088 (m, 12H), 6.933-6.841 (m, 2H), 5.244 (m, 1H), 4.279 (m, 1H), 3.814 (m, 1H), 3.788 (s, 3H), 3.642 (s, 2H), 3.261 (s, 3H), 3.136-2.513 (m, 10H), 2.818 (s, 3H), 2.141 (m, 2H), 1.690 (m, 1H), 1.586 (d, J=7.2 Hz, 3H), 1.370 (m, 2H).

N1-((2S,3R)-3-hydroxy-4-((1-(3-methoxybenzyl)piperidin-4-yl)methylamino)-1-phenylbutan-2-yl)-5-(N-methylmethylsulfonamido)-N3-((R)-1-phenylethyl)isophthalamide: $^1$H NMR (300 MHz, CDCl$_3$), δ: 8.012 (m, 1H), 7.872 (m, 1H), 7.742 (m, 1H), 7.369-7.081 (m, 11H), 6.850-6.750 (m, 3H), 5.245 (m, 1H), 4.302-4.234 (m, 1H), 3.764 (s, 3H), 3.730 (m, 1H), 3.436 (s, 2H), 3.256 (s, 3H), 3.104-2.814 (m, 6H), 2.816 (s, 3H), 2.725 (m, 2H), 2.496 (m, 2H), 1.932 (m, 2H), 1.653 (m, 2H), 1.564 (d, J=6.9 Hz, 3H), 1.461 (m, 1H).

N1-((2S,3R)-3-hydroxy-4-(3-methoxybenzylamino)-1-phenylbutan-2-yl)-N3-((R)-1-(3-methoxyphenyl)ethyl)-5-(N-methylmethylsulfonamido)isophthalamide: $^1$H NMR (300 MHz, CDCl$_3$), δ: 8.039 (m, 1H), 7.887 (m, 1H), 7.763 (m, 1H), 7.260-7.092 (m, 7H), 6.966-6.742 (m, 6H), 5.226 (m, 1H), 4.295 (m, 1H), 3.844-3.716 (m, 8H), 3.272 (s, 3H), 3.030-2.714 (m, 4H), 2.823 (s, 3H), 1.562 (d, J=6.9 Hz, 3H).

N1-((2S,3R)-4-(benzo[d][1,3]dioxol-5-ylmethylamino)-3-hydroxy-1-phenylbutan-2-yl)-5-(N-methylmethylsulfonamido)-N3-((R)-1-phenylethyl)isophthalamide: $^1$H NMR (300 MHz, CDCl$_3$), δ: 8.100 (m, 1H), 7.901 (m, 1H), 7.790 (m, 1H), 7.404-7.108 (m, 10H), 6.800-6.696 (m, 3H), 5.896 (s, 2H), 5.273 (m, 1H), 4.316 (m, 1H), 3.806-3.684 (m, 3H), 3.280 (s, 3H), 3.024-2.714 (m, 4H), 2.815 (s, 3H), 1.597 (d, J=6.9 Hz, 3H).

N1-((2S,3R)-3-hydroxy-1-phenyl-4-(3-(trifluoromethyl)benzylamino)butan-2-yl)-5-(N-methylmethylsulfonamido)-N3-((R)-1-phenylethyl)isophthalamide: 1H NMR (300 MHz, CDCl$_3$), δ: 8.038 (m, 1H), 7.896 (m, 1H), 7.770 (m, 1H), 7.565-7.111 (m, 14H), 5.277 (m, 1H), 4.330 (m, 1H), 3.924-3.722 (m, 3H), 3.283 (s, 3H), 2.992-2.761 (m, 4H), 2.818 (s, 3H), 1.584 (d, J=6.9 Hz, 3H).

N1-((2S,3R)-4-(3-(difluoromethoxy)benzylamino)-3-hydroxy-1-phenylbutan-2-yl)-5-(N-methylmethylsulfonamido)-N3-((R)-1-phenylethyl)isophthalamide: $^1$H NMR (300 MHz, CDCl$_3$), δ: 8.020 (m, 1H), 7.888 (m, 1H), 7.764 (m, 1H), 7.384-6.975 (m, 14H), 6.746 (s, 0.3H), 6.500 (s, 0.4H), 6.253 (s, 0.3H), 5.263 (m, 1H), 4.312 (m, 1H), 3.861-3.731 (m, 3H), 3.285 (s, 3H), 3.021-2.801 (m, 2H), 2.833 (s, 3H), 2.761 (m, 2H), 1.578 (d, J=7.2 Hz, 3H).

N1-((2S,3R)-3-hydroxy-4-((S)-1-(3-methoxyphenyl)ethylamino)-1-phenylbutan-2-yl)-5-(N-methylmethylsulfonamido)-N3-((R)-1-phenylethyl)isophthalamide: $^1$H NMR (300 MHz, CDCl$_3$), δ: 7.987 (m, 1H), 7.874 (m, 1H), 7.727 (m, 1H), 7.378-7.076 (m, 11H), 6.850-6.721 (m, 3H), 5.255 (m, 1H), 4.268 (m, 1H), 3.744 (s, 3H), 3.739-3.635 (m, 2H), 3.272 (s, 3H), 3.002-2.778 (m, 2H), 2.832 (s, 3H), 2.608 (m, 2H), 1.570 (d, J=6.9 Hz, 3H), 1.377 (d, J=6.6 Hz, 3H).

N1-((2S,3R)-3-hydroxy-1-phenyl-4-(3-(trifluoromethyl)benzylamino)butan-2-yl)-N3-methyl-N3-((4-methylthiazol-2-yl)methyl)isophthalamide: $^1$H NMR (300 MHz, CDCl$_3$), δ: 7.693-7.368 (m, 8H), 7.264-7.131 (m, 5H), 6.884 (s, 1H), 4.943 (br, 1.5H), 4.638 (br, 0.5H), 4.339 (m, 1H), 3.907-3.711 (m, 3H), 3.097-2.881 (m, 5H), 2.784 (d, J=5.2 Hz, 2H), 2.430 (s, 3H).

N1-((2S,3R)-4-(3-(difluoromethoxy)benzylamino)-3-hydroxy-1-phenylbutan-2-yl)-N3-methyl-N3-((4-methylthiazol-2-yl)methyl)isophthalamide: $^1$H NMR (300 MHz, CDCl$_3$), δ: 7.693-7.116 (m, 13H), 6.876 (s, 1H), 6.753 (s, 0.28H), 6.507 (s, 0.44H), 6.261 (s, 0.28H), 4.931 (br, 1.3H), 4.627 (br, 0.7H), 4.328 (m, 1H), 3.827-3.688 (m, 3H), 3.087-2.859 (m, 5H), 2.756 (d, J=4.5 Hz, 2H), 2.417 (s, 3H).

N1-((2S,3R)-3-hydroxy-4-(2-methoxybenzylamino)-1-phenylbutan-2-yl)-N3-methyl-N3-((4-methylthiazol-2-yl)methyl)isophthalamide: $^1$H NMR (300 MHz, CDCl$_3$), δ: 7.693-7.098 (m, 10H), 6.927-6.862 (m, 4H), 4.926 (br, 1.3H), 4.623 (br, 0.7H), 4.262 (m, 1H), 4.105-3.934 (m, 3H), 3.827 (s, 3H), 3.177-2.787 (m, 5H), 2.414 (s, 3H).

N1-((2S,3R)-3-hydroxy-1-phenyl-4-(3-(trifluoromethoxy)benzylamino)butan-2-yl)-5-(N-methylmethylsulfonamido)-N3-((R)-1-phenylethyl)isophthalamide: $^1$H NMR (300 MHz, CDCl$_3$), δ: 8.021 (m, 1H), 7.890 (m, 1H), 7.765 (m, 1H), 7.378-7.072 (m, 14H), 5.266 (m, 1H), 4.330 (m, 1H), 3.860-3.714 (m, 3H), 3.276 (s, 3H), 3.001-2.698 (m, 4H), 2.826 (s, 3H), 1.569 (d, J=6.6 Hz, 3H).

N1-((2S,3R)-3-hydroxy-4-(4-methoxybenzylamino)-1-phenylbutan-2-yl)-N3-methyl-N3-((4-methylthiazol-2-yl)methyl)isophthalamide: $^1$H NMR (300 MHz, CDCl$_3$), δ: 7.673-7.353 (m, 4H), 7.266-7.112 (m, 8H), 6.877-6.812 (m, 3H), 4.924 (br, 1.4H), 4.620 (br, 0.6H), 4.292 (m, 1H), 3.827-3.702 (m, 3H), 3.751 (s, 3H), 3.073-2.735 (m, 7H), 2.410 (s, 3H).

N1-((2S,3R)-3-hydroxy-1-phenyl-4-(3-(trifluoromethoxy)benzylamino)butan-2-yl)-N3-methyl-N3-((4-methylthiazol-2-yl)methyl)isophthalamide: $^1$H NMR (300 MHz, CDCl$_3$), δ: 7.672-7.505 (m, 3H), 7.411-7.076 (m, 10H), 6.878 (s, 1H), 4.930 (br, 1.3H), 4.627 (br, 0.7H), 4.320 (m, 1H), 3.842-3.699 (m, 3H), 3.083-2.852 (m, 5H), 3.177-2.787 (m, 5H), 2.754 (d, J=4.5 Hz, 2H), 2.416 (s, 3H).

N1-((2S,3R)-3-hydroxy-1-phenyl-4-(quinolin-3-ylmethylamino)butan-2-yl)-5-(N-methylmethylsulfonamido)-N3-((R)-1-phenylethyl)isophthalamide: $^1$H NMR (300 MHz, CDCl$_3$) δ 8.91-8.92 (m, 1H), 8.03-8.07 (m, 3H), 7.93 (s, 1H), 7.69-7.75 (m, 2H), 7.64-7.69 (m, 1H), 7.50-7.55 (m, 1H), 7.32-7.41 (m, 3H), 7.17-7.29 (m, 9H), 7.04-7.06 (m, 1H), 5.31-5.38 (m, 1H), 4.34-4.44 (m, 1H), 4.13-4.17 (d, 1H), 3.90-3.95 (d, 1H), 3.64-3.70 (m, 1H), 3.30 (s, 3H), 2.96-2.99 (d, 2H), 2.72-2.84 (m, 5H), 1.94 (s, 1H), 1.62-1.65 (d, 3H).

N1-((2S,3R)-3-hydroxy-4-((3-methylisoxazol-5-yl)methylamino)-1-phenylbutan-2-yl)-N3-methyl-N3-((4-methylthiazol-2-yl)methyl)isophthalamide: $^1$H NMR (300 MHz, CDCl$_3$) δ 7.65-7.83 (m, 2H), 7.48-7.58 (m, 1H), 7.39-7.44 (m, 1H), 7.14-7.29 (m, 6H), 6.80-6.99 (m, 2H), 5.99 (s, 1H), 4.96 (s, 2H), 4.33-4.45 (m, 1H), 3.83-3.94 (m, 2H), 3.62-3.72 (m, 1H), 2.94-3.15 (m, 6H), 2.73-2.85 (m, 2H), 2.44 (s, 3H), 2.26 (s, 3H).

N1-((2S,3R)-3-hydroxy-4-(3-methoxybenzylamino)-1-phenylbutan-2-yl)-N3-methyl-5-(N-methylmethylsulfonamido)-N3-((4-methylthiazol-2-yl)methyl)isophthalamide: $^1$H NMR (300 MHz, CDCl$_3$) δ 7.72-7.77 (m, 2H), 7.63-7.66 (d, 1H), 7.16-7.32 (m, 6H), 6.89-6.92 (m, 4H), 6.79-6.82 (m, 1H), 4.95 (s, 2H), 4.32-4.44 (m, 1H), 3.78-3.90 (m, 5H), 3.65-3.75 (m, 1H), 3.33 (s, 3H), 3.01-3.18 (m, 4H), 2.97-2.99 (d, 2H), 2.76-2.89 (m, 6H), 2.45 (s, 3H).

N1-((2S,3R)-3-hydroxy-4-(3-methoxybenzylamino)-1-phenylbutan-2-yl)-4,6-dimethyl-N3-((R)-1-phenylethyl)isophthalamide: $^1$H NMR (300 MHz, CDCl$_3$) δ 7.34-7.36 (d, 3H), 7.11-7.32 (m, 7H), 7.04-7.11 (m, 1H), 7.02 (s, 1H), 6.92 (s, 1H), 6.85-6.87 (m, 2H), 6.77-6.80 (m, 1H), 6.38-6.51 (m, 1H), 6.20-6.31 (m, 1H), 5.18-5.29 (m, 1H), 4.25-4.37 (m, 1H), 3.72-3.83 (m, 5H), 3.63-3.71 (m, 1H), 3.03-3.09 (m, 1H), 2.71-2.80 (m, 5H), 2.32 (s, 3H), 2.09 (s, 3H), 1.54-1.56 (d, 3H).

N1-((2S,3R)-4-((5-ethylpyridin-3-yl)methylamnino)-3-hydroxy-1-phenylbutan-2-yl)-5-(N-methylmethylsulfonamido)-N3-((R)-1-phenylethyl)isophthalamide: $^1$H NMR (300 MHz, CDCl$_3$) δ 8.48 (s, 1H), 8.20-8.21 (d, 1H), 8.13 (s, 1H), 8.01-8.04 (d, 1H), 7.97 (s, 1H), 7.70-7.73 (m, 1H), 7.41-7.44 (m, 2H), 7.17-7.36 (m, 10H), 6.77-6.90 (m, 1H), 5.33-5.42 (m, 1H), 4.30-4.42 (m, 1H), 4.01-4.06 (d, 1H), 3.65-3.69 (d, 1H), 3.55-3.63 (m, 1H), 3.32 (s, 3H), 3.00-3.02 (d, 2H), 2.80 (s, 3H), 2.55-2.62 (m, 4H), 2.02 (s, 1H), 1.65-1.67 (d, 3H), 1.17-1.22 (d, 3H).

N1-((2S,3R)-3-hydroxy-4-((5-methylisoxazol-3-yl)methylamino)-1-phenylbutan-2-yl)-5-(N-methylmethylsulfonamido)-N3-((R)-1-phenylethyl)isophthalamide: $^1$H NMR (300 MHz, CDCl$_3$) δ 8.03 (s, 1H), 7.95 (s, 1H), 7.82 (s, 1H), 7.63-7.74 (m, 1H), 7.15-7.34 (m, 12H), 6.90-7.00 (m, 1H), 5.96 (s, 1H), 5.25-5.35 (m, 1H), 4.33-4.45 (m, 1H), 3.77-3.88 (m, 2H), 3.66-3.74 (m, 1H), 3.29 (s, 3H), 2.84-3.02 (m, 4H), 2.80 (s, 3H), 2.38 (s, 3H), 1.57-1.59 (d, 3H).

N1-((2S,3R)-3-hydroxy-4-((5-methylisoxazol-3-yl)methylamino)-1-phenylbutan-2-yl)-N3-methyl-N3-((4-methylthiazol-2-yl)methyl)isophthalamide: $^1$H NMR (300 MHz, CDCl$_3$) δ 7.63-7.84 (m, 2H), 7.52-7.63 (m, 1H), 7.40-7.45 (m, 1H), 7.17-7.30 (m, 5H), 6.90 (s, 1H), 6.69-6.86 (m, 2H), 5.97 (s, 1H), 4.97 (s, 2H), 4.34-4.40 (m, 1H), 3.85 (s, 2H), 3.61-3.71 (m, 1H), 2.96-3.16 (m, 5H), 2.80-2.81 (d, 2H), 2.45 (s, 3H), 2.38 (s, 3H), 1.82 (s, 1H).

N1-((2S,3R)-4-((5-fluoropyridin-3-yl)methylamino)-3-hydroxy-1-phenylbutan-2-yl)-5-(N-methylmethylsulfonamido)-N3-((R)-1-phenylethyl)isophthalamide: $^1$H NMR (300 MHz, CDCl$_3$) δ 8.44 (s, 1H), 8.26-8.27 (d, 1H), 8.04 (s, 1H), 7.96 (s, 1H), 7.74 (s, 1H), 7.18-7.39 (m, 14H), 6.81-6.98 (m, 1H), 5.29-5.40 (m, 1H), 4.30-4.39 (m, 1H), 4.00-4.05 (d, 1H), 3.72-3.76 (d, 1H), 3.58-3.66 (m, 1H), 3.32-3.33 (m, 3H), 2.93-3.09 (m, 2H), 2.82 (s, 3H), 2.60-2.71 (m, 2H), 1.63-1.65 (d, 3H).

4,6-difluoro-N1-((2S,3R)-3-hydroxy-4-(3-methoxybenzylamnino)-1-phenylbutan-2-yl)-N3-((R)-1-phenylethyl)isophthalamide: $^1$H NMR (300 MHz, CDCl$_3$) δ 8.70-8.73 (d, 1H), 7.72-7.74 (d, 1H), 7.36-7.37 (d, 3H), 7.16-7.33 (m, 8H), 6.96-6.98 (m, 2H), 6.73-6.84 (m, 2H), 6.62-6.66 (d, 1H), 5.28-5.39 (m, 1H), 4.36-4.47 (m, 1H), 3.88-3.95 (m, 4H), 3.73-3.84 (m, 2H), 3.64-3.73 (m, 1H), 2.94-3.12 (m, 2H), 2.88-2.93 (m, 1H), 2.75-2.81 (m, 1H), 2.00 (s, 1H), 1.57-1.59 (d, 3H).

N1-((2S,3R)-3-hydroxy-4-((5-isopropoxypyridin-3-yl)methylamino)-1-phenylbutan-2-yl)-N3-methyl-N3-((4-methylthiazol-2-yl)methyl)isophthalamide: $^1$H NMR (300 MHz, CDCl$_3$) δ 8.17 (s, 1H), 8.11 (s, 1H), 7.68-7.86 (m, 1H), 7.63-7.66 (d, 1H), 7.49-7.60 (m, 1H), 7.38-7.43 (m, 1H), 7.27-7.15 (m, 6H), 6.94-7.05 (m, 1H), 6.89 (s, 1H), 4.96 (s, 2H), 4.52-4.63 (m, 1H), 4.28-4.44 (m, 1H), 3.75-3.85 (m, 2H), 3.61-3.74 (m, 1H), 2.88-3.16 (m, 6H), 2.80 (s 3H), 2.45 (s, 3H), 1.32-1.34 (d, 6H).

N1-((2S,3R)-3-hydroxy-4-((5-isopropoxypyridin-3-yl)methylamino)-1-phenylbutan-2-yl)-5-(N-methylmethylsulfonamido)-N3-((R)-1-phenylethyl)isophthalamide: $^1$H NMR (300 MHz, CDCl$_3$) δ 8.23 (s, 1H), 8.16 (s, 1H), 8.06-8.07 (d, 1H), 7.95-8.02 (m, 1H), 7.74 (s, 1H), 7.42-7.45 (m, 2H), 7.17-7.35 (m, 12H), 7.0-7.10 (m, 1H), 5.30-5.44 (m, 1H), 4.48-4.62(m, 1H), 4.29-4.40 (m, 1H), 4.03-4.08 (d, 1H), 3.62-3.84 (m, 2H), 3.31 (s, 3H), 2.93-3.08 (m, 2H), 2.80 (s, 3H), 2.65-2.73 (m, 2H), 1.65-1.67 (d, 3H), 1.29-1.31 (d, 6H).

N1-((2S,3R)-3-hydroxy-4-((5-isopropylpyridin-3-yl)methylamino)-1-phenylbutan-2-yl)-5-(N-methylmethylsulfonamido)-N3-((R)-1-phenylethyl)isophthalamide: $^1$H NMR (300 MHz, CDCl$_3$) δ 8.49 (s, 1H), 8.25 (s, 1H), 8.17 (s, 1H), 7.93-8.05 (m, 2H), 7.74 (s, 1H), 7.42-7.50 (m, 2H), 7.14-7.35 (m, 9H), 6.99-7.02 (d, 1H), 5.32-5.43 (m, 1H), 4.29-4.41 (m, 1H), 4.03-4.08 (d, 1H), 3.60-3.82 (m, 2H), 3.31 (s, 3H), 2.98-3.00 (d, 2H), 2.76-2.94 (m, 5H), 2.62-2.69 (m, 2H), 2.03 (s, 1H), 1.65-1.67 (d, 3H), 1.20-1.26 (m, 6).

N1-((2S,3R)-3-hydroxy-4-(1-(3-methylisoxazol-5-yl)ethylamino)-1-phenylbutan-2-yl)-5-(N-methylmethylsulfonamido)-N3-((R)-1-phenylethyl)isophthalamide: $^1$H NMR (300 MHz, CDCl$_3$) δ 8.14 (s, 1H), 7.98-7.99 (m, 1H), 7.73-7.77 (m, 1H), 7.54-7.57 (d, 1H), 7.07-7.42 (m, 11H), 6.85-6.94 (m, 1H), 5.95 (s, 1H), 5.27-5.41 (m, 1H), 4.31-4.45 (m, 1H), 4.03-4.15 (m, 1H), 3.89-4.00 (m, 1H), 3.54-3.65 (m, 1H), 3.33 (s, 3H), 2.96-3.04 (m, 2H), 2.83 (s, 3H), 2.58-2.77 (m, 2H), 2.16-2.19 (m, 3H), 1.61-1.64 (m, 3H), 1.48-1.54 (m, 3H).

N1-((2S,3R)-4-((5-ethoxypyridin-3-yl)methylamino)-3-hydroxy-1-phenylbutan-2-yl)-5-(N-methylmethylsulfonamido)-N3-((R)-1-phenylethyl)isophthalamide: $^1$H NMR (300 MHz, CDCl$_3$) δ 8.23 (s, 1H), 8.16 (s, 1H), 8.04-8.10 (m, 1H), 7.97-8.04 (m, 1H), 7.95 (s, 1H), 7.73 (s, 1H), 7.42-7.44 (m, 2H), 7.12-7.33 (m, 12H), 5.29-5.41 (m, 1H), 4.28-4.40 (m, 1H), 3.95-4.08 (m, 3H), 3.63-3.82 (m, 2H), 3.28 (s, 3H), 2.88-3.06 (m, 2H), 2.79 (s, 3H), 2.63-2.70 (m, 2H), 1.64-1.66 (d, 3H), 1.34-1.39 (m, 3H).

N1-((2S,3R)-3-hydroxy-4-((5-methoxypyridin-3-yl)methylamino)-1-phenylbutan-2-yl)-N3-methyl-N3-((4-methylthiazol-2-yl)methyl)isophthalamide: $^1$H NMR (300 MHz, CDCl$_3$) δ 8.19 (s, 1H), 8.14 (s, 1H), 7.71 (s, 1H), 7.61-7.64 (m, 1H), 7.47-7.57 (m, 1H), 7.35-7.40 (m, 1H), 7.14-7.26 (m, 7H), 7.04 (s, 1H), 6.88 (s, 1H), 4.96 (s, 2H), 4.27-4.42 (m, 1H), 3.74-3.88 (m, 5H), 3.65-3.74 (m, 1H), 3.36 (s, 3H), 2.91-3.15 (m, 5H), 2.78-2.79 (d, 2H), 2.44 (s, 3H).

N1-((2S,3R)-4-((5-ethoxypyridin-3-yl)methylamino)-3-hydroxy-1-phenylbutan-2-yl)-N3-methyl-N3-((4-methylthiazol-2-yl)methyl)isophthalamide: $^1$H NMR (300 MHz, CDCl$_3$) δ 8.21 (s, 1H), 8.16 (s, 1H), 7.71-7.87 (m, 1H), 7.62-7.71 (m, 1H), 7.47-7.57 (m, 1H), 7.30-7.47 (m, 2H), 7.13-7.30 (m, 6H), 6.90 (s, 1H), 4.96 (s, 2H), 4.28-4.43 (m, 1H), 4.09-4.02 (m, 2H), 3.86-3.97 (m, 2H), 3.69-3.82 (m, 1H), 2.93-3.16 (m, 7H), 2.77-2.93 (m, 2H), 2.45 (s, 3H), 1.38-1.43 (m, 3H).

N1-((2S,3R)-3-hydroxy-4-((5-isobutylpyridin-3-yl)methylamino)-1-phenylbutan-2-yl)-5-(N-methylmethylsulfonamido)-N3-((R)-1-phenylethyl)isophthalamide: $^1$H NMR (300 MHz, CDCl$_3$) δ 8.53 (s, 1H), 8.28-8.31 (m, 1H), 8.20 (s, 1H), 7.94 (s, 1H), 7.76 (s, 1H), 7.51 (s, 1H), 7.40-7.45 (m, 2H), 7.13-7.29 (m, 11H), 5.26-5.40 (m, 1H), 4.18-4.36 (m, 1H), 4.05-4.18 (m, 1H), 3.70-3.95 (m, 2H), 3.27-3.35 (m, 1H), 3.24 (s, 3H), 2.76-3.07 (m, 7H), 2.38-2.40 (d, 2H), 1.70-1.91 (m, 2H), 1.64-1.67 (d, 2H), 0.82-0.84 (d, 6H).

N1-((2S,3R)-3-hydroxy-4-((4-methoxypyridin-2-yl)methylamino)-1-phenylbutan-2-yl)-5-(N-methylmethylsulfonamido)-N3-((R)-1-phenylethyl)isophthalamide: $^1$H NMR (300 MHz, CDCl$_3$) δ 8.40-8.53 (m, 1H), 8.20-8.27 (m, 1H), 8.00 (s, 1H), 7.84-7.98 (m, 2H), 7.31-7.45 (m, 2H), 7.08-7.31 (m, 12H), 6.66-6.75 (m, 2H), 5.26-5.39 (m, 1H), 4.36-4.52 (m, 1H), 3.59-4.04 (m, 5H), 3.26 (s, 3H), 2.81-3.30 (m, 3H), 2.78 (s, 3H), 2.02 (s, 1H), 1.59-1.61 (d, 3H).

N1-((2S,3R)-3-hydroxy-4-((5-methylpyridin-3-yl)methylamino)-1-phenylbutan-2-yl)-N3-methyl-N3-((4-methylthiazol-2-yl)methyl)isophthalamide: $^1$H NMR (300 MHz, CDCl$_3$) δ 8.36 (s, 1H), 8.32 (s, 1H), 7.72-7.81 (m, 1H), 7.63-7.66 (m, 1H), 7.51 (s, 2H), 7.36-7.41 (m, 1H), 7.00-7.26 (m, 6H), 6.88 (s, 1H), 4.95 (s, 2H), 4.28-4.42 (m, 1H), 3.61-3.91 (m, 4H), 2.89-3.11 (m, 5H), 2.71-2.89 (m, 2H), 2.44 (s, 3H), 2.30 (s, 3H), 2.02 (s, 1H).

N1-((2S,3R)-3-hydroxy-4-((5-isobutylpyridin-3-yl)methylamino)-1-phenylbutan-2-yl)-N3-methyl-N3-((4-methylthiazol-2-yl)methyl)isophthalamide: $^1$H NMR (300 MHz, CDCl$_3$) δ 8.38 (s, 1H), 8.29 (s, 1H), 7.64-7.82 (m, 1H), 7.63-7.66 (m, 1H), 7.49-7.55 (m, 1H), 7.47 (s, 1H), 7.36-7.41 (m, 1H), 7.13-7.26 (m, 7H), 7.02-7.13 (m, 1H), 6.88 (s, 1H), 4.95 (s, 2H), 3.77-3.88 (m, 2H), 3.66-3.76 (m, 1H), 2.91-3.16 (m, 6H), 2.80-2.81 (d, 2H), 2.43-2.45 (m, 5H), 1.77-1.89 (m, 1H), 0.87-0.89 (d, 6H).

N1-((2S,3R)-3-hydroxy-4-((5-isobutoxypyridin-3-yl)methylamino)-1-phenylbutan-2-yl)-N3-methyl-N3-((4-methylthiazol-2-yl)methyl)isophthalamide: $^1$H NMR (300 MHz, CDCl$_3$) δ 8.20-8.21 (d, 1H), 8.14 (s, 1H), 7.69-7.83 (m, 1H), 7.65-7.67 (d, 1H), 7.49-7.58 (m, 1H), 7.37-7.43 (m, 1H), 7.15-7.27 (m, 7H), 6.92-7.03 (m, 1H), 6.89 (s, 1H), 4.96 (s, 2H), 4.30-4.45 (m, 1H), 3.79-3.93 (m, 2H), 3.74-3.76 (d, 2H), 2.93-3.17 (m, 7H), 2.77-2.87 (m, 2H), 2.45 (s, 3H), 2.01-2.17 (m, 1H), 1.01-1.03 (d, 6H).

N1-((2S,3R)-4-((5-(dimethylamino)pyridin-3-yl)methylamino)-3-hydroxy-1-phenylbutan-2-yl)-5-(N-methylmethylsulfonamido)-N3-((R)-1-phenylethyl)isophthalamide: $^1$H NMR (300 MHz, CDCl$_3$) δ 8.35-8.38 (d, 1H), 8.24 (s, 1H), 8.01 (s, 1H), 7.95 (s, 2H), 7.80-7.86 (m, 1H), 7.73 (s, 1H), 7.38-7.45 (m, 2H), 7.13-7.31 (m, 11H), 6.88-6.97 (m, 1H), 5.26-5.44 (m, 1H), 4.28-4.39 (m, 1H), 4.17-4.28 (m, 1H), 3.93-4.06 (m, 1H), 3.60-3.82 (m, 3H), 3.26 (s, 3H), 2.97 (s, 3H), 2.82-2.91 (m, 4H), 2.77 (s, 3H), 1.64-1.66 (d, 3H).

N1-((2S,3R)-4-((5-ethylpyridin-3-yl)methylamino)-3-hydroxy-1-phenylbutan-2-yl)-N3-methyl-N3-((4-methylthiazol-2-yl)methyl)isophthalamide: $^1$H NMR (300 MHz, CDCl$_3$) δ 8.34-8.37 (m, 2H), 7.68-7.84 (m, 1H), 7.59-7.68 (m, 1H), 7.51 (s, 2H), 7.36-7.41 (m, 1H), 7.10-7.27 (m 6H), 6.99-7.10 (m, 1H), 6.88 (s, 1H), 4.95 (s, 2H), 4.29-4.43 (m, 1H), 3.77-3.87 (m, 2H), 3.63-3.76 (m, 1H), 2.90-3.16 (m, 6H), 2.79-2.81 (d, 2H), 2.58-2.65 (m, 2H), 2.44 (s, 3H), 1.19-1.25 (m, 3H).

N1-((2S,3R)-3-hydroxy-4-((5-isobutoxypyridin-3-yl)methylamino)-1-phenylbutan-2-yl)-5-(N-methylmethylsulfonamido)-N3-((R)-1-phenylethyl)isophthalamide: $^1$H NMR (300 MHz, CDCl$_3$) δ 8.24 (s, 1H), 8.18 (s, 1H), 8.00-8.13 (m, 2H), 7.95 (s, 1H), 7.73 (s, 1H), 7.42-7.44 (m, 2H), 7.10-7.36 (m, 11H), 5.28-5.42 (m, 1H), 4.19-4.39 (m, 1H), 3.99-4.19 (m, 1H), 3.62-3.85 (m, 4H), 3.28 (s, 3H), 2.88-3.08 (m, 2H), 2.79-2.84 (m, 4H), (2.64-2.76, 2H), 1.96-2.12 (1H), 1.64-1.67 (d, 3H), 0.98-1.00 (d, 6H).

N1-((2S,3R)-4-(3-ethoxybenzylamino)-3-hydroxy-1-phenylbutan-2-yl)-5-(N-methylmethylsulfonamido)-N3-((R)-1-phenylethyl)isophthalamide: $^1$H NMR (300 MHz, CDCl$_3$) δ 8.13 (s, 1H), 7.92 (s, 1H), 7.81 (s, 1H), 7.67-7.78 (m, 1H), 7.38-7.41 (m, 2H), 7.11-7.33 (m, 12H), 6.87-6.93 (m, 2H), 6.76-6.85 (m, 1H), 5.24-5.36 (m, 1H), 4.28-4.39 (m, 1H), 3.94-4.01 (m, 2H), 3.76-3.92 (m, 3H), 3.26 (s, 3H), 2.78-2.91 (m, 4H), 2.76 (s, 3H), 1.61-1.63 (d, 3H), 1.34-1.38 (m, 3H).

N1-((2S,3R)-4-(3-ethoxybenzylamino)-3-hydroxy-1-phenylbutan-2-yl)-N3-methyl-N3-((4-methylthiazol-2-yl)methyl)isophthalamide: $^1$H NMR (300 MHz, CDCl$_3$) δ 7.70-7.86 (m, 1H), 7.65-7.67 (m, 1H), 7.48-7.60 (m, 1H), 7.36-7.41 (m, 1H), 7.12-7.29 (m, 8H), 6.84-6.93 (m, 2H), 6.78-6.82 (m, 1H), 4.96 (s, 2H), 4.33-4.45 (m, 1H), 3.97-4.04 (m, 2H), 3.77-3.89 (m, 2H), 3.66-3.79 (m, 3H), 2.92-3.16 (m, 5H), 2.73-2.92 (m, 2H), 2.44 (s, 3H), 1.36-1.41 (m, 3H).

N1-((2S,3R)-3-hydroxy-4-(3-isopropoxybenzylamino)-1-phenylbutan-2-yl)-N3-methyl-N3-((4-methylthiazol-2-yl)methyl)isophthalamide: $^1$H NMR (300 MHz, CDCl$_3$) δ 7.71-7.85 (m, 1H), 7.60-7.71 (m, 1H), 7.48-7.60 (m, 1H), 7.36-7.41 (m, 1H), 7.13-7.29 (m, 7H), 6.84-6.92 (m, 3H), 6.77-6.81 (m, 1H), 4.96 (s, 2H), 4.48-4.60 (m, 1H), 4.32-4.44 (m, 1H), 3.73-3.86 (m, 2H), 3.68-3.77 (m, 3H), 2.92-3.16 (m, 5H), 2.74-2.91 (m, 2H), 2.44 (s, 3H), 1.30-1.32 (d, 6H).

N1-((2S,3R)-3-hydroxy-4-(3-isobutoxybenzylamino)-1-phenylbutan-2-yl)-N3-methyl-N3-((4-methylthiazol-2-yl)methyl)isophthalamide: $^1$H NMR (300 MHz, CDCl$_3$) δ 7.75-7.86 (m, 1H), 7.66-7.69 (m, 1H), 7.51-7.60 (m, 1H), 7.38-7.43 (m, 1H), 7.15-7.33 (m, 6H), 6.86-6.94 (m, 4H), 6.81-6.84 (m, 1H), 4.97 (s, 2H), 4.34-4.46 (m, 1H), 2.82-3.95 (m, 2H), 3.64-3.78 (m, 4H), 2.95-3.18 (m, 5H), 2.75-2.95 (m, 2H), 2.45 (s, 3H), 1.99-2.13 (m, 2H), 1.00-1.02 (d, 6H).

N1-((2S,3R)-3-hydroxy-4-((5-isopropylpyridin-3-yl)methylamino)-1-phenylbutan-2-yl)-N3-methyl-N3-((4-methylthiazol-2-yl)methyl)isophthalamide: $^1$H NMR (300 MHz, CDCl$_3$) δ 8.38 (s, 2H), 7.69-7.84 (m, 1H), 7.63-7.66 (m, 1H), 7.48-7.59 (m, 1H), 7.39-7.43 (m, 1H), 7.15-7.29 (m, 7H), 6.70-6.90 (m, 2H), 4.96 (s, 2H), 4.32-4.43 (m, 1H), 3.77-3.87 (m, 2H), 3.64-3.74 (m, 1H), 2.95-3.16 (m, 6H), 2.85-2.96 (m, 1H), 2.79-2.80 (d, 2H), 2.44 (s, 3H), 1.23-1.26 (d, 6H).

N1-((2S,3R)-4-(3-ethylbenzylamino)-3-hydroxy-1-phenylbutan-2-yl)-5-(N-methylmethylsulfonamido)-N3-((R)-1-phenylethyl)isophthalamide: $^1$H NMR (300 MHz, CDCl$_3$): 1.18 (t, 3H, J=7.2 Hz), 1.58 (d, 3H, J=6.9 Hz), 2.56-2.84 (m, 9H), 3.21 (s, 3H), 3.67-3.85(m, 3H), 4.29-4.40(m, 1H), 5.23-5.32 (m, 1H), 7.05-7.36(m, 14H), 7.79(s, 1H), 7.91 (s, 1H), 8.06(s, 1H).

N1-((2S,3R)-3-hydroxy-4-(3-isopropylbenzylamino)-1-phenylbutan-2-yl)-5-(N-methylmethylsulfonamido)-N3-((R)-1-phenylethyl)isophthalamide: $^1$H NMR (300 MHz, CDCl$_3$): 1.19 (s, 3H), 1.21(s, 3H), 1.59(d, 3H, J=6.6 Hz), 2.77-2.94(m, 8H), 3.27 (s, 3H), 3.72-3.88(m, 3H), 4.22-4.41 (m, 1H), 5.26-5.33 (m, 1H), 7.11-7.39 (m, 14H), 7.77 (s, 1H), 7.92 (s, 1H), 8.07(s, 1H).

2-fluoro-2-fluoro-N1-((2S,3R)-3-hydroxy-4-(3-methoxybenzylamino)-1-phenylbutan-2-yl)-N3-methyl-N3-((4-methylthiazol-2-yl)methyl)isophthalamide: $^1$H NMR (300 MHz, CDCl$_3$): 2.85 (s, 3H), 2.90-3.18 (m, 7H), 3.81(s, 3H), 3.99-4.60 (m, 5H), 4.92-5.30 (m, 3H), 6.86(m, 4H), 7.17-7.45 (m, 7H), 7.45-7.52 (m, 1H), 7.81-7.83 (m, 1H).

N1-((2S,3R)-3-hydroxy-4-(3-isopropylbenzylamino)-1-phenylbutan-2-yl)-N3-methyl-N3-((4-methylthiazol-2-yl)methyl)isophthalamide: $^1$H NMR (300 MHz, CDCl$_3$): 1.21

(s, 3H), 1.23 (s, 3H), 2.44 (s, 3H), 2.75-3.20 (m, 8H), 3.63-3.86 (m, 3H), 4.35-4.43 (m, 1H), 4.92(s, 2H), 6.82 (s, 1H), 7.12-7.25 (m, 10H), 7.38-7.42 (m, 1H), 7.7.46-7.83(m, 2H).

N1-((2S,3R)-4-(3-(fluoromethyl)benzylamino)-3-hydroxy-1-phenylbutan-2-yl)-5-(N-methylmethylsulfonamido)-N3-((R)-1-phenylethyl)isophthalamide: $^1$H NMR (300 MHz, CDCl$_3$): 1.62 (d, 3H, J=7.2 Hz), 2.80-3.25 (m, 7H), 3.31 (s, 3H), 3.64-3.93 (m, 3H), 4.15-4.39 (m, 1H), 5.23-5.41 (m, 3H), 7.16-7.46 (m, 14H), 7.80 (s, 1H), 7.93 (s, 1H), 8.03 (s, 1H).

N1-((2S,3R)-4-(3-(fluoromethyl)benzylamino)-3-hydroxy-1-phenylbutan-2-yl)-N3-methyl-N3-((4-methylthiazol-2-yl)methyl)isophthalamide: $^1$H NMR (300 MHz, CDCl$_3$): 2.41 (s, 3H), 2.78-3.08 (m, 7H), 3.74-3.85 (m, 3H), 4.26-4.36 (m, 1H), 4.93 (s, 2H), 5.24-5.41 (d, 2H, J=47.4 Hz), 6.88 (s, 1H), 7.15-7.41 (m, 10H), 7.53-7.66 (m, 3H).

N1-((2S,3R)-4-(3-ethylbenzylamino)-3-hydroxy-1-phenylbutan-2-yl)-N3-methyl-N3-((4-methylthiazol-2-yl)methyl)isophthalamide: $^1$H NMR (300 MHz, CDCl$_3$):1.17-1.22 (t, 3H, J=7.8 Hz), 2.43 (s, 3H), 2.57-2.65 (q, 2H, J=7.8 Hz), 2.75-3.10 (m, 7H), 3.71-3.83 (m, 3H), 4.32-4.41 (m, 1H), 4.95 (s, 2H), 6.87 (s, 1H), 7.13-7.23 (m, 10H), 7.35-7.40 (m, 1H), 7.63-7.73 (m, 2H).

3-(2,2-dimethyl-1-((4-methylthiazol-2-yl)methyl)hydrazinecarbonyl)-N-((2S,3R)-3-hydroxy-4-(3-methoxybenzylamino)-1-phenylbutan-2-yl)benzamide: $^1$H NMR (300 MHz, CDCl$_3$): 2.43 (s, 3H), 2.72-3.02 (m, 4H), 3.43 (s, 6H), 3.46-3.73 (m, 6H), 4.28-4.38 (m, 1H), 5.17 (s, 2H), 6.75-6.88 (m, 4H), 6.99 (s, 1H), 7.09-7.26 (m, 6H), 7.66-7.69 (m, 1H), 7.99-8.02 (m, 1H), 8.17 (s, 1H).

N1-((2S,3R)-3-hydroxy-4-(3-methoxyphenethylamino)-1-phenylbutan-2-yl)-N3-methyl-N3-((4-methylthiazol-2-yl)methyl)isophthalamide: $^1$H NMR (300 MHz, CDCl$_3$): 2.42 (s, 3H), 2.79-3.16 (m, 11H), 3.76 (s, 3H), 3.81-3.90 (m, 1H), 4.25-4.34 (m, 1H), 4.93 (s, 2H), 6.73-6.78 (m, 3H), 6.88 (s, 1H), 7.13-7.25 (m, 7H), 7.42-7.46 (m, 1H), 7.69-7.72 (m, 2H).

N1-((2S,3R)-3-hydroxy-4-(4-methoxyphenethylamino)-1-phenylbutan-2-yl)-5-(N-methylmethylsulfonamido)-N3-((R)-1-phenylethyl)isophthalamide: $^1$H NMR (300 MHz, CDCl$_3$): 1.54 (d, 3H, J=7.2 Hz), 2.67-2.87 (m, 11H), 3.17 (s, 3H), 3.67 (s, 3H), 3.71-3.78 (s, 1H), 4.22-4.36 (m, 1H), 5.13-5.25 (m, 1H), 6.69-6.71 (d, 2H, J=7.4 Hz), 6.97-7.33 (m, 13H), 7.73 (s, 1H), 7.84 (s, 1H), 8.10 (s, 1H).

N1-((2S,3R)-3-hydroxy-4-(2-methoxyphenethylamino)-1-phenylbutan-2-yl)-5-(N-methylmethylsulfonamido)-N3-((R)-1-phenylethyl)isophthalamide: $^1$H NMR (300 MHz, CDCl$_3$): 1.69 (d, 3H, J=7.2 Hz), 2.78 (s, 3H), 2.97-3.31 (m, 11H), 3.73 9s, 3H), 3.89-4.16 (m, 1H), 4.35-4.43 (m, 1H), 5.22-5.34 (m, 1H), 6.76-6.81 (m, 1H), 7.02-7.25 (m, 14H), 7.46-7.49 (m, 1H), 7.95-7.98 (m, 1H), 8.57 (s, 1H).

N1-((2S,3R)-3-hydroxy-4-(3-isobutylbenzylamino)-1-phenylbutan-2-yl)-5-(N-methylmethylsulfonamido)-N3-((R)-1-phenylethyl)isophthalamide: $^1$H NMR (300 MHz, CDCl$_3$): 0.79 (d, 6H, J=6.2 Hz), 1.53 (d, 3H, J=7.2 Hz), 1.64-1.82 (m, 1H), 2.34-2.82 (m, 9H), 3.21 (s, 3H), 3.67-3.3.82 (m, 3H), 4.22-4.39 (m, 1H), 5.12-5.30, m, 1H), 6.97-7.30 (m, 14H), 7.74 (s, 1H), 7.85 (s, 1H), 8.00 (s, 1H).

N1-((2S,3R)-3-hydroxy-4-(3-methoxybenzylamino)-1-phenylbutan-2-yl)-N3-methyl-N3-((R)-1-(4-methylthiazol-2-yl)ethyl)isophthalamide: $^1$H NMR (300 MHz, CDCl$_3$): 1.88-1.94 (br d, 3H), 2.65 (s, 3H), 2.98-3.36 (m, 7H), 3.93-4.07 (m, 6H), 4.30-4.33 (m, 1H), 4.46-4.54 (m, 1H), 6.99-7.17 (m, 3H), 7.33-7.47 (m, 4H), 7.33-7.47 (m, 4H), 7.63-7.68 (m, 1H), 7.89-7.93 (m, 2H).

N1-((2S,3R)-3-hydroxy-4-(3-isobutylbenzylamino)-1-phenylbutan-2-yl)-N3-methyl-N3-((4-methylthiazol-2-yl)methyl)isophthalamide: $^1$H NMR (300 MHz, CDCl$_3$): 0.9 (d, 6H, J=6.2 Hz), 1.78-1.92 (m, 1H), 2.45 (s, 3H), 2.74-3.16 (m, 9H), 3.78-3.92 (m, 3H), 4.30-4.38 (m, 1H), 4.93 (s, 2H), 6.84-7.35 (m, 11H), 7.44-7.59 (m, 1H), 7.72-7.76 (m, 2H).

N1-((2S,3R)-3-hydroxy-4-(3-(3-methoxy-4-methylphenyl)propylamino)-1-phenylbutan-2-yl)-5-(N-methylmethylsulfonamido)-N3-((R)-1-phenylethyl)isophthalamide: $^1$H NMR (300 MHz, CDCl$_3$): 1.63 (d, 3H, J=7.3 Hz), 1.82-2.12 (m, 6H), 2.34-2.62 (m, 3H), 2.82-2.94 (m, 7H), 2.96-3.10 (m, 2H), 3.82 (s, 3H), 4.68-4.73 (m, 1H), 5.21-5.30 (m, 1H), 6.60 (s, 1H), 7.26-7.30 (m, 12H), 8.36-8.38 (m, 2H), 8.96 (s, 1H).

N1-((2S,3R)-1-(3,5-difluorophenyl)-3-hydroxy-4-(3-methoxybenzylamnino)butan-2-yl)-N3-methyl-N3-((4-methylthiazol-2-yl)methyl)isophthalamide: $^1$H NMR (300 MHz, CDCl$_3$): 2.40 (s, 3H), 2.72-2.85 (m, 3H), 2.98-3.06 (m, 4H), 3.67-3.84 (m, 6H), 4.22-4.28 (m, 1H), 4.93 (s, 2H), 6.53-6.77 (m, 1H), 6.78-7.05 (m, 6H), 7.24-7.26 (m, 1H), 7.38-7.43 (m, 1H), 7.69-7.72 (m, 2H).

N1-((2S,3R)-1-(3,5-difluorophenyl)-3-hydroxy-4-(3-methoxybenzylamino)butan-2-yl)-5-(N-methylmethylsulfonamido)-N3-((R)-1-phenylethyl)isophthalamide: $^1$H NMR (300 MHz, CDCl$_3$): 1.61 (d, 3H, J=7.2Hz), 2.71-2.87 (m, 7H), 3.31 (s, 3H), 3.71-3.90 (m, 6H), 4.25-4.36 (m, 1H), 5.22-5.33 (m, 1H), 6.58-6.91 (m, 7H), 7.18-7.27 (m, 5H), 7.83 (s, 1H), 7.94 (s, 1H), 8.03 (s, 1H).

N1-((2S,3R)-3-hydroxy-4-(3-methoxybenzylamino)-1-(thiazol-4-yl)butan-2-yl)-5-(N-methylmethylsulfonamido)-N3-((R)-1-phenylethyl)isophthalamide: $^1$H NMR (300 MHz, CDCl$_3$): 1.62 (d, 3H, J=7.2 Hz), 2.65-2.80 (m, 5H), 3.01-3.05 (m, 1H), 3.19-3.41 (m, 4H), 3.71-3.83 (m, 6H), 4.08-4.34 (m, 1H), 5.29-5.38 (m, 1H), 6.76-6.96 (m, 4H), 7.14-7.25 (m, 6H), 8.01 (s, 1H), 8.05 (s, 1H), 8.18 (s, 1H), 8.75 (s, 1H).

N1-((2S,3R)-3-hydroxy-4-(3-hydroxy-4-methoxyphenethylamino)-1-phenylbutan-2-yl)-5-(N-methylmethylsulfonamido)-N3-((R)-1-phenylethyl)isophthalamide: $^1$H NMR (300 MHz, CDCl$_3$): 1.63 (d, 3H, J=7.2 Hz), 2.60-2.89 (m, 11H), 3.18 (s, 3H), 3.64-3.78 (m, 4H), 4.22-4.34 (s, 1H), 5.14-5.32 (m, 1H), 6.51-6.67 (m, 3H), 7.06-7.38 (m, 10H), 7.69 (s, 1H), 7.86 (s, 1H), 8.10 (s, 1H).

N1-((2S,3R)-4-(3-ethynylbenzylamino)-3-hydroxy-1-phenylbutan-2-yl)-5-(N-methylmethylsulfonamido)-N3-((R)-1-phenylethyl)isophthalamide: $^1$H NMR (300 MHz, CDCl$_3$): 1.62 (d, 3H, J=7.2 Hz), 2.74-2.94 (m, 7H), 3.28 (s, 1H), 3.30 (s, 3H), 3.71-3.88 (m, 3H), 4.32-4.38 (m, 1H), 5.25-5.34 (m, 1H), 7.17-7.44 (m, 14H), 7.80 (s, 1H), 7.92 (s, 1H), 8.05 (s, 1H).

N1-((2S,3R)-4-(3-ethynylbenzylamino)-3-hydroxy-1-phenylbutan-2-yl)-N3-methyl-N3-((4-methylthiazol-2-yl)methyl)isophthalamide: $^1$H NMR (300 MHz, CDCl$_3$): 2.21 (s, 3H), 2.54-2.86 (m, 10H), 3.49-3.61 (m,3H), 4.07-4.13 (m, 1H), 4.72 (s, 2H), 6.67 (s, 1H), 6.95-7.22 (m, 10H0, 7.40-7.46 (m, 3H).

N1-((2S,3R)-4-(benzylamino)-3-hydroxy-1-phenylbutan-2-yl)-N3-methyl-N3-((4-methylthiazol-2-yl)methyl)isophthalamide: $^1$H NMR (300 MHz, CDCl$_3$): 2.43 (s, 3H), 2.80-3.09 (m, 7H), 3.63-3.87 (m, 3H), 4.28-4.37 (m, 1H), 4.94 (s, 2H), 6.88 (s, 1H), 7.21-7.70 (m, 14H).

N1-((2S,3R)-3-hydroxy-4-(2-methoxyphenethylamino)-1-phenylbutan-2-yl)-N3-methyl-N3-((4-methylthiazol-2-yl)methyl)isophthalamide: $^1$H NMR (300 MHz, CDCl$_3$): 2.40 (s, 3H), 2.85-3.19 (m, 11H), 3.66-3.78 (m, 4H), 4.23-4.32 (m, 1H), 4.91 (s, 2H), 6.81-6.87 (m, 4H), 7.09-7.20 (m, 7H), 7.39-7.43 (m, 1H), 7.69-7.72 (m, 2H).

N1-((2S,3R)-3-hydroxy-4-(4-methoxyphenethylamino)-1-phenylbutan-2-yl)-N3-methyl-N3-((4-methylthiazol-2-yl)methyl)isophthalamide: $^1$H NMR (300 MHz, CDCl$_3$): 2.41 (s, 3H), 2.72-3.19 (m, 11H), 3.75 (s, 3H), 3.82-3.92 (s, 1H), 4.59-4.68 (m, 1H), 4.93 (s, 1H), 6.79-6.88 (m, 3H), 7.08-7.27 (m, 8H), 7.40-7.44 (m, 1H), 7.69-7.72 (m, 2H).

N1-((2S,3R)-3-hydroxy-4-(3-methoxybenzylamino)-1-phenylbutan-2-yl)-N3-methyl-N3-((4-methylthiazol-2-yl)methyl)-5-nitroisophthalamide: $^1$H NMR (300 MHz, CDCl$_3$): 2.41 (s, 3H), 2.70-2.98 (m, 2H), 2.98-3.18 (m, 5H), 3.70-3.73 (m, 6H), 4.25-4.30 (m, 1H), 4.92 (s, 2H), 6.74-6.89 (m, 4H), 7.10-7.22 (m, 6H), 8.03 (s, 1H), 8.35 (s, 1H), 8.52 (s, 1H).

N1-((2S,3R)-3-hydroxy-4-(3-methoxybenzylamino)-1-phenylbutan-2-yl)-5-(methylsulfonylmethyl)-N3-((R)-1-phenylethyl)isophthalamide: $^1$H NMR (300 MHz, CDCl$_3$): 1.67 (d, 3H, J=7.2 Hz), 2.78 (s, 3H), 2.86-2.97 (m, 4H), 3.80-3.94 (m, 6H), 4.20 (s, 2H), 4.42-4.46 (m, 1H), 5.30-5.39 (m, 1H), 6.85-6.96 (m, 3H), 7.21-7.47 (m, 11H), 7.78 (s, 1H), 7.94 (s, 1H), 8.19 (s, 1H).

N1-((2S,3R)-3-hydroxy-4-(N-(3-methoxybenzyl)-4-(2-morpholinoethylamino)-4-oxobutanamido)-1-phenylbutan-2-yl)-5-(N-methylmethylsulfonamido)-N3-((R)-1-phenylethyl)isophthalamide: $^1$H NMR (300 MHz, CDCl$_3$+CD$_3$OD): 1.60 (d, 3H, J=7.2 Hz), 2.34-2.67 (m, 10H), 2.84 (s, 3H), 2.96-3.04 (m, 2H), 3.20-3.36 (m, 2H), 3.32 (s, 3H), 3.40-3.49 (m, 1H), 3.60-3.76 (m, 5H), 3.76 (s, 3H), 3.90-4.06 (m, 1H), 4.32-4.45 (m, 1H), 4.58-4.64 (m. 2H) 5.26-5.38 (m, 1H), 6.46-6.68 (m, 1H), 6.66-6.95 (m, 4H), 7.10-7.42 (m, 10H), 7.86-7.89 (m, 1H), 7.96-7.99 (m, 1H), 8.04-8.08 (m, 1H).

N1-((2S,3R)-3-hydroxy-4-(N-(3-methoxybenzyl)-4-oxo-4-(pyridin-3-ylmethylamino)butanamido)-1-phenylbutan-2-yl)-5-(N-methylmethylsulfonamido)-N3-((R)-1-phenylethyl)isophthalamide: $^1$H NMR (300 MHz, CDCl$_3$+CD$_3$OD): 1.48 (d, 3H, J=6.6 Hz), 2.34-3.32 (m, 6H), 2.80 (s, 3H), 3.22 (s, 3H), 3.76 (s, 3H), 3.80-4.78 (m, 8H), 5.20-5.32 (m, 1H), 6.64-6.82 (m, 3H), 7.00-7.36 (m, 12H), 7.42-8.48 (m, 6H)

N1-((2S,3R)-3-hydroxy-4-(N-(3-methoxybenzyl)-5-oxo-5-(pyridin-3-ylmethylamino)pentanamido)-1-phenylbutan-2-yl)-5-(N-methylmethylsulfonamnido)-N3-((R)-1-phenylethyl)isophthalamide: $^1$H NMR (300 MHz, CDCl$_3$+CD$_3$OD): 1.60 (d, 3H, J=7.2 Hz), 1.88-2.20 (m, 2H), 2.24-2.42 (m, 4H), 2.80 (s, 3H), 2.82-3.44 (m, 2H), 3.26 (s, 3H), 3.64-3.76 (m, 1H), 3.76 (s, 3H), 3.80-4.02 (m, 1H), 4.20-4.58 (m, 4H), 5.22-5.36 (m, 1H), 6.60-6.82 (m, 4H), 7.06-7.40 (m, 13H), 7.50-8.41 (m, 5H).

N1-((2S,3R)-3-hydroxy-4-(N-(3-methoxybenzyl)-5-(2-morpholinoethylamino)-5-oxopentanamido)-1-phenylbutan-2-yl)-5-(N-methylmethylsulfonamido)-N3-((R)-1-phenylethyl)isophthalamide: 1H NMR (300 MHz, CDCl$_3$+CD$_3$OD): 1.59 (d, 3H, J=6.6 Hz), 1.88-2.00 (m, 2H), 2.20-2.29 (m, 4H), 2.31-2.52 (m, 6H), 2.82 (s, 3H), 2.92-3.08 (m, 2H), 3.20-3.38 (m, 2H), 3.29 (s, 3H), 3.40-3.60 (m, 2H), 3.64-3.74 (m, 4H), 3.76 (s, 3H), 3.92-4.04 (m, 1H), 4.28-4.40 (m, 1H), 4.58-4.64 (m. 2H) 5.23-5.36 (m, 1H), 6.20-6.35 (m, 1H), 6.62-6.80 (m, 4H), 7.10-7.40 (m, 10H), 7.86-7.89 (m, 1H), 7.95-7.98 (m, 1H), 7.98-8.00 (m, 1H).

N1-((2S,3R)-3-hydroxy-4-(N-(3-methoxybenzyl)-5-(4-methylpiperazin-1-ylamino)-5-oxopentanamido)-1-phenylbutan-2-yl)-5-(N-methylmethylsulfonamnido)-N3-((R)-1-phenylethyl)isophthalamide: $^1$H NMR (300 MHz, CDCl$_3$+CD$_3$OD): 1.57 (d, 3H, J=6.6 Hz), 1.84-2.00 (m, 2H), 2.24-3.16 (m, 17H), 2.80 (s, 3H), 3.26 (s, 3H), 3.40-3.60 (m, 2H), 3.74 (s, 3H), 3.92-4.12 (m, 1H), 4.20-4.72 (m, 3H), 5.22-5.38 (m, 1H), 6.56-6.80 (m, 3H), 7.02-7.24 (m, 11H), 7.74-8.22 (m, 3H).

N1-((2S,3R)-3-hydroxy-4-(N-(3-methoxybenzyl)-5-oxo-5-(2-(piperidin-1-yl)ethylamino)pentanamido)-1-phenylbutan-2-yl)-5-(N-methylmethylsulfonamido)-N3-((R)-1-phe-nylethyl)isophthalamide: $^1$H NMR (300 MHz, CDCl$_3$+CD$_3$OD): 1.56 (d, 3H, J=6.6 Hz), 1.84-2.00 (m, 2H), 2.24-3.16 (m, 19H), 2.81 (s, 3H), 3.28 (s, 3H), 3.40-3.60 (m, 2H), 3.74 (s, 3H), 3.92-4.12 (m, 1H), 4.20-4.72 (m, 3H), 5.20-5.38 (m, 1H), 6.56-6.80 (m, 3H), 7.02-7.24 (m, 11H), 7.74-8.22 (m, 3H)

2-(3,4-bis(benzyloxy)-5-oxo-2,5-dihydrofuran-2-yl)-2-hydroxyethyl 4-(((2R,3S)-2-hydroxy-3-(3-(N-methylmeth-ylsulfonamido)-5-((R)-1-phenylethylcarbamoyl)benza-mido)-4-phenylbutyl)(3-methoxybenzyl)amino)-4-oxobutanoate: $^1$H NMR (300 MHz, CDCl$_3$+CD$_3$OD): 1.56 (m, 3H), 1.88-2.06 (m, 2H), 2.24-2.60 (m, 4H), 2.77 (s, 3H), 2.90-3.80 (m, 2H), 3.25 (s, 3H), 3.75 (s, 3H), 3.92-4.68 (m, 8H), 4.78-5.34 (m, 5H), 6.60-6.82 (m, 3H), 7.04-7.42(m, 21H), 7.74-8.26 (m, 3H)

2-(3,4-dihydroxy-5-oxo-2,5-dihydrofuran-2-yl)-2-hydroxyethyl 4-(((2R,3S)-2-hydroxy-3-(3-(N-methylmethyl-sulfonamido)-5-((R)-1-phenylethylcarbamoyl)benzamido)-4-phenylbutyl)(3-methoxybenzyl)amino)-4-oxobutanoate: $^1$H NMR (300 MHz, CDCl$_3$+CD$_3$OD): 1.55 (d, 3H, J=6.6 Hz), 2.40-3.42 (m, 9H), 2.83 (s, 3H), 3.25 (s, 3H), 3.74 (s, 3H), 3.90-4.36 (m, 5H), 4.60-4.74 (m, 2H), 5.18-5.28 (m, 1H), 6.60-6.80 (m, 3H), 7.04-7.39(m, 11H), 7.58-8.00 (m, 3H)

N1-((2S,3R)-3-hydroxy-4-(3-methoxybenzylamino)-1-phenylbutan-2-yl)-N3-((R)-1-(4-(hydroxymethyl)oxazol-2-yl)ethyl)-5-(N-methylmethylsulfonamido)isophthalarnide: $^1$H NMR (300 MHz, CDCl$_3$+CD$_3$OD): 1.59 (d, 3H, J=7.2 Hz), 2.60-3.02 (m, 4H), 2.83 (s, 3H), 3.26 (s, 3H), 3.66-3.82 (m, 3H), 3.73 (s, 3H), 4.24-4.36 (m, 1H), 4.44 (s. 2H) 5.32-5.42 (m, 1H), 6.74-6.83 (m, 3H), 7.04-7.24 (m, 6H), 7.53 (s. 1H) 7.75-7.77 (m, 1H), 7.92-7.96 (m, 1H), 8.05-8.08 (m, 1H).

N1-((2S,3R)-3-hydroxy-4-(3-methoxybenzylamino)-1-phenylbutan-2-yl)-N3-((4-(hydroxymethyl)oxazol-2-yl)methyl)-5-(N-methylmethylsulfonamido)isophthalaiide: $^1$H NMR (300 MHz, CDCl$_3$+CD$_3$OD): 2.70-3.08 (m, 4H), 2.84 (s, 3H), 3.27 (s, 3H), 3.68-3.85 (m, 3H), 3.73 (s, 3H), 4.26-4.35 (m, 1H), 4.46 (s. 2H), 4.64 (s. 2H), 6.74-6.88 (m, 3H), 7.07-7.24 (m, 6H), 7.53 (s. 1H) 7.75-7.77 (m, 1H), 7.93-7.96 (m, 1H), 8.05-8.08 (m, 1H).

N1-((2S,3R)-3-hydroxy-4-(3-methoxybenzylamino)-1-phenylbutan-2-yl)-5-(N-methylmethylsulfonamido)-N3-((R)-1-(4-methyloxazol-2-yl)ethyl)isophthalamide: $^1$H NMR (300 MHz, CDCl$_3$+CD$_3$OD): 1.63 (d, 3H, J=7.2 Hz), 2.70-3.04 (m, 4H), 2.85 (s, 3H), 3.31 (s, 3H), 3.74-3.88 (m, 3H), 3.75 (s, 3H), 4.32-4.39 (m, 1H), 5.36-5.44 (m, 1H), 6.76-6.90 (m, 3H), 7.12-7.26 (m, 6H), 7.30-7.32 (m. 1H) 7.83-7.84 (m, 1H), 7.97-7.99 (m, 1H), 8.10-8.12 (m, 1H).

N1-((2S,3R)-3-hydroxy-4-(3-methoxybenzylamino)-1-phenylbutan-2-yl)-N3-methyl-N3-((4-methyloxazol-2-yl)methyl)isophthalamide: $^1$H NMR (300 MHz, CDCl$_3$+CD$_3$OD): 2.17 (s, 3H), 2.74-3.16 (m, 7H) 3.64-3.90 (m, 3H), 3.78 (s, 3H), 4.34-4.44 (m, 1H), 4.77-4.84 (m, 2H), 6.79-6.96 (m, 3H), 7.00-7.50 (m, 7H), 7.50-7.89 (m. 4H).

N1-((2S,3R)-3-hydroxy-4-((R)-2-hydroxy-1-phenylethy-lamino)-1-phenylbutan-2-yl)-5-(N-methylmethylsulfona-mido)-N3-((R)-1-phenylethyl)isophthalamide: $^1$H NMR (300 MHz, CDCl$_3$+CD$_3$OD): 1.58 (d, 3H, J=6.6 Hz), 2.50-3.04 (m, 4H), 2.84 (s, 3H), 3.28 (s, 3H), 3.62-3.86 (m, 4H), 4.30-4.38 (m, 1H), 5.20-5.32 (m, 1H), 7.04-7.20 (m, 15H), 7.76-7.78 (m, 1H), 7.85-7.87 (m, 1H), 8.05-8.08 (m, 1H).

N1-((2,5-dimethyloxazol-4-yl)methyl)-N3-((2S,3R)-3-hydroxy-4-(3-methoxybenzylamino)-1-phenylbutan-2-yl)-N1-methylisophthalamide: $^1$H NMR (300 MHz, CDCl$_3$+CD$_3$OD): 2.24-2.60 (m, 6H), 2.76-3.14 (m, 7H) 3.64-3.88 (m, 3H), 3.76 (s, 3H), 4.28-4.36 (m, 1H), 4.40-4.60 (m, 2H), 6.79-6.92 (m, 3H), 7.00-7.50 (m, 6H), 7.50-7.89 (m. 4H).

N1-((2S,3R)-3-hydroxy-4-(3-methoxybenzylamino)-1-phenylbutan-2-yl)-5-(N-methylmethylsulfonamido)-N3-((R)-1-(thiazol-2-yl)ethyl)isophthalamide: $^1$H NMR (300 MHz, CDCl$_3$+CD$_3$OD): 1.72 (d, 3H, J=6.9 Hz), 2.70-3.01 (m, 4H), 2.84 (s, 3H), 3.29 (s, 3H), 3.70-3.89 (m, 3H), 3.75 (s, 3H), 4.27-4.36 (m, 1H), 5.54-5.66 (m, 1H), 6.76-6.90 (m, 3H), 7.08-7.30 (m, 6H), 7.67-7.69 (m. 1H) 7.81-7.83 (m, 1H), 7.95-7.98 (m, 1H), 8.10-8.13 (m, 1H).

N1-((2S,3R)-3-hydroxy-4-(3-methoxybenzylamino)-1-phenylbutan-2-yl)-5-(N-methylmethylsulfonamido)-N3-((R)-1-phenylethyl)isophthalamide: $^1$H NMR (300 MHz, CDCl$_3$+CD$_3$OD): 1.62 (d, 3H, J=7.2 Hz), 2.60-3.02 (m, 4H), 2.82 (s, 3H), 3.32 (s, 3H), 3.68-3.78 (m, 3H), 3.75 (s, 3H), 4.21-4.33 (m, 1H), 5.24-5.38 (m, 1H), 6.74-6.84 (m, 3H), 7.11-7.40 (m, 11H), 7.90-7.92 (m. 1H) 7.94-7.96 (m, 1H), 8.17-8.19 (m, 1H).

N1-((2S,3R)-3-hydroxy-4-(3-methoxybenzylamino)-1-phenylbutan-2-yl)-N3-methyl-N3-((2-methylthiazol-4-yl)methyl)isophthalamide: $^1$H NMR (300 MHz, CDCl$_3$+CD$_3$OD): 2.64 (s, 3H), 2.76-3.14 (m, 7H) 3.66-3.80 (m, 3H), 3.78 (s, 3H), 4.30-4.38 (m, 1H), 4.68-4.84 (m, 2H), 6.78-6.93 (m, 3H), 7.04-7.40 (m, 7H), 7.44-7.82 (m. 4H).

N1-((4-ethylthiazol-2-yl)methyl)-N3-((2S,3R)-3-hydroxy-4-(3-methoxybenzylamino)-1-phenylbutan-2-yl)-N1-methylisophthalamide: $^1$H NMR (300 MHz, CDCl$_3$+CD$_3$OD): 1.26 (t, 3H, J=7.5 Hz), 2.62-3.14 (m, 9H) 3.64-3.82 (m, 3H), 3.75 (s, 3H), 4.28-4.36 (m, 1H), 4.84-5.02 (m, 2H), 6.78-6.91 (m, 3H), 7.08-7.426 (m, 7H), 7.33-7.78(m, 4H).

N1-((2S,3R)-3-hydroxy-4-(3-methoxybenzylamino)-1-phenylbutan-2-yl)-N3-methyl-N3-((2-methyloxazol-4-yl)methyl)isophthalamide: $^1$H NMR (300 MHz, CDCl$_3$+CD$_3$OD): 2.54 (s, 3H), 2.74-3.10 (m, 7H) 3.68-3.84 (m, 3H), 3.75 (s, 3H), 4.27-4.36 (m, 1H), 4.48-4.62 (m, 2H), 6.76-6.90 (m, 3H), 7.07-7.27(m, 7H), 7.36-7.84 (m. 4H).

N1-((2S,3R)-3-hydroxy-4-((S)-1-(3-methoxyphenyl)ethylamino)-1-phenylbutan-2-yl)-N3-methyl-N3-((4-methylthiazol-2-yl)methyl)isophthalamide: $^1$H NMR (300 MHz, CDCl$_3$+CD$_3$OD), δ: 7.670 (m, 2H), 7.526 (m, 1H), 7.408 (m 1H), 7.237-7.107 (m, 6H), 6.889-6.739 (m, 4H), 4.931 (br, 1.3H), 4.630 (br, 0.7H), 4.293 (m, 1H), 3.765 (s, 3H), 3.783-3.633 (m, 2H), 3.020-2.858 (m, 5H), 2.646 (m, 2H), 2.421 (s, 3H), 1.398 (d, J=6.6 Hz, 3H).

N1-((2S,3R)-3-hydroxy-4-((R)-1-(3-methoxyphenyl)ethylamino)-1-phenylbutan-2-yl)-N3-methyl-N3-((4-methylthiazol-2-yl)methyl)isophthalamide: $^1$H NMR (300 MHz, CDCl$_3$+CD$_3$OD), δ: 7.732 (m, 2H), 7.532 (m, 1H), 7.387 (m 1H), 7.277-7.113 (m, 6H), 7.091-6.746 (m, 4H), 4.932 (br, 1.4H), 4.633 (br, 0.6H), 4.333 (m, 1H), 3.798-3.681 (m, 2H), 3.731 (s, 3H), 2.976 (s, 3H), 2.846 (m, 2H), 2.772-2.505 (m, 2H), 2.421 (s, 3H), 1.426 (d, J=6.3 Hz, 3H).

N1-((2S,3R)-3-hydroxy-4-(3-methoxybenzylamino)-1-phenylbutan-2-yl)-N3-methyl-N3-(pyrazin-2-ylmethyl)isophthalamide: 1H NMR (300 MHz, CDCl$_3$+CD$_3$OD): 2.54-3.06 (m, 7H), 3.65-3.84 (m, 6H), 4.25-4.36 (m, 1H), 4.76-4.92 (m, 2H), 6.74-6.90 (m, 3H), 7.08-7.82(m, 10H), 8.30-8.71 (m. 3H).

N1-((2S,3R)-3-hydroxy-4-(4-methylbenzylamino)-1-phenylbutan-2-yl)-N3-methyl-N3-((4-methylthiazol-2-yl)methyl)isophthalamide: $^1$H NMR (300 MHz, CDCl$_3$): 2.19 (s, 3H), 2.40 (s, 3H), 2.63-2.96 (m, 7H), 3.61-3.69 (m, 3H), 4.16-4.28 (m, 1H), 4.78-4.85 (s, 2H), 6.78 (s, 1H), 6.99-7.17 (m, 10H), 7.25-7.58 (m, 3H).

N1-((2S,3R)-3-hydroxy-4-(3-methoxybenzylamino)-1-phenylbutan-2-yl)-N3-methyl-5-(methylsulfonylmethyl)-N3-((4-methylthiazol-2-yl)methyl)isophthalamide: $^1$H NMR (300 MHz, CDCl$_3$): 2.42 (s, 3H), 2.62-3.18 (m, 10H), 3.72-3.83 (m, 6H), 4.2 (s, 2H), 4.14-4.20 (m, 1H), 4.82-4.90 (s, 2H), 6.76-6.92 (m, 4H), 7.21-7.38 (m, 6H), 7.67-8.18 (m, 3H).

N1-cyclohexyl-N3-((2S,3R)-3-hydroxy-4-(3-methoxybenzylamino)-1-phenylbutan-2-yl)-N1-((4-methylthiazol-2-yl)methyl)isophthalamide: 1H NMR (300 MHz, CDCl3) ☐7.69-7.15 (m, 14H), 7.05-6.81 (m, 5H), 4.93 (broad s, 2H), 4.40 (m, 1H), 3.87-3.68 (m, 6H), 3.49 (broad s, 1H), 3.03-2.81 (m, 5H), 2.43 (s, 4H), 1.72-1.54 (m, 7H), 1.01-0.86 (m, 4H).

N1-cyclopropyl-N3-((2S,3R)-3-hydroxy-4-(3-methoxybenzylamino)-1-phenylbutan-2-yl)-5-methoxy-N1-((4-methylthiazol-2-yl)methyl)isophthalamide: $^1$H NMR (300 MHz, CDCl$_3$) δ 7.32-7.16 (m, 10H), 6.93-6.79 (m, 4H), 4.98 (broad s, 2H), 4.37 (m, 1H), 4.00-3.74 (m, 9H), 3.10-2.77 (m, 4H), 2.45 (s, 3H), 0.58-0.48 (m, 4H).

N1-((2S,3S)-3-hydroxy-4-(3-methoxybenzylamino)-1-phenylbutan-2-yl)-5-(N-methylmethylsulfonamido)-N3-((R)-1-phenylethyl)isophthalamide: 1H NMR (300 MHz, CDCl$_3$+CD$_3$OD): 1.62 (d, 3H, J=7.2 Hz), 2.60-3.02 (m, 4H), 2.82 (s, 3H), 3.32 (s, 3H), 3.68-3.78 (m, 3H), 3.75 (s, 3H), 4.21-4.33 (m, 1H), 5.24-5.38 (m, 1H), 6.74-6.84 (m, 3H), 7.11-7.40 (m, 11H), 7.90-7.92 (m. 1H) 7.94-7.96 (m, 1H), 8.17-8.19 (m, 1H).

N1-cyclopropyl-N3-((2S,3R)-3-hydroxy-4-((5-isopropylpyridin-3-yl)methylamino)-1-phenylbutan-2-yl)-N1-((4-methylthiazol-2-yl)methyl)isophthalamide: $^1$H NMR (300 MHz, CDCl$_3$) δ 7.32-7.16 (m, 10H), 6.93-6.79 (m, 4H), 4.98 (broad s, 2H), 4.37 (m, 1H), 4.00-3.74 (m, 9H), 3.10-2.77 (m, 4H), 2.45 (s, 3H), 0.58-0.48 (m, 4H).

Example 5

Inhibition of Memapsin 1, Memapsin 2, and Cathepsin D Catalytic Activity

A substrate peptide NH$_3$-ELDLAVEFWHDR-CO$_2$ (SEQ ID NO.:1) (used for inhibition assay of memapsin 2, memapsin 1, and cathepsin D) was dissolved at 2 mg/ml in DMSO and diluted 1:100 in 0.1 M sodium acetate, pH 4.0 just prior to assay. Inhibitor dissolved in DMSO was diluted into 0.1 M sodium acetate, pH 4.0 (1:100 dilution). A 50 ml aliquot of the inhibitor solution in pH 4 buffer was combined with 150 ml of 0.1 M sodium acetate containing 100-200 nM of memapsin 1, memapsin 2, or cathepsin D. Following a pre-incubation at 37° C., the proteolytic assay was initated by addition of 50 ml of the substrate diluted into pH 4 buffer, and incubation continued at 37° C. Aliquots were removed at time intervals, and combined with an equal volume of MALDI-TOF matrix (α-hydroxycinnamic acid in acetone, 20 mg/ml) and immediately spotted in duplicate onto a stainless-steel MALDI sample plate. MALDI-TOF mass spectrometry was performed on a PE Biosystems Voyager DE instrument at the Molecular Biology Resource Center on campus. The instrument was operated at 25,000 accelerating volts in positive mode with a 150 ns delay. Ions with a mass-to-charge ratio (m/z) were detected in the range of 650-2000 atomic mass units. Data were analyzed by the Voyager Data Explorer module to obtain ion intensity data for mass species of substrates and corresponding products in a given mixture. Relative product formation was calculated as the ratio of signal intensity of the product to the sum of signal intensities of both product and the corresponding substrate. Relative product formed per unit time was obtained from non-linear regression analysis of the data representing the initial 15% formation of product using the model:

$$1-e^{-kT},$$

where k was the relative hydrolytic rate constant and T was time in seconds. Alternatively, relative hydrolytic rates were determined using a fluorogenic cleavage assay (Ermolieff, J. et al., *Biochemistry*, 39: 12450-12456 (2000)). Initial rates from either method were expressed relative to uninhibited controls and the inhibition constant $K_i$ was determined by a non-linear fit to a tight-binding model of competitive inhibition (Bieth, J., *Bayer-Symposium V: Proteinase Inhibitors*, pp 463-469, Spinger-Varlag, Berlin (1994)). Results are shown in Table 1 above (M2K, CDK, and M1K columns represent, respectively, the $K_1$ values obtained for memapsin 2, cathepsin D and memapsin 1).

Example 6

Cellular Aβ IC50 Determinations

The potency of compounds against memapsin 2 catalytic activity was determined in a cellular assay of Aβ production. Compounds that successfully penetrate the cell membrane demonstrated their ability to inhibit memapsin 2 catalytic activity in endosomal compartments, thus blocking the production of Aβ. Chinese hamster ovary cells that over-express human APP695 with the London and Swedish mutations were seeded in multi-well plates at 10% confluency. Compounds are dissolved in DMSO to concentrations near 1 mM, and diluted into culture media to a final concentration near 4 μM (final 0.4% DMSO). Compounds were diluted serially and applied to cells in multi-well plates 48 h after seeding. Incubation was continued in 5% $CO_2$ at 37 degrees C. for 24 h. Aliquots were removed and assayed for $A\beta_{40}$ content using a sandwich ELISA (BioSource International). Amount of $A\beta_{40}$ over the range of concentration of compounds, relative to control incubations, were fit to a 4-parameter $IC_{50}$ model. Results are provided in Table 1 above (Column labeled "Cell").

wherein $R^1$, $R^2$, $R^3$, and $R^4$ are hydrogen;

$R^5$ is halogen, —OH, —$CF_3$, —$NO_2$, —$N(R^8)R^9$, —$OR^{10}$, —$S(O)_nR^{11}$, —$C(O)R^{12}$, hydrogen, substituted or unsubstituted alkyl, substituted or unsubstituted heteroalkyl, substituted or unsubstituted cycloalkyl, substituted or unsubstituted aryl, or substituted or unsubstituted heteroaryl;

$R^6$ is substituted or unsubstituted alkyl, or substituted or unsubstituted cycloalkyl;

$R^7$ is —$S(O)_2R^{11}$, —$C(O)R^{12}$, —$N(R^8)R^9$, hydrogen, substituted or unsubstituted alkyl, substituted or unsubstituted cycloalkyl, substituted or unsubstituted heterocycloalkyl, substituted or unsubstituted aryl, or substituted or unsubstituted heteroaryl;

n is 2;

$R^8$ is independently —$C(O)R^{13}$, —$S(O)_2R^{14}$, hydrogen, substituted or unsubstituted alkyl, substituted or unsubstituted cycloalkyl, substituted or unsubstituted heterocycloalkyl, substituted or unsubstituted aryl, or substituted or unsubstituted heteroaryl;

$R^9$ is unsubstituted ($C_1$-$C_5$) alkyl;

$R^{10}$ is independently —$C(O)R^{13}$, substituted or unsubstituted alkyl, substituted or unsubstituted cycloalkyl, substituted or unsubstituted heterocycloalkyl, substituted or unsubstituted aryl, or substituted or unsubstituted heteroaryl;

$R^{11}$ is independently substituted or unsubstituted alkyl, —O-alkyl, substituted or unsubstituted cycloalkyl, substituted or unsubstituted heterocycloalkyl, substituted or unsubstituted aryl, substituted or unsubstituted heteroaryl, or —$N(R^{15})R^{16}$;

---

---

What is claimed is:

1. A compound having the formula:

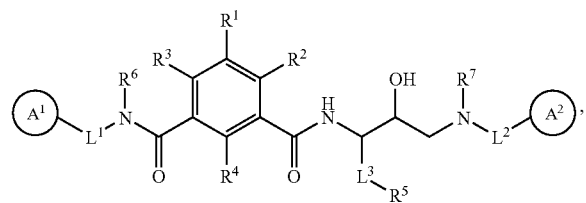

$R^{12}$ is independently —$NR^{18}R^{19}$, —$OR^{19}$, hydrogen, substituted or unsubstituted cycloalkyl, substituted or unsubstituted heterocycloalkyl, substituted or unsubstituted aryl, or substituted or unsubstituted heteroaryl;

$R^{13}$ is independently —$OR^{19}$, —$N(R^{18})R^{19}$, hydrogen, substituted or unsubstituted alkyl, substituted or unsubstituted cycloalkyl, substituted or unsubstituted heterocycloalkyl, substituted or unsubstituted aryl, or substituted or unsubstituted heteroaryl, $R^{14}$ is unsubstituted ($C_1$-$C_5$) alkyl;

$R^{18}$ and $R^{19}$ are independently hydrogen, substituted or unsubstituted alkyl, substituted or unsubstituted cycloalkyl, substituted or unsubstituted heterocycloalkyl, substituted or unsubstituted aryl, or substituted or unsubstituted heteroaryl;

$R^{15}$ and $R^{16}$ are independently hydrogen, substituted or unsubstituted alkyl, substituted or unsubstituted cycloalkyl, substituted or unsubstituted heterocycloalkyl, substituted or unsubstituted aryl, or substituted or unsubstituted heteroaryl;

$L^1$ is unsubstituted methylene or methylmethylene;

$L^2$ is unsubstituted methylene;

$L^3$ is a bond, $-N(R^{17})-$, $-S(O)_q-$, or substituted or unsubstituted alkylene;

$R^{17}$ is independently hydrogen, substituted or unsubstituted alkyl, substituted or substituted or unsubstituted cycloalkyl, substituted or unsubstituted heterocycloalkyl, substituted or unsubstituted aryl, or substituted or unsubstituted heteroaryl;

q is independently 0, 1, or 2;

$A^1$ is 2-(4-substituted)thiazolyl, 4-(2-substituted)thiazolyl, substituted 2-oxazolyl, or substituted 4-oxazolyl, $A^2$ is substituted phenyl, or substituted 3-pyridyl;

or a pharmaceutically acceptable salt, racemate, diastereomer, tautomer, or isotope thereof.

2. The compound of claim 1, wherein the compound has the stereochemistry as defined in the formula:

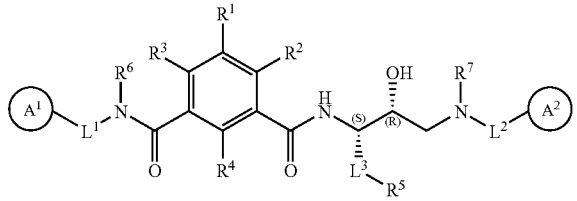

or a pharmaceutically acceptable salt thereof.

3. The compound of claim 1, wherein
$A^1$ and $A^2$ substituents are selected from $R^{24}$,
wherein $R^{24}$ is, independently, halogen, $-CN$, $-CF_3$, $-OCF_3$, $-OR^{27}$, $-S(O)_rR^{27}$, $-OCH_3$, $-C(O)R^{27}$, $-NR^{28}R^{29}$, $-NR^{28}C(O)R^{27}$, $-C(O)NR^{28}R^{29}$, $R^{25}$-substituted or unsubstituted $C_1$-$C_{20}$ alkyl, or $R^{25}$-substituted or unsubstituted 2 to 20 membered heteroalkyl,
wherein $R^{27}$, $R^{28}$, and $R^{29}$ are, independently, hydrogen, $R^{25}$-substituted or unsubstituted $C_1$-$C_{20}$ alkyl, or $R^{25}$-substituted or unsubstituted 2 to 20 membered heteroalkyl, and
wherein $R^{25}$ is independently oxo, halogen, $-CN$, $-OH$, $-CF_3$, $-OCF_3$, $-OCH_3$, unsubstituted $C_1$-$C_{20}$ alkyl, unsubstituted 2 to 20 membered heteroalkyl, unsubstituted $C_5$-$C_7$ cycloalkyl, unsubstituted 5 to 7 membered heterocycloalkyl, unsubstituted aryl, or unsubstituted heteroaryl.

4. The compound of claim 1, wherein
$R^5$ is $-OR^{10}$, substituted or unsubstituted cycloalkyl, substituted or unsubstituted aryl, or substituted or unsubstituted heteroaryl;
$R^7$ is hydrogen, substituted or unsubstituted alkyl;
$R^{10}$ is, independently, substituted or unsubstituted alkyl, substituted or unsubstituted cycloalkyl, substituted or unsubstituted heterocycloalkyl, substituted or unsubstituted aryl, or substituted or unsubstituted heteroaryl; and
$L^3$ is substituted or unsubstituted alkylene.

5. The compound of claim 1, wherein
$A^1$ is substituted 2-(4-substituted)thiazolyl or substituted 2-oxazolyl;
$R^5$ is substituted or unsubstituted aryl;
$R^6$ is unsubstituted alkyl, or cycloalkyl;
$L^1$ and $L^3$ are unsubstituted methylene.

6. The compound of claim 1, wherein
$A^1$ is 2-(4-substituted)thiazolyl);
$R^5$ is substituted or unsubstituted aryl;
$R^6$ is unsubstituted ($C_1$-$C_6$) alkyl, or unsubstituted ($C_3$-$C_6$) cycloalkyl;
$R^7$ is hydrogen; and
$L^1$ and $L^3$ are unsubstituted methylene.

7. The compound of claim 6, wherein
$A^1$ and $A^2$ substituents are selected from $R^{24}$,
wherein $R^{24}$ is, independently, halogen, $-CN$, $-CF_3$, $-OCF_3$, $-OR^{27}$, $-S(O)_rR^{27}$, $-OCH_3$, $-C(O)R^{27}$, $-NR^{28}R^{29}$, $-NR^{28}C(O)R^{27}$, $-C(O)NR^{28}R^{29}$, $R^{25}$-substituted or unsubstituted $C_1$-$C_{20}$ alkyl, or $R^{25}$-substituted or unsubstituted 2 to 20 membered heteroalkyl,
wherein $R^{27}$, $R^{28}$, and $R^{29}$ are, independently, hydrogen, $R^{25}$-substituted or unsubstituted $C_1$-$C_{20}$ alkyl, or $R^{25}$-substituted or unsubstituted 2 to 20 membered heteroalkyl, and
wherein $R^{25}$ is independently oxo, halogen, $-CN$, $-OH$, $-CF_3$, $-OCF_3$, $-OCH_3$, unsubstituted $C_1$-$C_{20}$ alkyl, unsubstituted 2 to 20 membered heteroalkyl, unsubstituted $C_5$-$C_7$ cycloalkyl, unsubstituted 5 to 7 membered heterocycloalkyl, unsubstituted aryl, or unsubstituted heteroaryl.

8. The compound of claim 6, wherein said compound has a memapsin 2 $K_i$ of less than 300 nM.

9. The compound of claim 6, wherein the compound has the stereochemistry as defined in the formula:

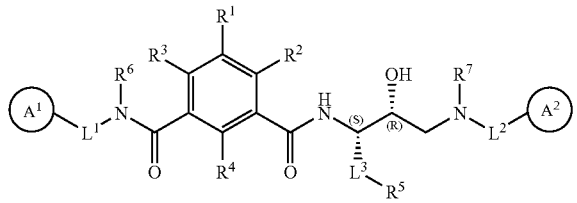

or a pharmaceutically acceptable salt thereof.

10. The compound of claim 6, wherein
$R^5$ is unsubstituted or substituted phenyl.

11. The compound of claim 6, wherein
$R^5$ is unsubstituted phenyl or dihalophenyl.

12. The compound of claim 6, wherein $R^5$ is unsubstituted phenyl.

13. The compound of claim 6, wherein
$A^1$ and $A^2$ are substituted with unsubstituted $C_1$-$C_5$ alkyl or $C_1$-$C_5$ haloalkyl.

14. The compound of claim 1, wherein
$A^1$ is 2-(4-methylthiazolyl).

15. The compound of claim 6, wherein
$A^1$ is 2-(4-methylthiazolyl).

16. The compound of claim 13, wherein
$A^1$ is 2-(4-methylthiazolyl).

17. The compound of claim 1, wherein
$A^2$ is substituted 3-pyridyl.

18. The compound of claim 6, wherein
$A^2$ is substituted 3-pyridyl.

19. The compound of claim 13, wherein
$A^2$ is substituted 3-pyridyl.

20. The compound of claim 1, wherein
A2 is 3-(5-substituted)pyridyl.

21. The compound of claim 6, wherein
$A^2$ is 3-(5-substituted)pyridyl.

22. The compound of claim 13, wherein A² is 3-(5-substituted)pyridyl.

23. The compound of claim 1, wherein A² is meta-substituted phenyl.

24. The compound of claim 6, wherein A² is meta-substituted phenyl.

25. The compound of claim 1, wherein
A¹ is 2-(4-substituted)thiazolyl;
A² is substituted 3-pyridyl;
R⁵ is unsubstituted or substituted phenyl;
R⁶ is unsubstituted (C₁-C₆) alkyl;
R⁷ is hydrogen; and
L³ is unsubstituted methylene.

26. The compound of claim 25, wherein
A¹ is 2-(4-methylthiazolyl);
A² is 3-(5-substituted)pyridyl; and
R⁵ is unsubstituted phenyl or dihalophenyl.

27. The compound of claim 26, wherein the 3-(5-substituted)pyridyl is substituted with unsubstituted C₁-C₅ alkyl or C₁-C₅ haloalkyl.

28. The compound of claim 25, wherein
A¹ and A² are R²⁴-substituted,
   wherein R²⁴ is, independently, halogen, —CN, —CF₃, —OCF₃, —OR₂₇, —S(O)ₓR²⁷, —OCH₃, —C(O)R²⁷, —NR²⁸R²⁹, —NR²⁸C(O)R²⁷, —C(O)NR²⁸R²⁹, R²⁵-substituted or unsubstituted C₁-C₂₀ alkyl, or or unsubstituted 2 to 20 membered heteroalkyl,
   wherein R²⁷, R²⁸, and R²⁹ are, independently, hydrogen, R²⁵-substituted or unsubstituted C₁-C₂₀ alkyl, or R²⁵-substituted or unsubstituted 2 to 20 membered heteroalkyl, and
   wherein R²⁵ is independently oxo, halogen, —CN, —OH, —CF₃, —OCF₃, —OCH₃, unsubstituted C₁-C₂₀ alkyl, unsubstituted 2 to 20 membered heteroalkyl, unsubstituted C₅-C₇ cycloalkyl, unsubstituted 5 to 7 membered heterocycloalkyl, unsubstituted aryl, or unsubstituted heteroaryl.

29. The compound of claim 25, wherein said compound has a memapsin 2 K_i of less than 300 nM.

30. The compound of claim 25,
wherein the compound has the stereochemistry as defined in the formula:

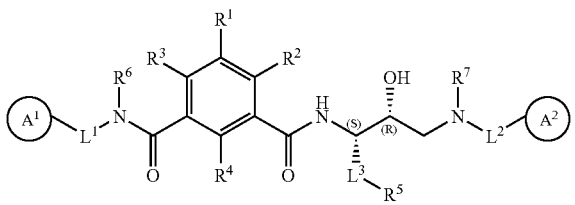

or a pharmaceutically acceptable salt thereof.

31. The compound of claim 1, wherein said compound has a memapsin 2 K_i of less than 300 nM.

32. A compound of claim 1 which is:
N1-(4-(3-(fluoromethyl)benzylamino)-3-hydroxy-1-phenylbutan-2-yl)-N3-methyl-N3-((4-methylthiazol-2-yl)methyl)isophthalamide;
N1-(3-hydroxy-4-((5-isopropoxypyridin-3-yl)methylamino)-1-phenylbutan-2-yl)-N3-methyl-N3-((4-methylthiazol-2-yl)methyl)isophthalamide;
N1-(3-hydroxy-4-(3-isobutylbenzylamino)-1-phenylbutan-2-yl)-N3-methyl-N3-((4-methylthiazol-2-yl)methyl)isophthalamide;
N1-(4-((5-ethoxypyridin-3-yl)methylamino)-3-hydroxy-1-phenylbutan-2-yl)-N3-methyl-N3-((4-methylthiazol-2-yl)methyl)isophthalamide;
N1-(3-hydroxy-4-((5-methoxypyridin-3-yl)methylamino)-1-phenylbutan-2-yl)-N3-methyl-N3-((4-methylthiazol-2-yl)methyl)isophthalamide;
N1-(3-hydroxy-4-((5-methylpyridin-3-yl)methylamino)-1-phenylbutan-2-yl)-N3-methyl-N3-((4-methylthiazol-2-yl)methyl)isophthalamide;
N1-(3-hydroxy-4-((5-isobutylpyridin-3-yl)methylamino)-1-phenylbutan-2-yl)-N3-methyl-N3-((4-methylthiazol-2-yl)methyl)isophthalamide;
N1-(3-hydroxy-4-((5-isobutoxypyridin-3-yl)methylamino)-1-phenylbutan-2-yl)-N3-methyl-N3-((4-methylthiazol-2-yl)methyl)isophthalamide;
N1-(4-((5-ethylpyridin-3-yl)methylamino)-3-hydroxy-1-phenylbutan-2-yl)-N3-methyl-N3-((4-methylthiazol-2-yl)methyl)isophthalamide;
N1-(3-hydroxy-4-(3-isobutoxybenzylamino)-1-phenylbutan-2-yl)-N3-methyl-N3-((4-methylthiazol-2-yl)methyl)isophthalamide;
N1-(3-hydroxy-4-((5-isopropylpyridin-3-yl)methylamino)-1-phenylbutan-2-yl)-N3-methyl-N3-((4-methylthiazol-2-yl)methyl)isophthalamide;
N1-(4-(3-(difluoromethoxy)benzylamino)-3-hydroxy-1-phenylbutan-2-yl)-N3-methyl-N3-((4-methylthiazol-2-yl)methyl)isophthalamide;
N1-(3-hydroxy-1-phenyl-4-(3-(trifluoromethoxy)benzylamino)butan-2-yl)-N3-methyl-N3-((4-methylthiazol-2-yl)methyl)isophthalamide;
N1-cyclopropyl-N3-(3-hydroxy-4-((5-isopropylpyridin-3-yl)methylamino)-1-phenylbutan-2-yl)-N1-((4-methylthiazol-2-yl)methyl)isophthalamide;

or a pharmaceutically acceptable salt, racemate, diastereomer, tautomer, or isotope thereof.

33. A compound of claim 1 which is:
N1-(3-hydroxy-4-(3-methoxybenzylamino)-1-phenylbutan-2-yl)-N3-methyl-N3-((4methylthiazol-2-yl)methyl)isophthalamide;
N1-cyclopropyl-N3-(3-hydroxy-4-(3-methoxybenzylamino)-1-phenylbutan-2-yl)-N1-((4-methylthiazol-2-yl)methyl)isophthalamide;
N1-(3-hydroxy-4-(3-isopropylbenzylamino)-1-phenylbutan-2-yl)-N3-methyl-N3-((4-methylthiazol-2-yl)methyl)isophthalamide;
N1-(4-(3-ethylbenzylamino)-3-hydroxy-1-phenylbutan-2-yl)-N3-methyl-N3-((4-methylthiazol-2-yl)methyl)isophthalamide;
N1-(1-(3,5-difluorophenyl)-3-hydroxy-4-(3-methoxybenzylamino)butan-2-yl)-N3-methyl-N3-((4-methylthiazol-2-yl)methyl)isophthalamide;
N1-(3-hydroxy-4-(3-methoxybenzylamino)-1-phenylbutan-2-yl)-N3-methyl-N3-((4-methyloxazol-2-yl)methyl)isophthalamide;
N1-(4-(3-ethynylbenzylamino)-3-hydroxy-1-phenylbutan-2-yl)-N3-methyl-N3-((4-methylthiazol-2-yl)methyl)isophthalamide;
N1-(3-hydroxy-4-(3-methoxybenzylamino)-1-phenylbutan-2-yl)-N3-isopropyl-N3-((4-methylthiazol-2-yl)methyl)isophthalamide;
N1-(3-hydroxy-4-(3-methoxybenzylamino)-1-phenylbutan-2-yl)-N3-isobutyl-N3-((4-methylthiazol-2-yl)methyl)isophthalamide;
N1-(4-(3-ethoxybenzylamino)-3-hydroxy-1-phenylbutan-2-yl)-N3-methyl-N3-((4-methylthiazol-2-yl)methyl)isophthalamide;
N1-(3-hydroxy-4-(3-isopropoxybenzylamino)-1-phenylbutan-2-yl)-N3-methyl-N3-((4-methylthiazol-2-yl)methyl)isophthalamide;

N1-(3-hydroxy-1-phenyl-4-(3-(trifluoromethyl)benzy-
lamino)butan-2-yl)-N3-methyl-N3-((4-methylthiazol-
2-yl)methyl)isophthalamide;
N1-ethyl-N3-(3-hydroxy-4-(3-methoxybenzylamino)-1-
phenylbutan-2-yl)-N1-((4-methylthiazol-2-yl)methyl)
isophthalamide;
N1-(3-hydroxy-4-(3-methoxybenzylamino)-1-phenylbu-
tan-2-yl)-N3-methyl-N3-((2-methylthiazol-4-yl)me-
thyl)isophthalamide;
N1-((4-ethylthiazol-2-yl)methyl)-N3-(3-hydroxy-4-(3-
methoxybenzylamino)-1-phenylbutan-2-yl)-N1-meth-
ylisoplithalamide;
N1-cyclopentyl-N3-(3-hydroxy-4-(3-methoxybenzy-
lamino)-1-phenylbutan-2-yl)-N1-((4-methylthiazol-2-
yl)methyl)isophthalamide;
N1-(3-hydroxy-4-(3-methoxybenzylamino)-1-phenylbu-
tan-2-yl)-N3-methyl-N3-((2-methyloxazol-4-yl)me-
thyl)isophthalamide;
or a pharmaceutically acceptable salt, racemate, diastere-
omer, tautomer, or isotope thereof.

34. A compound which is:
N1-(3-hydroxy-4-((5-isopropylpyridin-3-yl)methy-
lamino)-1-phenylbutan-2-yl)-N3-methyl-N3-((4-meth-
ylthiazol-2-yl)methyl)isophthalamide;
or a pharmaceutically acceptable salt, racemate, diastere-
omer, tautomer, or isotope thereof.

35. A compound which is:
N1-((2S ,3R)-3-hydroxy-4-((5-isopropylpyridin-3-yl)me-
thylamino)-1-phenylbutan-2-yl)-N3-methyl-N3-((4-
methylthiazol-2-yl)methyl)isophthalamide;
or a pharmaceutically acceptable salt thereof.

36. A compound having the formula:

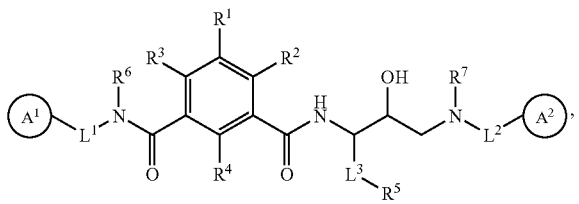

wherein
$A^1$ is 2-(4-substituted)thiazolyl;
$A^2$ is 3-(5-substituted)pyridyl;
$R^1$, $R^2$, $R^3$, and $R^4$ are hydrogen;
$R^5$ is unsubstituted or substituted phenyl
$R^6$ is unsubstituted ($C_1$-$C_6$) alkyl or unsubstituted ($C_3$-$C_6$) cycloalkyl;
$R^7$ is hydrogen; and
$L^1$, $L^2$, and $L^3$ are unsubstituted methylene;
or a pharmaceutically acceptable salt, racemate, diastere-
omer, tautomer, or isotope thereof.

37. The compound of claim 36 wherein
$A^1$ is 2-(4-methylthiazolyl);
$R^5$ is unsubstituted phenyl or dihalophenyl.

38. The compound of claim 36, wherein
the 3-(5-substituted)pyridyl is substituted with unsubsti-
tuted $C_1$-$C_5$ alkyl or $C_1$-$C_5$ haloalkyl.

39. The compound of claim 37, wherein
the 3-(5-substituted)pyridyl is substituted with unsubsti-
tuted $C_1$-$C_5$ alkyl or $C_1$-$C_5$ haloalkyl.

40. The compound of claim 36,
wherein the compound has the stereochemistry as defined in the formula:

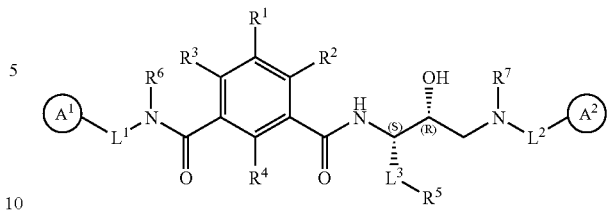

or a pharmaceutically acceptable salt thereof.

41. A compound having the formula:

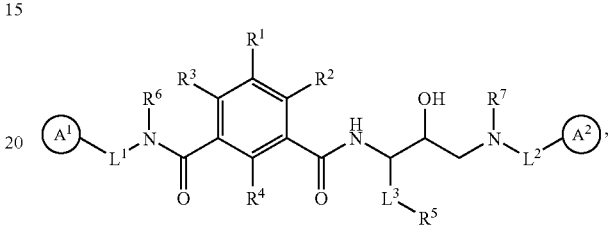

wherein
$R^1$, $R^2$, $R^3$, and $R^4$ are hydrogen;
$R^5$ is phenyl or difluorophenyl;
$R^6$ is unsubstituted $C_1$-$C_6$ alkyl, unsubstituted $C_3$-$C_6$ cycloalkyl or benzyl;
$R^7$ is hydrogen;
$L^1$ and $L^2$ are, independently, unsubstituted methylene or methylmethylene;
$L^3$ is unsubstituted methylene;
$A^1$ is selected from the group consisting of 2-(4-methyl)
thiazolyl, 2-(4-ethyl)thiazolyl, 4-(2-methyl)thiazolyl,
2-(4-methyl)oxazolyl, 4-(2-methyl)oxazolyl ,and 4-(2,
5-dimethyl)oxazolyl; and
$A^2$ is a 3-(5-substituted)pyridyl or meta-substituted phe-
nyl;
or a pharmaceutically acceptable salt, racemate, diastere-
omer, tautomer, or isotope thereof.

42. The compound of claim 41 wherein
$R^5$ is phenyl or 3,5-difluorophenyl;
$R^6$ is methyl, ethyl, isopropyl, isobutyl, cyclopropyl, or cyclopentyl;
$R^7$ is hydrogen;
$L^1$, $L^2$, and $L^3$ are unsubstituted methylene;
$A^1$ is selected from the group consisting of 2-(4-methyl)
thiazolyl, 2-(4-ethyl)thiazolyl, 4-(2-methyl)thiazolyl,
2-(4-methyl)oxazolyl, 4-(2-methyl)oxazolyl ,and 4-(2,
5-dimethyl)oxazolyl; and
$A^2$ is selected from the group consisting of 3-methoxyphe-
nyl, 3-ethoxyphenyl, 3-isopropoxyphenyl, 3-isobutox-
yphenyl, 3-difluoromethoxyphenyl, 3-trifluoromethox-
yphenyl, 3-ethylphenyl, 3-isopropylphenyl,
3-isobutylphenyl, 3-fluoromethylphenyl, 3-trifluorom-
ethylphenyl, 3-ethynylphenyl, 3-(5-methoxy)pyridinyl,
3-(5-ethoxy)pyridinyl, 3-(5-isopropoxy)pyridinyl, 3-(5-
isobutoxy)pyridinyl, 3-(5-methyl)pyridinyl, 3-(5-ethyl)
pyridinyl, 3-(5-isopropyl)pyridinyl, and 3-(5-isobutyl)
pyridinyl.

43. The compound of claim 42, wherein
$A^1$ is 2-(4-methyl)thiazolyl.

44. The compound of claim 41,
wherein the compound has the stereochemistry as defined in the formula:

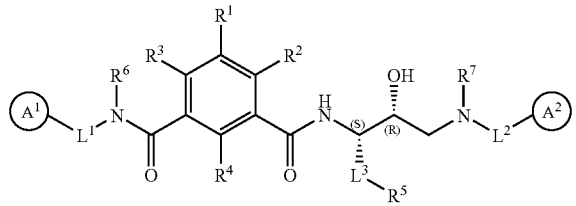

or a pharmaceutically acceptable salt thereof.

45. The compound of claim 41, wherein said compound has a memapsin 2 $K_i$ of less than 300 nM.

46. The compound of claim 36, wherein said compound has a memapsin 2 $K_i$ of less than 300 nM.

47. A composition comprising a compound of claim 1 and a pharmaceutically acceptable carrier.

48. A composition comprising a compound of claim 34 and a pharmaceutically acceptable carrier.

* * * * *

UNITED STATES PATENT AND TRADEMARK OFFICE
CERTIFICATE OF CORRECTION

PATENT NO. : 7,504,420 B2
APPLICATION NO. : 11/463558
DATED : March 17, 2009
INVENTOR(S) : Arun K. Ghosh et al.

It is certified that error appears in the above-identified patent and that said Letters Patent is hereby corrected as shown below:

- On the title page item (56), under OTHER PUBLICATIONS please add:

-- ABBOTT, N.J. et al. (1992). Physiology and Pharmacology of the Blood-Brain Barrier, Bradbury, M.W.B. ed., Springer-Verlag:Berlin, Germany, pp. XI-XXIII. (Table of Contents Only.)

ABBOTT, N.J. et al. (March 1996). "Transporting Therapeutics Across the Blood-Brain Barrier," *Mol. Med. Today* 2(3):106-113.

BRAGA, D. et al. (2005, e-pub. June 15, 2005). "Making Crystals from Crystals: A Green Route to Crystal Engineering and Polymorphism," *Chem. Commun.* pp. 3625-3645. (cited by examiner)

International Search Report mailed August 28, 2006 for PCT Application No. PCT/US2006/013342 filed April 10, 2006, 6 pages. (cited by examiner)

MedicineNet.com. (2007). "Tacrine," located at <http://www.medicinenet.com/tacrine/article.htm>, last visited July 21, 2007, three pages. (cited by examiner)

Varghese, J. (March 2006). "Human β-Secretase (BACE) and BACE Inhibitors: Progress Report," *Current Topics in Medicinal Chemistry* 6(6):569-578.

XUE, Q. et al. (2007). "Preparation of 2-hydroxy-1,3-diaminoalkanes Including Spiro Substituted Chroman Derivatives as β-Secretase Modulators and Their use for Treatment Alzheimer's Disease and Related Condition," Caplus Database DN 147:30947; AN 2007:585478, two pages. (cited by examiner) --.

- Column 1, line 27; please replace "inter alia," with -- *inter alia*, --.

- Column 4, line 34; please replace "at least one carbon atoms" with -- at least one carbon atom --.

- Column 4, line 38; please replace "quatemized." with -- quaternized. --.

- Column 8, line 46; please replace "ex vivo" with -- *ex vivo* --.

UNITED STATES PATENT AND TRADEMARK OFFICE
CERTIFICATE OF CORRECTION

PATENT NO. : 7,504,420 B2
APPLICATION NO. : 11/463558
DATED : March 17, 2009
INVENTOR(S) : Arun K. Ghosh et al.

It is certified that error appears in the above-identified patent and that said Letters Patent is hereby corrected as shown below:

- Column 9, line 25 and 26; please replace "tert-" with -- *tert-* --.

- Column 16, line 43; please replace "may be 20" with -- may be --.

- Column 16, line 46 should be a continuation of the previous paragraph. Please delete the break and indent.

- Column 17, line 33; please replace "Formula (II)" with -- Formula (IV) --.

- Column 18, line 62; please replace "include *t* any one" with -- include any one --.

- Column 21, line 2; please replace "thereby preventing to escape" with -- thereby preventing escape --.

- Column 21, line 19; please replace "some ebociments," with -- some embodiments, --.

- Column 21, line 20; please replace "may includes" with -- may include --.

- Column 21, line 24; please replace "in vitro" with -- *in vitro* --.

- Column 21, line 27; please replace "in vitro" with -- *in vitro* --.

- Column 25, line 64; please replace "in vitro" with -- *in vitro* --.

- Column 26, line 16; please replace "in vitro" with -- *in vitro* --.

- Column 26, line 64; please replace "in vitro" with -- *in vitro* --.

- Column 26, line 66; please replace "standard in vitro or in vivo assays" with -- standard *in vitro* or *in vivo* assays --.

- Column 27, lines 35-36; please replace "with a nucleic acid constructs" with -- with a nucleic acid construct --.

- Column 29, line 60; please replace "form the 5 preparation" with -- form the preparation --.

UNITED STATES PATENT AND TRADEMARK OFFICE
CERTIFICATE OF CORRECTION

PATENT NO. : 7,504,420 B2
APPLICATION NO. : 11/463558
DATED : March 17, 2009
INVENTOR(S) : Arun K. Ghosh et al.

It is certified that error appears in the above-identified patent and that said Letters Patent is hereby corrected as shown below:

- Column 30, line 45; please replace "inter alia," with -- *inter alia*, --.

- Column 30, line 48; please replace "to achieve the desires result" with -- to achieve the desired result --.

- Column 33, line 32; please replace "in vitro," with -- *in vitro*, --.

- Column 33, line 33; please replace "in vitro" with -- *in vitro* --.

- Column 33, line 36; please replace "in vitro" with -- *in vitro* --.

- Column 34, line 2; please replace "reduces P3-secretase" with -- reduces β-secretase --.

- Column 34, line 67; please replace "groups at one end" with -- group at one end --.

- Column 35, line 2; please replace "include, fro" with -- include, for --.

- Column 38, line 40; please replace "tert-butyl-" with -- *tert*-butyl- --.

- Column 38, line 59; please replace "cc" with -- ά --.

- Column 38, line 59; please replace "methylbezy-" with -- methylbenzy- --.

- Column 38, line 65; please replace "tert-butyl-" with -- *tert*-butyl- --.

- Column 39, line 44; please replace "cc" with -- α --.

- Column 39, line 44; please replace "methylbezylamine" with -- methylbenzylamine --.

- Column 43, line 51; please replace "was dried over" with -- were dried over --.

- Column 44, line 24; please replace "4.14 imol," with -- 4.14 mmol, --.

- Column 45, line 11; please replace "mono-Methyl" with -- *mono*-Methyl --.

UNITED STATES PATENT AND TRADEMARK OFFICE
CERTIFICATE OF CORRECTION

PATENT NO.      : 7,504,420 B2
APPLICATION NO. : 11/463558
DATED           : March 17, 2009
INVENTOR(S)     : Arun K. Ghosh et al.

It is certified that error appears in the above-identified patent and that said Letters Patent is hereby corrected as shown below:

- Column 45, line 14; please replace "removed in vacuo." with -- removed *in vacuo*. --.

- Column 45, line 25; please replace "removed in vacuo" with -- removed *in vacuo* --.

- Column 49, line 3; please replace "0.45 nmol" with -- 0.45 mmol --.

- Column 49; line 28; please replace "4.3 grn," with -- 4.3 gm, --.

- Column 49, line 42; please replace "1.74 gin," with -- 1.74 gm, --.

- Column 78, line 1; please replace "((R or S)-i-(3-fluorophenyl)" with -- ((R or S)-1-(3-fluorophenyl) --.

- Column 79, line 4; please replace "((2 S,3R)" with -- ((2S,3R) --.

- Column 79, line 59; please replace "((3-methyl-i H-pyrazol-5-yl)" with -- ((3-methyl-1-H-pyrazol-5-yl) --.

- Column 85, line 15; please replace "(m, 12), 6.66-6.75" with -- (m, 12H), 6.66-6.75 --.

- Column 87, line 3; please replace "7.7.46-7.83(m, 2H)" with -- 7.46-7.83(m, 2H) --.

- Column 87, line 49; please replace "3.73 9s, 3H)," with -- 3.73 (s, 3H), --.

- Column 87, line 57; please replace "3.3.82 (m, 3H)," with -- 3.82 (m, 3H), --.

- Column 88, line 51; please replace "6.95-7.22 (m, 10H0," with -- 6.95-7.22 (m, 10H), --.

- Column 89, line 24; please replace "4.58-4.64 (m. 2H)" with -- 4.58-4.64 (m, 2H), --.

- Column 89, line 53; please replace "4.58-4.64 (m. 2H)" with -- 4.58-4.64 (m, 2H), --.

UNITED STATES PATENT AND TRADEMARK OFFICE
CERTIFICATE OF CORRECTION

PATENT NO. : 7,504,420 B2
APPLICATION NO. : 11/463558
DATED : March 17, 2009
INVENTOR(S) : Arun K. Ghosh et al.

It is certified that error appears in the above-identified patent and that said Letters Patent is hereby corrected as shown below:

- Column 90, line 27; please replace "isophthalarnide" with -- isophthalamide --.

- Column 90, line 31; please replace "7.53 (s." with -- 7.53 (s, --.

- Column 90, line 35; please replace "(-N-methylmethylsulfonamido)isophthalaiide:" with -- (-N-methylmethylsulfonamido)isophthalamide: --.

- Column 90, line 39; please replace "7.53 (s. 1H)" with -- 7.53 (s, 1H), --.

- Column 90, line 47; please replace "7.30-7.32 (m. 1H)" with -- 7.30-7.32 (m, 1H), --.

- Column 90, line 54; please replace "7.50-7.89 (m. 4H)." with -- 7.50-7.89 (m, 4H). --.

- Column 90, line 67; please replace "7.50-7.89 (m. 4H)." with -- 7.50-7.89 (m, 4H). --.

- Column 91, line 7; please replace "7.67-7.69 (m. 1H)" with -- 7.67-7.69 (m, 1H), --.

- Column 91, line 34; please replace "7.36-7.84 (m. 4H)." with -- 7.36-7.84 (m, 4H). --.

- Column 91, line 38; please replace "8: 7.60 (m, 2H)," with -- δ: 7.60 (m, 2H), --.

- Column 91, line 54; please replace "isophthalamide: 1H NMR" with -- isophthalamide: $^1$H NMR --.

- Column 91, line 57; please replace "8.30-8.71 (m. 3H)." with -- 8.30-8.71 (m, 3H). --.

- Column 92, line 6; please replace "isophthalamide: 1H NMR (300 MHz, CDCl3)" with -- isophthalamide: $^1$H NMR (300 MHz, CDCl$_3$) --.

UNITED STATES PATENT AND TRADEMARK OFFICE
CERTIFICATE OF CORRECTION

PATENT NO. : 7,504,420 B2
APPLICATION NO. : 11/463558
DATED : March 17, 2009
INVENTOR(S) : Arun K. Ghosh et al.

It is certified that error appears in the above-identified patent and that said Letters Patent is hereby corrected as shown below:

- Column 92, line 7; please replace "☐7.69-7.15" with -- δ 7.69-7.15 --.

- Column 92, line 19; please replace "isophthalamide: 1H NMR" with -- isophthalamide: $^1$H NMR --.

- Column 92, line 23; please replace "7.90-7.92 (m. 1H)" with -- 7.90-7.92 (m, 1H), --.

In the Claims:

- In Claim 1, column 95, line 17; please replace "substituted 4-oxazolyl," with -- substituted 4-oxazolyl; --.

- In Claim 20, column 96, line 65; please replace "A2 is" with -- $A^2$ is --.

- In Claim 28, column 97, line 24; please replace "—OR$_{27}$," with -- —OR$^{27}$, --.

- In Claim 28, column 97, line 26; please replace "$C_1$-$C_{20}$ alkyl, or or unsubstituted" with -- $C_1$-$C_{20}$ alkyl, or $R^{25}$ substituted or unsubstituted --.

Signed and Sealed this

Tenth Day of November, 2009

David J. Kappos
*Director of the United States Patent and Trademark Office*

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic construct

<400> SEQUENCE: 1

Glu Leu Asp Leu Ala Val Glu Phe Trp His Asp Arg
1               5                   10